United States Patent
Gedulin et al.

(10) Patent No.: US 10,251,880 B2
(45) Date of Patent: Apr. 9, 2019

(54) BILE ACID RECYCLING INHIBITORS AND SATIOGENS FOR TREATMENT OF DIABETES, OBESITY, AND INFLAMMATORY GASTROINTESTINAL CONDITIONS

(71) Applicant: SATIOGEN PHARMACEUTICALS, INC., San Diego, CA (US)

(72) Inventors: Bronislava Gedulin, Del Mar, CA (US); Andrew A. Young, Chapel Hill, NC (US); Howard E. Greene, Frankfort, MI (US)

(73) Assignee: SATIOGEN PHARMACEUTICALS, INC., San Diego, CA (US)

( * ) Notice: Subject to any disclaimer, the term of this patent is extended or adjusted under 35 U.S.C. 154(b) by 96 days.

(21) Appl. No.: 14/555,290

(22) Filed: Nov. 26, 2014

(65) Prior Publication Data

US 2015/0087642 A1     Mar. 26, 2015

Related U.S. Application Data

(63) Continuation of application No. 13/116,988, filed on May 26, 2011, now abandoned.

(Continued)

(51) Int. Cl.
    *A61K 31/575*        (2006.01)
    *A61K 31/496*        (2006.01)
    (Continued)

(52) U.S. Cl.
CPC .......... *A61K 31/496* (2013.01); *A61K 9/0031* (2013.01); *A61K 9/02* (2013.01); *A61K 9/286* (2013.01); *A61K 31/155* (2013.01); *A61K 31/16* (2013.01); *A61K 31/18* (2013.01); *A61K 31/19* (2013.01); *A61K 31/191* (2013.01); *A61K 31/216* (2013.01); *A61K 31/38* (2013.01);

(Continued)

(58) Field of Classification Search
CPC .. A61K 31/4995; A61K 45/06; A61K 31/496; A61K 31/155; A61K 31/5377
USPC ....... 514/321.2, 249, 315, 326, 408, 252.12, 514/635
See application file for complete search history.

(56) References Cited

U.S. PATENT DOCUMENTS

| 5,234,697 A | 8/1993 | Sipos |
| 5,415,872 A | 5/1995 | Sipos |

(Continued)

FOREIGN PATENT DOCUMENTS

| CN | 1284953 | 2/2001 |
| CN | 1439638 | 9/2003 |

(Continued)

OTHER PUBLICATIONS

Deacon. Dipeptidyl peptidase 4 inhibition with sitagliptin: a new therapy for type 2 diabetes. Expert Opin Investig Drugs 16:533-545 (2007).

(Continued)

*Primary Examiner* — Craig D Ricci
*Assistant Examiner* — Janet L. Coppins
(74) *Attorney, Agent, or Firm* — Wilson Sonsini Goodrich & Rosati

(57) ABSTRACT

Provided herein are methods of utilizing bile acid transport inhibitors and/or enteroendocrine peptide enhancing agents for the treatment of obesity, diabetes, and inflammatory gastrointestinal conditions.

12 Claims, 26 Drawing Sheets

Related U.S. Application Data

(60) Provisional application No. 61/348,666, filed on May 26, 2010, provisional application No. 61/348,669, filed on May 26, 2010.

(51) Int. Cl.

| | | |
|---|---|---|
| *A61K 9/00* | (2006.01) | |
| *A61K 9/02* | (2006.01) | |
| *A61K 9/28* | (2006.01) | |
| *A61K 31/155* | (2006.01) | |
| *A61K 31/16* | (2006.01) | |
| *A61K 31/18* | (2006.01) | |
| *A61K 31/19* | (2006.01) | |
| *A61K 31/191* | (2006.01) | |
| *A61K 31/216* | (2006.01) | |
| *A61K 31/38* | (2006.01) | |
| *A61K 31/40* | (2006.01) | |
| *A61K 31/42* | (2006.01) | |
| *A61K 31/452* | (2006.01) | |
| *A61K 31/454* | (2006.01) | |
| *A61K 31/495* | (2006.01) | |
| *A61K 31/4985* | (2006.01) | |
| *A61K 31/4995* | (2006.01) | |
| *A61K 31/513* | (2006.01) | |
| *A61K 31/5377* | (2006.01) | |
| *A61K 31/55* | (2006.01) | |
| *A61K 31/554* | (2006.01) | |
| *A61K 31/655* | (2006.01) | |
| *A61K 31/7042* | (2006.01) | |
| *A61K 45/06* | (2006.01) | |
| *C07C 279/14* | (2006.01) | |
| *C07D 295/13* | (2006.01) | |
| *C07D 401/12* | (2006.01) | |

(52) U.S. Cl.
CPC .............. *A61K 31/40* (2013.01); *A61K 31/42* (2013.01); *A61K 31/452* (2013.01); *A61K 31/454* (2013.01); *A61K 31/495* (2013.01); *A61K 31/4985* (2013.01); *A61K 31/4995* (2013.01); *A61K 31/513* (2013.01); *A61K 31/5377* (2013.01); *A61K 31/55* (2013.01); *A61K 31/554* (2013.01); *A61K 31/575* (2013.01); *A61K 31/655* (2013.01); *A61K 31/7042* (2013.01); *A61K 45/06* (2013.01); *C07C 279/14* (2013.01); *C07D 295/13* (2013.01); *C07D 401/12* (2013.01)

(56) References Cited

U.S. PATENT DOCUMENTS

| | | |
|---|---|---|
| 5,589,358 A | 12/1996 | Dawson |
| 5,663,165 A | 9/1997 | Brieaddy |
| 5,723,458 A | 3/1998 | Brieaddy et al. |
| 5,817,652 A | 10/1998 | Brieaddy et al. |
| 5,900,233 A | 5/1999 | Day |
| 5,908,830 A | 6/1999 | Smith et al. |
| 5,910,494 A | 6/1999 | Brieaddy et al. |
| 5,994,391 A | 11/1999 | Lee et al. |
| 5,998,400 A | 12/1999 | Brieaddy |
| 6,020,330 A | 2/2000 | Enhsen et al. |
| 6,107,494 A | 8/2000 | Lee et al. |
| 6,114,322 A | 9/2000 | Enhsen et al. |
| 6,268,392 B1 | 7/2001 | Keller et al. |
| 6,303,661 B1 | 10/2001 | Demuth et al. |
| 6,309,663 B1 | 10/2001 | Patel et al. |
| 6,329,405 B1 | 12/2001 | Kurata et al. |
| 6,387,924 B2 | 5/2002 | Lee et al. |
| 6,420,417 B1 | 7/2002 | Keller et al. |
| 6,458,851 B1 | 10/2002 | Keller et al. |
| 6,465,451 B1 | 10/2002 | Handlon |
| 6,642,268 B2 | 11/2003 | Keller et al. |
| 6,740,663 B2 | 5/2004 | Tremont et al. |
| 6,784,201 B2 | 8/2004 | Lee et al. |
| 6,852,753 B2 | 2/2005 | Koeller et al. |
| 6,861,053 B1 | 3/2005 | Lin et al. |
| 6,875,877 B2 | 4/2005 | Li et al. |
| 6,890,898 B2 | 5/2005 | Bachovchin et al. |
| 6,906,058 B2 | 6/2005 | Starke et al. |
| 6,943,189 B2 | 9/2005 | Keller et al. |
| 7,125,864 B2 | 10/2006 | Starke et al. |
| 7,132,416 B2 | 11/2006 | Starke et al. |
| 7,179,792 B2 | 2/2007 | Glombik et al. |
| 7,192,945 B2 | 3/2007 | Starke et al. |
| 7,192,946 B2 | 3/2007 | Starke et al. |
| 7,226,943 B2 | 6/2007 | Starke et al. |
| 7,238,684 B2 | 7/2007 | Starke et al. |
| 7,514,421 B2 | 4/2009 | Abrahamsson et al. |
| 7,956,085 B2 | 6/2011 | Frick et al. |
| 8,106,026 B2 | 1/2012 | Nabel et al. |
| 9,345,715 B2 | 5/2016 | Young et al. |
| 2003/0139434 A1 | 7/2003 | Balkan et al. |
| 2003/0149010 A1 | 8/2003 | Keller et al. |
| 2003/0199482 A1* | 10/2003 | Seibert ................. A61K 31/19 514/171 |
| 2003/0219472 A1 | 11/2003 | Giovannie et al. |
| 2004/0014806 A1 | 1/2004 | Bhat et al. |
| 2004/0122033 A1 | 6/2004 | Nargund et al. |
| 2004/0138145 A1 | 7/2004 | Canton et al. |
| 2004/0176438 A1 | 9/2004 | Tremont et al. |
| 2005/0009805 A1 | 1/2005 | Sasahara et al. |
| 2005/0124557 A1 | 6/2005 | Lindqvist |
| 2005/0131068 A1 | 6/2005 | Alstermark et al. |
| 2006/0094884 A1 | 5/2006 | Starke et al. |
| 2006/0193895 A1 | 8/2006 | Miura |
| 2006/0199797 A1* | 9/2006 | Abrahamsson ...... A61K 31/554 514/211.08 |
| 2006/0269510 A1 | 11/2006 | Barbier et al. |
| 2007/0025953 A1 | 2/2007 | Jones |
| 2007/0032420 A1 | 2/2007 | Polidori et al. |
| 2007/0190041 A1 | 8/2007 | Sasahara et al. |
| 2008/0031968 A1 | 2/2008 | Bianco et al. |
| 2008/0065136 A1 | 3/2008 | Young |
| 2008/0096921 A1 | 4/2008 | Navas et al. |
| 2008/0145453 A1 | 6/2008 | Lopez et al. |
| 2008/0167356 A1 | 7/2008 | Caldwell et al. |
| 2008/0221161 A1 | 9/2008 | Pinkerton et al. |
| 2009/0118201 A1 | 5/2009 | Chen et al. |
| 2010/0035834 A1 | 2/2010 | Glombik et al. |
| 2010/0130426 A1 | 5/2010 | Young |
| 2010/0130472 A1 | 5/2010 | Young |
| 2011/0065676 A1 | 3/2011 | Perelman et al. |
| 2011/0294767 A1 | 12/2011 | Gedulin et al. |
| 2012/0157399 A1 | 6/2012 | Young et al. |
| 2013/0059807 A1 | 3/2013 | Gedulin et al. |
| 2013/0190281 A1 | 7/2013 | Young et al. |
| 2016/0220577 A1 | 8/2016 | Young et al. |

FOREIGN PATENT DOCUMENTS

| | | |
|---|---|---|
| EP | 0509335 | 10/1992 |
| EP | 1273659 | 1/2003 |
| EP | 1347052 | 9/2003 |
| EP | 1173205 | 6/2005 |
| EP | 1535913 | 6/2005 |
| GB | 2465677 | 6/2010 |
| JP | S63-96138 | 4/1988 |
| JP | 2000-026300 | 7/1998 |
| JP | 2002-542208 | 12/2002 |
| JP | 2005097216 A | 4/2005 |
| JP | 2008-517921 | 5/2008 |
| JP | 2008-534523 | 8/2008 |
| KR | 970005178 | 12/1993 |
| WO | WO-9733882 A1 | 9/1997 |
| WO | WO1998-038182 | 9/1998 |
| WO | WO2000-01687 | 1/2000 |
| WO | WO2000-062810 | 10/2000 |
| WO | WO2002-008211 | 1/2002 |
| WO | WO-02078626 A2 | 10/2002 |

(56) References Cited

FOREIGN PATENT DOCUMENTS

| | | |
|---|---|---|
| WO | WO2003-018024 | 3/2003 |
| WO | WO2004-020421 | 3/2004 |
| WO | WO2006-031931 | 3/2006 |
| WO | WO2006-57637 | 6/2006 |
| WO | WO2006-105912 | 10/2006 |
| WO | WO2006-105913 | 10/2006 |
| WO | WO2006-116814 | 11/2006 |
| WO | WO2007-041368 | 4/2007 |
| WO | WO-2007041368 A2 * | 4/2007 ............ A61K 31/40 |
| WO | WO2007-095174 | 8/2007 |
| WO | WO2007-127505 | 11/2007 |
| WO | WO2008-002573 | 1/2008 |
| WO | WO2008-058628 | 5/2008 |
| WO | WO2008-058631 | 5/2008 |
| WO | WO2008-067219 | 6/2008 |
| WO | WO2008-091540 | 7/2008 |
| WO | WO2010-059853 | 5/2010 |
| WO | WO-2010062861 A2 | 6/2010 |
| WO | WO2012/064266 | 5/2012 |
| WO | WO2012/064267 | 5/2012 |
| WO | WO2012/064268 | 5/2012 |

OTHER PUBLICATIONS

Green et al. Inhibition of dipeptidylpeptidase IV activity as a therapy of type 2 diabetes. Expert Opin Emerg Drugs 11(3):525-539 (2006).
U.S. Appl. No. 12/623,977 Office Action dated Mar. 16, 2015.
Adrian et al. Deoxycholate is an important releaser of peptide YY and enteroglucagon from the human colon. Gut 34:1219-1224 (1993).
Balas et al. The Dipeptidyl Peptidase IV Inhibitor Vildagliptin Suppresses Endogenous Glucose Production and Enhances Islet Function after Single-Dose Administration in Type 2 Diabetic Patients. The Journal of Clinical Endocrinology & Metabolism 92(4):1249-1255 (2007).
Bhat et al. Inhibition of ileal bile acid transport and reduced atherosclerosis in apoE−/−mice by SC-435. J Lipid Res 44(9):1614-21 (2003).
Brinton. Novel pathways for glycaemic control in type 2 diabetes: focus on bile acid modulation. Diabetes, Obesity and Metabolism. 10(11):1004-1011 (May 2008).
Cannon. Chapter Nineteen in Burger's Medicinal Chemistry and Drug Discovery, Fifth Edition, vol. 1: Principles and Practice, Wiley-Interscience 1995, pp. 783-802.
Chen et al. Liver Receptor Homologue-1 Mediates Species- and Cell Line-specific Bile Acid-dependent Negative Feedback Regulation of the Apical Sodium-dependent Bile Acid Transporter. J. Biol. Chem. 2003, 278:19909-19916.
Crosignani et al. Clinical pharmacokinetics of therapeutic bile acids. Clin. Pharmacokinet. 30: 333-358 (1996).
Definition of 'conceivable,' from the Free Dictionary, [online] 2009 [Retrieved on Jul. 30, 2012] Retrieved from the internet: http://www.thefreedictionary.com/conceivable.
Dumoulin et al. Peptide YY, Glucagon-Like Peptide-1, and Neurotensin Responses to Luminal Factors in the Isolated Vascularly Perfused Rat Ileum. Endocrinology 139(9):3780-3786 (1998).
Edney et al. Cholesterol Drugs Have 'Small' Increased Diabetes Risk, U.S. FDA Says. Bloomberg [online] Feb. 28, 2012 [Retrieved on Jul. 30, 2012] Retrieved from the internet: http://www.bloomberg.com/news/2012-02-28/cholesterol-drugs-have-small-increased-diabetes-risk-u-s-fda-says.html.
El-Shattawy et al. Effectiveness of rectal insulin suppositories containing sodium cholate in normal and insulin dependent diabetic subjects. Pharmaceutical Res 8:S157 (1991).
Enhsen et al. Bile acids in drug discovery. Drug Discover Today 3(9):409-418 (1998).
EP11787464.4 Extended European Search Report dated Nov. 13, 2013.
GB0920703.6 Search Report dated Mar. 10, 2010.

GB0920704.4 Examination Report dated Jul. 1, 2011.
GB1021390.8 Search Report dated Mar. 24, 2011.
Genet et al. Structure-Activity Relationship Study of Betulinic Acid, A Novel and Selective TGR5 Agonist, and Its Synthetic Derivatives: Potential Impact in Diabetes. J. Med. Chem. 53:178-190 (2010).
Geyer et al. The solute carrier family SLC10: More than a family of bile acid transporters regarding function and phylogenetic relationships. Naunyn-Schmiedeberg's Archives of Pharmacology 372(6):413-431 (2006).
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.
Hosny et al. Evaluation of efficiency of insulin suppository formulations containing sodium salicylate or sodium cholate in insulin dependent diabetic patients. Bollettino Chiico Farmceutico 142:361-366 (2003).
Hosny et al. Effect of Different Bile Salts on the Relative Hypoglycemia of Witepsol W35 Suppositories Containing Insulin in Diabetic Beagle Dogs. Drug. Dev. Ind. Pharm. 2001, 27:837-845.
Hosny. Relative Hypoglycemia of Rectal Insulin Suppositories Containing Deoxycholic Acid, Sodium Taurocholate, Polycarbophil, and Their Combinations in Diabetic Rabbits. Drug Dev. Ind. Pharm. 25:745-752 (1999).
Huang et al. Discovery of potent, nonsystemic apical sodium-codependent bile acid transporter inhibitors (Part 1). J Med Chem 48(18):5837-52 (2005).
Huang et al. Discovery of potent, nonsystemic apical sodium-codependent bile acid transporter inhibitors (Part 2). J Med Chem 48(18):5853-68 (2005).
Katsuma et al. Bile acids promote glucagon-like peptide-1 secretion through TGR5 in a murine enteroendocrine cellline STC-1. Biochem Biophys Res Commun 329(1):386-390 (2005).
Kawamata et al. A G Protein-coupled Receptor Responsive to Bile Acid. J. Biol. Chem. 278:9435-9440 (2003).
Khailova et al. Inhibition of the apical sodium-dependent bile acid transporter in experimental necrotizing enterocolitis. Database BIOSIS Apr. 2007 XP002715581, Database accession No. PREV200700602750 * abstract * & Gastroenterology 132(4 Suppl. 2):A57 (2007).
Kramer et al. Bile acid reabsorption inhibitors (BARI): novel hypolipidemic drugs. Curr Med Chem (9):997-1016 (2006).
Lee et al. Metforming Decreases Food Consumption and Induces Weight Loss in Subjects with Obesity with Type II Non-Insulin-Dependent Diabetes. Obesity Research 6(1):47-53 (1998).
Lim et al. Glucagon-like peptide 1 secretion by the L-cell. Diabetes 55(Supp 2):S70-77 (2006).
Macchiarulo et al. Molecular field analysis and 3D-quantitative structure-activity relationship study (MFA 3D-QSAR) unveil novel features of bile acid recognition at TGR5. J Chem Inf Model 48(9):1792-801 (2008).
Namba et al. GLP-1 derivatives, for the prevention and treatment of type 2 diabetes mellitus. Magazine of Japanese Society of Gastroenterology 102(11):1398-1404 (2005) (w/English trans).
Onaga et al. Multiple regulation of peptide YY secretion in the digestive tract. Peptides 17(5):279-290 (2002).
PCT/US09/65587 International Search Report dated Jul. 27, 2010.
PCT/US2011/038251 International Search Report dated Jan. 19, 2012.
Pellicciari et al. Nongenomic actions of bile acids. Synthesis and preliminary characterization of 23- and 6,23-alkyl-substituted bile acid derivatives as selective modulators for the G-protein coupled receptor TGR5. J Med Chem 50(18):4265-8 (2007).
Raun et al. Liraglutide, a Long-Action Glucagon-Like Peptide-1 Analog, Reduces Body Weight and Food Intake in Obese Candy-Fed Rats, Whereas a Dipeptidyl Peptidase-IV Inhibitor, Vildagliptin, Does No. Diabetes 56:8-15 (2007).
Reimann et al. Signaling mechanisms underlying the release of glucagon-like peptide 1. Diabetes 55(Supp 2):S78-85 (2006).
Root et al. Ileal bile acid transporter inhibition, CYP7A1 induction, and antilipemic action of 264W94. J Lipid Res 43(8):1320-30 (2002).

(56) References Cited

OTHER PUBLICATIONS

Sato et al. Anti-hyperglycemic activity of a TGR5 agonist isolated from Olea europaea. Biochem Biophys Res Commun 362(4):793-8 (2007).
Sato et al. Novel potent and selective bile acid derivatives as TGR5 agonists: biological screening, structure-activity relationships, and molecular modeling studies. J Med Chem 51(6):1831-41 (2008).
Spangeus et al. Large intestinal endocrine cells in non-obese diabetic mice. J Diabetes Complications 12(6):321-7 (1998).
Tenjarla et al. Release of 5-Aminosalicylate from and MMX mesalamine tablet during transit through a simulated gastrointestinal tract system. Advances in Therapy 23: 826-940 (2007).
Thomas et al, Decreased developmental of experimental necrotizing enterocolitis in apical sodium-dependent bile acid transporter knock-out mice. Gastroenterology, (May 2009) vol. 136, No. 5 Suppl. 1, p. A41.
Tozaki et al. Chitosan capsules for colon-specific drug delivery: improvement of insulin absorption from the rat colon. J Pharm Sci 86:1016-1021 (1997).
Tremont et al. Discovery of potent, nonsystemic apical sodium-codependent bile acid transporter inhibitors (Part 1). Journal of Medicinal Chemistry 48:5837-5852 (2005).
U.S. Appl. No. 12/623,977 Office Action dated Apr. 26, 2013.
U.S. Appl. No. 12/623,977 Office Action dated Jan. 31, 2012.
U.S. Appl. No. 12/623,977 Office Action dated Oct. 24, 2014.
U.S. Appl. No. 12/623,977 Office Action dated Sep. 25, 2012.
U.S. Appl. No. 12/624,345 Notice of Allowance dated Sep. 21, 2012.
U.S. Appl. No. 12/624,345 Office Action dated Feb. 15, 2012.
U.S. Appl. No. 12/624,345 Office Action dated May 26, 2011.
U.S. Appl. No. 12/624,345 Office Action dated Nov. 16, 2011.
U.S. Appl. No. 13/116,988 Office Action dated Jul. 30, 2014.
U.S. Appl. No. 13/116,988 Office Action dated Nov. 15, 2013.
U.S. Appl. No. 13/402,763 Office Action dated May 29, 2014.
U.S. Appl. No. 13/402,763 Office Action dated Oct. 9, 2014.
U.S. Appl. No. 13/402,819 Office Action dated Aug. 1, 2014.
U.S. Appl. No. 13/402,819 Office Action dated Jan. 14, 2014.
Watanabe. Functional Food 2(1):57-63 (w/English Translation) (Apr. 2008).
West et al. SC-435, an ileal apical sodium-codependent bile acid transporter inhibitor alters mRNA levels and enzyme activities of selected genes involved in hepatic cholesterol and lipoprotein metabolism in guinea pigs. Journal of Nutritional Biochemistry 16(12):722-728 (2005).
Wu et al. Expression of bitter taste receptors of the T2R family in the gastrointestinal tract and enteroendocrine STC-1 cells. Proc. Natl. Acad. Sci. 99:2392-2397 (2002).
Wynne et al. Appetite control. J Endocrinol 184:291-318 (2005).
Yamamoto et al. Colon-specific delivery of peptide drugs and anti-inflammatory drugs using chitosan capsules. Sciences Techniqus et Pratiques 10: 23-34 (2000).
Ziv et al. Bile Salts Promote the Absorption of Insulin from the Rat Colon. Life Sci. 29:803-809 (1981).
Anand et al. Role of metformin in experimentally-induced inflammatory bowel disease. ARS Pharmaceutica 49(4):267-281. Database Accession No. EMB-2009271947 (2008) Abstract.
Dowling et al. Biliary Lipid Secretion and Bile Composition after Acute and Chronic Interruption of the Enterohepatic Circulation in the Rhesus Monkey IV. Primate Biliary Physiology. J. Clin Invest 50:1917-1926 (1971).
Dowling et al. Effects of controlled interruption of the enterohepatic circulation of bile salts by biliary diversion and by ileal resection on bile salt secretion, synthesis, and pool size in the rhesus monkey. J Clin Invest 49:232-242 (1970).
Khailova et al. Inhibition of the apical sodium-dependent bile acid transporter in experimental necrotizing enterocolits. Gastroenterology 132(4 Sup 2):A57. Digestive Disease Week Meeting/108th Annual Meeting of the American-Gastroenterological-Association. Washington, D.C. May 19-24, 2007. Database Accession No. PREV200700602750.
Morsy et al. Gastroprotective effects of the insulin sensitizers rosiglitazone and metformin against indomethacin-induced gastric ulcers in Type 2 diabetic rats. Clin Exp Pharmacol Physiol. 37(2):173-177 (2010).
The Merk Manual, 18th Ed., Japanese Version, the third impression of the first edition, p. 1371-1375 (Apr. 25, 2007).
Tucker et al. Metformin kinetics in healthy subjects and in patients with diabetes mellitus.Br J Clin Pharmacol. 12(2):235-246 (1981).
U.S. Appl. No. 13/402,819 Office Action dated Jul. 7, 2015.
Journal of Pharmaceutical Sciences 125(6):379-384 (2005).
U.S. Appl. No. 13/402,819 Office Action dated Aug. 22, 2016.
U.S. Appl. No. 13/402,819 Office Action dated Feb. 10, 2016.
U.S. Appl. No. 13/402,819 Office Action dated May 26, 2017.
U.S. Appl. No. 15/097,203 Office Action dated Jun. 9, 2017.
Abraham et al. Surgical and nonsurgical management of gallstones. Am Fam Physician 89(10):795-802 (2014).
EP0982974.1 Extended Search Report dated Nov. 22, 2012.
U.S. Appl. No. 13/402,819 Office Action dated Apr. 5, 2018.
U.S. Appl. No. 15/097,203 Office Action dated May 18, 2018.

* cited by examiner

Compound 100B + DPP-IV inhbitor

Compound 100B alone

L-cell activation
↓
anorexigenic
hormones

BILE ACID RECYCLING INHIBITORS AND SATIOGENS FOR TREATMENT OF DIABETES, OBESITY, AND INFLAMMATORY GASTROINTESTINAL CONDITIONS

CROSS-REFERENCE TO RELATED APPLICATIONS

This application is a continuation of U.S. application Ser. No. 13/116,988, filed on May 26, 2011, which claims the benefit under 35 U.S.C. § 119(e) of U.S. Provisional Application No. 61/348,666, filed May 26, 2010, and U.S. Provisional Application No. 61/348,669, filed May 26, 2010, each of which is incorporated herein by reference in its entirety.

BACKGROUND OF THE INVENTION

Diabetes and obesity affect numerous humans throughout the world, and are associated with or induces other diseases or conditions. In particular, diabetes and obesity are serious risk factors for diseases and conditions such as hypertension, gallbladder disease, cancer, polycystic ovary disease and arteriosclerosis and can contribute to elevated levels of cholesterol in the blood. Overeating and obesity, which frequently leads to diabetes, have become a problem in the general population. Consequently there is interest in reducing food intake, losing weight, and reducing elevated blood glucose.

Inflammatory gastrointestinal conditions affect millions of people. For example, necrotizing enterocolitis (NEC) affects thousands of newborns each year and is the most common gastrointestinal emergency of premature infants. Mortality rates of NEC are between 10 to 50%, and thus NEC remains a major cause of morbidity and mortality in premature infants. The pathophysiology of NEC is poorly understood. An effective treatment of NEC as well as other inflammatory gastrointestinal conditions is needed.

SUMMARY OF THE INVENTION

Provided herein, in certain embodiments, are therapeutic methods using compounds that inhibit the Apical Sodium-dependent Bile Transporter (ASBT) or any recuperative bile salt transporter. In certain instances, use of the compounds provided herein reduces or inhibits recycling of bile acid salts in the gastrointestinal tract. In some embodiments, the methods provided herein reduce intraenterocyte bile acids or reduce necrosis and/or damage to ileal architecture. In some embodiments, the bile transport inhibitors are non-systemic compounds. In other embodiments, the bile acid transporter inhibitors are systemic compounds. In certain embodiments, the bile transport inhibitors described herein enhance L-cell secretion of enteroendocrine peptides.

In certain embodiments, provided herein are methods for treating or preventing an inflammatory intestinal condition or a metabolic disorder comprising administering a therapeutically effective amount of an ASBT inhibitor (ASBTI) and/or an enteroendocrine peptide enhancing agent and/or a nuclear farnesoid X receptor (FXR) agonist to an individual in need thereof. In certain embodiments, provided herein is an ASBTI and/or an enteroendocrine peptide enhancing agent and/or a FXR agonist for use in the treatment of an inflammatory intestinal condition comprising administering a therapeutically effective amount of an ASBTI and/or an enteroendocrine peptide enhancing agent and/or a FXR agonist to an individual in need thereof. In some embodiments, an ASBTI and/or an enteroendocrine peptide enhancing agent and/or a FXR agonist is minimally absorbed. In some embodiments, an ASBTI and/or an enteroendocrine peptide enhancing agent and/or a FXR agonist is non-systemically administered to the distal ileum of an individual in need thereof. In some embodiments, an ASBTI and/or an enteroendocrine peptide enhancing agent and/or a FXR agonist is non-systemically administered to the colon or the rectum of an individual in need thereof. In some embodiments, less than 50%, less than 40%, less than 30%, less than 20%, less than 10%, less than 9%, less than 8%, less than 7%, less than 6%, less than 5%, less than 4%, less than 3%, less than 2%, or less than 1% of the ASBTI and/or the enteroendocrine peptide enhancing agent and/or a FXR agonist is systemically absorbed.

In some embodiments, the methods provided herein treat inflammatory intestinal conditions including but not limited to necrotizing enterocolitis, gastritis, ulcerative colitis, inflammatory bowel disease, irritable bowel syndrome, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection.

In some embodiments, the individual is a newborn or prematurely born infant. In some embodiments, the individual is enterally-fed infant or formula-fed infant.

In some embodiments, the methods described herein reduce intraenterocyte bile acids in an individual in need thereof. In some embodiments, the methods described herein reduce accumulation of bile acids in ileal enterocytes of an individual in need thereof. In some embodiments, the methods described herein inhibit transport of bile acids from ileal lumen into enterocytes of an individual in need thereof. In some embodiments, the methods described herein increase ileal luminal bile acids of an individual in need thereof. In some embodiments, the methods described herein reduce necrosis or damage to ileal architecture or ileal cells in an individual in need thereof.

In some embodiments of the methods described above, the ASBTI is a compound of Formula I as described herein. In some embodiments of the methods described above, the ASBTI is a compound of Formula II as described herein. In some embodiments of the methods described above, the ASBTI is a compound of Formula III as described herein. In some embodiments of the methods described above, the ASBTI is a compound of Formula IV as described herein. In some embodiments of the methods described above, the ASBTI is a compound of Formula V as described herein. In some embodiments of the methods described above, the ASBTI is a compound of Formula VI or Formula VID as described herein.

In certain embodiments, an ASBTI is any compound described herein that inhibits recycling of bile acids in the gastrointestinal tract of an individual. In certain embodiments, an ASBTI is (−)-(3R,5R)-trans-3-butyl-3-ethyl-2,3,4,5-tetrahydro-7,8-dimethoxy-5-phenyl-1,4-benzothiazepine 1,1-dioxide; ("Compound 100A") or any other salt or analog thereof. In certain of any of the aforementioned embodiments, an ASBTI is 1-[4-[4-[(4R,5R)-3,3-dibutyl-7-(dimethylamino)-2,3,4,5-tetrahydro-4-hydroxy-1,1-di-oxido-1-benzothiepin-5-yl]phenoxy]butyl]4-aza-1-azoni-abicyclo[2.2.2]octane methane sulfonate salt ("Compound 100B") or any other salt or analog thereof. In certain embodiments, an ASBTI is N,N-dimethylimido-dicarbonimidic diamide ("Compound 100C") or any salt or analog thereof. In certain embodiments, an ASBTI is any commercially available ASBTI including but not limited to SD-5613, A-3309, 264W94, S-8921, SAR-548304, BARI-1741, HMR-1453, TA-7552, R-146224, or SC-435. In some embodiments, an ASBTI is 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine; 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl]amino]-1-deoxy-D-glucitol; or Potassium((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl)sulphate ethanolate, hydrate.

In certain embodiments, an enteroendocrine peptide secretion enhancing agent is a bile acid, a bile salt, a bile acid mimic, a bile salt mimic, TGR5 agonist, or a combination thereof. In some embodiments, the enteroendocrine peptide secretion enhancing agent is a glucagon-like peptide secretion enhancing agent, optionally in combination with a bile acid, a bile salt, a bile acid mimic, or a bile salt mimic. In certain embodiments, the glucagon-like peptide secretion enhancing agent is a glucagon-like peptide-1 (GLP-1) secretion enhancing agent or a glucagon-like peptide-2 (GLP-2) secretion enhancing agent, optionally in combination with a bile acid, a bile salt, a bile acid mimic, or a bile salt mimic. In some embodiments, the enteroendocrine peptide secretion enhancing agent is a pancreatic polypeptide-fold peptide secretion enhancing agent, optionally in combination with a bile acid, a bile salt, a bile acid mimic, or a bile salt mimic. In some embodiments, the pancreatic polypeptide-fold peptide secretion enhancing agent is a peptide YY (PYY) secretion enhancing agent.

In certain embodiments, the FXR agonist is GW4064, GW9662, INT-747, T0901317, WAY-362450, fexaramine, a cholic acid, a deoxycholic acid, a glycocholic acid, a glycodeoxycholic acid, a taurocholic acid, a taurodihydrofusidate, a taurodeoxycholic acid, a cholate, a glycocholate, a deoxycholate, a taurocholate, a taurodeoxycholate, a chenodeoxycholic acid, or a salt thereof, or a combination thereof.

Provided in certain embodiments herein are methods and dosage forms (e.g., oral or rectal dosage form) for use in the treatment of diabetes, obesity, or an inflammatory intestinal condition comprising a therapeutically effective amount of a bile acid, bile salt, or mimetic thereof, and a carrier. In some embodiments, the bile acid, bile salt, or mimetic thereof is a minimally absorbed bile acid, bile salt, or mimetic thereof. In specific embodiments, the dosage form is an enteric formulation, an ileal-pH sensitive release, or a suppository or other suitable form.

In some embodiments, provided herein is a method for treating diabetes, obesity, or an inflammatory intestinal condition comprising rectally administering a therapeutically effective amount of a minimally absorbed bile acid, bile salt, or mimetic thereof.

In some embodiments, the methods provided herein further comprise administering a therapeutically effective amount of an inhibitor of Dipeptidyl Peptidase-4. In some embodiments, the inhibitor of Dipeptidyl Peptidase-4 is administered orally or rectally. In some embodiments, the inhibitor of Dipeptidyl Peptidase-4 is co-administered with an ASBTI, an enteroendocrine peptide enhancing agent, a FXR agonist, bile acid, bile salt, or mimetic thereof. In some embodiments, the inhibitor of Dipeptidyl Peptidase-4 is an absorbable or systemically absorbed inhibitor of Dipeptidyl Peptidase-4.

In certain embodiments, a bile acid mimetic is a TGR5 agonist, M-BAR agonist, GPR119 agonist, GPR120 agonist, GPR131 agonist, GPR140 agonist, GPR143 agonist, GPBAR1 agonist, BG37 agonist, farnesoid-X receptor agonist. In some instances, a bile acid mimetic promotes L-cell secretions. In certain instances, a bile acid mimetic promotes the secretion of GLP-1, GLP-2, PYY, OXM, or a combination thereof.

In some embodiments, the methods described above further comprise administration of a second agent selected from a liver receptor homolog 1 (LRH-1), a DPP-IV inhibitor, a proton pump inhibitor, H2 antagonist, prokinetic agent, a biguanide, an incretin mimetic, a thiazolidinone, a mucoadhesive agent, and GLP-1 or an analog thereof, and a TGR5 agonist. In some embodiments, the second agent is a DPP-IV inhibitor.

In some embodiments, the composition administered comprises at least one of a spreading agent or a wetting agent. In some embodiments, the absorption inhibitor is a mucoadhesive agent (e.g., a mucoadhesive polymer). In certain embodiments, the mucoadhesive agent is selected from methyl cellulose, polycarbophil, polyvinylpyrrolidone, sodium carboxymethyl cellulose, and combinations thereof. In some embodiments, a pharmaceutical composition administered further comprises an enteroendocrine peptide.

In some embodiments, provided herein is a method for lowering elevated blood glucose in a mammal resulting from food intake comprising orally administering to said mammal a therapeutically effective amount of a minimally absorbed Apical Sodium-dependent Bile Transporter inhibitor. In some embodiments, provided herein is a method further comprising administering to said mammal a therapeutically effective amount of an inhibitor of Dipeptidyl Peptidase-4.

In specific instances, provided herein is a method for lowering elevated body weight or lowering elevated blood glucose in a mammal resulting from food intake comprising orally administering to said mammal a therapeutically effective amount of a minimally absorbed Apical Sodium-dependent Bile Transporter inhibitor and/or an inhibitor of Dipeptidyl Peptidase-4. In other embodiments, provided herein is a method for lowering elevated body weight or lowering elevated blood glucose in a mammal resulting from food intake comprising orally co-administering to said mammal a therapeutically effective amount of a minimally absorbed Apical Sodium-dependent Bile Transporter inhibitor and an inhibitor of Dipeptidyl Peptidase-4.

Also provided herein is a method of promoting stimulation of L-cell secretion in an individual in need thereof, the method comprising orally or rectally administering an effective amount of a minimally absorbed bile acid, bile salt, or mimetic thereof. In specific instances, the individual in need thereof is suffering from a disorder ameliorated by L-cell secreted products.

In certain embodiments, increased L-cell secretion of enteroendocrine peptides is associated with reduced necrosis and/or reduced damage to ileal architecture. In certain instances, increased L-cell secretion of enteroendocrine peptides is associated with induction of satiety and/or reduction of food intake (caloric intake) and subsequent weight loss. In some embodiments, increased L-cell secretion of enteroendocrine peptides is associated with a reduction in blood and/or plasma glucose levels in a hyperglycemic individual. In some instances, increased L-cell secretion of enteroendocrine peptides is associated with increased insulin sensitivity.

In some embodiments, provided herein is a pharmaceutical composition formulated for non-systemic ileal, rectal or colonic delivery of the enteroendocrine peptide secretion enhancing agent. In certain embodiments, provided herein is an enteroendocrine peptide secretion enhancing agent such as a TGR5 agonist, a bile acid, a bile salt, a bile acid mimic, a bile salt mimic, or a combination thereof. In some embodiments, the enteroendocrine peptide secretion enhancing agent is a glucagon-like peptide secretion enhancing agent, optionally in combination with a bile acid, a bile salt, a bile acid mimic, or a bile salt mimic. In certain embodiments, the glucagon-like peptide secretion enhancing agent is a glucagon-like peptide-1 (GLP-1) secretion enhancing agent or a glucagon-like peptide-2 (GLP-2) secretion enhancing agent, optionally in combination with a bile acid, a bile salt, a bile acid mimic, or a bile salt mimic. In some embodiments, the enteroendocrine peptide secretion enhancing agent is a pancreatic polypeptide-fold peptide secretion enhancing agent, optionally in combination with a bile acid, a bile salt, a bile acid mimic, or a bile salt mimic. In some embodiments, the pancreatic polypeptide-fold peptide secretion enhancing agent is a peptide YY (PYY) secretion enhancing agent.

In certain embodiments, the composition further comprises at least one of a cholesterol absorption inhibitor, a spreading agent or a wetting agent. In some embodiments, the absorption inhibitor is a mucoadhesive agent. In specific embodiments, the polymer having mucoadhesive properties is selected from methyl cellulose, polycarbophil, polyvinylpyrrolidone, sodium carboxymethyl cellulose, and combinations thereof. In some embodiments, the enteroendocrine peptide secretion enhancing agent is covalently linked to the absorption inhibitor.

In certain embodiments, the carrier is a rectally suitable carrier. In certain embodiments, any pharmaceutical composition described herein is formulated as a suppository, an enema solution, a rectal foam, or a rectal gel. In some embodiments, any pharmaceutical composition described herein comprises an orally suitable carrier. In certain embodiments, the pharmaceutical composition comprises an enteric coating.

Provided in certain embodiments herein is a method for treating a metabolic disease or a condition associated with a metabolic disease comprising administering to the lower ileum, the colon and/or the rectum of an individual in need thereof, a pharmaceutical composition comprising a therapeutically effective amount of an enteroendocrine peptide secretion enhancing agent. Provided in certain embodiments herein is a method for treating a metabolic disease or a condition associated with a metabolic disease or an inflammatory intestinal condition comprising administering (e.g., orally or rectally administering) to an individual in need thereof, a pharmaceutical composition comprising a therapeutically effective amount of an enteroendocrine peptide secretion enhancing agent and a carrier. In some embodiments, compositions provided herein further comprise administering a therapeutically effective amount of ASBTI. In some embodiments, administered is a pharmaceutical composition that further comprises an absorption inhibitor, wherein the absorption inhibitor inhibits the absorption of the enteroendocrine peptide secretion enhancing agent across the rectal or colonic mucosa. In some embodiments, the composition administered comprises an orally suitable carrier. In certain embodiments, the pharmaceutical composition is formulated for enteric delivery. In some embodiments, the pharmaceutical composition comprises an enteric coating.

Provided in certain embodiments herein is a method for treating obesity, diabetes, or an inflammatory intestinal condition comprising administering to the lower ileum, the colon and/or the rectum of an individual in need thereof, a pharmaceutical composition comprising a therapeutically effective amount of an enteroendocrine peptide secretion enhancing agent. Provided in some embodiments herein is a method for treating obesity, diabetes, or an inflammatory intestinal condition comprising administering (e.g., orally or rectally administering) to an individual in need thereof, a pharmaceutical composition comprising a therapeutically effective amount of an enteroendocrine peptide secretion enhancing agent and a carrier. In some embodiments, compositions provided herein further comprise administering a therapeutically effective amount of ASBTI. In some embodiments, administered is a pharmaceutical composition that further comprises an absorption inhibitor, wherein the absorption inhibitor inhibits the absorption of the enteroendocrine peptide secretion enhancing agent across the rectal or colonic mucosa. In some embodiments, the composition administered comprises an orally suitable carrier. In certain embodiments, the pharmaceutical composition is formulated for enteric delivery. In some embodiments, the pharmaceutical composition comprises an enteric coating.

In certain other embodiments, provided herein is a method of treating (e.g., preventing, prophylactically treating or reducing the incidences of) pancreatic and other cancers comprising contacting the distal ileum of an individual in need thereof with an Apical Sodium-dependent Bile Transporter inhibitor.

Provided in certain embodiments herein is a method for preventing or treating pancreatic cancers comprising administering to the lower ileum, the colon and/or the rectum of an individual in need thereof, a pharmaceutical composition comprising a therapeutically effective amount of an enteroendocrine peptide secretion enhancing agent. Provided in some embodiments herein is a method for preventing or treating pancreatic cancers comprising administering (e.g., orally or rectally administering) to an individual in need thereof, a pharmaceutical composition comprising a therapeutically effective amount of an enteroendocrine peptide secretion enhancing agent and a carrier. In some embodiments, administered is a pharmaceutical composition that further comprises an absorption inhibitor, wherein the absorption inhibitor inhibits the absorption of the enteroendocrine peptide secretion enhancing agent across the rectal or colonic mucosa. In some embodiments, the composition administered comprises an orally suitable carrier. In certain embodiments, the pharmaceutical composition is formulated for enteric delivery. In some embodiments, the pharmaceutical composition comprises an enteric coating.

In some embodiments, administered according to a method described herein is a composition comprising a rectally suitable carrier. In some embodiments, the administered pharmaceutical composition is formulated as a suppository, an enema solution, a rectal foam, or a rectal gel.

In certain embodiments, a composition administered according to a method described herein comprises an enteroendocrine peptide secretion enhancing agent that is a bile acid, bile salt, bile acid mimic or bile salt mimic. In some embodiments, the enteroendocrine peptide secretion enhancing agent is a glucagon-like peptide secretion enhancing agent. In certain embodiments, the enteroendocrine peptide secretion enhancing agent is a glucagon-like peptide-1 (GLP-1) secretion enhancing agent or a glucagon-like peptide-2 (GLP-2) secretion enhancing agent. In some embodiments, the enteroendocrine peptide secretion enhancing agent is a pancreatic polypeptide-fold peptide secretion enhancing agent. In specific embodiments, the enteroendocrine peptide secretion enhancing agent is a peptide YY (PYY) secretion enhancing agent. In some embodiments, a composition administered according to a method described herein comprises any one or more of the enteroendocrine peptide secretion enhancing agents described herein.

Without limiting their utility to appetite suppression, agents delivered rectally that invoke enteroendocrine signals will be termed, for convenience, "rectal satiogens". As an example of how this definition should not be limiting, the stimulation of enteroendocrine regulatory peptides can benefit not only metabolic diseases by the above effects, but can benefit a number of other conditions via mechanisms that may be entirely independent of the control of nutrient flux. Examples of conditions in which enhanced enteroendocrine secretion can be beneficial are described in US 2009/0264808, and include: diabetes, impaired glucose tolerance, glucose metabolic disorders, insulin resistance, obesity, acute coronary syndrome, hibernating myocardium, ventricular dysfunction, cardiac risk, post myocardial infarction mortality, post-surgical or sepsis-related or critical illness-related catabolism and mortality, critical illness polyneuropathy, congestive heart failure, toxic hypervolemia, renal failure, ischemia-reperfusion injury, mortality and morbidity from stroke and neurodegenerative disease, neuropathy, inflammatory intestinal conditions, inflamatory bowel disease, necrotizing enterocolitis, gastritis, ulcerative colitis, inflammatory bowel disease, irritable bowel syndrome, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection, bowel mucosal injury, impaired bowel integrity, osteopenia, and bone fractures and bone disorders.

Provided herein are methods and uses for treating obesity or diabetes or an inflammatory intestinal condition comprising contacting the distal ileum of an individual in need thereof with an Apical Sodium-dependent Bile Transporter Inhibitor (ASBTI) and/or enteroendocrine peptide enhancing agent and/or a FXR agonist.

In some embodiments of the methods and uses, contacting the distal ileum of an individual in need thereof with an ASBTI and/or enteroendocrine peptide enhancing agent and/or a FXR agonist:
  a. reduces intraenterocyte bile acids;
  b. reduces necrosis and/or damage to ileal architecture;
  c. reduces food intake in the individual;
  d. induces satiety in the individual;
  e. reduces blood and/or plasma glucose levels in the individual;
  f. treats a metabolic disorder in the individual;
  g. reduces the weight of the individual;
  h. stimulates L-cells in the distal gastrointestinal tract of the individual;
  i. increases the concentration of bile acids and salts thereof in the vicinity of L-cells in the distal gastrointestinal tract of the individual;
  j. enhances enteroendocrine peptide secretion in the individual; or
  k. any combination thereof.

In some embodiments, the ASBTI and/or the enteroendocrine peptide enhancing agent and/or a FXR agonist is not systemically absorbed. In some other embodiments, the ASBTI and/or the enteroendocrine peptide enhancing agent and/or a FXR agonist is systemically absorbed.

In some embodiments of the methods, the individual is an obese or morbidly overweight individual. In some embodiments of the methods, the individual is a diabetic individual. In some embodiments of the methods, the individual is a non-diabetic individual.

In some embodiments, provided herein are methods for the treatment of obesity, diabetes, or an inflammatory intestinal condition comprising administration of a therapeutically effective amount of a combination of an ASBTI and a DPP-IV inhibitor to an individual in need thereof. In some embodiments, provided herein are methods for the treatment of obesity, diabetes, or an inflammatory intestinal condition comprising administration of a therapeutically effective amount of a combination of an ASBTI and an enteroendocrine peptide enhancing agent and/or a FXR agonist to an individual in need thereof. In some embodiments, provided herein are methods for the treatment of obesity, diabetes, or an inflammatory intestinal condition comprising administration of a therapeutically effective amount of a combination of an ASBTI and a thiazolidinedione to an individual in need thereof. In some embodiments, provided herein are methods for the treatment of obesity, diabetes, or an inflammatory intestinal condition comprising administration of a therapeutically effective amount of a combination of an ASBTI and an incretin mimic to an individual in need thereof. In some embodiments, provided herein are methods for the treatment of obesity, diabetes, or an inflammatory intestinal condition comprising administration of a therapeutically effective amount of a combination of an ASBTI and GLP-1 or an analog thereof to an individual in need thereof. In some embodiments, provided herein are methods for the treatment of obesity, diabetes, or an inflammatory intestinal condition comprising administration of a therapeutically effective amount of a combination of an ASBTI and a biguanide to an individual in need thereof.

In some embodiments, the methods described herein reduce intraenterocyte bile acids in an individual in need thereof. In some embodiments, the methods described herein reduce necrosis or damage to ileal architecture in an individual in need thereof. In some embodiments, the methods described herein reduce food intake (caloric intake) in an individual in need thereof. In some embodiments, the methods described herein induce satiety in an individual in need thereof. In some embodiments, the methods described herein treat metabolic disorders in an individual in need thereof. In some embodiments, the methods described herein reduce the weight of an individual in need thereof. In some embodiments, the methods described herein stimulate L-cells in the distal gastrointestinal tract of an individual in need thereof. In some embodiments, the methods described herein increase the concentration of bile acid and salts thereof in the vicinity of L-cells in the distal gastrointestinal tract of an individual.

Provided herein are methods for reducing food intake in an individual in need thereof comprising administration of an Apical Sodium-dependent Bile Acid Transporter Inhibitor (ASBTI) to an individual in need thereof wherein the ASBTI is delivered or released non-systemically in the distal ileum of the individual.

Provided herein are methods for reducing circulating blood or plasma glucose levels in an individual in need thereof comprising administration of an Apical Sodium-dependent Bile Acid Transporter Inhibitor (ASBTI) to an individual in need thereof wherein the ASBTI is delivered or released non-systemically in the distal ileum of the individual.

Provided herein are methods for increasing insulin secretion in an individual in need thereof comprising administration of an Apical Sodium-dependent Bile Acid Transporter Inhibitor (ASBTI) to an individual in need thereof wherein the ASBTI is delivered or released non-systemically in the distal ileum of the individual.

In some embodiments, the methods described herein enhance enteroendocrine peptide secretion in an individual in need thereof. In some of such embodiments, the enteroendocrine peptide is GLP-1, GLP-2, PYY, oxyntomodulin, or a combination thereof.

In some embodiments, contacting the distal ileum of an individual in need thereof with an ASBTI and/or an enterendocrine peptide enhancing agent and/or a FXR agonist increases the level of GLP-1 in the blood and/or plasma of the individual by from about 2 times to about 6 times the level of GLP-1 in the blood and/or plasma of the individual prior to contacting the distal ileum of the individual with the ASBTI.

In some embodiments, contacting the distal ileum of an individual in need thereof with an ASBTI reduces the level of glucose in the blood and/or plasma of the individual by at least 30% compared to the level of glucose in the blood and/or plasma of the individual prior to contacting the distal ileum of the individual with the ASBTI.

In some embodiments, contacting the distal ileum of an individual in need thereof with an ASBTI maintains reduced blood and/or plasma glucose levels in the individual for at least 24 hours compared to blood and/or plasma glucose levels in the individual prior to contacting the distal ileum of the individual with the ASBTI.

In some embodiments, the ASBTI and/or the enterendocrine peptide enhancing agent and/or the FXR agonist is administered orally. In some embodiments, the ASBTI and/or the enterendocrine peptide enhancing agent and/or the FXR agonist is administered as an ileal-pH sensitive release formulation that delivers the ASBTI and/or the enterendocrine peptide enhancing agent and/or the FXR agonist to the distal ileum, colon and/or rectum of an individual. In some embodiments, the ASBTI and/or the enterendocrine peptide enhancing agent and/or the FXR agonist is administered as an enterically coated formulation. In some embodiments, oral delivery of an ASBTI and/or an enterendocrine peptide enhancing agent and/or a FXR agonist provided herein can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (the ileum) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

In some embodiments of the methods described above, the ASBTI and/or the enterendocrine peptide enhancing agent and/or the FXR agonist is administered before ingestion of food. In some embodiments of the methods described above, the ASBTI and/or the enterendocrine peptide enhancing agent and/or the FXR agonist is administered less than about 60 minutes before ingestion of food. In some embodiments of the methods described above, the ASBTI and/or the enterendocrine peptide enhancing agent and/or the FXR agonist is administered less than about 30 minutes before ingestion of food. In some embodiments of the methods described above, the ASBTI and/or the enterendocrine peptide enhancing agent and/or the FXR agonist is administered after ingestion of food.

Provided herein are methods for prevention and/or treatment of congestive heart failure, ventricular dysfunction, toxic hypervolemia, polycystic ovary syndrome, inflammatory bowel disease, impaired bowel integrity, short bowel syndrome, gastritis, peptic ulcer, or irritable bowel disease comprising contacting the distal ileum of an individual in need thereof with an ASBTI and/or an enterendocrine peptide enhancing agent and/or a FXR agonist. In some embodiments, the methods further comprise administration of a DPP-IV inhibitor, a TGR5 agonist, a biguanide, an incretin mimetic, or GLP-1 or an analog thereof. Provided herein are methods for prevention and/or treatment of radiation enteritis comprising contacting the distal ileum of an individual in need thereof with an ASBTI and/or an enterendocrine peptide enhancing agent and/or a FXR agonist. In some embodiments, the methods further comprise administration of a DPP-IV inhibitor, a TGR5 agonist, a biguanide, an incretin mimetic, or GLP-1 or an analog thereof.

Provided herein are compositions for reducing intra-enterocyte bile acids in an individual in need thereof comprising an Apical Sodium-dependent Bile Acid Transporter Inhibitor (ASBTI) and/or an enterendocrine peptide enhancing agent and/or a FXR agonist, and a pharmaceutically acceptable carrier, wherein the ASBTI is delivered or released non-systemically in the distal ileum of the individual. Provided herein are compositions for reducing necrosis and/or damage to ileal architecture in an individual in need thereof comprising an Apical Sodium-dependent Bile Acid Transporter Inhibitor (ASBTI) and/or an enterendocrine peptide enhancing agent and/or a FXR agonist, and a pharmaceutically acceptable carrier, wherein the ASBTI and/or the enterendocrine peptide enhancing agent and/or the FXR agonist is delivered or released non-systemically in the distal ileum of the individual. Provided herein are compositions for reducing caloric intake in an individual in need thereof comprising an Apical Sodium-dependent Bile Acid Transporter Inhibitor (ASBTI) and/or an enterendocrine peptide enhancing agent and/or a FXR agonist, and a pharmaceutically acceptable carrier, wherein the ASBTI and/or the enterendocrine peptide enhancing agent and/or the FXR agonist is delivered or released non-systemically in the distal ileum of the individual. Provided herein are compositions for reducing circulating blood and/or plasma glucose levels in an individual in need thereof comprising an Apical Sodium-dependent Bile Acid Transporter Inhibitor (ASBTI) and/or an enterendocrine peptide enhancing agent and/or a FXR agonist, and a pharmaceutically acceptable carrier, wherein the ASBTI is delivered or released non-systemically in the distal ileum of the individual. Provided herein are compositions for increasing insulin secretion in an individual in need thereof comprising an Apical Sodium-dependent Bile Acid Transporter Inhibitor (ASBTI) and/or an enterendocrine peptide enhancing agent and/or a FXR agonist, and a pharmaceutically acceptable carrier, wherein the ASBTI is delivered or released non-systemically in the distal ileum of the individual. Provided herein are compositions for preventing pancreatic and other cancers comprising contacting the distal ileum of an individual in need thereof with an ASBTI. In any of the aforementioned embodiments, the compositions further comprise a DPP-IV inhibitor, a TGR5 agonist, a biguanide, an incretin mimetic, or GLP-1 or an analog thereof.

Provided herein, in some embodiments, are ASBTIs for reducing intraenterocyte bile acids, reducing necrosis and/or damage to ileal architecture, reducing food intake (caloric intake), or for reducing circulating blood or plasma glucose levels wherein the ASBTI is not absorbed systemically following oral administration. In some of such embodiments, the ASBTI is a compound of Formula I, II, III, IV, V or VI as described herein. In some of such embodiments, the ASBTI is prevented from being absorbed in the stomach by its presence in a formulation that releases it in the ileum. In some of such embodiments, the ASBTI is administered in combination with a second therapeutic agent selected from a DPP-IV inhibitor, a biguanide, a thiazolidinedione, an incretin mimetic, GLP-1 or an analog thereof, or a TGR5 agonist.

Provided in some embodiments herein is a kit comprising any composition described herein (e.g., a pharmaceutical composition formulated for rectal administration) and a device for localized delivery within the rectum or colon. In certain embodiments, the device is a syringe, bag, or a pressurized container.

BRIEF DESCRIPTION OF FIGURES

FIG. 11A illustrates the plasma PYY concentrations in the caecum, transverse colon, and sigmoid as a result of bile salt administration. FIG. 11B illustrates the plasma enteroglucagon concentrations in the caecum, transverse colon, and sigmoid as a result of bile salt administration.

DETAILED DESCRIPTION OF THE INVENTION

Figure 1:
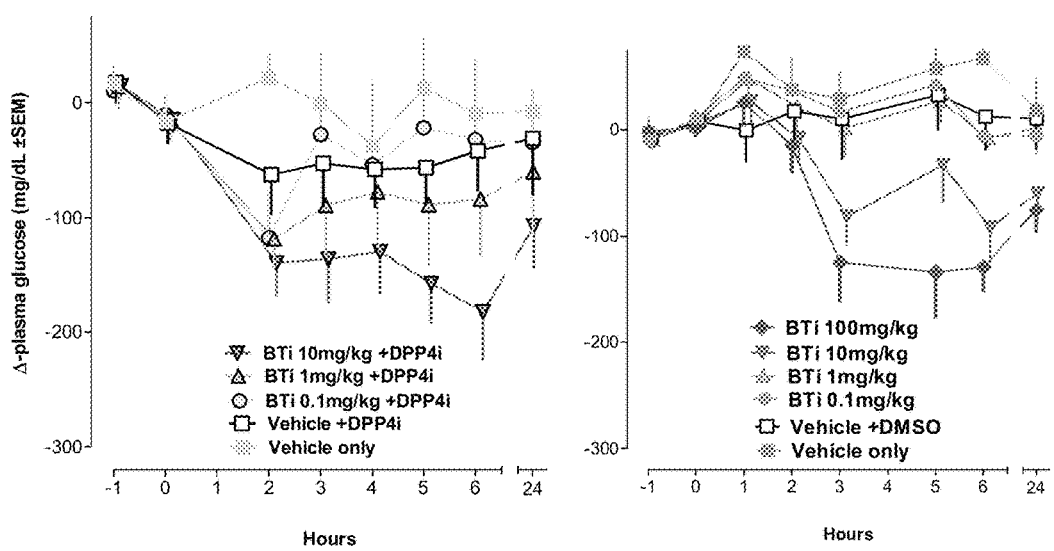
FIG. 1 illustrates the change in plasma glucose level in diabetic db/db mice after oral administration of a combination of the ASBTI (−)-(3R,5R)-trans-3-butyl-3-ethyl-2,3,4,5-tetrahydro-7,8-dimethoxy-5-phenyl-1,4-benzothiazepinel,1-dioxide at doses of 0, 0.1, 1, 10 mg/kg and 30 mg/kg sitagliptin (DPP-IV inhibitor) and the ASBTI alone.

Described herein is the use of inhibitors of the Apical Sodium-dependent Bile Transporter (ASBT) or any recuperative bile salt transporter that are active in the gastrointestinal (GI) tract.

In certain embodiments, the methods provided herein are utilized in methods for treating or preventing an inflammatory intestinal condition or induction of weight loss in an individual in need thereof. In certain embodiments, the methods provided herein comprise administering a therapeutically effective amount of an ASBT inhibitor (ASBTI) and/or an enteroendocrine peptide enhancing agent and/or a FXR agonist to an individual in need thereof. In some embodiments, such ASBT inhibitors and/or enteroendocrine peptide enhancing agents and/or FXR agonists are not systemically absorbed. In some embodiments, such ASBT inhibitors and/or enteroendocrine peptide enhancing agents and/or FXR agonists are systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some embodiments, the ASBTIs are formulated for delivery to the distal ileum. In some embodiments, an ASBTI and/or an enteroendocrine peptide enhancing agent and/or a FXR agonist is minimally absorbed. In some embodiments, an ASBTI and/or an enteroendocrine peptide enhancing agent and/or a FXR agonist is non-systemically administered to the colon or the rectum of an individual in need thereof. In some embodiments, less than 50%, less than 40%, less than 30%, less than 20%, less than 10%, less than 9%, less than 8%, less than 7%, less than 6%, less than 5%, less than 4%, less than 3%, less than 2%, or less than 1% of the ASBTI and/or the enteroendocrine peptide enhancing agent and/or a FXR agonist is systemically absorbed. In certain embodiments, ASBTIs described herein inhibit scavenging of bile salts by recuperative bile acid salt transporters in the distal gastrointestinal tract (e.g., the distal ileum, the colon and/or the rectum).

In some instances, the inhibition of bile salt recycling results in higher concentrations of bile salts in the lumen of the distal gastrointestinal tract or portions thereof (e.g., the distal small bowel and/or colon and/or rectum). As used herein, the distal gastrointestinal tract includes the region from the distal ileum to the anus. In some embodiments, the compounds described herein reduce intraenterocyte bile acids or accumulation thereof. In some embodiments, the compounds described herein reduce necrosis and/or damage to ileal architecture. In certain embodiments, the higher concentration of bile salts in the distal small bowel and/or colon and/or rectum modulates (e.g., enhances) the secretion of enteroendocrine peptides in the distal gastrointestinal tract. In some embodiments, the compounds described herein enhance the secretion of enteroendocrine peptides (e.g., GLP-1, GLP-2, oxyntomodulin, PYY, or a combination thereof) from L-cells that are present in the distal ileum, colon and/or the rectum. In certain embodiments, the enhanced secretion of L-cell enteroendocrine peptides modulates (e.g., slows or inhibits) gastric emptying and gastric acid secretion. In certain instances the enhanced secretion of L-cell enteroendocrine peptides induces a feeling of satiety. In some embodiments, the enhanced secretion of L-cell enteroendocrine peptides reduces food intake thereby inducing weight loss.

Also described herein is the use of such compounds for reducing or maintaining weight in individuals (e.g., individuals interested in losing weight, reducing weight, and/or maintaining a healthy body weight and lifestyle). In certain instances, the compounds described herein are useful in the treatment of diseases or conditions that are modulated by enteroendocrine peptides secreted by L-cells of the distal gastrointestinal tract, including L-cells in the distal ileum, the colon and/or the rectum. In some instances, enhanced enteroendocrine peptide secretion (e.g., increase in GLP-1 secretion) reduces blood or plasma glucose levels. In some embodiments, the compounds described herein are also useful in the treatment of metabolic disorders (e.g., diabetes, metabolic syndrome or the like) because they do not cause side effects (e.g., weight gain) that are associated with conventional therapies for metabolic disorders.

Compounds

In some embodiments, provided herein are ASBT inhibitors that reduce or inhibit bile acid recycling in the distal gastrointestinal (GI) tract, including the distal ileum, the colon and/or the rectum. In certain embodiments, the ASBTIs are systemically absorbed. In certain embodiments, the ASBTIs are not systemically absorbed. In some embodiments, ASBTIs described herein are modified or substituted (e.g., with a -L-K group) to be non-systemic. In certain embodiments, any ASBT inhibitor is modified or substituted with one or more charged groups (e.g., K) and optionally, one or more linker (e.g., L), wherein L and K are as defined herein.

In some embodiments, an ASBTI suitable for the methods described herein is a compound of Formula I:

Formula I

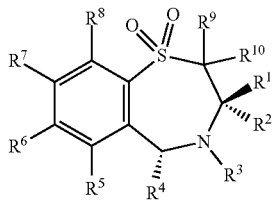

wherein:
R¹ is a straight chained $C_{1-6}$ alkyl group;
R² is a straight chained $C_{1-6}$ alkyl group;
R³ is hydrogen or a group $OR^{11}$ in which $R^{11}$ is hydrogen, optionally substituted $C_{1-6}$alkyl or a $C_{1-6}$ alkylcarbonyl group;
R⁴ is pyridyl or optionally substituted phenyl or $-L_z-K_z$; wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;
R⁵, R⁶, R⁷ and R⁸ are the same or different and each is selected from hydrogen, halogen, cyano, $R^5$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, OCN, SCN, NHCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$, $O(CH_2)_pN^+R^{12}R^{13}R^{14}$ and $—W—R^{31}$, wherein W is O or NH and $R^{31}$ is selected from

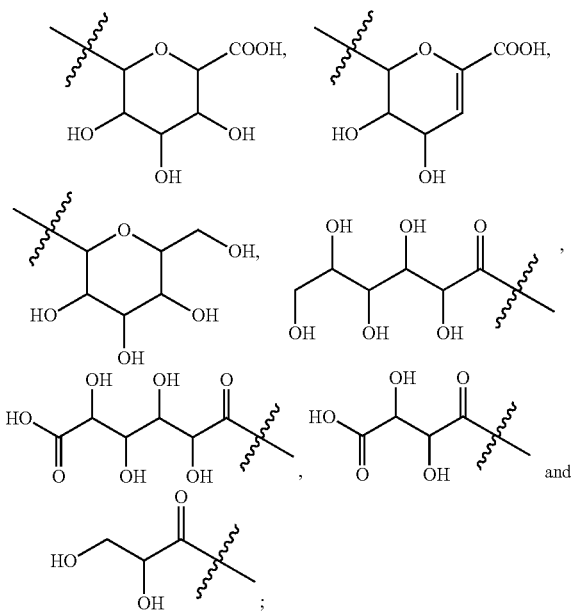

wherein p is an integer from 1-4, n is an integer from 0-3 and, $R^{12}$, $R^{13}$, $R^{14}$ and $R^{15}$ are independently selected from hydrogen and optionally substituted $C_{1-6}$ alkyl; or R⁶ and R⁷ are linked to form a group

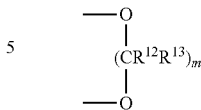

wherein $R^{12}$ and $R^{13}$ are as hereinbefore defined and m is 1 or 2; and
R⁹ and R¹⁰ are the same or different and each is selected from hydrogen or $C_{1-6}$ alkyl; and salts, solvates and physiologically functional derivatives thereof.

In some embodiments of the methods, the compound of Formula I is a compound
wherein
R¹ is a straight chained $C_{1-6}$ alkyl group;
R² is a straight chained $C_{1-6}$ alkyl group;
R³ is hydrogen or a group $OR^{11}$ in which $R^{11}$ is hydrogen, optionally substituted $C_{1-6}$ alkyl or a $C_{1-6}$ alkylcarbonyl group;
R⁴ is optionally substituted phenyl;
R⁵, R⁶ and R⁸ are independently selected from hydrogen, $C_{1-4}$ alkyl optionally substituted by fluorine, $C_{1-4}$ alkoxy, halogen, or hydroxy;
R⁷ is selected from halogen, cyano, $R^{15}$-acetylide, $OR^{15}$, optionally substituted $C_{1-6}$ alkyl, $COR^{15}$, $CH(OH)R^5$, $S(O)_nR^{15}$, $P(O)(OR^{15})_2$, $OCOR^{15}$, $OCF_3$, OCN, SCN, HNCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)R^{15}$, $O(CH_2)_pSO_3R^{15}$, $O(CH_2)_pNR^{12}R^{13}$ and $O(CH_2)_pN^+R^{12}R^{13}R^{14}$;
wherein n, p and $R^{12}$ to $R^{15}$ are as hereinbefore defined;
with the proviso that at least two of R⁵ to R⁸ are not hydrogen; and
salts solvates and physiologically functional derivatives thereof.

In some embodiments of the methods described herein, the compound of Formula I is a compound
wherein
R¹ is a straight chained $C_{1-6}$ alkyl group;
R² is a straight chained $C_{1-6}$ alkyl group;
R³ is hydrogen or a group $OR^{11}$ in which $R^{11}$ is hydrogen, optionally substituted $C_{1-6}$ alkyl or a $C_{1-6}$ alkylcarbonyl group;
R⁴ is un-substituted phenyl;
R⁵ is hydrogen or halogen;
R⁶ and R⁸ are independently selected from hydrogen, $C_{1-4}$ alkyl optionally substituted by fluorine, $C_{1-4}$ alkoxy, halogen, or hydroxy;
R⁷ is selected from $OR^{15}$, $S(O)_nR^{15}$, $OCOR^{15}$, $OCF_3$, OCN, SCN, CHO, $OCH_2OR^{15}$, $OCH=CHR^{15}$, $O(CH_2CH_2O)nR^{15}$, $O(CH_2)_pSO_3R^{15}$, $O(CH_2)_pNR^{12}R^{13}$ and $O(CH_2))_pN^+R^{12}R^{13}R^{14}$ wherein p is an integer from 1-4, n is an integer from 0-3, and $R^{12}$, $R^{13}$, $R^{14}$, and $R^{15}$ are independently selected from hydrogen and optionally substituted $C_{1-6}$ alkyl;
R⁹ and R¹⁰ are the same or different and each is selected from hydrogen or $C_{1-6}$ alkyl; and salts, solvates and physiologically functional derivatives thereof.

In some embodiments of the methods, wherein the compound of Formula I is a compound wherein
R¹ is methyl, ethyl or n-propyl;
R² is methyl, ethyl, n-propyl, n-butyl or n-pentyl;
R³ is hydrogen or a group $OR^{11}$ in which $R^{11}$ is hydrogen, optionally substituted $C_{1-6}$ alkyl or a $C_{1-6}$ alkylcarbonyl group;

R⁴ is un-substituted phenyl;
R⁵ is hydrogen;
R⁶ and R⁸ are independently selected from hydrogen, $C_{1-4}$ alkyl optionally substituted by fluorine, $C_{1-4}$ alkoxy, halogen, or hydroxy;
R⁷ is selected from $OR^{15}$, $S(O)_nR^{15}$, $OCOR^{15}$, $OCF_3$, OCN, SCN, CHO, $OCH_2OR^{15}$, $OCH=CHR^{15}$, $O(CH_2CH_2O)_n R^{15}$, $O(CH_2)_pSO_3R^{15}$, $O(CH_2)_pNR^{12}R^{13}$ and $O(CH_2)_pN^+ R^{12}R^{13}R^{14}$ wherein p is an integer from 1-4, n is an integer from 0-3, and $R^{12}$, $R^{13}$, $R^{14}$, and $R^{15}$ are independently selected from hydrogen and optionally substituted $C_{1-6}$ alkyl;
R⁹ and R¹⁰ are the same or different and each is selected from hydrogen or $C_{1-6}$ alkyl; and
salts, solvates and physiologically functional derivatives thereof.

In some embodiments of the methods, the compound of Formula I is a compound
wherein
R¹ is methyl, ethyl or n-propyl;
R² is methyl, ethyl, n-propyl, n-butyl or n-pentyl;
R³ is hydrogen or a group $OR^{11}$ in which $R^{11}$ is hydrogen, optionally substituted $C_{1-6}$ alkyl or a $C_{1-6}$ alkylcarbonyl group;
R⁴ is un-substituted phenyl;
R⁵ is hydrogen;
R⁶ is $C_{1-4}$ alkoxy, halogen, or hydroxy;
R⁷ is $OR^{15}$, wherein $R^{15}$ is hydrogen or optionally substituted $C_{1-6}$ alkyl;
R⁸ is hydrogen or halogen;
R⁹ and R¹⁰ are the same or different and each is selected from hydrogen or $C_{1-6}$ alkyl; and
salts, solvates and physiologically functional derivatives thereof.

In some embodiments of the methods, the compound of Formula I is
(3R,5R)-3-Butyl-3-ethyl-2,3,4,5-tetrahydro-7,8-dimethoxy-5-phenyl-1,4-benzothiazepine 1,1-dioxide;
(3R,5R)-3-Butyl-3-ethyl-2,3,4,5-tetrahydro-7,8-dimethoxy-5-phenyl-1,4-benzothiazepin-4-ol 1,1-dioxide;
(±)-Trans-3-butyl-3-ethyl-2,3,4,5-tetrahydro-7,8-dimethoxy-5-phenyl-1,4-benzothiazepine 1,1-dioxide;
(±)-Trans-3-butyl-3-ethyl-2,3,4,5-tetrahydro-7,8-dimethoxy-5-phenyl-1,4,-benzothiazepin-4-ol 1,1-dioxide;
(3R,5R)-7-Bromo-3-butyl-3-ethyl-2,3,4,5-tetrahydro-8-methoxy-5-phenyl-1,4-benzothiazepine 1,1-dioxide;
(3R,5R)-7-Bromo-3-butyl-3-ethyl-2,3,4,5-tetrahydro-8-methoxy-5-phenyl-1,4-benxothiaxepin-4-ol 1,1-dioxide;
(3R,5R)-3-Butyl-3-ethyl-2,3,4,5-tetrahydro-5-phenyl-1,4-benzothiazepine-7,8-diol 1,1-dioxide;
(3R,5R)-3-Butyl-3-ethyl-2,3,4,5-tetrahydro-8-methoxy-5-phenyl-1,4-benzothiazepin-7-ol 1,1-dioxide;
(3R,5R)-3-Butyl-3-ethyl-2,3,4,5-tetrahydro-7-methoxy-5-phenyl-1,4-benzothiazepin-8-ol 1,1-dioxide;
(±)-Trans-3-butyl-3-ethyl-2,3,4,5-tetrahydro-8-methoxy-5-phenyl-1,4-benzothiazepine 1,1-dioxide;
(±)-Trans-3-butyl-3-ethyl-2,3,4,5-tetrahydro-5-phenyl-1,4-benzothiazepin-8-ol 1,1-dioxide;
(±)-Trans-3-butyl-3-ethyl-2,3,4,5-tetrahydro-5-phenyl-1,4-benzothiazepine-4,8-diol;
(±)-Trans-3-butyl-3-ethyl-2,3,4,5-tetrahydro-5-phenyl-1,4-benzothiazepin-8-thiol 1,1-dioxide;
(±)-Trans-3-butyl-3-ethyl-2,3,4,5-tetrahydro-5-phenyl-1,4-benzothiazepin-8-sulfonic acid 1,1-dioxide;
(±)-Trans-3-butyl-3-ethyl-2,3,4,5-tetrahydro-8,9-dimethoxy-5-phenyl-1,4-benzothiazepine 1,1-dioxide;
(3R,5R)-3-butyl-7,8-diethoxy-2,3,4,5-tetrahydro-5-phenyl-1,4-benzothiazepine 1,1-dioxide;
(±)-Trans-3-butyl-8-ethoxy-3-ethyl-2,3,4,5-tetrahydro-5-phenyl-1,4-benzothiazepine 1,1-dioxide;
(±)-Trans-3-butyl-3-ethyl-2,3,4,5-tetrahydro-8-isopropoxy-5-phenyl-1,4-benzothiazepine 1,1-dioxide hydrochloride;
(±)-Trans-3-butyl-3-ethyl-2,3,4,5-tetrahydro-5-phenyl-1,4-benzothiazepin-8-carbaldehyde-1,1-dioxide;
3,3-Diethyl-2,3,4,5-tetrahydro-7,8-dimethoxy-5-phenyl-1,4-benzothiazepine 1,1-dioxide;
3,3-Diethyl-2,3,4,5-tetrahydro-8-methoxy-5-phenyl-1,4-benzothiazepine 1,1-dioxide;
3,3-Diethyl-2,3,4,5-tetrahydro-5-phenyl-1,4-benzothiazpin-4,8-diol 1,1-dioxide;
(RS)-3,3-Diethyl-2,3,4,5-tetrahydro-4-hydroxy-7,8-dimethoxy-5-phenyl-1,4-benzothiazepine 1,1-dioxide;
(±)-Trans-3-butyl-8-ethoxy-3-ethyl-2,3,4,5-tetrahydro-5-phenyl-1,4-benzothiazepin-4-ol-1-dioxide;
(±)-Trans-3-butyl-3-ethyl-2,3,4,5-tetrahydro-8-isopropoxy-5-phenyl-1,4-benzothiazepin-4-ol 1,1-dioxide;
(±)-Trans-3-butyl-3-ethyl-2,3,4,5-tetrahydro-7,8,9-trimethoxy-5-phenyl-1,4-benzothiazepin-4-ol 1,1-dioxide;
(3R,5R)-3-butyl-3-ethyl-2,3,4,5-tetrahydro-5-phenyl-1,4-benzothiazepin-4,7,8-triol 1,1-dioxide;
(±)-Trans-3-butyl-3-ethyl-2,3,4,5-tetrahydro-4,7,8-trimethoxy-5-phenyl-1,4-benzothiazepine 1,1-dioxide;
3,3-Diethyl-2,3,4,5-tetrahydro-5-phenyl-1,4-benzothiazepin-8-ol 1,1-dioxide;
3,3-Diethyl-2,3,4,5-tetrahydro-7-methoxy-5-phenyl-1,4-benzothiazepin-8-ol 1,1-dioxide;
3,3-Dibutyl-2,3,4,5-tetrahydro-5-phenyl-1,4-benzothiazepin-8-ol 1,1-dioxide;
(±)-Trans-3-Butyl-3-ethyl-2,3,4,5-tetrahydro-1,1-dioxo-5-phenyl-1,4-benzothiazepin-8-yl hydrogen sulfate;
or
3,3-Diethyl-2,3,4,5-tetrahydro-1,1-dioxo-5-phenyl-1,4-benzothiazepin-8-yl hydrogen sulfate.

In some embodiments, the compound of Formula I is

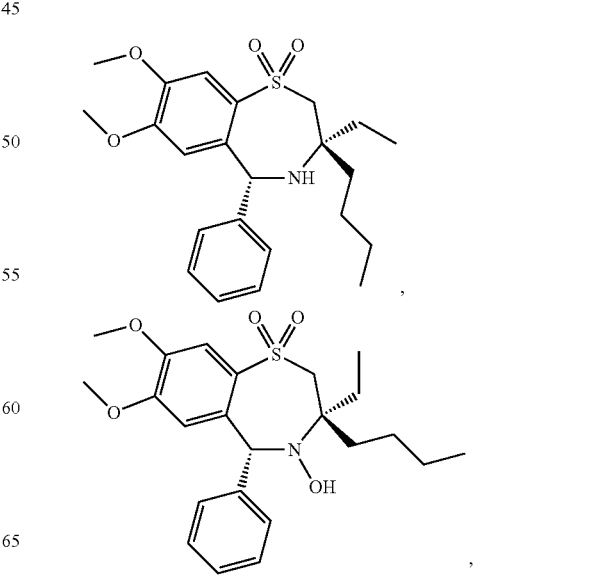

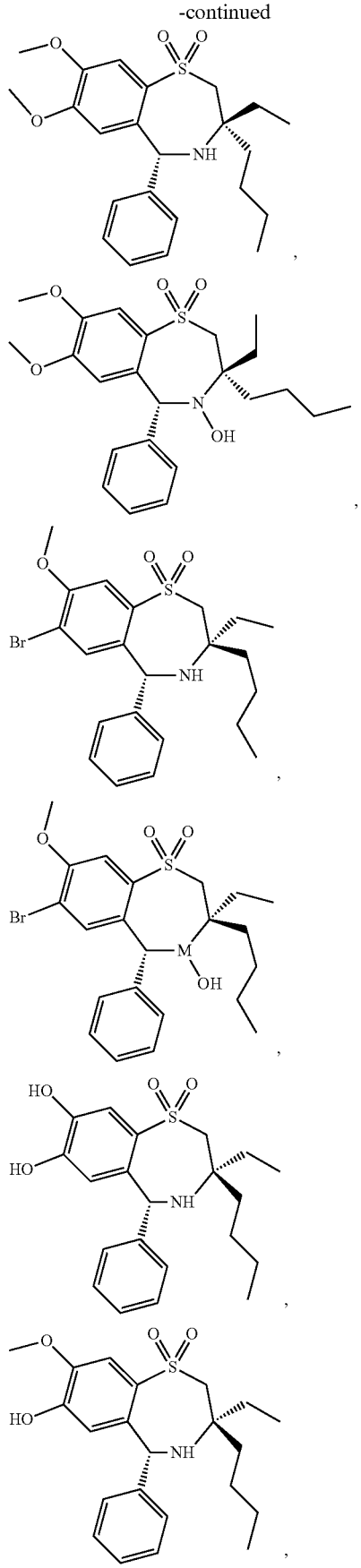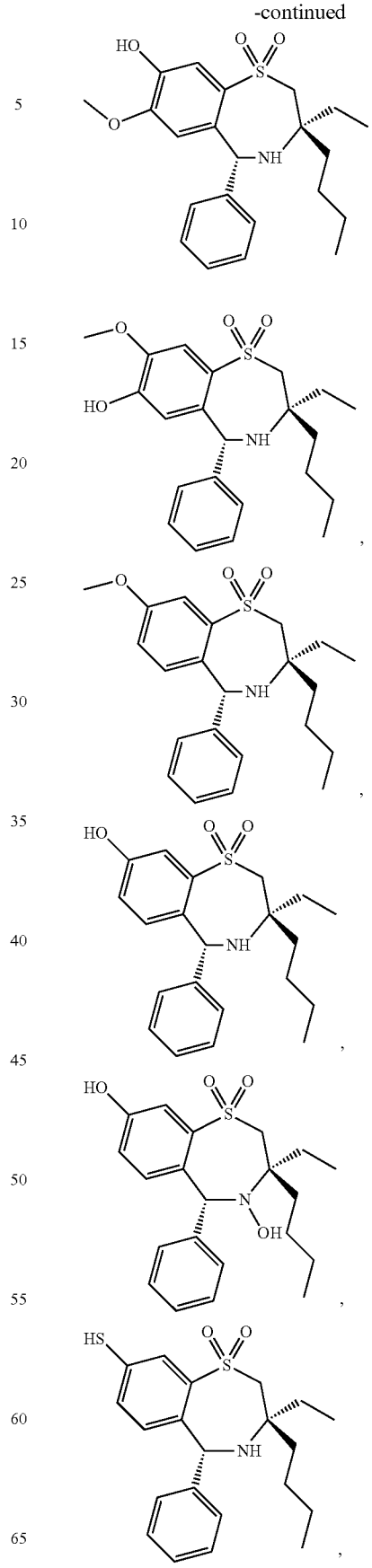

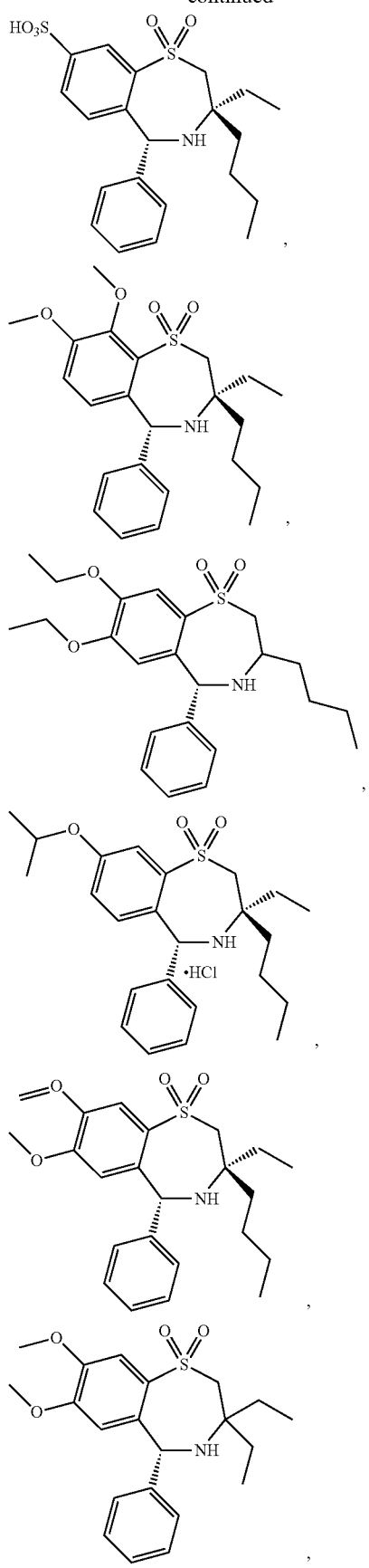
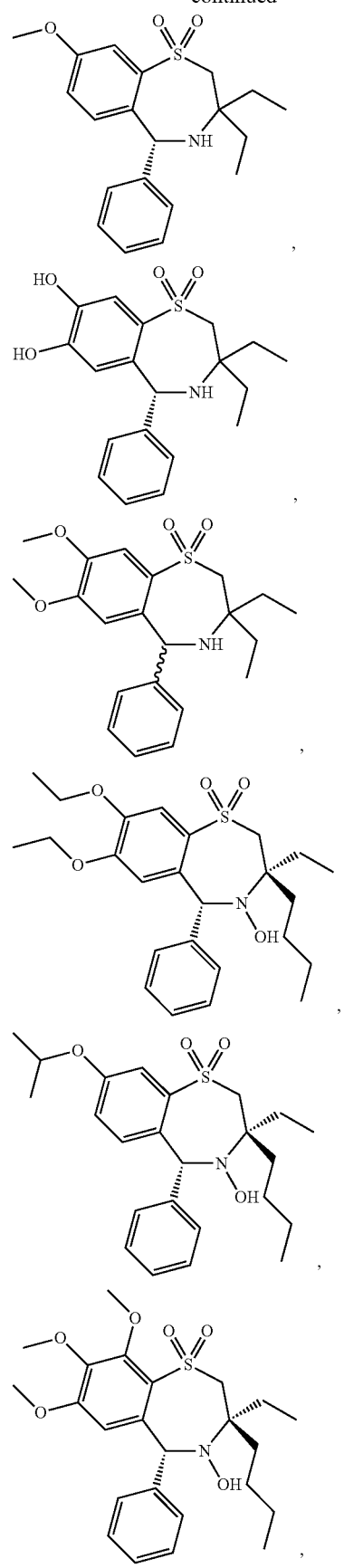

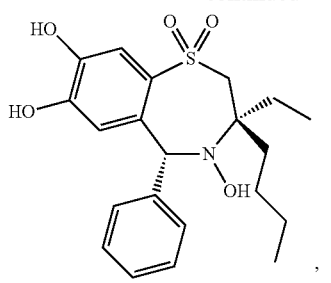
,
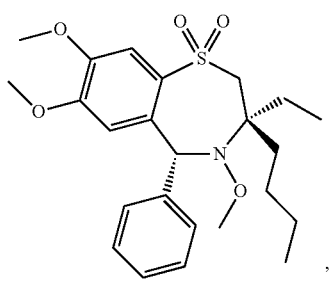
,
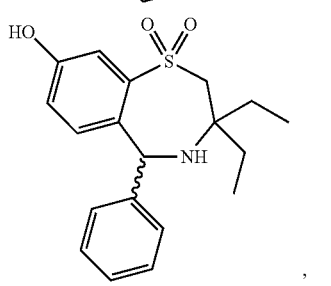
,
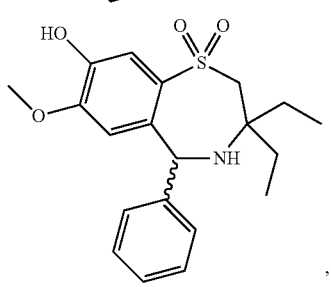
,
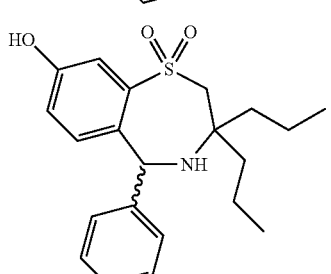
,
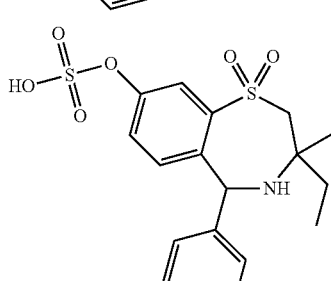
, or

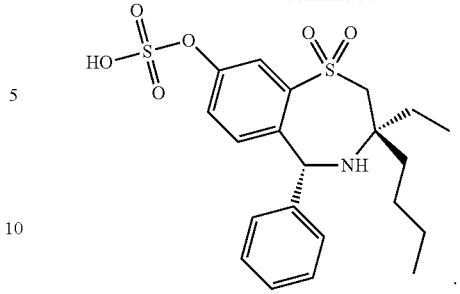

In some embodiments of the methods, the compound of Formula I is

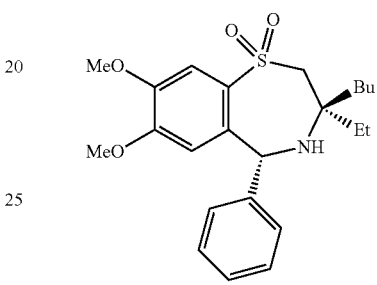

In some embodiments, an ASBTI suitable for the methods described herein is a compound of Formula II Formula II

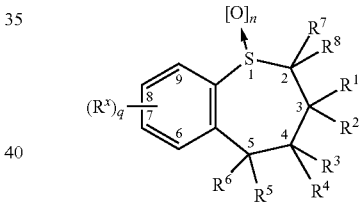

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $S^+R^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or
$R^1$ and $R^2$ taken together with the carbon to which they are attached form $C_3$-$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, quaternary heterocycle, quaternary heteroaryl, $OR^{30}$, $SR^9$, $S(O)R^9$, $SO_2R^9$, $SO_3R^9$, and -$L_z$-$K_z$;

wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $SR^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, amino acid, peptide, or polypeptide, and $R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, S(O), $NR^{18}$, $NR^{13}R^{18}$, $NR^{18}R^{14}$, $N^+12^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)M, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_3R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen or SH;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof In some embodiments of the methods, the compound of Formula II is a compound
wherein
$R^5$ and $R^6$ are independently selected from the group consisting of H, aryl, heterocycle, quaternary heterocycle, and quarternary heteroaryl
wherein the aryl, heteroaryl, quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^3OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, $N^+R^9R^{11}R^{12}A^-$ and $-L_z-K_z$.

In some embodiments of the methods, the compound of Formula II is a compound
wherein
$R^5$ or $R^6$ is —Ar—$(R^y)_t$
t is an integer from 0 to 5;
Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and
one or more $R^y$ are independently selected from the group consisting of alkyl, alkenyl, alkynyl, polyalkyl, polyether, aryl, halo alkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, $N^+R^9R^{11}R^{12}A^-$ and $-L_z-K_z$;
wherein said alkyl, alkenyl, alkynyl, polyalkyl, polyether, aryl, haloalkyl, cycloalkyl, and heterocycle can be further substituted with one or more substituent groups selected from the group consisting of $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR)OR^8$, and or phenylene;
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene.

In some embodiments of the methods, the compound of Formula II is a compound wherein $R^5$ or $R^6$ is

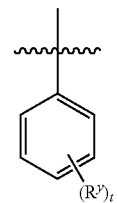

In some embodiments of the methods, the compound of Formula II is a compound wherein n is 1 or 2. In some embodiments of the methods, the compound of Formula II is a compound wherein $R^1$ and $R^2$ are independently H or $C_{1-7}$ alkyl. In some embodiments of the methods, the compound of Formula II is a compound wherein each $C_{1-7}$ alkyl is independently ethyl, n-propyl, n-butyl, or isobutyl. In some embodiments of the methods, the compound of Formula II is a compound wherein $R^3$ and $R^4$ are independently H or $OR^9$. In some embodiments of the methods, compound of Formula II is a compound wherein $R^9$ is H In some embodiments of the methods, the compound of Formula II is a compound wherein one or more $R^x$ are in the 7-, 8- or 9-position of the benzo ring of Formula II. In some embodiments of the methods, the compound of Formula II is a compound wherein $R^x$ is in the 7-position of the benzo ring of Formula II. In some embodiments of the methods, the compound of Formula II is a compound wherein one or more $R^x$ are independently selected from $OR^{13}$ and $NR^{13}R^{14}$.

In some embodiments of the methods, the compound of Formula II is a compound
wherein:
q is 1 or 2;
n is 2;
$R^1$ and $R^2$ are each alkyl;
$R^3$ is hydroxy;
$R^4$ and $R^6$ are hydrogen;
$R^5$ has the formula

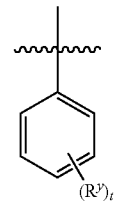

wherein
t is an integer from 0 to 5;
one or more $R^Y$ are $OR^{13}$;
$R^{13}$ is selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl;
said $R^{13}$ alkyl, alkenyl, alkynyl, arylalkyl, heterocycle, and polyalkyl groups optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide;
$R^{13}$ is optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein A is a pharmaceutically acceptable anion, and M is a pharmaceutically acceptable cation, $R^9$ and $R^{1°}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{1°}$ are as defined above, provided that both $R^3$ and $R^4$ cannot be OH, $NH_2$, and SH; or $R^{11}$ and $R^{12}$ together with the nitrogen or carbon atom to which they are attached form a cyclic ring; and $R^{16}$ and $R^{17}$ are independently selected from the substituents constituting $R^9$ and M;

$R^7$ and $R^8$ are hydrogen; and one or more $R^x$ are independently selected from the group consisting of alkoxy, alkylamino and dialkylamino and —W—$R^{31}$, wherein W is O or NH and $R^{31}$ is selected from

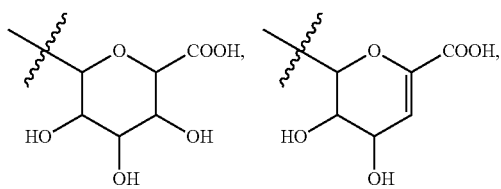

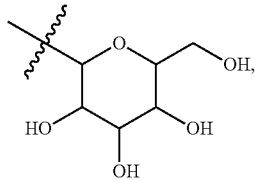

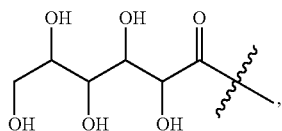

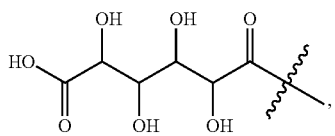

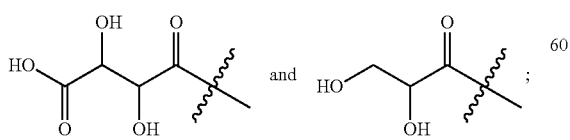

or a pharmaceutically acceptable salt, solvate, or prodrug thereof.

In some embodiments, a compound of Formula II is

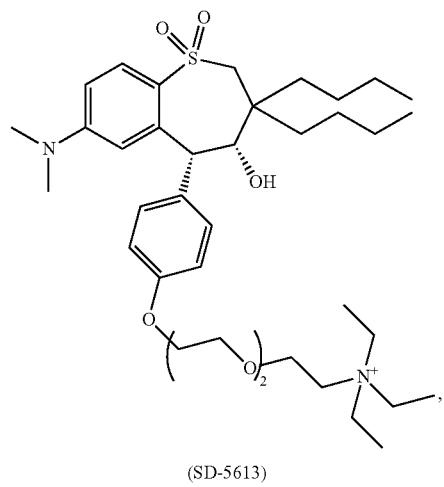

(SD-5613)

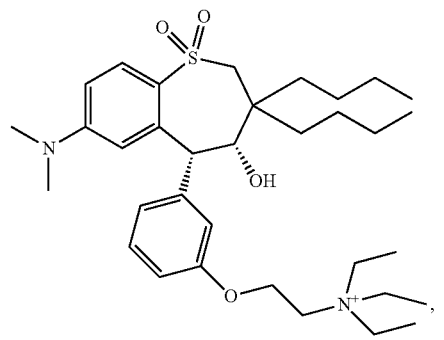

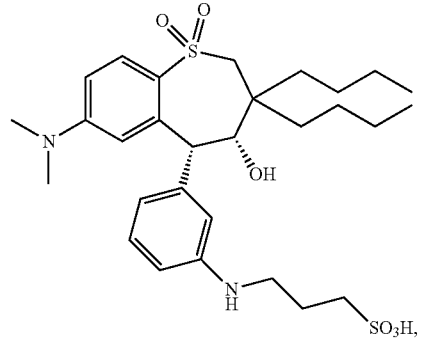

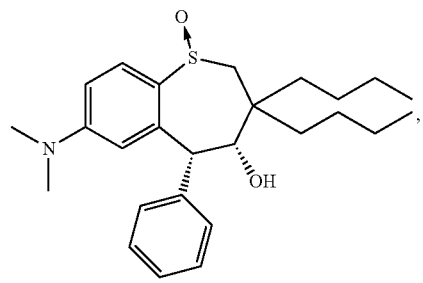

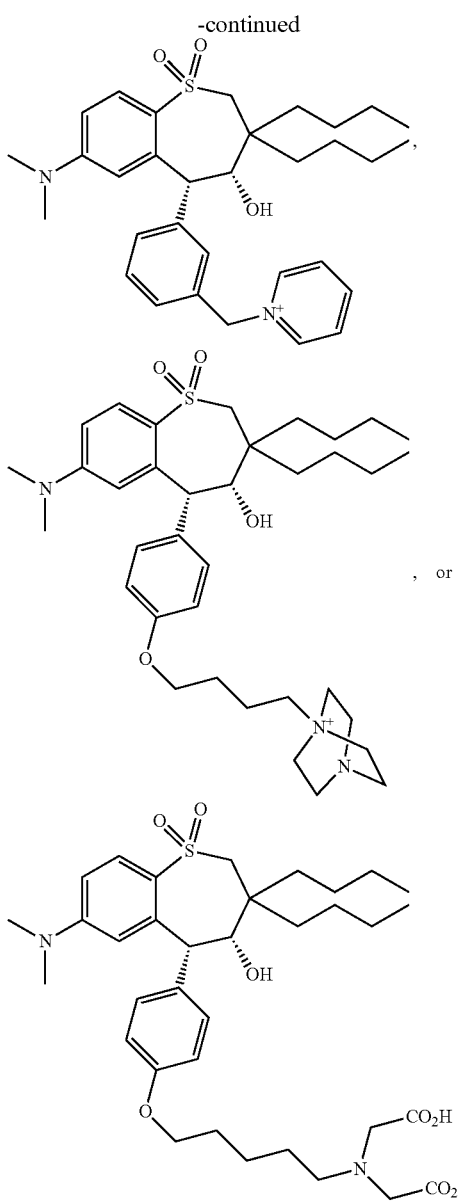

, or or the like.

In some embodiments of the methods, the compound of Formula II is

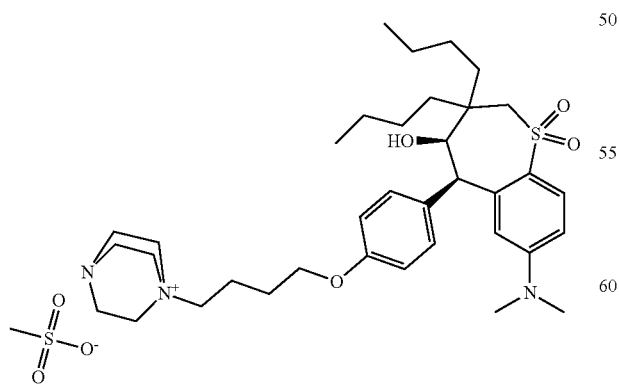

In certain embodiments, ASBTIs suitable for the methods described herein are non-systemic analogs of Compound 100C. Certain compounds provided herein are Compound 100C analogues modified or substituted to comprise a charged group. In specific embodiments, the Compound 100C analogues are modified or substituted with a charged group that is an ammonium group (e.g., a cyclic or acyclic ammonium group). In certain embodiments, the ammonium group is a non-protic ammonium group that contains a quarternary nitrogen.

In some embodiments, a compound of Formula II is

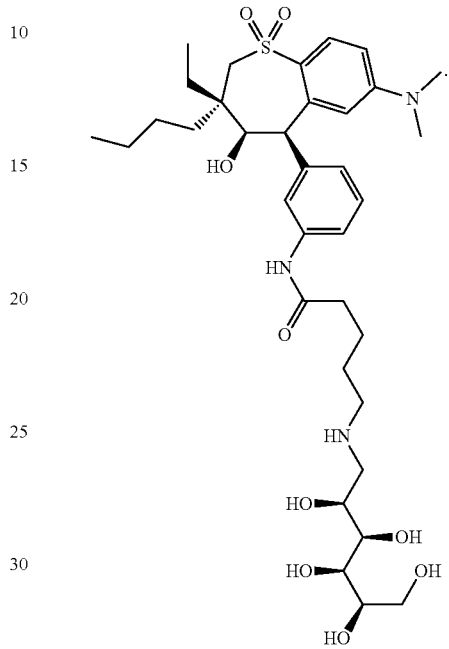

In some embodiments, a compound of Formula II is 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl]amino]-1-deoxy-D-glucitol or SA HMR1741 (a.k.a. BARI-1741).

In some embodiments, a compound of Formula II is

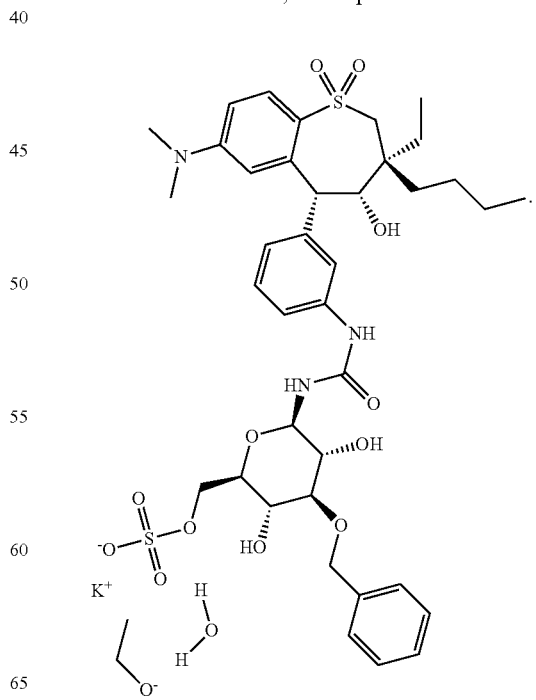

In some embodiments, a compound of Formula II is potassium((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl) sulphate ethanolate, hydrate or SAR548304B (a.k.a. SAR-548304).

In some embodiments, an ASBTI suitable for the methods described herein is a compound of Formula III:

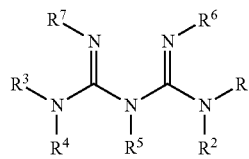

Formula III wherein:
each $R^1$, $R^2$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;

each $R^3$, $R^4$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

$R^5$ is H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, each $R^6$, $R^7$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;

each X is independently NH, S, or O;
each Y is independently NH, S, or O;

$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
each A is independently NR$^1$, S(O)$_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;

n is 0-7;

K is a moiety that prevents systemic absorption;

provided that at least one of $R^1$, $R^2$, $R^3$ or $R^4$ is -L-K;

or a pharmaceutically acceptable prodrug thereof.

In some embodiments of a compound of Formula III, $R^1$ and $R^3$ are -L-K. In some embodiments, $R^1$, $R^2$ and $R^3$ are -L-K.

In some embodiments, at least one of $R^1$, $R^2$, $R^3$, $R^4$, $R^5$, $R^6$ and $R^7$ is H. In certain embodiments, $R^5$, $R^6$, $R^7$ are H and $R^1$, $R^2$, $R^3$ and $R^4$ are alkyl, aryl, alkyl-aryl, or heteroalkyl. In some embodiments, $R^1$ and $R^2$ are H. In some embodiments, $R^1$, $R^2$, $R^5$, $R^6$ and $R^7$ are H. In some embodiments, $R^6$ and $R^7$ together form a bond. In certain embodiments, $R^5$, $R^6$ and $R^7$ are H, alkyl or O-alkyl.

In some embodiments, $R^1$ and $R^3$ are -L-K. In some embodiments, $R^1$, $R^2$ and $R^3$ are -L-K. In some embodiments, $R^3$ and $R^4$ are -L-K. In some embodiments, $R^1$ and $R^2$ together with the nitrogen to which they are attached form a 3-8 membered ring and the ring is substituted with -L-K. In some embodiments, $R^1$ or $R^2$ or $R^3$ or $R^4$ are aryl optionally substituted with -L-K. In some embodiments, $R^3$ or $R^2$ or $R^3$ or $R^4$ are alkyl optionally substituted with -L-K. In some embodiments, $R^1$ or $R^2$ or $R^3$ or $R^4$ are alky-aryl optionally substituted with -L-K. In some embodiments, $R^1$ or $R^2$ or $R^3$ or $R^4$ are heteroalkyl optionally substituted with -L-K.

In some embodiments, L is a $C_1$-$C_7$alkyl. In some embodiments, L is heteroalkyl. In certain embodiments, L is $C_1$-$C_7$alkyl-aryl. In some embodiments, L is $C_1$-$C_7$alkyl-aryl-$C_1$-$C_7$alkyl.

In certain embodiments, K is a non-protic charged group. In some specific embodiments, each K is a ammonium group. In some embodiments, each K is a cyclic non-protic ammonium group. In some embodiments, each K is an acyclic non-protic ammonium group.

In certain embodiments, each K is a cyclic non-protic ammonium group of structure:

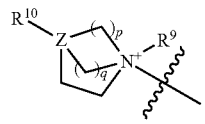

In certain embodiments, K is an acyclic non-protic ammonium group of structure:

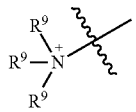

wherein p, q, $R^9$, $R^{10}$ and Z are as defined above. In certain embodiments, p is 1. In other embodiments, p is 2. In further embodiments, p is 3. In some embodiments, q is 0. In other embodiments, q is 1. In some other embodiments, q is 2.

The compounds further comprise 1, 2, 3 or 4 anionic counterions selected from $Cl^-$, $Br^-$, $I^-$, $R^{11}SO_3^-$, $(SO_3^-—R^{11}—SO_3^-)$, $R^{11}CO_2^-$, $(CO_2^-—R^{11}—CO_2^-)$, $(R^{11})_2(P=O)O^-$ and $(R^{11})(P=O)O_2^{2-}$ wherein $R^{11}$ is as defined above. In some embodiments, the counterion is $Cl^-$, $Br^-$, $I^-$, $CH_2CO_2^-$, $CH_3SO_3^-$, or $C_6H_5SO_3^-$ or $CO_2^-—(CH_2)_2—CO_2^-$. In some embodiments, the compound of Formula III has one K group and one counterion. In other embodiments, the compound of Formula III has one K group, and two molecules of the compound of Formula III have one counterion. In yet other embodiments, the compound of Formula III has two K groups and two counterions. In some other embodiments, the compound of Formula III has one K group comprising two ammonium groups and two counterions.

Also described herein are compounds having the Formula IIIA:

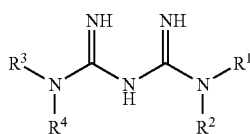

Formula IIIA wherein:
each $R^1$, $R^2$ is independently H, substituted or unsubstituted alkyl, or -L-K; or $R^1$ and $R^2$ together with the nitrogen to which they are attached form a 3-8-membered ring that is optionally substituted with $R^8$;
and $R^3$, $R^4$, $R^8$, L and K are as defined above.

In some embodiments of compounds of Formula IIIA, L is $A_n$, wherein each A is substituted or unsubstituted alkyl, or substituted or unsubstituted heteroalkyl, and n is 0-7. In certain specific embodiments of the compound of Formula IIIA, $R^1$ is H. In some embodiments of Formula IIIA, $R^1$ and $R^2$ together with the nitrogen to which they are attached form a 3-8-membered ring that is optionally substituted with -L-K.

Also described herein are compounds having the Formula IIIB:

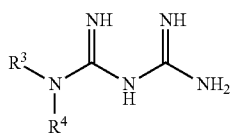

Formula IIIB wherein:
each $R^3$, $R^4$ is independently H, substituted or unsubstituted alkyl, substituted or unsubstituted heteroalkyl, substituted or unsubstituted aryl, substituted or unsubstituted alkyl-aryl, or -L-K;
and $R^1$, $R^2$, L and K are as defined above.

In certain embodiments of Formula IIIB, $R^3$ is H. In certain embodiments, $R^3$ and $R^4$ are each -L-K. In some embodiments, $R^3$ is H and $R^4$ is substituted or unsubstituted alkyl, substituted or unsubstituted heteroalkyl, substituted or unsubstituted aryl, substituted or unsubstituted alkyl-aryl containing one or two -L-K groups.

In some embodiments, an ASBTI suitable for the methods described herein is a compound of Formula IIIC

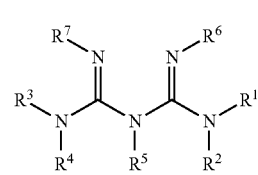

Formula IIIC wherein:
each $R^1$, $R^2$ is independently H, hydroxy, alkyl, alkoxy, $—C(=X)YR^8$, $—YC(=X)R^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;
each $R^3$, $R^4$ is independently H, hydroxy, alkyl, alkoxy, $—C(=X)YR^8$, $—YC(=X)R^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;
$R^5$ is H, hydroxy, alkyl, alkoxy, $—C(=X)YR^8$, $—YC(=X)R^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl,
each $R^6$, $R^7$ is independently H, hydroxy, alkyl, alkoxy, $—C(=X)YR^8$, $—YC(=X)R^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;
each X is independently NH, S, or O;
each Y is independently NH, S, or O;

$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
  each A is independently $NR^1$, $S(O)_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;
  n is 0-7;
K is a moiety that prevents systemic absorption;
or a pharmaceutically acceptable salt thereof.

In some specific embodiments of Formula I, II or III, K is selected from

[chemical structures]

In some embodiments, an ASBTI suitable for the methods described herein is a compound of Formula IV:

[structure IV]

wherein
$R^1$ is a straight chain $C_{1-6}$ alkyl group;
$R^2$ is a straight chain $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is pyridyl or an optionally substituted phenyl;
$R^5$, $R^6$ and $R^8$ are the same or different and each is selected from:
  hydrogen, halogen, cyano, $R^{15}$-acetylide, $OR^{15}$, optionally substituted $C_{1-6}$ alkyl, $COR^{15}$, CH(OH) $R^{15}$, $S(O)_nR^{15}$, $P(O)(OR^{15})_2$, $OCOR^{15}$, $OCF_3$, OCN, SCN, NHCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, OCH=$CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein
p is an integer from 1-4,
n is an integer from 0-3 and
$R^2$, $R^{13}$, $R^{14}$ and $R^{15}$ are independently selected from hydrogen and optionally substituted $C^{1-6}$ alkyl;
$R^7$ is a group of the formula

[chemical structures]

wherein the hydroxyl groups may be substituted by acetyl, benzyl,
  or —($C_1$-$C_6$)-alkyl-$R^{17}$,
wherein the alkyl group may be substituted with one or more hydroxyl groups;
$R^{16}$ is —COOH, —$CH_2$—OH, —$CH_2$—O-Acetyl, —COOMe or —COOEt;
$R^{17}$ is H, —OH, —$NH_2$, —COOH or $COOR^{18}$;
$R^{18}$ is ($C_1$-$C_4$)-alkyl or —NH—($C_1$-$C_4$)-alkyl;
X is —NH— or —O—; and
$R^9$ and $R^{10}$ are the same or different and each is hydrogen or $C_1$-$C_6$ alkyl; and salts thereof.

In some embodiments, a compound of Formula IV has the structure of Formula IVA or Formula IVB:

[structure Formula IVA]

[structure Formula IVB]

In some embodiments, a compound of Formula IV has the structure of Formula IVC:

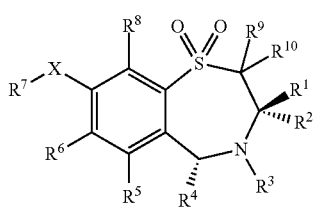

IVC

In some embodiments of Formula IV, X is O and $R^7$ is selected from

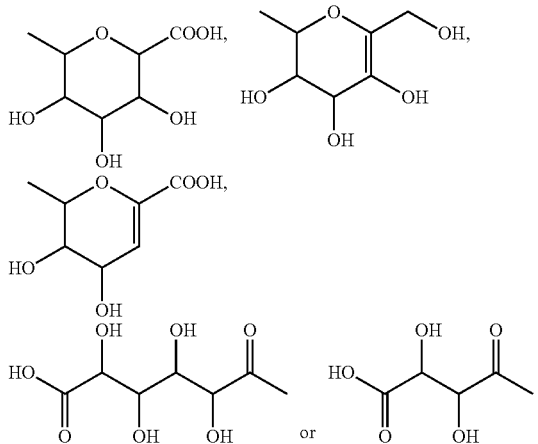

In some embodiments, a compound of Formula IV is:

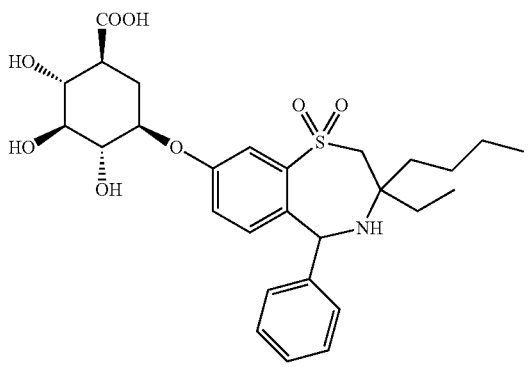 [SMILES: CCCCC1(CC)CS(=O)(=O)c2cc(O[C@@H]3C[C@H](C(=O)O)[C@@H](O)[C@H](O)[C@H]3O)ccc2C(c2ccccc2)N1]

In some embodiments, an ASBTI suitable for the methods described herein is a compound of Formula V:

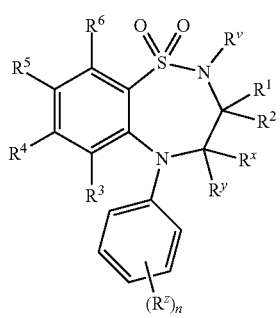

V wherein:
$R^v$ is selected from hydrogen or $C_{1-6}$alkyl;
One of $R^1$ and $R^2$ are selected from hydrogen or $C_{1-6}$alkyl and the other is selected from $C_{1-6}$alkyl;
$R^x$ and $R^y$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2;
$R^z$ is selected from halo, nitr, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
n is 0-5;
one of $R^4$ and $R^5$ is a group of formula (VA):

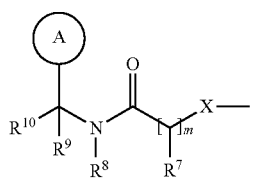

VA $R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
wherein $R^3$ and $R^6$ and the other of $R^4$ and $R^5$ may be optionally substituted on carbon by one or more $R^{17}$;
X is —O—, —N($R^a$)—, —S(O)$_b$— or —CH($R^a$)—;
wherein $R^a$ is hydrogen or $C_{1-6}$alkyl and b is 0-2;
Ring A is aryl or heteroaryl;
wherein Ring A is optionally substituted on carbon by one or more substituents selected from $R^{18}$;
$R^7$ is hydrogen, $C_{1-6}$alkyl, carbocyclyl or heterocyclyl;
wherein $R^7$ is optionally substituted on carbon by one or more substituents selected from $R^{19}$; and wherein if said heterocyclyl contains an —NH— group, that nitrogen may be optionally substituted by a group selected from $R^{20}$;
$R^8$ is hydrogen or $C_{1-6}$-alkyl;
$R^9$ is hydrogen or $C_{1-6}$alkyl;
$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkynyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)-$R^{21}$—($C_{1-10}$alkylene)$_q$- or heterocyclyl-(C$_{1-10}$alkylene)$_r$-R$^{22}$—(C$_{1-10}$alkylene)$_s$-; wherein R$^{10}$ is optionally substituted on carbon by one or more substituents selected from R$^{23}$; and wherein if said heterocyclyl contains an —NH— group, that nitrogen may be optionally substituted by a group selected from R$^{24}$; or R$^{10}$ is a group of formula (VB):

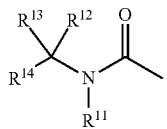

VB wherein:
R$^{11}$ is hydrogen or C$_{1-6}$-alkyl;
R$^{12}$ and R$^{13}$ are independently selected from hydrogen, halo, carbamoyl, sulphamoyl, C$_{1-10}$alkyl, C$_{2-10}$alkynyl, C$_{2-10}$alkynyl, C$_{1-10}$alkanoyl, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, carbocyclyl or heterocyclyl; wherein R$^{12}$ and R$^{13}$ may be independently optionally substituted on carbon by one or more substituents selected from R$^{25}$; and wherein if said heterocyclyl contains an —NH— group, that nitrogen may be optionally substituted by a group selected from R$^{26}$;
R$^{14}$ is selected from hydrogen, halo, carbamoyl, sulphamoyl, hydroxyaminocarbonyl, C$_{1-10}$alkyl, C$_{2-10}$alkenyl, C$_{2-10}$alkynyl, C$_{1-10}$alkanoyl, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{27}$—(C$_{1-10}$alkylene)$_q$- or heterocyclyl-(C$_{1-10}$alkylene)$_r$-R$^{28}$—(C$_{1-10}$alkylene)$_s$-; wherein R$^{14}$ may be optionally substituted on carbon by one or more substituents selected from R$^{29}$; and wherein if said heterocyclyl contains an —NH— group, that nitrogen may be optionally substituted by a group selected from R$^{30}$; or R$^{14}$ is a group of formula (VC):

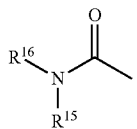

VC

R$^{15}$ is hydrogen or C$_{1-6}$alkyl; and R$^{16}$ is hydrogen or C$_{1-6}$alkyl; wherein R$^{16}$ may be optionally substituted on carbon by one or more groups selected from R$^{31}$;
or R$^{15}$ and R$^{16}$ together with the nitrogen to which they are attached form a heterocyclyl; wherein said heterocyclyl may be optionally substituted on carbon by one or more R$^{37}$; and wherein if said heterocyclyl contains an —NH— group, that nitrogen may be optionally substituted by a group selected from R$^{38}$
m is 1-3; wherein the values of R$^7$ may be the same or different;

R$^{17}$, R$^{18}$, R$^{19}$, R$^{23}$, R$^{25}$, R$^{29}$, R$^{31}$ and R$^{37}$ are independently selected from halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$ amino, N,N,N—(C$_{1-10}$alkyl)$_3$ammonio, C$_{1-10}$alkanoylamino, N—(C$_{1-10}$alkyl)carbamoyl, N,N—(C$_{1-10}$alkyl)$_2$ carbamoyl, C$_{1-10}$alkylS(O)$_a$ wherein a is 0 to 2, N—(C$_{1-10}$alkyl)sulphamoyl, N,N—(C$_{1-10}$ alkyl)$_2$ sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{32}$—(C$_{1-10}$alkylene)$_q$- or heterocyclyl-(C$_{1-10}$alkylene)$_r$-R$^{33}$—(C$_{1-10}$alkylene)$_s$-; wherein R$^{17}$, R$^{18}$, R$^{19}$, R$^{23}$, R$^{25}$, R$^{29}$, R$^{31}$ and R$^{37}$ may be independently optionally substituted on carbon by one or more R$^{34}$; and wherein if said heterocyclyl contains an —NH— group, that nitrogen may be optionally substituted by a group selected from R$^{35}$;
R$^{21}$, R$^{22}$, R$^{27}$, R$^{28}$, R$^{32}$ or R$^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein R$^{36}$ is selected from hydrogen or C$_{1-6}$alkyl, and x is 0-2;
p, q, r and s are independently selected from 0-2;
R$^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;
R$^{20}$, R$^{24}$, R$^{26}$, R$^{30}$, R$^{35}$ and R$^{38}$ are independently selected from C$_{1-6}$alkyl, C$_{1-6}$alkanoyl, C$_{1-6}$alkylsulphonyl, C$_{1-6}$alkoxycarbonyl, carbamoyl, N—(C$_{1-6}$alkyl)carbamoyl, N,N—(C$_{1-6}$alkyl)carbamoyl, benzyl, benzyloxycarbonyl, benzoyl and phenylsulphonyl; and
wherein a "heteroaryl" is a totally unsaturated, mono or bicyclic ring containing 3-12 atoms of which at least one atom is chosen from nitrogen, sulphur and oxygen, which heteroaryl may, unless otherwise specified, be carbon or nitrogen linked;
wherein a "heterocyclyl" is a saturated, partially saturated or unsaturated, mono or bicyclic ring containing 3-12 atoms of which at least one atom is chosen from nitrogen, sulphur and oxygen, which heterocyclyl may, unless otherwise specified, be carbon or nitrogen linked, wherein a —CH$_2$— group can optionally be replaced by a —C(O)— group, and a ring sulphur atom may be optionally oxidised to form an S-oxide; and
wherein a "carbocyclyl" is a saturated, partially saturated or unsaturated, mono or bicyclic carbon ring that contains 3-12 atoms; wherein a —CH$_2$— group can optionally be replaced by a —C(O) group;
or a pharmaceutically acceptable salt or in vivo hydrolysable ester or amide formed on an available carboxy or hydroxy group thereof.

In some embodiments, compound of Formula V is 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-

α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine; or 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine.

In some embodiments, compound of Formula V is

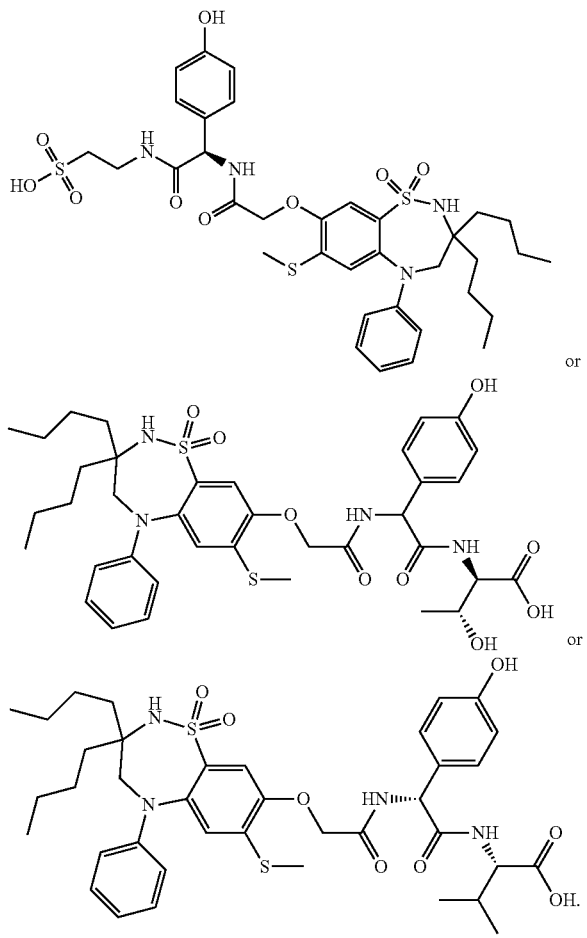

In some embodiments, an ASBTI suitable for the methods described herein is a compound of Formula VI:

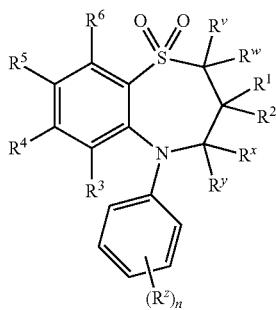

VI wherein:
R$^v$ and R$^w$ are independently selected from hydrogen or C$_{1-6}$alkyl;
one of R$^1$ and R$^2$ is selected from hydrogen or C$_{1-6}$alkyl and the other is selected from C$_{1-6}$alkyl;
R$^x$ and R$^y$ are independently selected from hydrogen or C$_{1-6}$alkyl, or one of Rx and R$^y$ is hydrogen or C$_{1-6}$alkyl and the other is hydroxy or C$_{1-6}$alkoxy;
R$^z$ is selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl;
n is 0-5;
one of R$^4$ and R$^5$ is a group of formula (VIA):

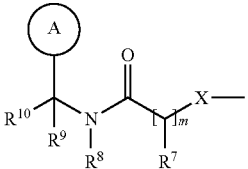

VIA

R$^3$ and R$^6$ and the other of R$^4$ and R$^5$ are independently selected from hydrogen, halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl; wherein R$^3$ and R$^6$ and the other of R$^4$ and R$^5$ may be optionally substituted on carbon by one or more R$^{17}$;
X is —O—, —N(R$^a$)—, —S(O)$_b$— or —CH(R$^a$)—; wherein R$^a$ is hydrogen or C$_{1-6}$alkyl and b is 0-2;
Ring A is aryl or heteroaryl; wherein Ring A is optionally substituted on carbon by one or more substituents selected from R$^{18}$;
R$^7$ is hydrogen, C$_{1-6}$alkyl, carbocyclyl or heterocyclyl; wherein R$^7$ is optionally substituted on carbon by one or more substituents selected from R$^{19}$; and wherein if said heterocyclyl contains an —NH— group, that nitrogen may be optionally substituted by a group selected from R$^{20}$;
R$^8$ is hydrogen or C$_{1-6}$alkyl;
R$^9$ is hydrogen or C$_{1-6}$alkyl;
R$^{10}$ is hydrogen, halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, N,N,N—(C$_{1-10}$alkyl)$_3$ammonio, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)-R$^{21}$—(C$_{1-10}$alkylene)$_q$- or heterocyclyl-(C$_{1-10}$alkylene)$_r$-R$^{22}$—(C$_{1-10}$alkylene)$_s$-; wherein R$^{10}$ is optionally substituted on carbon by one or more substituents selected from R$^{23}$; and wherein if said heterocyclyl contains an —NH— group, that nitrogen may be optionally substituted by a group selected from $R^{24}$; or $R^{10}$ is a group of formula (VIB):

$$\text{VIB}$$

wherein:
- $R^{11}$ is hydrogen or $C_{1-6}$alkyl;
- $R^{12}$ and $R^{13}$ are independently selected from hydrogen, halo, nitro, cyano, hydroxy, amino, carbamoyl, mercapto, sulphamoyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;
- $R^{14}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$ amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$ carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclylC$_{1-10}$alkyl, heterocyclyl, heterocyclylC$_{1-10}$alkyl, carbocyclyl-($C_{1-10}$ alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (VIC):

$$\text{VIC}$$

- $R^{15}$ is hydrogen or $C_{1-6}$alkyl;
- $R^{16}$ is hydrogen or $C_{1-6}$alkyl; wherein $R^{16}$ may be optionally substituted on carbon by one or more groups selected from $R^{31}$;
- n is 1-3; wherein the values of $R^7$ may be the same or different;
- $R^{17}$, $R^{18}$, $R^{19}$, $R^{23}$, $R^{25}$, $R^{29}$ or $R^{31}$ are independently selected from halo, nitro, cyano, hydroxy, amino, carbamoyl, mercapto, sulphamoyl, hydroxyaminocarbonyl, amidino, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, ($C_{1-10}$ alkyl)$_3$silyl, N—($C_{1-10}$alkyl)amino, N,N—($C_{1-10}$ alkyl)$_2$ amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclylC$_{1-10}$alkyl, heterocyclyl, heterocyclylC$_{1-10}$alkyl, carbocyclyl-($C_{1-10}$alkylene)$_p$-$R^{32}$—($C_{1-10}$alkylene)$_q$- or heterocyclyl-($C_{1-10}$alkylene)-$R^{33}$—($C_{1-10}$ alkylene)$_s$-; wherein $R^{17}$, $R^{18}$, $R^{19}$, $R^{23}$, $R^2$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;
- $R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O) NR$^{36}$—, —NR$^{36}$C(S)NR$^{36}$—, —OC(O)N=C—, —NR$^{36}$C(O)— or —C(O)NR$^{36}$—; wherein $R^{36}$ is selected from hydrogen or $C_{1-6}$alkyl, and x is 0-2;
- p, q, r and s are independently selected from 0-2;
- $R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;
- $R^{20}$, $R^{24}$, $R^{26}$, $R^{30}$ or $R^{35}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

In some embodiments, a compound of Formula VI has the structure of Formula VID:

$$\text{VID}$$

wherein:
- $R^1$ and $R^2$ are independently selected from $C_{1-6}$alkyl; one of $R^4$ and $R^5$ is a group of formula (VIE):

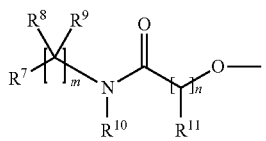

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{14}$;

$R^7$ is carboxy, sulpho, sulphino, phosphono, —P(O)(OR$^a$)(OR$^b$), P(O)(OH)(OR$_a$), —P(O)(OH)(R$^a$) or P(O)(OR$^a$)(R$^b$), wherein R$^a$ and R$^b$ are independently selected from $C_{1-6}$alkyl; or $R^7$ is a group of formula (VIF):

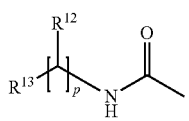

$R^8$ and $R^9$ are independently hydrogen, $C_{1-4}$alkyl or a saturated cyclic group, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; and wherein if said saturated cyclic group contains an —NH— moiety, that nitrogen may be optionally substituted by one or more $R^{20}$;

$R^{10}$ is hydrogen or $C_{1-4}$alkyl; wherein $R^{10}$ is optionally substituted on carbon by one or more substituents selected from $R^{24}$;

$R^{11}$ is hydrogen, $C^{1-4}$alkyl, carbocyclyl or heterocyclyl; wherein $R^{11}$ is optionally substituted on carbon by one or more substituents selected from $R^{16}$; and wherein if said heterocyclyl contains an —NH— moiety, that nitrogen may be optionally substituted by one or more $R^{21}$;

$R^{12}$ is hydrogen or $C_{1-4}$alkyl, carbocyclyl or heterocyclyl; wherein $R^{12}$ optionally substituted on carbon by one or more substituents selected from $R^{17}$; and wherein if said heterocyclyl contains an —NH— moiety, that nitrogen may be optionally substituted by one or more $R^{22}$;

$R^{13}$ is carboxy, sulpho, sulphino, phosphono, —P(O)(OR$^c$)(OR$^d$), —P(O)(OH)(OR$^c$), —P(O)(OH)(R$^c$) or —P(O)(OR$^c$)(R$^d$) wherein R$^c$ and R$^d$ are independently selected from $C_{1-6}$alkyl;

m is 1-3; wherein the values of $R^8$ and $R^9$ may be the same or different;

n is 1-3; wherein the values of $R^{11}$ may be the same or different;

p is 1-3; wherein the values of $R^{12}$ may be the same or different;

$R^{14}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{14}$ and $R^{16}$ may be independently optionally substituted on carbon by one or more $R^{18}$;

$R^{15}$ and $R^{17}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl, sulpho, sulphino, amidino, phosphono, —P(O)(OR$^e$)(OR$^f$), —P(O)(OH)(OR$^e$), —P(O)(OH)(R$^e$) or —P(O)(OR$^e$)(R$^f$), wherein R$^e$ and R$^f$ are independently selected from $C_{1-6}$alkyl; wherein $R^{15}$ and $R^{17}$ may be independently optionally substituted on carbon by one or more $R^{19}$; and wherein if said heterocyclyl contains an —NH— moiety, that nitrogen may be optionally substituted by one or more $R^{23}$;

$R^{18}$, $R^{19}$ and $R^{25}$ are independently selected from halo, hydroxy, cyano, carbamoyl, ureido amino nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{20}$, $R^{21}$, $R^{22}$, $R^{23}$ and $R^{26}$ are independently $C_{1-4}$alkyl, $C_{1-4}$alkanoyl, $C_{1-4}$alkylsulphonyl, sulphamoyl, N—($C_{1-4}$alkyl)sulphamoyl, N,N—($C_{1-4}$alkyl)$_2$sulphamoyl, $C_{1-4}$alkoxycarbonyl, carbamoyl, N—($C_{1-4}$alkyl)carbamoyl, N,N—($C_{1-4}$alkyl)$_2$carbamoyl, benzyl, phenethyl, benzoyl, phenylsulphonyl and phenyl;

$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

wherein any saturated cyclic group is a totally or partially saturated, mono or bicyclic ring containing 3-12 atoms of which 0-4 atoms are chosen from nitrogen, sulphur or oxygen, which may be carbon or nitrogen linked;

wherein any heterocyclyl is a saturated, partially saturated or unsaturated, mono or bicyclic ring containing 3-12 atoms of which at least one atom is chosen from nitrogen, sulphur or oxygen, which may be carbon or nitrogen linked, wherein a —CH$_2$— group can optionally be replaced by a —C(O)— or a ring sulphur atom may be optionally oxidised to form the S-oxides; and wherein any carbocyclyl is a saturated, partially saturated or unsaturated, mono or bicyclic carbon ring that contains 3-12 atoms, wherein a —CH$_2$— group can optionally be replaced by a —C(O)—;

or a pharmaceutically acceptable salt thereof.

In some embodiments, any compound described herein is covalently conjugated to a bile acid using any suitable method. In some embodiments, compounds described herein are covalently bonded to a cyclodextrin or a biodegradable polymer (e.g., a polysaccharide).

In certain embodiments compounds described herein are not systemically absorbed. Moreover, provided herein are compounds that inhibit bile salt recycling in the gastrointestinal tract of an individual. In some embodiments, compounds described herein, may not be transported from the gut lumen and/or do not interact with ASBT. In some embodiments, compounds described herein, do not affect, or minimally affect, fat digestion and/or absorption. In certain embodiments, the administration of a therapeutically effective amount of any compound described herein does not result in gastrointestinal disturbance or lactic acidosis in an individual. In certain embodiments, compounds described herein are administered orally. In some embodiments, an ASBTI is released in the distal ileum. An ASBTI compatible with the methods described herein may be a direct inhibitor, an allosteric inhibitor, or a partial inhibitor of the Apical Sodium-dependent Bile acid Transporter.

In certain embodiments, compounds that inhibit ASBT or any recuperative bile acid transporters are compounds that are described in EP1810689, U.S. Pat. Nos. 6,458,851, 7,413,536, 7,514,421, US Appl. Publication Nos. 2002/0147184, 2003/0119809, 2003/0149010, 2004/0014806, 2004/0092500, 2004/0180861, 2004/0180860, 2005/0031651, 2006/0069080, 2006/0199797, 2006/0241121, 2007/0065428, 2007/0066644, 2007/0161578, 2007/0197628, 2007/0203183, 2007/0254952, 2008/0070888, 2008/0070892, 2008/0070889, 2008/0070984, 2008/0089858, 2008/0096921, 2008/0161400, 2008/0167356, 2008/0194598, 2008/0255202, 2008/0261990, WO 2002/50027, WO2005/046797, WO2006/017257, WO2006/105913, WO2006/105912, WO2006/116499, WO2006/117076, WO2006/121861, WO2006/122186, WO2006/124713, WO2007/050628, WO2007/101531, WO2007/134862, WO2007/140934, WO2007/140894, WO2008/028590, WO2008/033431, WO2008/033464, WO2008/031501, WO2008/031500, WO2008/033465, WO2008/034534, WO2008/039829, WO2008/064788, WO2008/064789, WO2008/088836, WO2008/104306, WO2008/124505, and WO2008/130616; the compounds described therein that inhibit recuperative bile acid transport are hereby incorporated herein by reference.

In certain embodiments, compounds that inhibit ASBT or any recuperative bile acid transporters are compounds described in WO93/16055, WO94/18183, WO94/18184, WO96/05188, WO96/08484, WO96/16051, WO97/33882, WO98/38182, WO99/35135, WO98/40375, WO99/64409, WO99/64410, WO00/01687, WO00/47568, WO00/61568, DE 19825804, WO00/38725, WO00/38726, WO00/38727 (including those compounds with a 2,3,4,5-tetrahydro-1-benzothiepine 1,1-dioxide structure), WO00/38728, WO01/66533, WO02/50051, EP0864582 (e.g. (3R,5R)-3-butyl-3-ethyl-1,1-dioxido-5-Phenyl-2,3,4,5-tetrahydro-1,4-benzothiazepin-8-yl (∪-D-glucopyranosiduronic acid, WO94/24087, WO98/07749, WO98/56757, WO99/32478, WO99/35135, WO00/20392, WO00/20393, WO00/20410, WO00/20437, WO01/34570, WO00/35889, WO01/68637, WO01/68096, WO02/08211, WO03/020710, WO03/022825, WO03/022830, WO03/0222861, JP10072371, U.S. Pat. Nos. 5,910,494; 5,723,458; 5,817,652; 5,663,165; 5,998,400; 6,465,451, 5,994,391; 6,107,494; 6,387,924; 6,784,201; 6,875,877; 6,740,663; 6,852,753; 5,070,103, 6,114,322, 6,020,330, 7,179,792, EP251315, EP417725, EP489-423, EP549967, EP573848, EP624593, EP624594, EP624595, EP869121, EP1070703, WO04/005247, compounds disclosed as having IBAT activity in Drugs of the Future, 24, 425-430 (1999), Journal of Medicinal Chemistry, 48, 5837-5852, (2005) and Current Medicinal Chemistry, 13, 997-1016, (2006); the compounds described therein that inhibit recuperative bile acid transport are hereby incorporated herein by reference.

In some embodiments, compounds that inhibit ASBT or any recuperative bile acid transporter are benzothiepines, benzothiazepines (including 1,2-benzothiazepines; 1,4-benzothiazepines; 1,5-benzothiazepines; and/or 1,2,5-benzothiadiazepines). In some embodiments, compounds that inhibit ASBT or any recuperative bile acid transporter include and are not limited to S-8921 (disclosed in EP597107, WO 93/08155), 264W94 (GSK) disclosed in WO 96/05188; SC-435 (1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt), SC-635 (Searle); 2164U90 (3-butyl-3-ethyl-2,3,4,5-tetrahydro-5-phenyl-1,4-benzothiazepine 1,1-dioxide); BARI-1741 (Aventis SA), AZD 7508 (Astra Zeneca); barixibat (11-(D-gluconamido)-N-{2-[(1S,2R,3S)-3-hydroxy-3-phenyl-2-(2-pyridyl)-1-(2-pyridylamino)propyl]phenyl}undecanamide) or the like, or combinations thereof. In some embodiments, an ASBTI is:

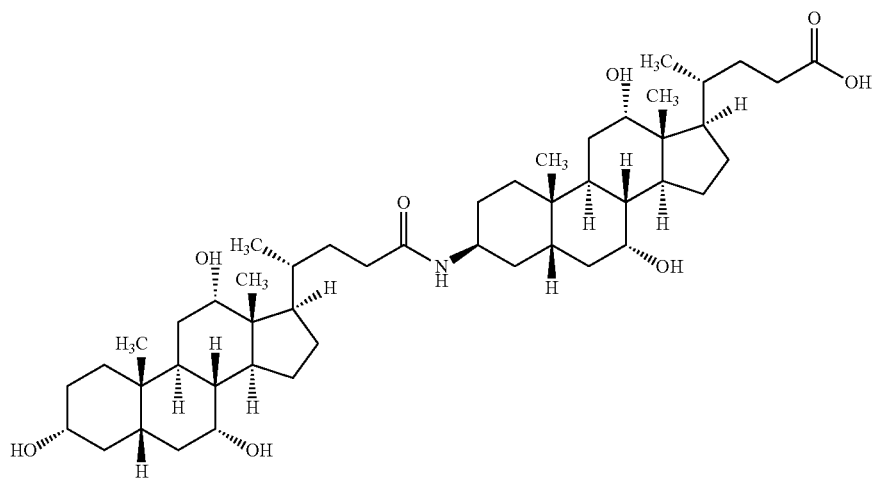

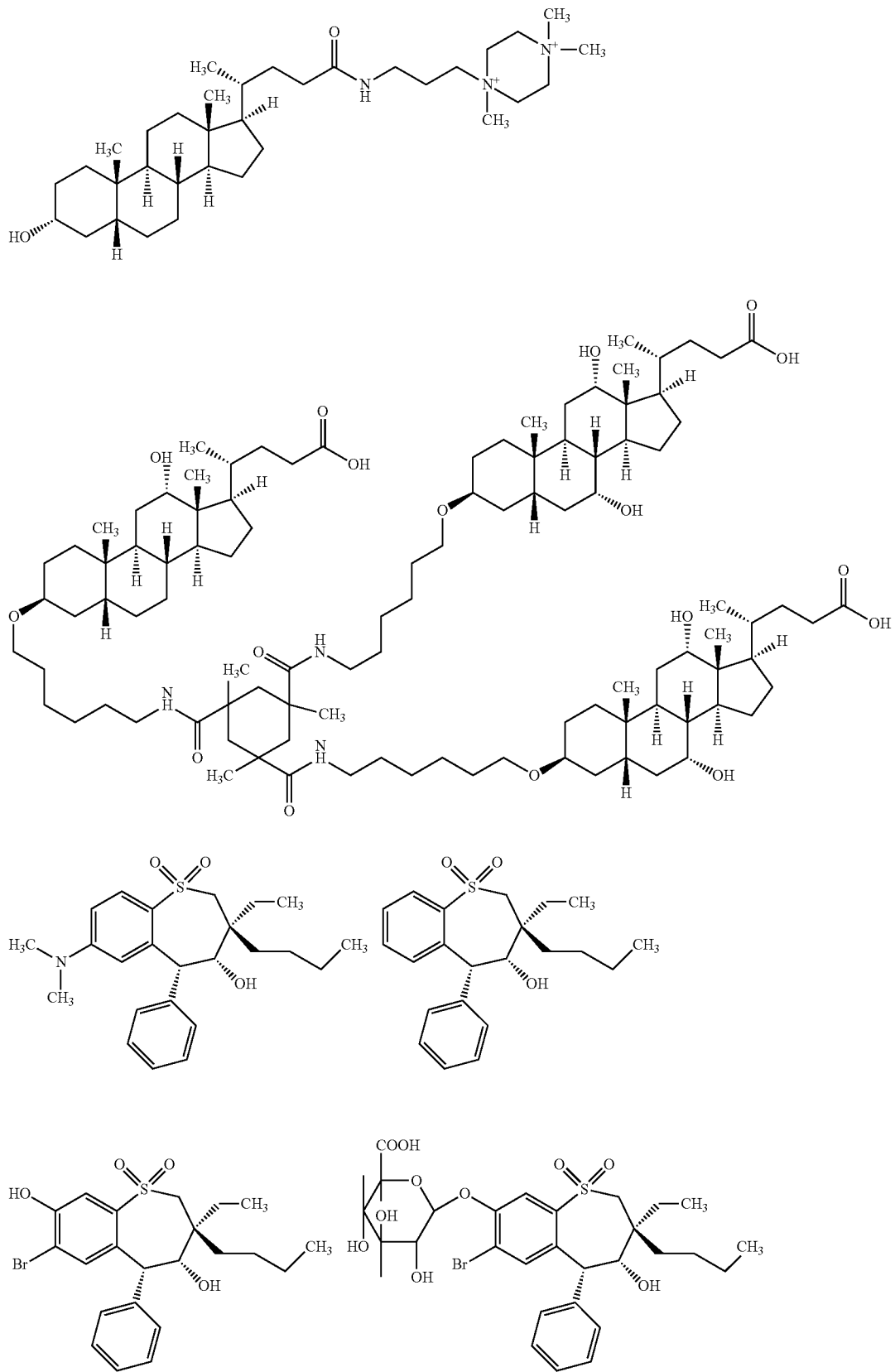

-continued

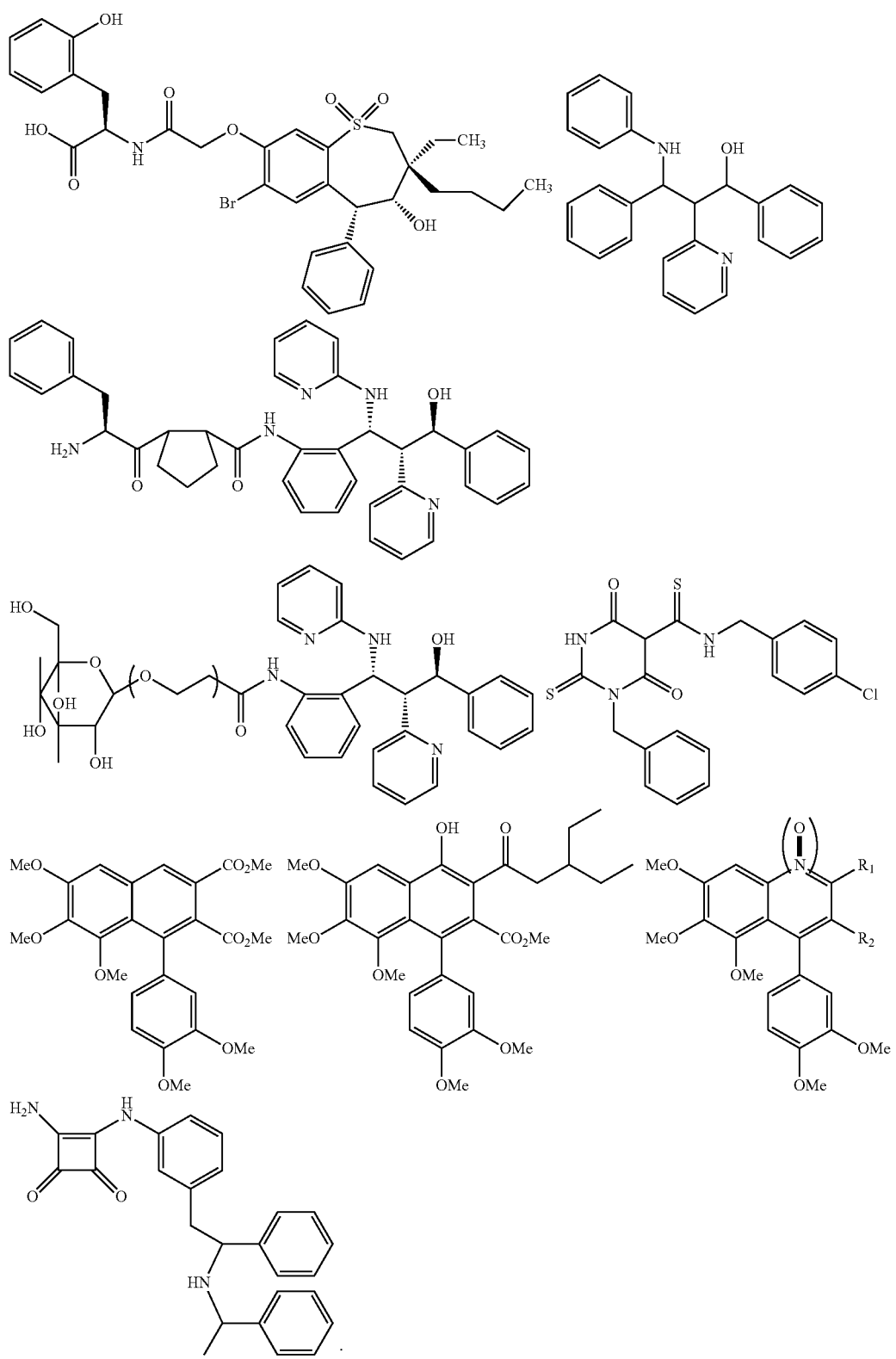

In certain embodiments, compounds described herein have one or more chiral centers. As such, all stereoisomers are envisioned herein. In various embodiments, compounds described herein are present in optically active or racemic forms. It is to be understood that the compounds of the present invention encompasses racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contains one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference for such disclosure). General methods for the preparation of compound as described herein are modified by the use of appropriate reagents and conditions, for the introduction of the various moieties found in the formulae as provided herein. As a guide the following synthetic methods are utilized.

Formation of Covalent Linkages by Reaction of an Electrophile with a Nucleophile The compounds described herein are modified using various electrophiles and/or nucleophiles to form new functional groups or substituents. Table A entitled "Examples of Covalent Linkages and Precursors Thereof" lists selected non-limiting examples of covalent linkages and precursor functional groups which yield the covalent linkages. Table A is used as guidance toward the variety of electrophiles and nucleophiles combinations available that provide covalent linkges. Precursor functional groups are shown as electrophilic groups and nucleophilic groups.

TABLE A

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |

TABLE A-continued

Examples of Covalent Linkages and Precursors Thereof

| Covalent Linkage Product | Electrophile | Nucleophile |
|---|---|---|
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments it is contemplated that each protective group be removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in then presence of acid- and base-protecting groups since the former are stable and are subsequently removed by metal or pi-acid catalysts. For example, an allyl-blocked carboxylic acid is deprotected with a Pd⁰-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups are selected from:

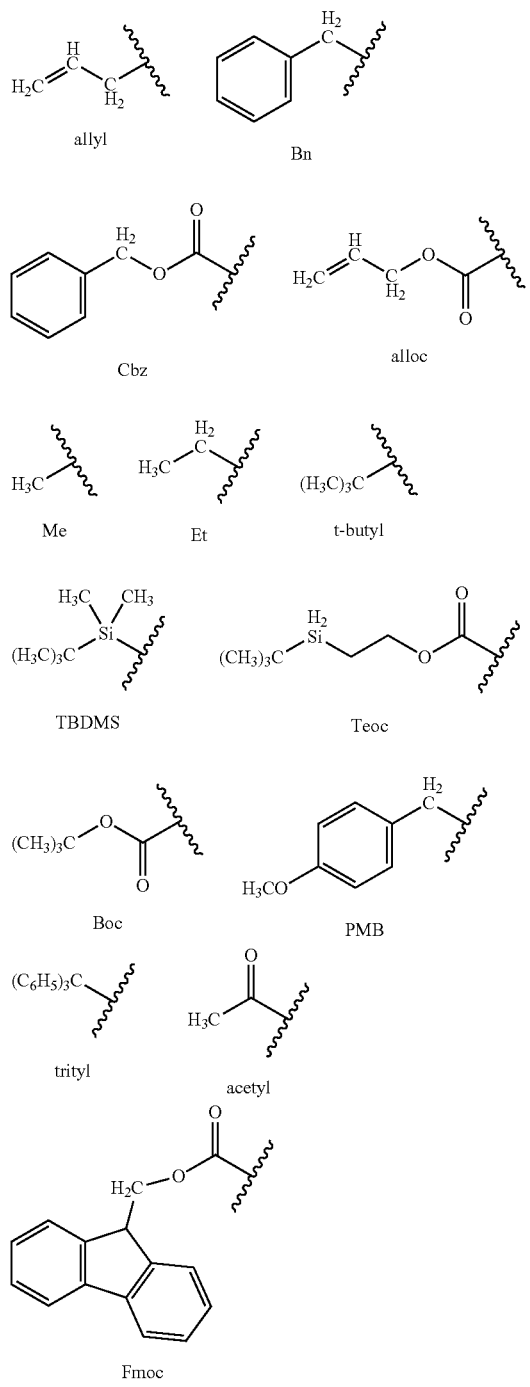

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, ASBTIs described herein are synthesized as described in, for example, WO 96/05188, U.S. Pat. Nos. 5,994,391; 7,238,684; 6,906,058; 6,020,330; and 6,114,322. In some embodiments, ASBTIs described herein are synthesized starting from compounds that are available from commercial sources or that are prepared using procedures outlined herein. In some embodiments, compounds described herein are prepared according to the process set forth in Scheme 1:

Scheme 1:

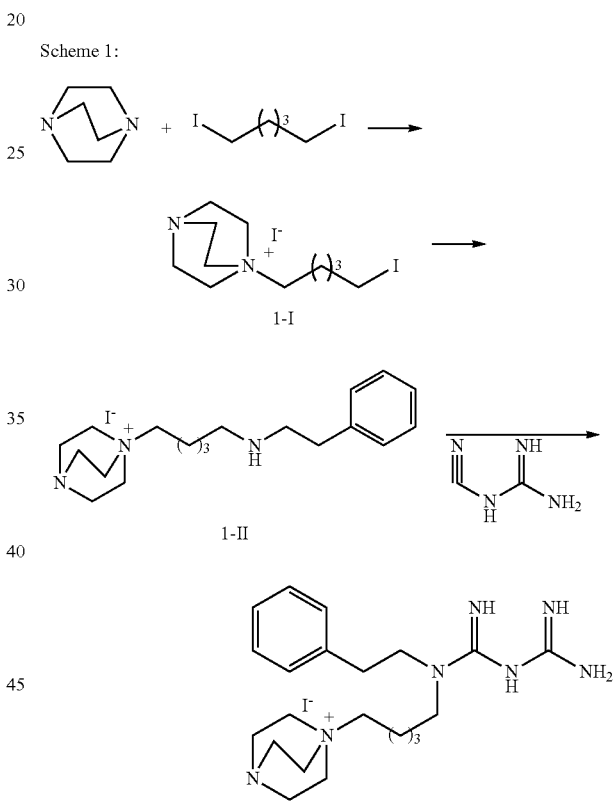

In certain embodiments, the synthesis begins with a reaction of 1,4-diazabicyclo[2.2.2]octane with 4-iodo-1-chloro butane to provide a compound of structure 1-I. Such compounds are prepared in any suitable manner, e.g., as set forth in Tremont, S. J. et. al., *J. Med. Chem.* 2005, 48, 5837-5852. The compound of structure 1-I is then subjected to a reaction with phenethylamine to provide a compound of structure 1-II. The compound of structure 1-II is then allowed to react with dicyanodiamide to provide a compound of Formula I.

In some embodiments, a first compound of Formula III is subjected to a further reaction to provide a second compound of Formula III as shown in Scheme 2 below.

Scheme 2:

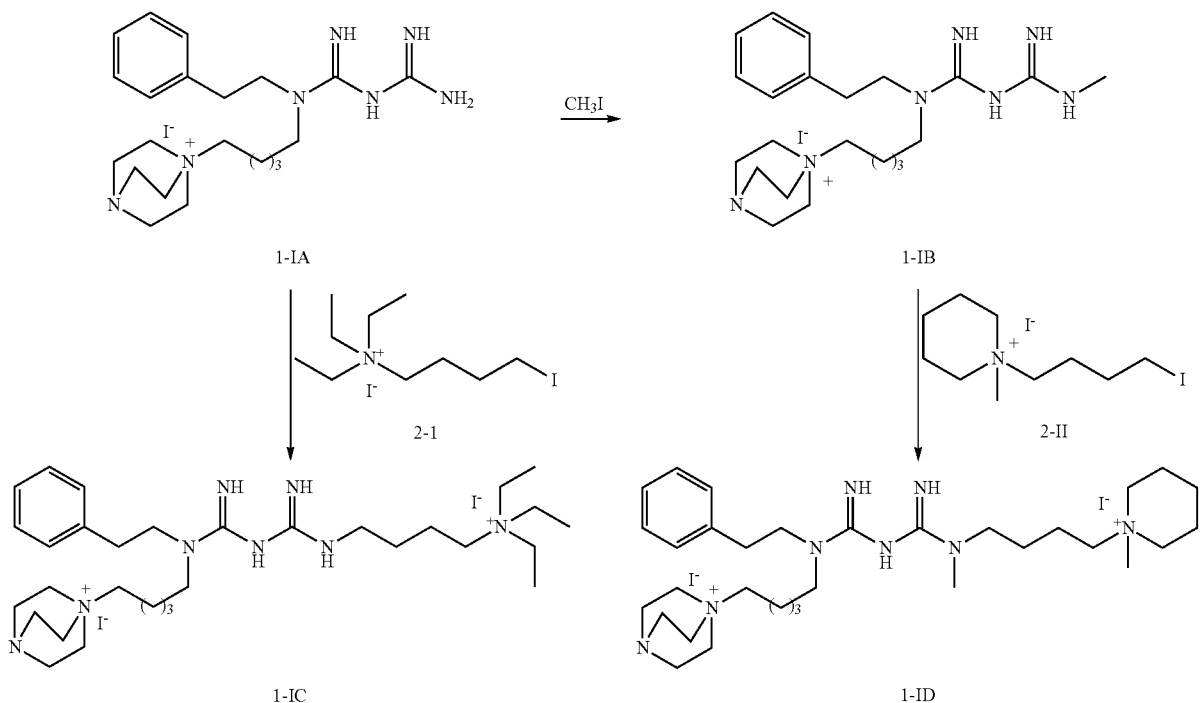

A first compound of Formula III, 1-IA, is alkylated with iodomethane to provide a second compound of Formula III, 1-IB. Alkylation of 1-IB with a compound of structure 2-II provides a further compound of Formula III, IC. In an alternative embodiment, a first compound of Formula III, 1-IA, is alkylated with a compound of structure 2-I to provide a second compound of Formula III, 1-IC.

General Definitions

The term "bile acid," as used herein, includes steroid acids (and/or the carboxylate anion thereof), and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocolate, and the like. Taurocholic acid and/or taurocholate are referred to herein as TCA. Any reference to a bile acid used herein includes reference to a bile acid, one and only one bile acid, one or more bile acids, or to at least one bile acid. Therefore, the terms "bile acid," "bile salt," "bile acid/salt," "bile acids," "bile salts," and "bile acids/salts" are, unless otherwise indicated, utilized interchangeably herein. Any reference to a bile acid used herein includes reference to a bile acid or a salt thereof. Furthermore, pharmaceutically acceptable bile acid esters are optionally utilized as the "bile acids" described herein, e.g., bile acids conjugated to an amino acid (e.g., glycine or taurine). Other bile acid esters include, e.g., substituted or unsubstituted alkyl ester, substituted or unsubstituted heteroalkyl esters, substituted or unsubstituted aryl esters, substituted or unsubstituted heteroaryl esters, or the like. For example, the term "bile acid" includes cholic acid conjugated with either glycine or taurine: glycocholate and taurocholate, respectively (and salts thereof). Any reference to a bile acid used herein includes reference to an identical compound naturally or synthetically prepared. Furthermore, it is to be understood that any singular reference to a component (bile acid or otherwise) used herein includes reference to one and only one, one or more, or at least one of such components. Similarly, any plural reference to a component used herein includes reference to one and only one, one or more, or at least one of such components, unless otherwise noted. Moreover, as used herein, bile acid/salt mimics or mimetics described herein are compounds that mimic the agonist signaling properties of the bile acid/salt, especially at TGR5 (GPBAR1, BG37, Axor109) receptors. Examples includes those described in WO 2010/014836, which is incorporated herein for such disclosure. In some embodiments, bile acid mimetics include triterpenoid, such as oleanoic acid, ursolic acid, or the like.

The term "subject", "patient" or "individual" are used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The term "colon," as used herein, includes the cecum, ascending colon, hepatic flexure, splenic flexure, descending colon, and sigmoid.

The term "composition," as used herein includes the disclosure of both a composition and a composition administered in a method as described herein. Furthermore, in some embodiments, the composition of the present invention is or comprises a "formulation," an oral dosage form or a rectal dosage form as described herein.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

Where combination treatments or prevention methods are contemplated, it is not intended that the agents described herein be limited by the particular nature of the combination. For example, the agents described herein are optionally administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent. Furthermore, combination treatments are optionally administered separately or concomitantly.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to a patient simultaneously in the form of a single entity or dosage. The term "non-fixed combination" means that at least one of the agents described herein, and at least one co-agent, are administered to a patient as separate entities either simultaneously, concurrently or sequentially with variable intervening time limits, wherein such administration provides effective levels of the two or more agents in the body of the patient. In some instances, the co-agent is administered once or for a period of time, after which the agent is administered once or over a period of time. In other instances, the co-agent is administered for a period of time, after which, a therapy involving the administration of both the co-agent and the agent are administered. In still other embodiments, the agent is administered once or over a period of time, after which, the co-agent is administered once or over a period of time. These also apply to cocktail therapies, e.g. the administration of three or more active ingredients.

As used herein, the terms "co-administration", "administered in combination with" and their grammatical equivalents are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical Sciences (current edition), Mack Publishing Co., Easton, Pa. In certain embodiments, the agents and compositions described herein are administered orally.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "carrier" as used herein, refers to relatively nontoxic chemical agents that, in certain instances, facilitate the incorporation of an agent into cells or tissues.

The term "non-systemic" or "minimally absorbed" as used herein refers to low systemic bioavailability and/or absorption of an administered compound. In some instances a non-systemic compound is a compound that is substantially not absorbed systemically. In some embodiments, ASBTI compositions described herein deliver the ASBTI to the distal ileum, colon, and/or rectum and not systemically (e.g., a substantial portion of the ASBTI is not systemically absorbed. In some embodiments, the systemic absorption of a non-systemic compound is <0.1%, <0.3%, <0.5%, <0.6%, <0.7%, <0.8%, <0.9%, <1%, <1.5%, <2%, <3%, or <5% of the administered dose (wt. % or mol %). In some embodiments, the systemic absorption of a non-systemic compound is <15% of the administered dose. In some embodiments, the systemic absorption of a non-systemic compound is <25% of the administered dose. In an alternative approach, a non-systemic ASBTI is a compound that has lower systemic bioavailability relative to the systemic bioavailability of a systemic ASBTI (e.g., compound 100A, 100C). In some embodiments, the bioavailability of a non-systemic ASBTI described herein is <30%, <40%, <50%, <60%, or <70% of the bioavailability of a systemic ASBTI (e.g., compound 100A, 100C).

In another alternative approach, the compositions described herein are formulated to deliver <10% of the administered dose of the ASBTI systemically. In some embodiments, the compositions described herein are formulated to deliver <20% of the administered dose of the ASBTI systemically. In some embodiments, the compositions described herein are formulated to deliver <30% of the administered dose of the ASBTI systemically. In some embodiments, the compositions described herein are formulated to deliver <40% of the administered dose of the ASBTI systemically. In some embodiments, the compositions described herein are formulated to deliver <50% of the administered dose of the ASBTI systemically. In some embodiments, the compositions described herein are formulated to deliver <60% of the administered dose of the ASBTI systemically. In some embodiments, the compositions described herein are formulated to deliver <70% of the administered dose of the ASBTI systemically. In some embodiments, systemic absorption is determined in any suitable manner, including the total circulating amount, the amount cleared after administration, or the like.

The term "ASBT inhibitor" refers to a compound that inhibits apical sodium-dependent bile transport or any recuperative bile salt transport. The term Apical Sodium-dependent Bile Transporter (ASBT) is used interchangeably with the term Ileal Bile Acid Transporter (IBAT).

The term "reducing food intake" refers to consumption of a lower amount of food by an individual undergoing therapy with any ASBTI described herein compared to the amount of food consumed in the absence of ASBTI therapy.

The term "induction of satiety" or "inducing satiety" or "satiety" refers to a feeling of fullness and/or a reduction of the sensation of hunger.

The term "metabolic disorder" refers to any disorder that involves an alteration in the normal metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, GLP-2, oxyntomodulin, PYY or the like), the neural control system (e.g., GLP-1 in the brain) or the like. Examples of metabolic disorders include and are not limited to diabetes, insulin resistance, dyslipidemia, metabolic syndrome, or the like.

The term "enhancing enteroendocrine peptide secretion" refers to a sufficient increase in the level of the enteroendocrine peptide agent to, for example, decrease hunger in a subject, to curb appetite in a subject and/or decrease the food intake of a subject or individual and/or treat any disease or disorder described herein. In some embodiments, enhanced enteroendocrine peptide secretion reverses or alleviates symptoms of congestive heart failure, ventricular dysfunction, toxic hypervolemia, polycystic ovary syndrome, inflammatory bowel disease, impaired bowel integrity, short bowel syndrome, gastritis, peptic ulcer, or irritable bowel syndrome.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p-toluenenesulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halo, alkoyl, alkoyloxo, isocyanato, thiocyanato, isothiocyanato, nitro, haloalkyl, haloalkoxy, fluoroalkyl, amino, alkyl-amino, dialkyl-amino, amido.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NHR or —NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

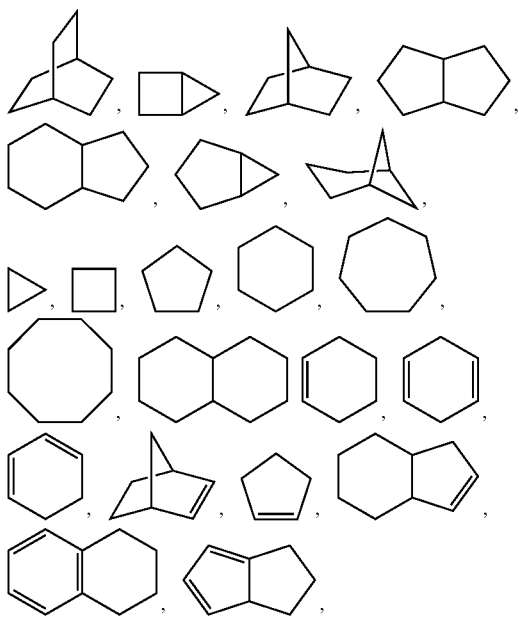

and the like. Monocyclic cycloalkyls include, but are not limited to, cyclopropyl, cyclobutyl, cyclopentyl, cyclohexyl, cycloheptyl, and cyclooctyl.

The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Illustrative examples of heteroaryl groups include the following moieties:

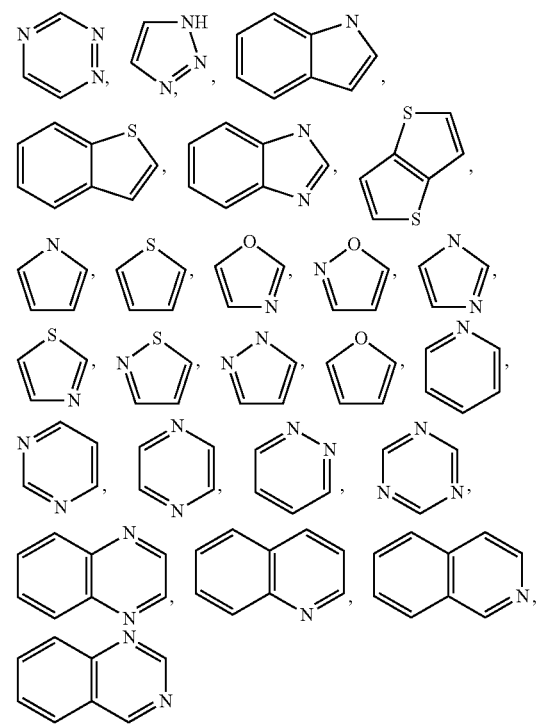

and the like.

A "heteroalicyclic" group or "heterocyclo" group refers to a cycloalkyl group, wherein at least one skeletal ring atom is a heteroatom selected from nitrogen, oxygen and sulfur. In various embodiments, the radicals are with an aryl or heteroaryl. Illustrative examples of heterocyclo groups, also referred to as non-aromatic heterocycles, include:

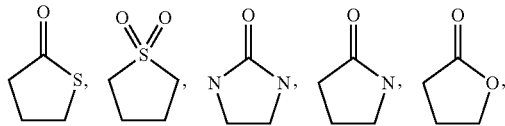

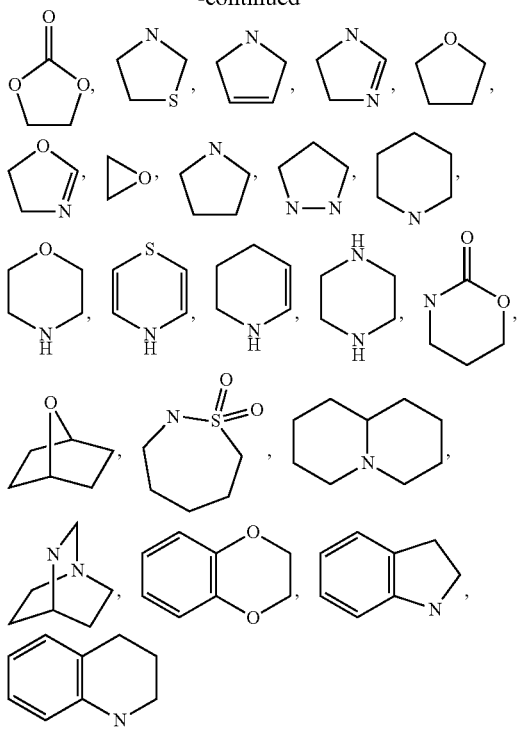

and the like. The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In some embodiments, up to two heteroatoms are consecutive, such as, by way of example, —$CH_2$—NH—$OCH_3$ and —$CH_2$—O—Si($CH_3$)$_3$.

A "cyano" group refers to a —CN group.

An "isocyanato" group refers to a —NCO group.

A "thiocyanato" group refers to a —CNS group.

An "isothiocyanato" group refers to a —NCS group.

"Alkoyloxy" refers to a RC(=O)O— group.

"Alkoyl" refers to a RC(=O)— group.

The term "modulate," as used herein refers to having some affect on (e.g., increasing, enhancing or maintaining a certain level).

The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art and may be found in references such as Greene and Wuts, above. In some embodiments, alkyl groups described herein are optionally substituted with an O that is connected to two adjacent carbon atoms (i.e., forming an epoxide).

The term "therapeutically effective amount" or an "effective amount" as used herein, refers to a sufficient amount of a therapeutically active agent to provide a desired effect in a subject or individual. In some embodiments, a "therapeutically effective amount" or an "effective amount" of an enteroendocrine peptide secretion enhancing agent refers to a sufficient amount of the enteroendocrine peptide secretion enhancing agent to a treat a metabolic disorder in a subject or individual. In some embodiments, a "therapeutically effective amount" or an "effective amount" of an enteroendocrine peptide secretion enhancing agent refers to a sufficient amount of the enteroendocrine peptide secretion enhancing agent to increase the secretion of enteroendocrine peptide(s) in a subject or individual. In specific embodiments, the "therapeutically effective amount" is an amount that when delivered to the colon or rectum it produces an anorectal response (e.g., it increase the secretion of enteroendocrine peptide(s) in the rectum and/or colon, particularly in the L-cells, of an individual). In some embodiments, a "therapeutically effective amount" or an "effective amount" of an enteroendocrine peptide secretion enhancing agent refers to a sufficient amount of the enteroendocrine peptide secretion enhancing agent to decrease hunger in a subject, to curb appetite in a subject and/or decrease the food intake of a subject or individual.

L-Cells

L-cells are scattered throughout the epithelial layer of the gut from the duodenum to the rectum, with the highest numbers occurring in the ileum, colon, and rectum. They are characterized by an open-cell morphology, with apical microvilli facing into the gut lumen and secretory vesicles located adjacent to the basolateral membrane, and are therefore in direct contact with nutrients in the intestinal lumen. Furthermore, L-cells are located in close proximity to both neurons and the microvasculature of the intestine, thereby allowing the L-cell to be affected by both neural and hormonal signals. As well as Glucagon-Like Peptide 1 (GLP-1) and Glucagon-Like Peptide 2 (GLP-2), L-cells also secrete the anorexigenic hormone, peptide YY (PYY), and glutamate. The cells are just one member of a much larger family of enteroendocrine cells that secrete a range of hormones, including ghrelin, GIP, cholecystokinin, somatostatin, and secretin, which are involved in the local coordination of gut physiology, as well as in playing wider roles in the control of insulin release and appetite. L-cells are unevenly distributed in the gastrointestinal tract, within higher concentrations in the distal portion of the gastrointestinal tract (e.g., in the distal ileum, colon and rectum).

Proglucagon Products

The proglucagon gene product is expressed in the L-cells of the small intestine, in -cells of the pancreas and in the central nervous system. Tissue-specific expression of isoforms of the enzyme prohormone convertase directs post-translational synthesis of specific proglucagon-derived peptides in the L-cell and α-cell. Specifically, cleavage of proglucagon by prohormone convertase ⅓, which is expressed in the L-cell, forms GLP-1 and GLP-2, as well as the glucagon-containing peptides, glicentin and oxyntomodulin. In contrast, α-cell expression of prohormone convertase 2 forms glucagon, glicentin-related pancreatic peptide, and the major proglucagon fragment, which contains within its sequence both the GLP-1 and GLP-2 sequences.

Glucagon-like peptide 1 (GLP-1) is an intestinal hormone that effects in the regulation of glycemia, stimulating glucose-dependent insulin secretion, proinsulin gene expression, and 1-cell proliferative and anti-apoptotic pathways, as well as inhibiting glucagon release, gastric emptying, and food intake. The anorexigenic effect of GLP-1 is mediated by GLP-1 receptors which are present in both the NTS and hypothalamus, and in the pancreas, lung, brain, kidney, gastrointestinal tract and heart. Reduced secretion of GLP-1 contributes to the pathogenesis of obesity and enhanced/or normal secretion restores satiety.

The primary physiological stimulus of GLP-1 secretion from L-cells is ingestion of carbohydrates, luminal glucose (not systemic glucose) fat, and protein. Protein hydrolysate are also potent triggers of GLP-1 release, and certain amino acids such as, but not limited to, alanine, serine, glutamine, asparagine, and glycine stimulate GLP-1 release. Within the fat group, the long-chain unsaturated fatty acid and short-chain fatty acid subgroups are potent triggers of GLP-1 release, while the short-chain fatty acids also stimulate peptide YY release. In addition to luminal nutrients, intestinal peptides, neurotransmitters, as well as systemic hormones, modulate GLP-1 secretion. Such intestinal peptides include, but are not limited to, somatostatin (forms SS14 and SS28), and such neurotransmitters include, but are not limited to, acetylcholine and -aminobutyric acid (GABA) (both of which enhance GLP-1 release), and □-adrenergic agonists, (which respectively inhibit and/or stimulate GLP-1 secretion from L-cells). Peripheral hormones that participate in energy homeostasis, such as the adipocyte hormone leptin, also stimulate GLP-1 release. Other GLP-1 secretegoues include bile acids/salts, insulin, gastrin-releasing peptide (GRP), several gut peptides including, but not limited to, Gastric Inhibitory Polypeptide (GIP) and calcitonin gene-related protein (CGRP). CGRP is a peptide found throughout the enteric nervous system. Thus, GLP-1 secretagogues include, but are not limited to, nutrients, neurotransmitters, neuropeptides, intestinal peptide, peripheral hormones, and bile acis/salts.

Within about 15 minutes of food ingestion the circulating GLP-1 levels increase and remain elevated for up to 3 hours, depending on the composition of the meal. Circulating GLP-1 exists in two equipotent forms, GLP-1$^{7-36NH2}$ and GLP-1$^{7-37}$, with GLP-1$^{7-36NH2}$ being the predominant form. Secreted GLP-1 is rapidly degraded by the ubiquitous enzyme dipeptidyl peptidase-4 (DPP-4), resulting in an extremely short half-life for GLP-1 of about 30 seconds to about 2 minutes. Therefore, levels of circulating GLP-1 are maintained by inhibiting DPP-4 activity, or alternatively, by enhancing GLP-1 secretion.

Figure 19:
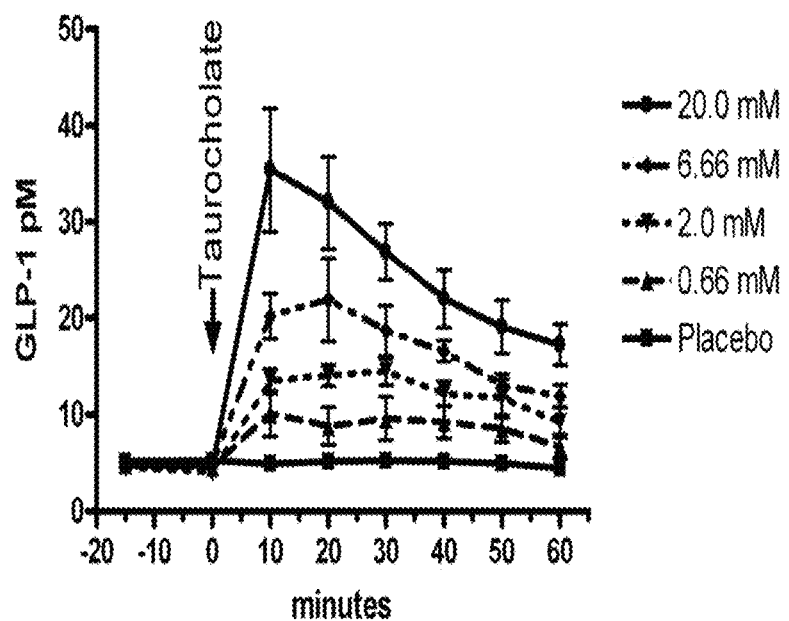
FIG. 19 illustrates the acute release of GLP-1 in response to rectal administration of bile acids in obese diabetic humans treated with a DPP4 inhibitor.

In some embodiments, provided herein is a method of increasing circulating GLP (e.g., GLP-1) levels by administering to the distal gastrointestinal tract (e.g., distal ileum, colon and/or rectum) an effective amount of an enteroendocrine peptide secretion enhancing agent (e.g., a bile acid). In certain embodiments, the method is included in a method of treating a metabolic disorder. In some embodiments, the method is included in a method of treating obesity or diabetes. FIG. 19 illustrates the increase of circulating GLP-1 levels following rectal administration of an enteroendocrine peptide secretion enhancing agent (e.g., a bile acid). FIG. 19 illustrates the increase of circulating GLP-1 levels following rectal administration of taurocholic acid.

Pancreatic Polypeptide (PP)-Fold Peptides

The Pancreatic Polypeptide (PP)-fold peptides include Peptide YY (PYY), Pancreatic Polypeptide (PP) and Neuropeptide Y (NPY), which all share sequence homology and contain several tyrosine residues. They have a common tertiary structure which consists of an -helix and polyproline helix, connected by a β-turn, resulting in a characteristic U-shaped peptide, the PP-fold.

Neuropeptide Y (NPY) is one of the most abundant neurotransmitters in the brain. Hypothalamic levels of NPY reflect the body's nutritional status, wherein the levels of hypothalamic NPY mRNA and NPY release increase with fasting and decrease after feeding.

Pancreatic Polypeptide (PP) is produced by cells at the periphery of the islets of the endocrine pancreas, and to a lesser extent in the exocrine pancreas, colon and rectum. The release of PP is biphasic and occurs in proportion to the number of calories ingested, with the levels remaining elevated for up to 6 hours post-prandially. The circulating levels of PP are increased by gastric distension, ghrelin, motilin and secretin and reduced by somatostatin. In addition, circulating PP exhibits a diurnal rhythm, with levels low in the early hours of the morning and highest in the evening. The levels of PP have been found to reflect long-term energy stores, with lower levels and reduced second phase of release in obese subjects, and higher levels in anorexic subjects. Circulating PP is unable to cross the blood-brain barrier, but exerts its anorectic effect by sending anorectic signals via brainstem pathways, hypothalamic neuropeptides and by modulating expression of other gut hormones such as ghrelin.

Figure 18:
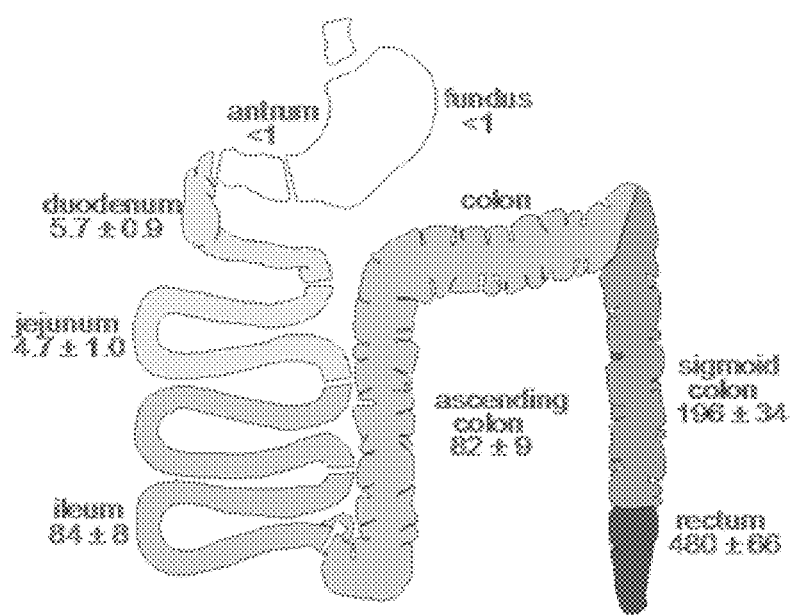
FIG. 18 illustrates the normal GI distribution of PYY (pmol/g).

Peptide YY (PYY) is secreted predominantly from the distal gastrointestinal tract, particularly the ileum, colon and rectum. FIG. 18 illustrates the concentration of PYY at various locations in the gastrointestinal tract. The L-cells of the intestine release PYY in proportion to the amount of calories ingested, and occurs before the nutrients reach the cells in the distal tract. Thus, release may be mediated via a neural reflex as well as direct contact with nutrients. Post-prandially, the circulating PYY levels rise rapidly to a plateau after 1-2 hours and remain elevated for up to 6 hours. The levels of PYY are also influenced by meal composition, with higher levels obtained following fat intake relative to carbohydrate or protein intake. Other signals, such as gastric acid, CCK and luminal bile salts, insulin-like growth factor 1, bombesin and calcitonin-gene-related peptide increase PYY levels, whereas gastric distension has no effect, and levels are reduced by GLP-1. The N-terminal of circulating PYY allows it to cross the blood-brain barrier.

Figure 20:
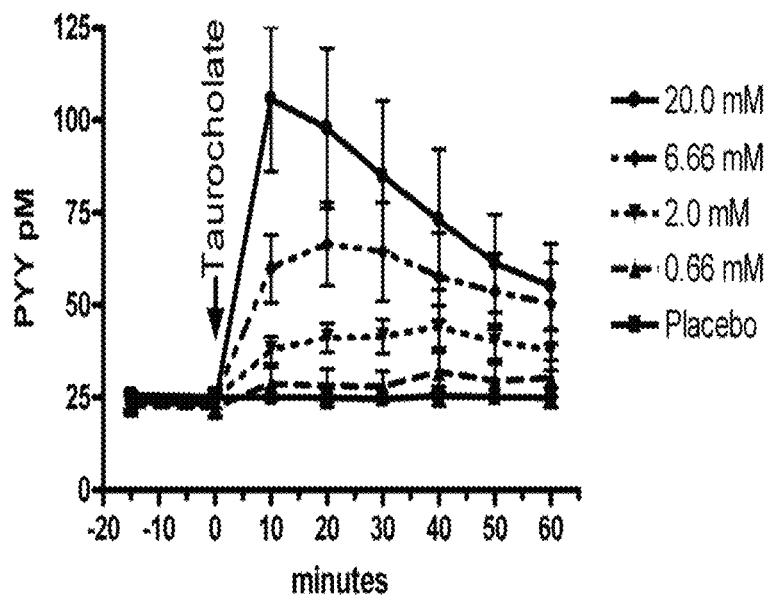
FIG. 20 illustrates the acute release of PYY in response to rectal administration of bile acids in obese diabetic humans treated with a DPP4 inhibitor.
Figure 21:
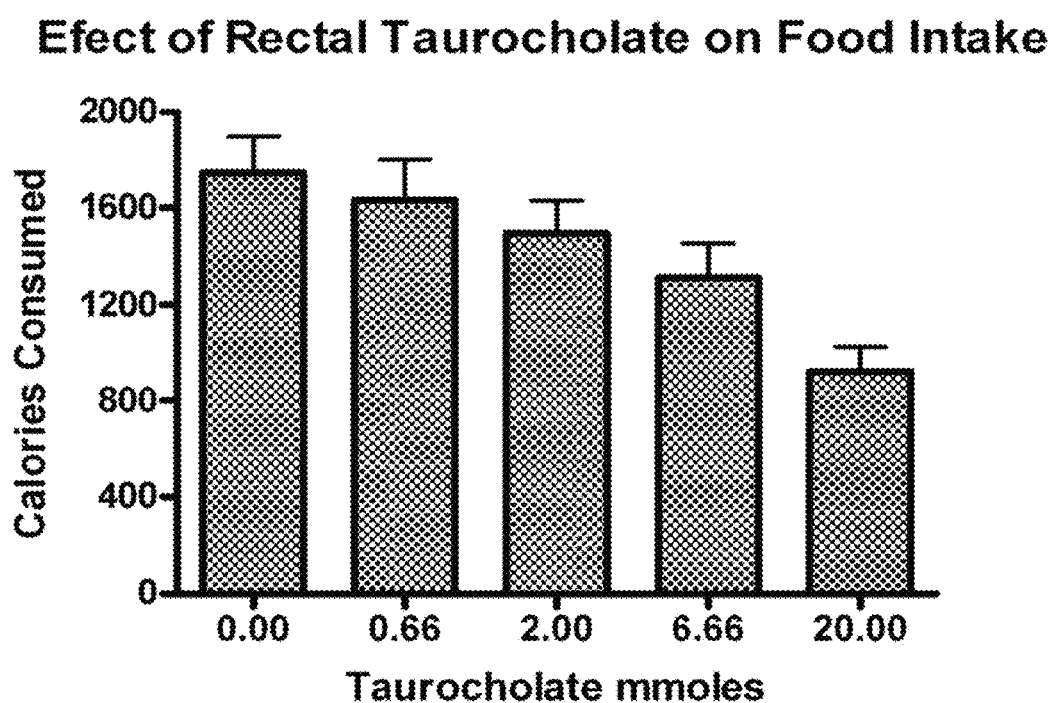
FIG. 21 illustrates the reduction of spontaneous food intake in response to rectal administration of bile acids in obese diabetic humans treated with a DPP4 inhibitor.
Figure 22:
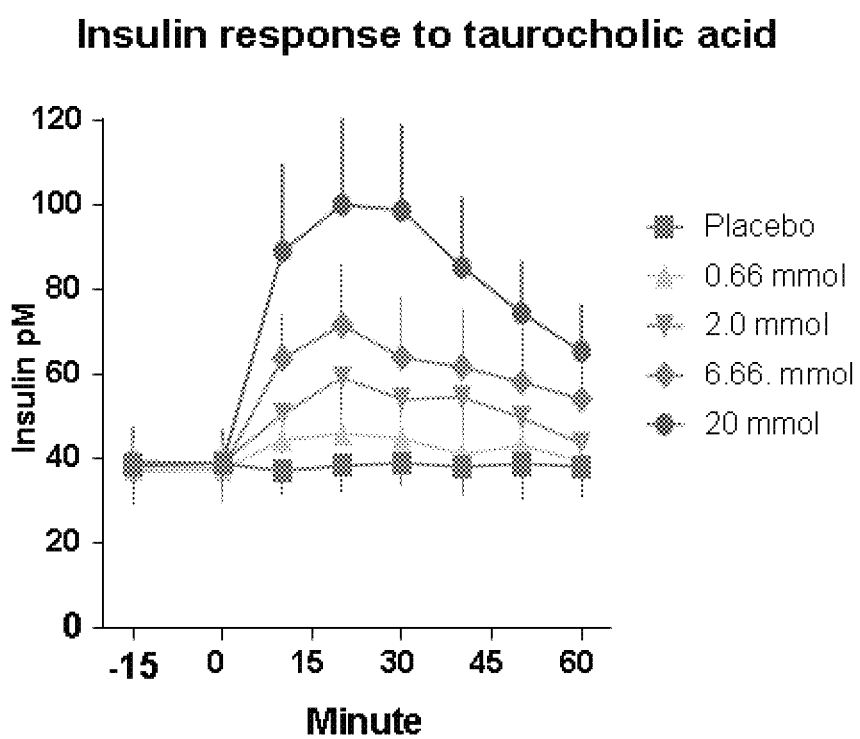
FIG. 22 illustrates the acute release of insulin and in response to rectal administration of bile acids in obese diabetic humans treated with a DPP4 inhibitor.
Figure 23:
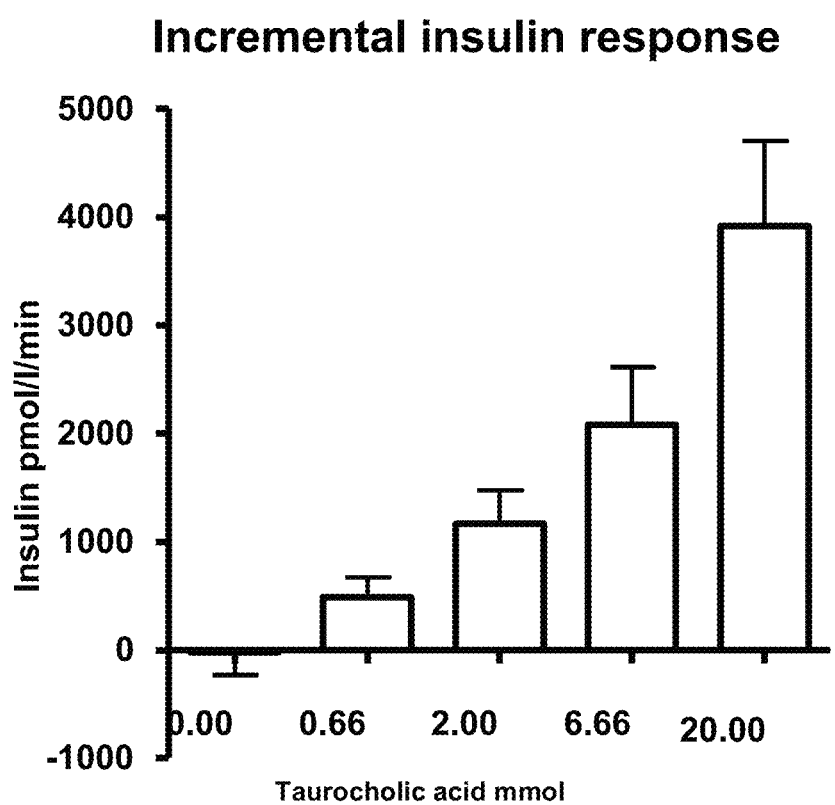
FIG. 23 illustrates the incremental integrated response of insulin to rectal administration of bile acids in obese diabetic humans treated with a DPP4 inhibitor.
Figure 24:
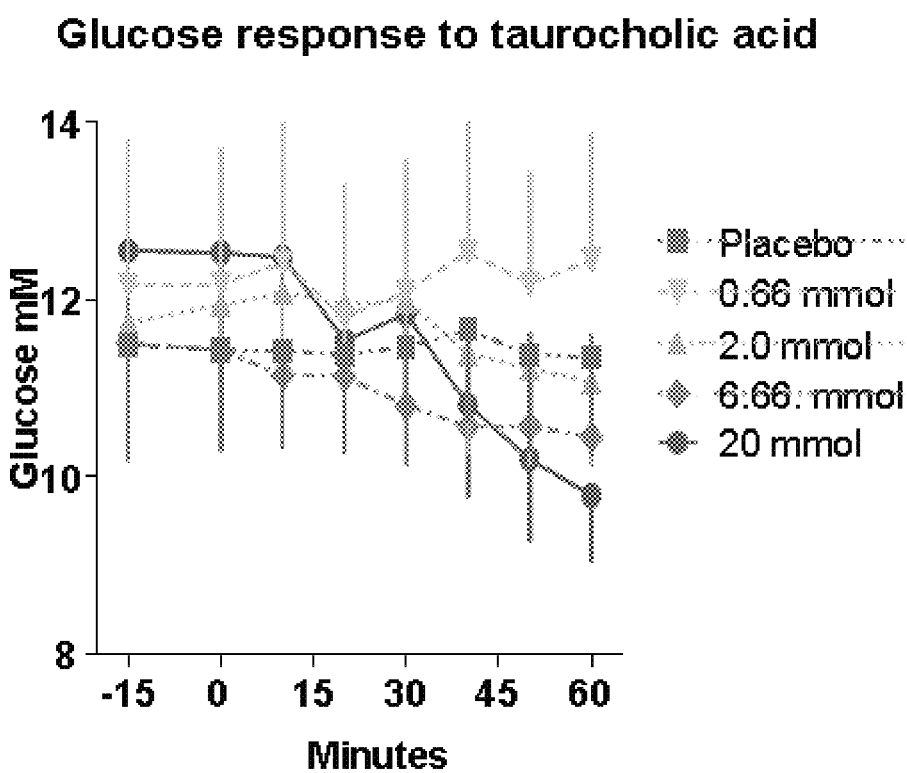
FIG. 24 illustrates the acute reduction of plasma glucose concentration in response to rectal administration of bile acids in obese diabetic humans treated with a DPP4 inhibitor.
Figure 25:
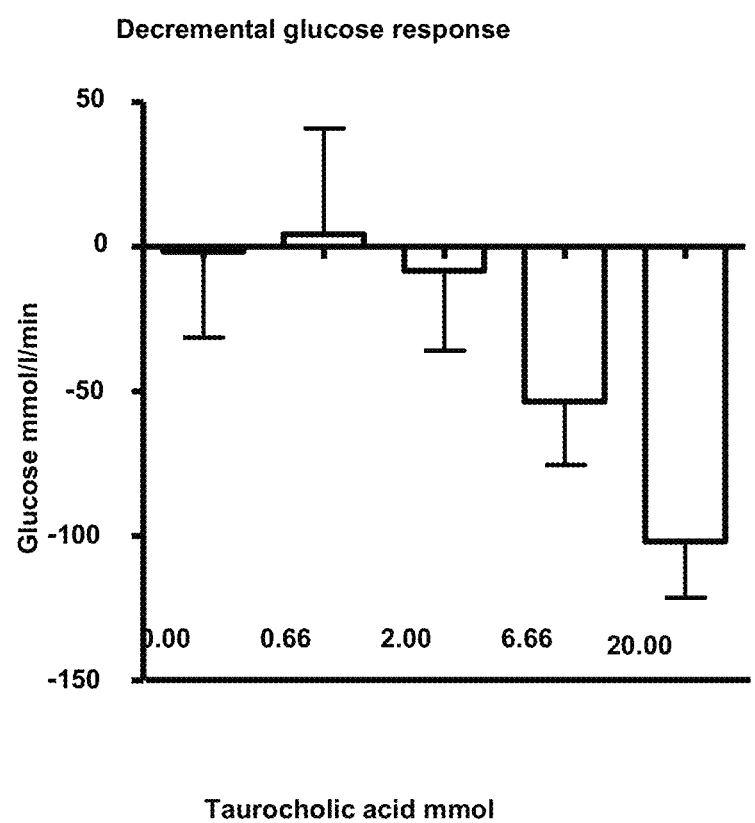
FIG. 25 illustrates the incremental integrated response of plasma glucose concentration to rectally administered bile acids in obese diabetic humans treated with a DPP4 inhibitor.
Figure 26:
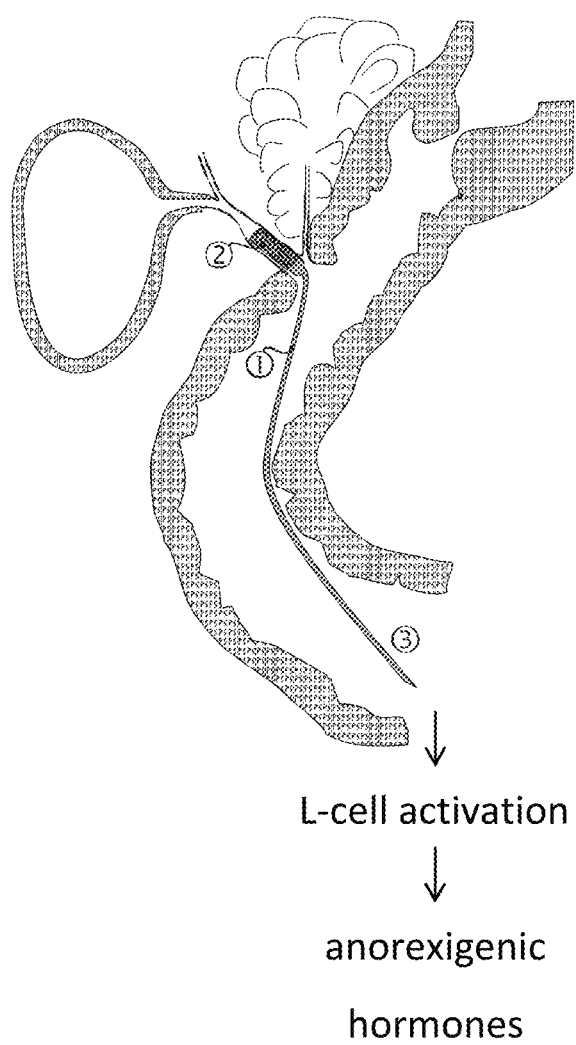
FIG. 26 illustrates delivery of bile acid salts to the lower gut via a biliary shunt.

In some embodiments, provided herein is a method of increasing circulating PYY levels by administering to the distal gastrointestinal tract (e.g., distal ileum, colon and/or rectum) an effective amount of an enteroendocrine peptide secretion enhancing agent (e.g., a bile acid). In certain embodiments, the method is included in a method of treating a metabolic disorder. In some embodiments, the method is included in a method of treating obesity or diabetes. FIG. 20 illustrates the increase of circulating PYY levels following rectal administration of an enteroendocrine peptide secretion enhancing agent (e.g., a bile acid).

Enteroendocrine Peptide Secretion Enhanced Treatment

Intravenous administration of GLP-1 decreases food intake in both lean and obese individuals in a dose-dependent manner, although the effect is small when infusions achieve post-prandial circulating levels. In addition, obese subjects given subcutaneous GLP-1 prior to each meal, reduce their caloric intake. Thus, modulation/control of GLP-1 secretion restore satiety and controls appetite and food intake. Similarly, infusion of PP decreases appetite and food intake. Obese humans have a relatively low level of circulating PYY and a relative deficiency of post-prandial secretion of PYY. Administration of PYY causes a delay in gastric emptying, a delay in secretions from the pancreas and stomach, and increases the absorption of fluids and electrolytes from the ileum after a meal. In addition, intravenous administration of PYY decreases appetite, inhibits food intake and reduces weight gain.

Appetite, weight gain and food intake are controlled by the circulating or systemic levels of GLP-1, PYY and PP. The methods and composition described herein use, by way of non-limiting example, the administration of bile acids/salts and bile acids/salts mimics to modulate (e.g., increase) the circulating levels of GLP-1, PYY and PP. In certain embodiments of the present invention, such administration decreases food intake and weight gain while suppressing appetite.

Bile Acid

Bile contains water, electrolytes and a numerous organic molecules including bile acids, cholesterol, phospholipids and bilirubin. Bile is secreted from the liver and stored in the gall bladder, and upon gall bladder contraction, due to ingestion of a fatty meal, bile passes through the bile duct into the intestine. Bile acids are critical for digestion and absorption of fats and fat-soluble vitamins in the small intestine. Adult humans produce 400 to 800 mL of bile daily. The secretion of bile can be considered to occur in two stages. Initially, hepatocytes secrete bile into canaliculi, from which it flows into bile ducts and this hepatic bile contains large quantities of bile acids, cholesterol and other organic molecules. Then, as bile flows through the bile ducts, it is modified by addition of a watery, bicarbonate-rich secretion from ductal epithelial cells. Bile is concentrated, typically five-fold, during storage in the gall bladder.

The flow of bile is lowest during fasting, and a majority of that is diverted into the gallbladder for concentration. When chyme from an ingested meal enters the small intestine, acid and partially digested fats and proteins stimulate secretion of cholecystokinin and secretin, both of which are important for secretion and flow of bile. Cholecystokinin (cholecysto=gallbladder and kinin=movement) is a hormone which stimulates contractions of the gallbladder and common bile duct, resulting in delivery of bile into the gut. The most potent stimulus for release of cholecystokinin is the presence of fat in the duodenum. Secretin is a hormone secreted in response to acid in the duodenum, and it simulates biliary duct cells to secrete bicarbonate and water, which expands the volume of bile and increases its flow out into the intestine.

Bile acids are derivatives of cholesterol. Cholesterol, ingested as part of the diet or derived from hepatic synthesis, are converted into bile acids in the hepatocyte. Examples of such bile acids include cholic and chenodeoxycholic acids, which are then conjugated to an amino acid (such as glycine or taurine) to yield the conjugated form that is actively secreted into cannaliculi. The most abundant of the bile salts in humans are cholate and deoxycholate, and they are normally conjugated with either glycine or taurine to give glycocholate or taurocholate respectively.

Free cholesterol is virtually insoluble in aqueous solutions, however in bile it is made soluble by the presence of bile acids and lipids. Hepatic synthesis of bile acids accounts for the majority of cholesterol breakdown in the body. In humans, roughly 500 mg of cholesterol are converted to bile acids and eliminated in bile every day. Therefore, secretion into bile is a major route for elimination of cholesterol. Large amounts of bile acids are secreted into the intestine every day, but only relatively small quantities are lost from the body. This is because approximately 95% of the bile acids delivered to the duodenum are absorbed back into blood within the ileum, by a process is known as "Enterohepatic Recirculation".

Venous blood from the ileum goes straight into the portal vein, and hence through the sinusoids of the liver. Hepatocytes extract bile acids very efficiently from sinusoidal blood, and little escapes the healthy liver into systemic circulation. Bile acids are then transported across the hepatocytes to be resecreted into canaliculi. The net effect of this enterohepatic recirculation is that each bile salt molecule is reused about 20 times, often two or three times during a single digestive phase. Bile biosynthesis represents the major metabolic fate of cholesterol, accounting for more than half of the approximate 800 mg/day of cholesterol that an average adult uses up in metabolic processes. In comparison, steroid hormone biosynthesis consumes only about 50 mg of cholesterol per day. Much more that 400 mg of bile salts is required and secreted into the intestine per day, and this is achieved by re-cycling the bile salts. Most of the bile salts secreted into the upper region of the small intestine are absorbed along with the dietary lipids that they emulsified at the lower end of the small intestine. They are separated from the dietary lipid and returned to the liver for re-use. Re-cycling thus enables 20-30 g of bile salts to be secreted into the small intestine each day.

Bile acids are amphipathic, with the cholesterol-derived portion containing both hydrophobic (lipid soluble) and polar (hydrophilic) moieties while the amino acid conjugate is generally polar and hydrophilic. This amphipathic nature enables bile acids to carry out two important functions: emulsification of lipid aggregates and solubilization and transport of lipids in an aqueous environment. Bile acids have detergent action on particles of dietary fat which causes fat globules to break down or to be emulsified. Emulsification is important since it greatly increases the surface area of fat available for digestion by lipases which cannot access the inside of lipid droplets. Furthermore, bile acids are lipid carriers and are able to solubilize many lipids by forming micelles and are critical for transport and absorption of the fat-soluble vitamins.

Pharmaceutical Compositions and Methods of Use

In some embodiments, compositions described herein are administered for delivery of enteroendocrine peptide secretion enhancing agents to a subject or individual. In certain embodiments, any compositions described herein are formulated for ileal, rectal and/or colonic delivery. In more specific embodiments, the composition is formulated for non-systemic or local delivery to the rectum and/or colon. It is to be understood that as used herein, delivery to the colon includes delivery to sigmoid colon, transverse colon, and/or ascending colon. In still more specific embodiments, the composition is formulated for non-systemic or local delivery to the rectum and/or colon is administered rectally. In other specific embodiments, the composition is formulated for non-systemic or local delivery to the rectum and/or colon is administered orally.

In some embodiments, provided herein is a composition comprising an enteroendocrine peptide secretion enhancing agent and, optionally, a pharmaceutically acceptable carrier for reducing food intake in an individual. In some embodiments, provided herein is a composition comprising an enteroendocrine peptide secretion enhancing agent and, optionally, a pharmaceutically acceptable carrier for reducing circulating glucose levels in an individual. In some embodiments, provided herein is a composition comprising an enteroendocrine peptide secretion enhancing agent and, optionally, a pharmaceutically acceptable carrier for increasing insulin levels in an individual. In specific embodiments, the composition is formulated for delivering the enteroendocrine peptide secretion enhancing agent to the distal gastrointestinal tract of the individual. Generally, a therapeutically effective amount of an enteroendocrine peptide secretion enhancing agent is provided.

In certain embodiments, the composition comprises an enteroendocrine peptide secretion enhancing agent and an absorption inhibitor. In specific embodiments, the absorption inhibitor is an inhibitor that inhibits the absorption of the (or at least one of the) specific enteroendocrine peptide secretion enhancing agent with which it is combined. In some embodiments, the composition comprises an enteroendocrine peptide secretion enhancing agent, an absorption inhibitor and a carrier (e.g., an orally suitable carrier or a rectally suitable carrier, depending on the mode of intended administration). In certain embodiments, the composition comprises an enteroendocrine peptide secretion enhancing agent, an absorption inhibitor, a carrier, and one or more of a cholesterol absorption inhibitor, an enteroendocrine peptide, a peptidase inhibitor, a spreading agent, and a wetting agent.

In certain embodiments enteroendocrine peptide secretion enhancing agents are selected from, by way of non-limiting example, bile acids, bile acid mimic and/or modified bile acids. In more specific embodiments, compositions described herein are formulated for non-systemic or local delivery of a bile acid, bile acid mimic and/or modified bile acid (as the active component or components) to the rectum and/or colon, including the sigmoid colon, transverse colon, and/or ascending colon. In certain embodiments, the compositions described herein are administered rectally for non-systemic or local delivery of the bile acid active component to the rectum and/or colon, including the sigmoid colon, transverse colon, and/or ascending colon. In other embodiments, the compositions described herein are administered orally for non-systemic delivery of the bile salt active component to the rectum and/or colon, including the sigmoid colon, transverse colon, and/or ascending colon. In specific embodiments, compositions formulated for oral administration are, by way of non-limiting example, enterically coated or formulated oral dosage forms, such as, tablets and/or capsules. It is to be understood that the terms "subject" and "individual" are utilized interchangeably herein and include, e.g., humans and human patients in need of treatment.

Enteroendocrine Peptide Enhancing Agents

In some embodiments, enteroendocrine peptide enhancing agents provided herein include, by way of non-limiting example, enteroendocrine peptide secretion (e.g., of the L-cells) enhancing agents, inhibitors of degradation of enteroendocrine peptides (e.g., of the L-cells), or combinations thereof.

In certain embodiments, the enteroendocrine peptide secretion enhancing agents used in the methods and compositions described herein include, by way of non-limiting example, a steroid acid or a nutrient. In specific embodiments, the steroid acid or nutrient described herein is a steroid acid or nutrient that enhances the secretion of an enteroendocrine peptide. In specific embodiments, the steroid acid is an oxidize cholesterol acid. In some embodiments, an enteroendocrine peptide secretion enhancing agent, bile acid, or bile acid mimic used in any composition or method described herein is a compound of Formula VII:

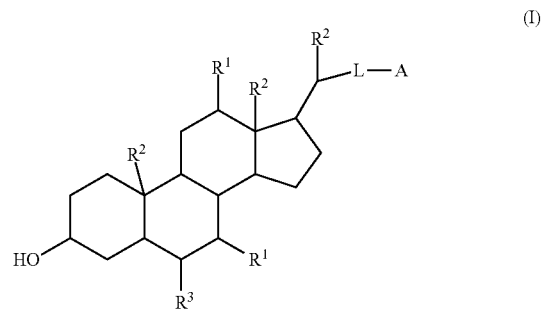

(I)

In certain embodiments, each $R^1$ is independently H, OH, O-lower alkyl (e.g., $OCH_3$, or OEt). In some embodiments, each $R^1$ is independently H, OH, lower (e.g., $C_1$-$C_6$ or $C_1$-$C_3$) alkyl, or lower (e.g., $C_1$-$C_6$ or $C_1$-$C_3$) heteroalkyl. In certain embodiments, L is a substituted or unsubstituted alkyl or substituted or unsubstituted heteroalkyl. In some embodiments, $R^2$ is H, OH, lower alkyl, or lower heteroalkyl (e.g., OMe). In certain embodiments, $R^3$ is H, OH, O-lower alkyl, lower alkyl, or lower heteroalkyl (e.g., OMe). In some embodiments, A is $COOR^4$, $S(O)_nR^4$, or $OR^5$. In certain embodiments, $R^4$ is H, an anion, a pharmaceutically acceptable cation (e.g., an alkali metal cation, alkaline earth metal cation, or any other pharmaceutically acceptable cation) substituted or unsubstituted alkyl, substituted or unsubstituted heteroalkyl, substituted or unsubstituted aryl, substituted or unsubstituted heteroaryl, an amino acid, or the like; and n is 1-3. Each $R^5$ is independently selected from lower alkyl and H.

In specific embodiments, L is unsubstituted branched or straight chain alkyl. In more specific embodiments, L is unsubstituted branched or straight chain lower alkyl. In some embodiments, L is $(CR^{52})_m$—$CONR^5$—$(CR^{52})_p$. Each m is 1-6 and n is 1-6. In specific embodiments, m is 2 and n is 1. In other specific embodiments, m is 2 and n is 2. In certain embodiments, A is COOH or COO—. In some embodiments, A is $SO_3H$ or $SO_3$—.

In specific embodiments, the compound of Formula VII has a structure represented by:

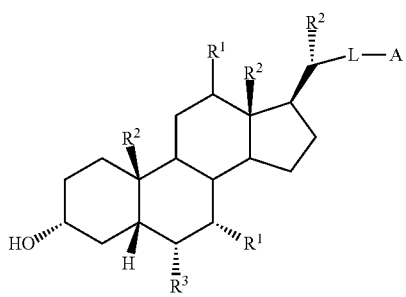

(Ia)

In some embodiments, bile acid mimics include, by way of non-limiting example, 6-methyl-2-oxo-4-thiophen-2-yl-1,2,3,4-tetrahydro-phyrimidine-5-carboxylic acid benzyl ester (or TGR5-binding analogs thereof), oleanolic acid (or TGR5-binding analogs thereof), crataegolic acid, 6α-ethyl-23(S)-methylcholic acid (S-EMCA, INT-777), (3R)-3-Hydroxy-3-(2-propen-1-yl)-lup-20(29)-en-28-oic acid hydrate (RG-239), or the like.

In some embodiments, a bile acid mimic is

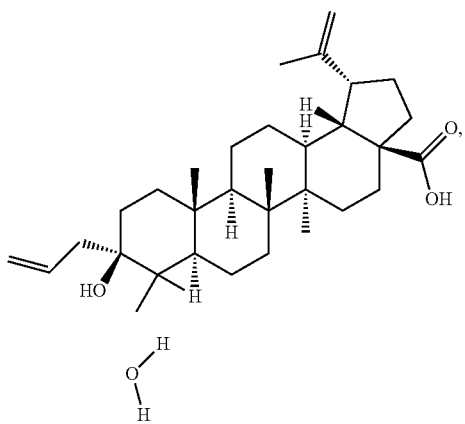

RG-239

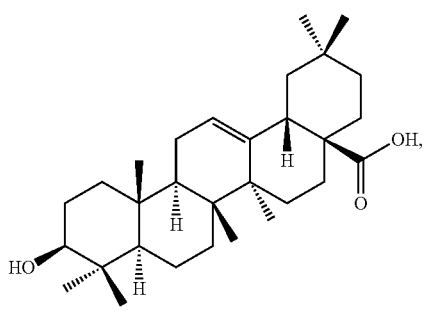

Oleanolic acid

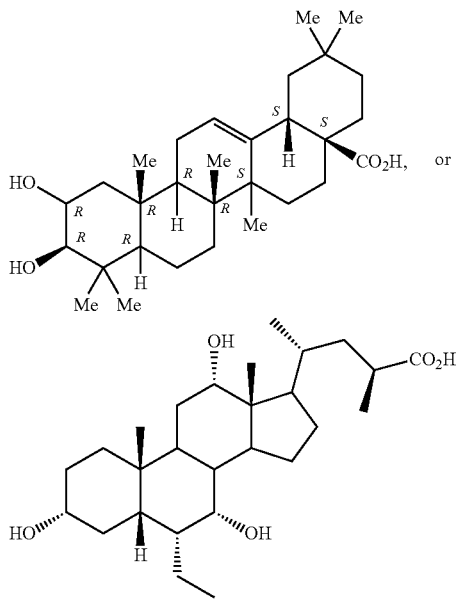

Crataegolic acid or

Figure 11A:
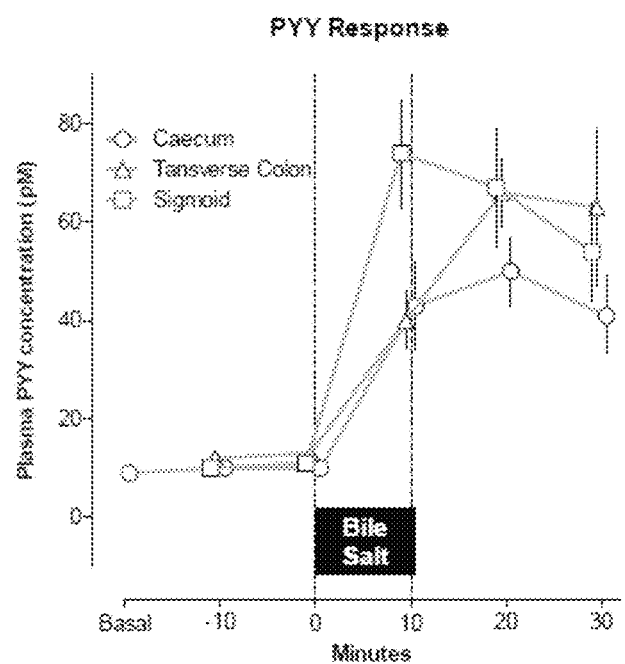
FIG. 11A and FIG. 11B illustrate the response of enteroendocrine peptides to administration of bile salts.
Figure 11B:
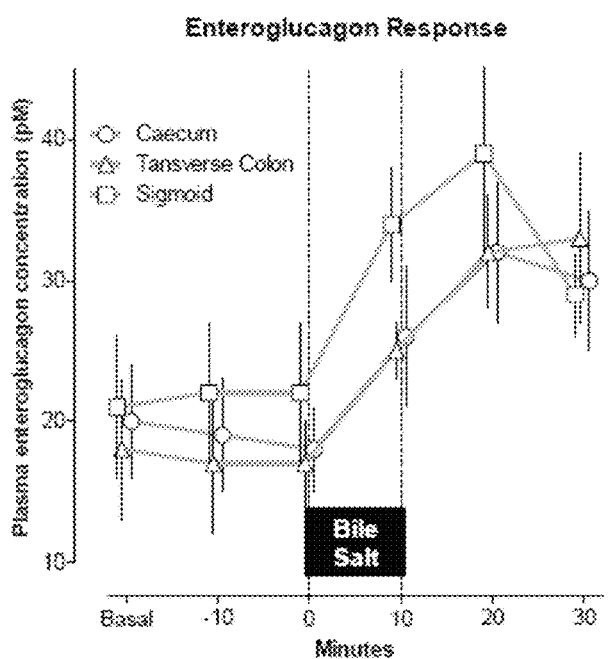

In certain embodiments, enteroendocrine peptide secretion enhancing agents used in the methods and compositions described herein enhance the secretion of an enteroendocrine peptide secreted by L-cells (e.g., GLP-1, GLP-2, PYY, and the like). FIG. 11 (FIGS. 11A and 11B) illustrates the response of enteroendocrine peptides to administration of bile salts.

In some embodiments, the enteroendocrine peptide secretion enhancing agent is a steroid acid, such as a bile acid/salt, a bile acid/salt mimic, a modified bile acid/salt, or a combination thereof. The bile acids or salts thereof used in the methods and compositions described herein include, by way of non-limiting example, cholic acid, deoxycholic acid, glycocholic acid, glycodeoxycholic acid, taurocholic acid, taurodihydrofusidate, taurodeoxycholic acid, cholate, glycocholate, deoxycholate, taurocholate, taurodeoxycholate, chenodeoxycholic acid, ursodeoxycholic acid and combinations thereof. In certain embodiments, bile salts used in the methods and compositions described herein are pharmaceutically acceptable salts including, by way of non-limiting example, the sodium and potassium salts thereof. In specific embodiments, the enteroendocrine peptide secretion enhancing agent is a pharmaceutically acceptable bile acid salt including, by way of non-limiting example, sodium glycocholate, sodium taurocholate and combinations thereof. In some embodiments, more than one bile acid and/or salt is used in a methods and/or composition described herein. In certain embodiments, the bile acid/salt used herein has a low or relatively low solubility in water.

Although bile acids facilitate digestion and absorption of lipids in the small intestine, they are generally used in pharmaceutical formulations as excipients. As excipients, bile acids find uses as surfactants and/or as agents that enhance the transfer of active components across mucosal membranes, for systemic delivery of a pharmaceutically active compound. In certain embodiments of the methods and pharmaceutical compositions described herein, however, a bile acid, a bile acid mimic and/or a modified bile acid is the active agent used to enhance secretion of enteroendocrine peptides.

In certain specific embodiments, the enteroendocrine peptide secretion enhancing agents used in the methods and compositions described herein are modified bile acids/salts. In certain embodiments, the bile acid/salt is modified in such a way so as to inhibit absorption of the bile acid/salt across the rectal or colonic mucosa.

In certain embodiments, the enteroendocrine peptide secretion enhancing agents described herein are a glucagon-like peptide secretion enhancing agent. In a specific embodiment, the glucugen-like peptide secretion enhancing agent is a bile acid, a bile acid mimic or a modified bile acid. In some embodiments, the glucagon-like peptide secretion enhancing agents are selected from, by way of non-limiting example, glucagon-like peptide-1 (GLP-1) secretion enhancing agents or glucagon-like peptide-2 (GLP-2) secretion enhancing agents. In some embodiments, the glucagon-like peptide secretion enhancing agents enhance both GLP-1 and GLP-2. In a specific embodiment, the GLP-1 and/or GLP-2 secretion enhancing agent is selected from bile acids, bile acid mimics or modified bile acids.

In certain embodiments, the enteroendocrine peptide secretion enhancing agent described herein is a pancreatic polypeptide-fold peptide secretion enhancing agent. In more specific embodiments, the pancreatic polypeptide-fold peptide secretion enhancing agent is selected from, by way of non-limiting example, peptide YY (PYY) secretion enhancing agents. In specific embodiments, the pancreatic polypeptide-fold peptide secretion enhancing agent or the PYY secretion enhancing agent is selected from a bile acid, a bile acid mimic, a modified bile acid or a fatty acid or salt thereof (e.g., a short chain fatty acid).

In some embodiments, the enteroendocrine peptide secretion enhancing agent is selected from, by way of non-limiting example, carbohydrates, glucose, fats, and proteins. In certain embodiments, the enteroendocrine peptide secretion enhancing agent is selected from fatty acids, including long chain fatty acids and short chain fatty acids. Short chain fatty acids and salts include, by way of non-limiting example, propionic acid, butyric acid, propionate, and butyrate.

In some embodiments, the enteroendocrine peptide secretion enhancing agent is selected from, by way of non-limiting example, carbohydrates, glucose, fat, protein, protein hydrolysate, amino acids, nutrients, intestinal peptides, peripheral hormones that participate in energy homeostasis, such as the adipocyte hormone leptin, bile acids/salts, insulin, gastrin-releasing peptide (GRP), gut peptides, gastric acid, CCK, insulin-like growth factor 1, bombesin, calcitonin-gene-related peptide and combinations thereof that enhance the secretion of enteroendocrine peptides.

In certain embodiments, the inhibitors of degradation of L-cell enteroendocrine peptide products include DPP-IV inhibitors, TGR5 modulators (e.g., TGR5 agonists), or combinations thereof. In certain instances, the administration of a DPP-IV inhibitor in combination with any of the compounds disclosed herein reduces or inhibits degradation of GLP-1 or GLP-2. In certain instances, administration of a TGR5 agonist in combination with any of the compounds disclosed herein enhances the secretion of enteroendocrine peptide products from L-cells. In some instances, the enteroendocrine peptide enhancing agent agonizes or partially agonizes bile acid receptors (e.g., TGR5 receptors or Farnesoid-X receptors) on in the gastrointestinal tract.

DPP-IV inhibitors include (2S)-1-{2-[(3-hydroxy-1-adamantyl)amino]acetyl}pyrrolidine-2-carbonitrile (vildaglip-tin), (3R)-3-amino-1-[9-(trifluoromethyl)-1,4,7,8-tetrazabicyclo[4.3.0]nona-6,8-d ien-4-yl]-4-(2,4,5-trifluorophenyl) butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin). TGR5 modulators (e.g., agonists) include the compounds disclosed in, e.g, WO2008/091540, WO 2008067219 and US Appl. No. 2008/0221161, the TGR5 modulators (e.g., agonists) of which are hereby incorporated herein by reference.

In some embodiments, the enteroendocrine peptide secretion enhancing agents used in the methods and compositions described herein may or may not be substrates for bile acid scavenger systems. In some embodiments, the enteroendocrine peptide secretion enhancing agents may not form micelles and/or assist in fat absorption. In certain embodiments, the enteroendocrine peptide secretion enhancing agents may or may not enhance permeability and/or promote inflammation. In certain embodiments, the enteroendocrine peptide secretion enhancing agent may not irritate the bowel or promote diarrhea. In some embodiments, the enteroendocrine peptide secretion enhancing agent is selected from, by way of non-limiting example, toll or toll-like receptor ligands.

Figure 12:
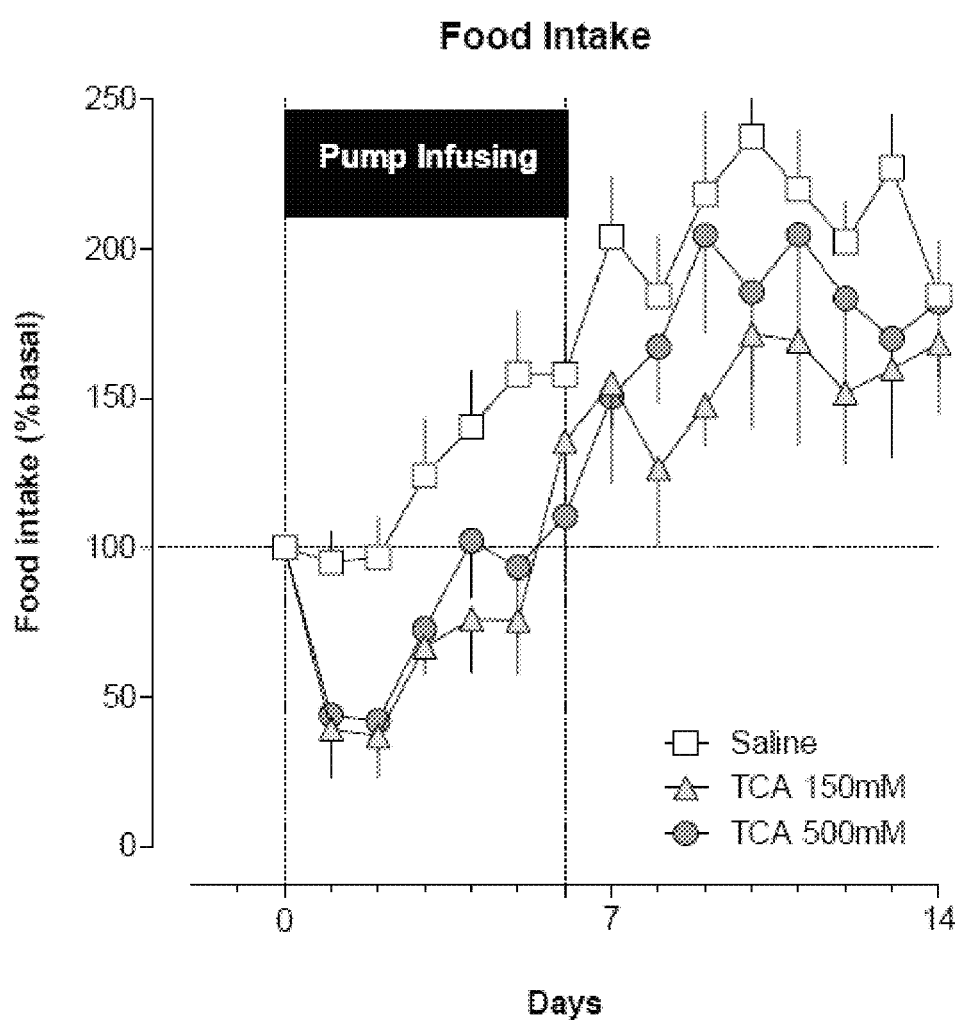
FIG. 12 illustrates the affect on food intake of pump infusion of TCA.
Figure 13:
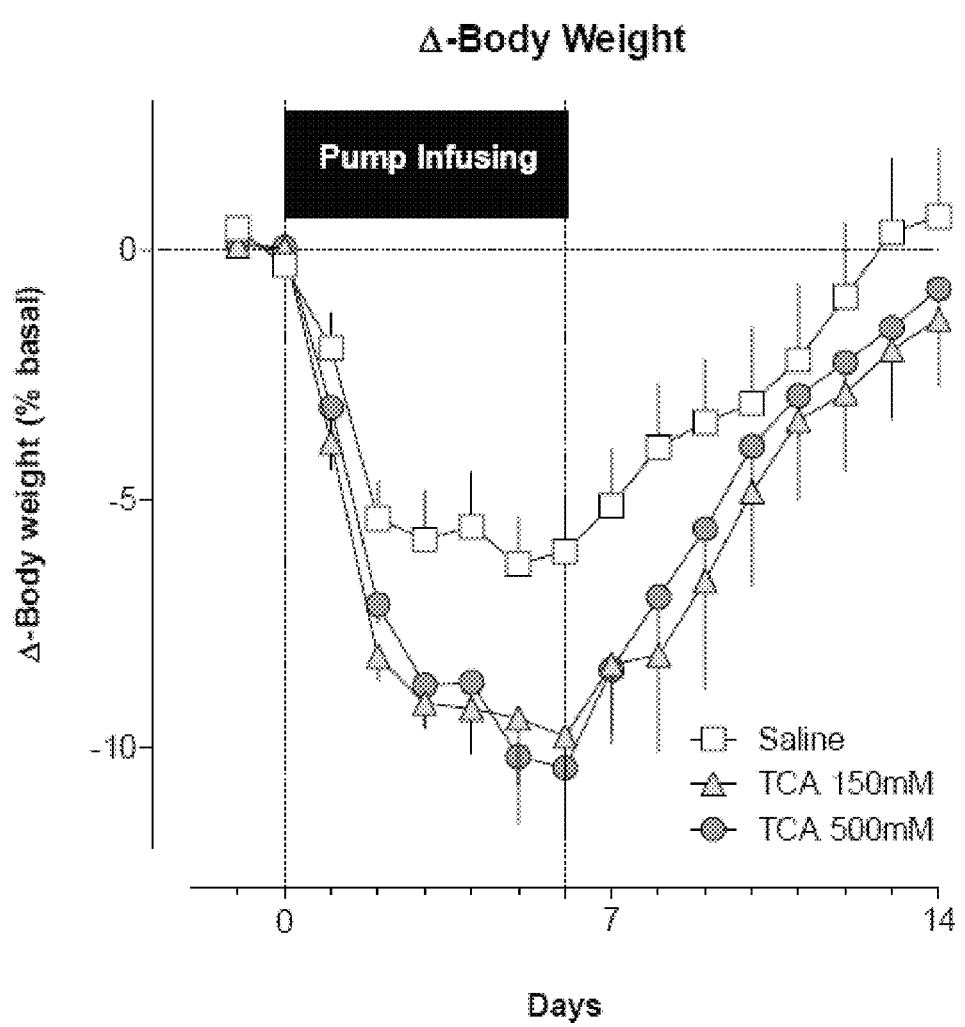
FIG. 13 illustrates the affect on body weight of pump infusion of TCA.

FIG. 12 illustrates the affect on food intake of pump infusion of TCA in concentrations of 150 mM and 500 mM. FIG. 13 illustrates the affect on body weight of pump infusion of TCA in concentrations of 150 mM and 500 mM.

FXR Agonists

In some embodiments, FXR agonist is GW4064, GW9662, INT-747, T0901317, WAY-362450, fexaramine, a cholic acid, a deoxycholic acid, a glycocholic acid, a glycodeoxycholic acid, a taurocholic acid, a taurodihydrofusi-date, a taurodeoxycholic acid, a cholate, a glycocholate, a deoxycholate, a taurocholate, a taurodeoxycholate, a chenodeoxycholic acid.

Absorption Inhibitors

In certain embodiments, the compositions described herein are and the methods described herein include administering a composition that is formulated for the non-systemic delivery of enteroendocrine peptide secretion enhancing agents to the rectum and/or colon (sigmoid, transverse, and/or ascending colon). As previously discussed, enteroendocrine peptide secretion enhancing agents include, by way of non-limiting example, bile acids, bile salts, bile acid mimics, bile salt mimics, modified bile acids, modified bile salts and combinations thereof. In certain embodiments, the composition described herein as being formulated for the non-systemic delivery of enteroendocrine peptide secretion enhancing agents further includes an absorption inhibitor. As used herein, an absorption inhibitor includes an agent or group of agents that inhibit absorption of the enteroendocrine peptide secretion enhancing agent across the rectal or colonic mucosa. In specific embodiments, the absorption inhibitor is an absorption inhibitor that inhibits the absorption of the specific enteroendocrine peptide secretion enhancing agent with which it is combined.

Suitable bile acid absorption inhibitors (also described herein as absorption inhibiting agents) include, by way of non-limiting example, anionic exchange matrices, polyamines, quaternary amine containing polymers, quaternary ammonium salts, polyallylamine polymers and copolymers, colesevelam, colesevelam hydrochloride, Cholesta-Gel (N,N,N-trimethyl-6-(2-propenylamino)-1-hexanaminium chloride polymer with (chloromethyl) oxirane, 2-propen-1-amine and N-2-propenyl-1-decanamine hydrochloride), cyclodextrins, chitosan, chitosan derivatives, carbohydrates which bind bile acids, lipids which bind bile acids, proteins and proteinaceous materials which bind bile acids, and antibodies and albumins which bind bile acids. Suitable cyclodextrins include those that bind bile acids such as, by way of non-limiting example, β-cyclodextrin and hydroxypropyl-β-cyclodextrin. Suitable proteins, include those that bind bile acids such as, by way of non-limiting example, bovine serum albumin, egg albumin, casein, $\alpha^U$-acid glycoprotein, gelatin, soy proteins, peanut proteins, almond proteins, and wheat vegetable proteins.

In certain embodiments the absorption inhibitor is cholestyramine. In specific embodiments, cholestyramine is combined with a bile acid. Cholestyramine, an ion exchange resin, is a styrene polymer containing quaternary ammonium groups crosslinked by divinylbenzene. In other embodiments, the absorption inhibitor is colestipol. In specific embodiments, colestipol is combined with a bile acid. Colestipol, an ion exchange resin, is a copolymer of diethylenetriamine and 1-chloro-2,3-epoxypropane.

In certain embodiments of the compositions and methods described herein the enteroendocrine peptide secretion enhancing agent is linked to an absorption inhibitor, while in other embodiments the enteroendocrine peptide secretion enhancing agent and the absorption inhibitor are separate molecular entities. In specific embodiments the bile acid, bile acid mimic or the modified bile acid is linked to a bile acid adsorption inhibitor described herein.

Cholesterol Absorption Inhibitors

In certain embodiments, a composition described herein optionally includes at least one cholesterol absorption inhibitor. Suitable cholesterol absorption inhibitors include, by way of non-limiting example, ezetimibe (SCH 58235), ezetimibe analogs, ACT inhibitors, stigmastanyl phosphorylcholine, stigmastanyl phosphorylcholine analogues, -lactam cholesterol absorption inhibitors, sulfate polysaccharides, neomycin, plant sponins, plant sterols, phytostanol preparation FM-VP4, Sitostanol, -sitosterol, acyl-CoA:cholesterol-O-acyltransferase (ACAT) inhibitors, Avasimibe, Implitapide, steroidal glycosides and the like. Suitable enzetimibe analogs include, by way of non-limiting example, SCH 48461, SCH 58053 and the like. Suitable ACT inhibitors include, by way of non-limiting example, trimethoxy fatty acid anilides such as CI-976, 3-[decyldimethylsilyl]-N-[2-(4-methylphenyl)-1-phenylethyl]-propanamide, melinamide and the like. ||-lactam cholesterol absorption inhibitors include, by way of non-limiting example, (3R-4S)-1,4-bis-(4-methoxyphenyl)-3-(3-phenylpropyl)-2-azetidinone and the like.

Enteroendocrine Peptides

In certain embodiments, the compositions described herein optionally include at least one enteroendocrine peptide. Suitable enteroendocrine peptides include, by way of non-limiting example, glucagon-like peptides GLP-1 and/or GLP-2, or pancreatic polypeptide-fold peptides pancreatic polypeptide (PP), neuropeptide Y (NPY) and/or peptide YY (PYY).

Peptidase Inhibitors

In some embodiments, the compositions described herein optionally include at least one peptidase inhibitor. Such peptidase inhibitors include, but are not limited to, dipeptidyl peptidase-4 inhibitors (DPP-4), neutral endopeptidase inhibitors, and converting enzyme inhibitors. Suitable dipeptidyl peptidase-4 inhibitors (DPP-4) include, by way of non-limiting example, Vildaglipti, 2S)-1-{2-[(3-hydroxy-1-adamantyl)amino]acetyl}pyrrolidine-2-carbonitrile, Sitagliptin, (3R)-3-amino-1-[9-(trifluoromethyl)-1,4,7,8-tetrazabicyclo[4.3.0]nona-6,8-d ien-4-yl]-4-(2,4,5-trifluorophenyl)butan-1-one, Saxagliptin, and (1S,3S,5S)-2-[(2S)-2-amino-2-(3-hydroxy-1-adamantyl)acetyl]-2-azabicyclo[3.1.0]hexane-3-carbonitrile. Such neutral endopeptidase inhibitors include, but are not limited to, Candoxatrilat and Ecadotril.

Spreading Agents/Wetting Agents

In certain embodiments, the composition described herein optionally comprises a spreading agent. In some embodiments, a spreading agent is utilized to improve spreading of the composition in the colon and/or rectum. Suitable spreading agents include, by way of non-limiting example, hydroxyethylcellulose, hydroxypropymethyl cellulose, polyethylene glycol, colloidal silicon dioxide, propylene glycol, cyclodextrins, microcrystalline cellulose, polyvinylpyrrolidone, polyoxyethylated glycerides, polycarbophil, di-n-octyl ethers, Cetiol™OE, fatty alcohol polyalkylene glycol ethers, Aethoxal™B), 2-ethylhexyl palmitate, Cegesoft™C 24), and isopropyl fatty acid esters.

In some embodiments, the compositions described herein optionally comprise a wetting agent. In some embodiments, a wetting agent is utilized to improve wettability of the composition in the colon and rectum. Suitable wetting agents include, by way of non-limiting example, surfactants. In some embodiments, surfactants are selected from, by way of non-limiting example, polysorbate (e.g., 20 or 80), stearyl hetanoate, caprylic/capric fatty acid esters of saturated fatty alcohols of chain length $C_{12}$-$C_{18}$, isostearyl diglycerol isostearic acid, sodium dodecyl sulphate, isopropyl myristate, isopropyl palmitate, and isopropyl myristate/isopropyl stearate/isopropyl palmitate mixture.

Methods

Provided herein, in certain embodiments, are methods for treating obesity, diabetes, or an inflammatory intestinal condition comprising administration of a therapeutically effective amount of an ASBTI and/or an enteroendocrine peptide enhancing agent and/or a FXR agonist to an individual in need thereof. Provided herein, in certain embodiments, are methods for treating obesity, diabetes, or an inflammatory intestinal condition comprising contacting the distal gastrointestinal tract, including the distal ileum and/or the colon and/or the rectum, of an individual in need thereof with an ASBTI and/or an enteroendocrine peptide enhancing agent and/or a FXR agonist. Also provided herein are methods for reducing intraenterocyte bile acids, reducing necrosis and/or damage to ileal architecture, or reducing blood or plasma glucose levels of an individual comprising administration of a therapeutically effective amount of an ASBTI and/or an enteroendocrine peptide enhancing agent and/or a FXR agonist to an individual in need thereof. Provided herein are methods for stimulating L-cells in the distal gastrointestinal tract, including L-cells in the distal ileum and/or colon and/or rectum, of an individual comprising administration of a therapeutically effective amount of an ASBTI and/or an enteroendocrine peptide enhancing agent and/or a FXR agonist to an individual in need thereof. Provided herein are methods for enhancing enteroendocrine peptide secretion from L-cells in the distal gastrointestinal tract, including L-cells in the distal ileum and/or colon and/or rectum, of an individual comprising administration of a therapeutically effective amount of an ASBTI and/or an enteroendocrine peptide enhancing agent and/or a FXR agonist to an individual in need thereof. Provided herein are methods for increasing the concentration of bile acids and salts thereof in the vicinity of L-cells lining the distal gastrointestinal tract, including L-cells in the distal ileum, and/or the colon and/or the rectum of an individual, comprising administration of a therapeutically effective amount of an ASBTI and/or an enteroendocrine peptide enhancing agent and/or a FXR agonist to an individual in need thereof. In some of the aforementioned embodiments, the ASBTI is contacted with the distal ileum of the individual in need thereof. In some of the aforementioned embodiments, the ASBTI is not absorbed systemically. In some other embodiments, the ASBTI is absorbed systemically.

In some embodiments of the methods provided herein, inhibition of bile acid transporters and/or bile acid recycling increases the concentration of bile acids in the vicinity of L-cells to concentrations that are higher than physiological levels of bile acids in individuals that have not been treated with an ASBTI. In some embodiments of the methods described herein, an increase in concentration of bile acids in the vicinity of L-cell increases the secretion of enteroendocrine peptides, including GLP-1, GLP-2, PYY and/or oxyntomodulin from L-cells. In some instances a higher concentration of GLP-1 and/or GLP-2 and/or PYY and/or oxynotmodulin in the blood and/or plasma of an individual, increases insulin sensitivity of the individual, reduces intra-enterocyte bile acids, reduces necrosis and/or damage to ileal architecture, and/or slows down gastric emptying and/or induces a feeling of satiety thereby reducing food intake and/or inducing weight loss.

Provided herein are methods for reducing necrosis and/or damage to ileal architecture or cells comprising administration of a therapeutically effective amount of an ASBTI and/or an enteroendocrine peptide enhancing agent and/or a FXR agonist to an individual in need thereof. In certain embodiments, provided herein are methods for reducing intra-enterocyte bile acids comprising administration of a therapeutically effective amount of an ASBTI and/or an enteroendocrine peptide enhancing agent and/or a FXR agonist to an individual in need thereof. In certain embodiments, provided herein are methods for reducing food intake in an individual comprising administration of a therapeutically effective amount of an ASBTI to an individual in need thereof. In certain embodiments, provided herein is a method for reducing food intake in an individual in need thereof comprising contacting the distal gastrointestinal tract, including the distal ileum and/or colon and/or rectum, of the individual with a therapeutically effective amount of an ASBTI. Provided herein are methods for reducing weight of an individual comprising administration of a therapeutically effective amount of an ASBTI to an individual in need thereof. In certain embodiments, provided herein is a method of reducing weight of an individual in need thereof comprising contacting the distal gastrointestinal tract, including the distal ileum and/or colon and/or rectum, of the individual with a therapeutically effective amount of an ASBT inhibitor. In some embodiments, the method provides for inhibition of bile salt recycling upon administration of any of the compounds described herein to an individual. In some embodiments, an ASBTI described herein is systemically absorbed upon administration. In some embodiments, an ASBTI described herein is not absorbed systemically. In some embodiments, an ASBTI described herein is administered to the individual orally, enterically or rectally. In some embodiments, an ASBTI described herein is delivered and/or released in the distal ileum of an individual. In some embodiments, an ASBTI described herein increases the concentration of bile acids in the distal ileum, the colon and/or the rectum thereby increasing secretion of enteroendocrine peptide products from L-cells in the gastrointestinal tract. In certain instances administration of a therapeutically effective amount of an ASBTI described herein to an individual in need thereof increases the secretion of enteroendocrine peptide products (e.g., GLP-1, GLP-2, PYY, oxyntonmodulin or the like) from L-cells that line the gastrointestinal tract. In some embodiments, elevated levels of GLP-1 slow down gastric emptying, and/or inhibit or reduce meal-stimulated gastric secretion, thereby reducing food intake in the individual. In some embodiments, an ASBTI described herein is administered in combination with a DPP-IV inhibitor. In some instances, inhibition of DPP-IV reduces the degradation of enteroendocrine peptide products (e.g. GLP-1) thereby prolonging the delay in gastric emptying and thereby reducing food intake. In some of such embodiments, an ASBTI described herein is administered to a non-diabetic individual for reducing food intake in the non-diabetic individual. In some of such embodiments, an ASBTI described herein is administered to a diabetic individual for reducing food intake in the diabetic individual. In some embodiments, the methods described herein are methods for reducing food intake in obese or morbidly overweight individuals. In some embodiments, a reduction in food intake reduces the weight of an individual (e.g., an obese or morbidly overweight individual)

Provided herein are methods for inducing satiety in an individual comprising administration of a therapeutically effective amount of an ASBTI to an individual in need thereof. In certain embodiments, provided herein is a method for inducing satiety in an individual in need thereof comprising contacting the distal gastrointestinal tract, including distal ileum and/or the colon and/or the rectum, of the individual with a therapeutically effective amount of an ASBT inhibitor. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI described herein is administered to the individual orally, enterically or rectally. In some embodiments, an ASBTI described herein is delivered and/or released in the distal ileum of an individual. In some embodiments, an ASBTI described herein increases the concentration of bile acids in the distal ileum, the colon and/or the rectum and induces secretion of enteroendocrine peptide products from L-cells of the distal gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the gastrointestinal tract. In some embodiments, elevated levels of GLP-1 slow down gastric emptying, and induce a feeling of fullness in an individual. In some embodiments, an ASBTI described herein is administered in combination with a DPP-IV inhibitor. In some instances, inhibition of DPP-IV reduces the degradation of enteroendocrine peptide products (e.g. GLP-1) thereby prolonging the delay in gastric emptying and sustaining the feeling of satiety and/or fullness. In some of such embodiments, an ASBTI described herein is administered to a non-diabetic individual. In some of such embodiments, an ASBTI described herein is administered to a diabetic individual. In some of such embodiments, an ASBTI described herein is administered to an obese or morbidly overweight individual.

Provided herein are methods for preventing or treating metabolic disorders in an individual comprising administration of a therapeutically effective amount of an ASBTI and/or an enteroendocrine peptide enhancing agent and/or a FXR agonist to an individual in need thereof. In certain embodiments, the metabolic disorders include but not limited to necrotizing enterocolitis, gastritis, ulcerative colitis, inflammatory bowel disease, irritable bowel syndrome, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In certain embodiments, provided herein is a method for treating metabolic disorders in an individual in need thereof comprising contacting the distal gastrointestinal tract, including distal ileum and/or the colon and/or the rectum, of the individual with a therapeutically effective amount of an ASBTI and/or an enteroendocrine peptide enhancing agent and/or a FXR agonist. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI described herein is administered to the individual orally, enterically or rectally. In some embodiments, an ASBTI and/or an enteroendocrine peptide enhancing agent and/or a FXR agonist described herein is delivered and/or released in the distal ileum of an individual. In some embodiments, an ASBTI and/or an enteroendocrine peptide enhancing agent and/or a FXR agonist described herein increases the concentration of bile acids in the distal ileum, the colon and/or the rectum and induces secretion of enteroendocrine peptide products from the L-cells of the gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the distal gastrointestinal tract. In some embodiments, elevated levels of GLP-1 reduce glucose levels in blood. In some instances, elevated levels of GLP-1 increase insulin sensitivity in a hyperglycemic individual. In some embodiments, an ASBTI and/or an enteroendocrine peptide enhancing agent and/or a FXR agonist described herein is administered in combination with a DPP-IV inhibitor. In some instances, inhibition of DPP-IV reduces the degradation of enteroendocrine peptide products (e.g. GLP-1) thereby prolonging the effect of GLP-1 in reducing blood glucose levels. In some of such embodiments, an ASBTI described herein is administered to a non-diabetic individual. In some of such embodiments, an ASBTI described herein is administered to a diabetic individual. In some of such embodiments, an ASBTI described herein is administered to an obese or morbidly overweight individual.

Provided herein are methods for preventing or treating radiation induced enteritis in an individual comprising administration of a therapeutially effective amount of an ASBTI and/or an enteroendocrine peptide enhancing agent and/or a FXR agonist to an individual in need thereof. In certain embodiments, provided herein is a method for treating radiation enteritis in an individual in need thereof comprising contacting the distal gastrointestinal tract, including distal ileum and/or the colon and/or the rectum, of the individual with a therapeutically effective amount of an ASBTI and/or an enteroendocrine peptide enhancing agent and/or a FXR agonist. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI and/or an enteroendocrine peptide enhancing agent and/or a FXR agonist described herein is administered to the individual orally, enterically or rectally. In some embodiments, an ASBTI described herein is delivered and/or released in the distal ileum of an individual. In some embodiments, an ASBTI and/or an enteroendocrine peptide enhancing agent and/or a FXR agonist described herein increases the concentration of bile acids in the distal ileum, the colon and/or the rectum and induces secretion of enteroendocrine peptide products from the L-cells of the gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the distal gastrointestinal tract. In some embodiments, elevated levels of GLP-2 has a regenerative effect on radiation-induced injuries of the gastrointestinal tract (e.g., after radiation therapy for treatment of cancer, or accidental exposure to radiation). In some embodiments, prophylactic administration of an ASBTI and/or an enteroendocrine peptide enhancing agent and/or a FXR agonist reduces or prevents intestinal inflammation (gastrointestinal enteritis), for example in a cancer patient undergoing radiation therapy. In some embodiments, an ASBTI described herein is administered in combination with a DPP-IV inhibitor. In some instances, inhibition of DPP-IV reduces the degradation of enteroendocrine peptide products (e.g. GLP-2) thereby prolonging the effect of GLP-2 in regeneration and/or healing of gastronintestinal tissue.

Provided herein are methods for preventing or treating pancreatic and other cancers in an individual comprising administration of a therapeutially effective amount of an ASBTI and/or an enteroendocrine peptide enhancing agent and/or a FXR agonist to an individual in need thereof. Other cancers include but are not limited to colon, breast, bowel and lung. In certain embodiments, provided herein is a method for preventing or treating pancreatic and other cancers cancer in an individual in need thereof comprising contacting the distal gastrointestinal tract, including distal ileum and/or the colon and/or the rectum, of the individual with a therapeutically effective amount of an ASBTI. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI and/or an enteroendocrine peptide enhancing agent and/or a FXR agonist described herein is administered to the individual orally, enterically or rectally. In some embodiments, an ASBTI described herein is delivered and/or released in the distal ileum of an individual. In some embodiments, an ASBTI and/or an enteroendocrine peptide enhancing agent and/or a FXR agonist described herein increases the concentration of bile acids in the distal ileum, the colon and/or the rectum and induces secretion of enteroendocrine peptide products from the L-cells of the gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the distal gastrointestinal tract. In some embodiments, elevated levels of enteroendocrine peptide products have a protective effect against pancreatic and other cancers. In some embodiments, prophylactic administration of an ASBTI reduces or prevents pancreatic and other cancers. In some embodiments, an ASBTI and/or an enteroendocrine peptide enhancing agent and/or a FXR agonist described herein is administered in combination with a DPP-IV inhibitor. In some instances, inhibition of DPP-IV reduces the degradation of enteroendocrine peptide products (e.g., GLP-1) thereby prolonging the effect of GLP-1 in prevention of pancreatic and other cancers. In some of such embodiments, an ASBTI described herein is administered to an individual with pancreatic and other cancers. In some of such embodiments, an ASBTI described herein is administered to an individual at risk of pancreatic and other cancers. In some of such embodiments, an ASBTI described herein is administered to an individual at risk of pancreatic and other cancers and having other metabolic disorders (e.g., diabetes).

In some embodiments, administration of an ASBT inhibitor and/or an enteroendocrine peptide enhancing agent and/or a FXR agonist described herein allows for treatment of a metabolic disorder without the side effects associated with conventional therapies (e.g., biguanides such as metformin, DDPIV inhibitors or the like) for metabolic disorders. In some embodiments, the administration of an ASBT inhibitor described herein reduces the incidence of gastrointestinal distress and/or lactic acidosis that is associated with biguanide therapy and/or treatment with a DPP-IV inhibitor. In some embodiments, the administration of an ASBT inhibitor described herein avoids weight gain that is associated with biguanide therapy and/or treatment with a DPP-IV inhibitor and/or an enteroendocrine peptide enhancing agent and/or a FXR agonist. Metabolic disorders that are amenable to treatment with compounds described herein include diabetes, insulin resistance, and metabolic syndrome.

In some embodiments, provided herein is a method of decreasing the dose of a biguanide or a DPP-IV inhibitor to treat a metabolic disorder in an individual in need thereof by replacing treatment with a biguanide (e.g., metformin) or a DPP-IV inhibitor with a treatment comprising administering a therapeutically effective amount of an ASBT inhibitor described herein to the individual. In some embodiments, provided herein is a method for treating a metabolic disease or disorder comprising administering to an individual in need thereof a therapeutically effective amount of an ASBT inhibitor described herein in combination with a reduced dose of a biguanide (e.g., metformin) or a DPP-IV inhibitor (e.g., sitagliptin) or an enteroendocrine peptide enhancing agent or a FXR agonist.

In some embodiments of any of the methods described herein, administration of an ASBT inhibitor and/or an enteroendocrine peptide enhancing agent and/or a FXR agonist described herein increases the level of GLP-1 in the blood and/or plasma of an individual by from about 1.1 times to about 30 times compared to the level of GLP-1 in the blood and/or plasma of the individual prior to administration of the ASBTI. In some embodiments of any of the methods described herein, administration of an ASBT inhibitor described herein increases the level of GLP-1 in the blood and/or plasma of an individual by from about 1.1 times to about 20 times compared to the level of GLP-1 in the blood and/or plasma of the individual prior to administration of the ASBTI. In some embodiments of any of the methods described herein, administration of an ASBT inhibitor and/or an enteroendocrine peptide enhancing agent and/or a FXR agonist described herein increases the level of GLP-1 in the blood and/or plasma of an individual by from about 1.5 times to about 10 times compared to the level of GLP-1 in the blood and/or plasma of the individual prior to administration of the ASBTI and/or an enteroendocrine peptide enhancing agent and/or a FXR agonist. In some embodiments of any of the methods described herein, administration of an ASBT inhibitor and/or an enteroendocrine peptide enhancing agent and/or a FXR agonist described herein increases the level of GLP-1 in the blood and/or plasma of an individual by from about 2 times to about 8 times compared to the level of GLP-1 in the blood and/or plasma of the individual prior to administration of the ASBTI and/or an enteroendocrine peptide enhancing agent and/or a FXR agonist. In some embodiments of any of the methods described herein, administration of an ASBT inhibitor and/or an enteroendocrine peptide enhancing agent and/or a FXR agonist described herein increases the level of GLP-1 in the blood and/or plasma of an individual by from about 2 times to about 6 times compared to the level of GLP-1 in the blood and/or plasma of the individual prior to administration of the ASBTI and/or an enteroendocrine peptide enhancing agent and/or a FXR agonist. In some instances, an increase in GLP-1 level of from about 2 times to about 3 times following the administration of an ASBT inhibitor and/or an enteroendocrine peptide enhancing agent and/or a FXR agonist described herein compared to the level of GLP-1 in the blood and/or plasma of the individual prior to administration of the ASBTI and/or an enteroendocrine peptide enhancing agent and/or a FXR agonist is associated with an anti-diabetic effect. In some instances, an increase in GLP-1 level of from about 3 times to about 8 times following the administration of an ASBT inhibitor and/or an enteroendocrine peptide enhancing agent and/or a FXR agonist described herein compared to the level of GLP-1 in the blood and/or plasma of the individual prior to administration of the ASBTI and/or an enteroendocrine peptide enhancing agent and/or a FXR agonist is associated with reduction in food intake and/or induction of satiety and/or weight loss.

In certain embodiments of any of the methods described herein, administration of an ASBTI and/or an enteroendocrine peptide enhancing agent and/or a FXR agonist reduces blood and/or plasma sugar levels by at least 20%, at least 30%, at least 40%, at least 50% at least 60%, at least 70% or at least 80% compared to blood and/or plasma sugar levels prior to administration of the ASBTI and/or an enteroendocrine peptide enhancing agent and/or a FXR agonist. In some embodiments of any of the methods described herein, administration of an ASBTI and/or an enteroendocrine peptide enhancing agent and/or a FXR agonist reduces blood and/or plasma sugar levels by at least 20% compared to blood and/or plasma sugar levels prior to administration of the ASBTI and/or an enteroendocrine peptide enhancing agent and/or a FXR agonist. In some embodiments of any of the methods described herein, administration of an ASBTI and/or an enteroendocrine peptide enhancing agent and/or a FXR agonist reduces blood and/or plasma sugar levels by at least 30% compared to blood and/or plasma sugar levels prior to administration of the ASBTI and/or an enteroendocrine peptide enhancing agent and/or a FXR agonist. In some embodiments of any of the methods described herein, administration of an ASBTI and/or an enteroendocrine peptide enhancing agent and/or a FXR agonist reduces blood and/or plasma sugar levels by at least 40% compared to blood and/or plasma sugar levels prior to administration of the ASBTI and/or an enteroendocrine peptide enhancing agent and/or a FXR agonist.

In some embodiments of any of the methods described herein, administration of an ASBTI reduces blood and/or plasma sugar levels for a longer period of time (e.g., at least 24 hours) compared to reduction in blood and/or plasma sugar levels upon administration of metformin or a DPP-IV inhibitor. In some embodiments of any of the methods described herein, administration of a single dose of an ASBTI sustains reduced blood and/or plasma sugar levels for at least 6 hours, at least 12 hours, at least 14 hours, at least 16 hours, at least 18 hours, at least 20 hours, at least 24 hours, at least 30 hours, at least 36 hours or at least 48 hours compared to reduction in blood and/or plasma sugar levels upon administration of a single dose of metformin or a DPP-IV inhibitor.

In some embodiments of any of the methods described herein, administration of an ASBTI and/or an enteroendocrine peptide enhancing agent and/or a FXR agonist results in higher levels of GLP-1 in blood and/or plasma of an individual compared to levels of GLP-1 in blood and/or plasma of a normal individual. In some embodiments of any of the methods described herein, administration of an ASBTI and/or an enteroendocrine peptide enhancing agent and/or a FXR agonist results in higher levels of GLP-1 in blood and/or plasma of an individual compared to levels of GLP-1 in blood and/or plasma of an individual that has been administered a DPP-IV inhibitor.

Also provided herein is a method for treating conditions that are ameliorated by increased secretion of L-cell enteroendocrine peptides comprising contacting the distal gastrointestinal tract, including distal ileum and/or the colon and/or the rectum, of an individual in need thereof with a therapeutically effective amount of any ASBTI compound and/or an enteroendocrine peptide enhancing agent and/or a FXR agonist described herein. L-cells are highly specialized gut enteroendocrine cells expressed along the gastrointestinal tract. The majority of L cells are located in the distal gastrointestinal tract, predominantly in the ileum and colon. The L-cells in the enteric endocrine system do not secrete their hormone continuously. Instead, they respond to changes in the environment within the lumen of the digestive tube, including changes in bile acid concentrations in the lumen of the digestive tube. The apical border of L-cells is in contact with the contents of the gastrointestinal lumen. Enteroendocrine peptides secreted by L-cells include GLP-1, GLP-2, PYY and oxyntomodulin. In certain instances, the methods described herein enhance L-cell secretion of one or more metabolic and/or enteroendocrine hormones. In some embodiments, the methods described herein enhance L-cell secretion of GLP-1, GLP-2, PYY or oxyntomodulin or combinations thereof. In certain embodiments, enhanced secretion of multiple enteroendocrine hormones (e.g., enhanced secretion of PYY and/or GLP-1 and/or GLP-2 and/or oxyntomodulin) is more effective for long term weight reduction compared to enhanced secretion of any single enteroendocrine hormone. In certain embodiments, enhanced secretion of multiple enteroendocrine hormones (e.g., enhanced secretion of PYY and/or GLP-1 and/or GLP-2 and/or oxyntomodulin) is more effective for long term improvement of peripheral insulin sensitivity compared to enhanced secretion of any single enteroendocrine hormone. Thus, advantageously, administration of a single therapeutic agent (e.g., any ASBTI described herein) has the potential to simultaneously impact multiple metabolic pathways (as opposed to administration of multiple therapeutic agents each of which impacts a different metabolic pathway).

In certain instances, contacting the distal ileum of an individual with an ASBTI (e.g., any ASBTI described herein) inhibits bile acid reuptake and increases the concentration of bile acids in the vicinity of L-cells in the distal ileum and/or colon and/or rectum, thereby reducing intra-enterocyte bile acids, enhancing the release of enteroendocrine peptides, and/or reducing necrosis or damage to ileal architecture. Without being limited to any particular theory, bile acids and/or bile salts interact with TGR5 receptors on the apical surface of L-cells to trigger the release of one or more enteroendocrine hormones into systemic circulation and/or the gastrointestinal lumen. Under physiological conditions, the concentration of enteroendocrine hormones varies in the gastrointestinal tract. By way of example, in the absence of an ASBTI, PYY concentrations in the upper small intestine are about ~5 pmol/g tissue, about ~80 pmol/g tissue in the distal ileum and ascending colon, ~200 pmol/g tissue in the sigmoid colon, and ~500 pmol/g tissue in the rectum. In some embodiments, the administration of one or more ASBTIs, according to methods described herein, increases concentrations of one or more enteroendocrine peptides in the gastrointestinal lumen and/or systemic circulation compared to physiological concentrations of the enteroendocrine peptides in the absence of an ASBTI.

Conditions that are mediated by L-cell enteroendocrine peptides include obesity, diabetes, congestive heart failure, ventricular dysfunction, toxic hypervolemia, polycystic ovary syndrome, inflamatory bowel disease, impaired bowel integrity, short bowel syndrome, gastritis, peptic ulcer, necrotizing enterocolitis, ulcerative colitis, celiac disease, intestinal celiac disease, gastroenteritis, radiation induced enteritis, chemotherapy induced enteritis, non-ulcer dyspepsia (NUD), gastrointestinal complications following bariatric surgery, gastric carcinogenesis, irritable bowel disease, gastroesophageal reflux disease (GERD), Barrett's esophagus or the like.

Administration of a compound described herein is achieved in any suitable manner including, by way of non-limiting example, by oral, enteric, parenteral (e.g., intravenous, subcutaneous, intramuscular), intranasal, buccal, topical, rectal, or transdermal administration routes. Any compound or composition described herein is administered in a method or formulation appropriate to treat a new born or an infant. Any compound or composition described herein is administered in an oral formulation (e.g., solid or liquid) to treat a new born or an infant. Any compound or composition described herein is administered prior to ingestion of food, with food or after ingestion of food.

In certain embodiments, a compound or a composition comprising a compound described herein is administered for prophylactic and/or therapeutic treatments. In therapeutic applications, the compositions are administered to an individual already suffering from a disease or condition, in an amount sufficient to cure or at least partially arrest the symptoms of the disease or condition. In various instances, amounts effective for this use depend on the severity and course of the disease or condition, previous therapy, the individual's health status, weight, and response to the drugs, and the judgment of the treating physician.

In prophylactic applications, compounds or compositions containing compounds described herein are administered to an individual susceptible to or otherwise at risk of a particular disease, disorder or condition. In certain embodiments of this use, the precise amounts of compound administered depend on the individual's state of health, weight, and the like. Furthermore, in some instances, when a compound or composition described herein is administered to an individual, effective amounts for this use depend on the severity and course of the disease, disorder or condition, previous therapy, the individual's health status and response to the drugs, and the judgment of the treating physician.

In certain instances, wherein following administration of a selected dose of a compound or composition described herein, an individual's condition does not improve, upon the doctor's discretion the administration of a compound or composition described herein is optionally administered chronically, that is, for an extended period of time, including throughout the duration of the individual's life in order to ameliorate or otherwise control or limit the symptoms of the individual's disorder, disease or condition.

In certain embodiments, an effective amount of a given agent varies depending upon one or more of a number of factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In some embodiments, doses administered include those up to the maximum tolerable dose. In some embodiments, doses administered include those up to the maximum tolerable dose by a newborn or an infant. In certain embodiments, about 0.001-5000 mg per day, from about 0.001-1500 mg per day, about 0.001 to about 100 mg/day, about 0.001 to about 50 mg/day, or about 0.001 to about 30 mg/day, or about 0.001 to about 10 mg/day of a compound described herein is administered. In various embodiments, the desired dose is conveniently presented in a single dose or in divided doses administered simultaneously (or over a short period of time) or at appropriate intervals, for example as two, three, four or more sub-doses per day. In various embodiments, a single dose is from about 0.001 mg/kg to about 500 mg/kg. In various embodiments, a single dose is from about 0.001, 0.01, 0.1, 1, or 10 mg/kg to about 10, 50, 100, or 250 mg/kg. In various embodiments, a single dose of an ASBTI is from about 0.001 mg/kg to about 100 mg/kg. In various embodiments, a single dose of an ASBTI is from about 0.001 mg/kg to about 50 mg/kg. In various embodiments, a single dose of an ASBTI is from about 0.001 mg/kg to about 10 mg/kg. In various embodiments, a single dose of an ASBTI is administered every 6 hours, every 12 hours, every 24 h hours, every 48 hours, every 72 hours, every 96 hours, every 5 days, every 6 days, or once a week. In some embodiments the total single dose of an ASBTI and/or an enteroendocrine peptide enhancing agent and/or a FXR agonist is in the range described above.

In the case wherein the patient's status does improve, upon the doctor's discretion an ASBTI is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%. In some embodiments the total single dose of an ASBTI and/or an enteroendocrine peptide enhancing agent and/or a FXR agonist is in the range described above.

Once improvement of the patient's conditions has occurred (e.g., weight loss), a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms (e.g., weight gain).

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. In certain embodiments, data obtained from cell culture assays and animal studies are used in formulating a range of dosage for use in human. In specific embodiments, the dosage of compounds described herein lies within a range of circulating concentrations that include the $ED_{50}$ with minimal toxicity. The dosage optionally varies within this range depending upon the dosage form employed and the route of administration utilized.

In some embodiments, the systemic exposure of a therapeutically effective amount of any non-systemic ASBTI described herein (e.g., an ASBTI that comprises a group L-K) is reduced when compared to the systemic exposure of a therapeutically effective amount of any systemically absorbed ASBTI (e.g. Compounds 100A, 100C). In some embodiments, the AUC of a therapeutically effective amount of any non-systemic ASBTI described herein (e.g., an ASBTI that comprises a group L-K) is at least 10%, at least 20%, at least 30%, at least 40%, at least 50%, at least 60%, at least 70%, at least 80% or at least 90% reduced when compared to the AUC of any systemically absorbed ASBTI (e.g. Compounds 100A, 100C).

In some embodiments, the systemic exposure of a therapeutically effective amount of a compound of Formula I that is not systemically absorbed (e.g., a compound of Formula I that comprises a group L-K) is reduced when compared to the systemic exposure of a therapeutically effective amount of Compound 100A. In some embodiments, the AUC of a therapeutically effective amount of a compound of Formula I that is not systemically absorbed (e.g., a compound of Formula I that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula I that is not systemically absorbed (e.g., a compound of Formula I that comprises a group L-K) is about 50% reduced when compared to the AUC of a therapeutically effective amount of Compound 100A. In other embodiments, the AUC of a therapeutically effective amount of a compound of Formula I that is not systemically absorbed (e.g., a compound of Formula I that comprises a group L-K) is about 75% reduced when compared to the AUC of a therapeutically effective amount of Compound 100A.

In some embodiments, the systemic exposure of a therapeutically effective amount of a compound of Formula II that is not systemically absorbed (e.g., a compound of Formula II that comprises a group L-K) is reduced when compared to the systemic exposure of a therapeutically effective amount of Compound 100A. In some embodiments, the AUC of a therapeutically effective amount of a compound of Formula II that is not systemically absorbed (e.g., a compound of Formula II that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula II that is not systemically absorbed (e.g., a compound of Formula II that comprises a group L-K) is about 50% reduced when compared to the AUC of a therapeutically effective amount of Compound 100A. In other embodiments, the AUC of a therapeutically effective amount of a compound of Formula II that is not systemically absorbed (e.g., a compound of Formula II that comprises a group L-K) is about 75% reduced when compared to the AUC of a therapeutically effective amount of Compound 100A.

In some embodiments, the systemic exposure of a therapeutically effective amount of a compound of Formula III, IIIA, IIIB or IIIC is reduced when compared to the systemic exposure of a therapeutically effective amount of Compound 100C. In some embodiments, the AUC of a therapeutically effective amount of a compound of Formula III, IIIA, IIIB or IIIC is about 10%, about 20%, about 30%, about 40%, about 50%, about 60%, about 70%, about 80% or about 90% reduced when compared to the AUC of a therapeutically effective amount of Compound 100C. In some embodiments, the AUC of a therapeutically effective amount of a compound of Formula III, IIIA, IIIB or IIIC is about 50% reduced when compared to the AUC of a therapeutically effective amount of Compound 100C. In other embodiments, the AUC of a therapeutically effective amount of a compound of Formula III, IIIA, IIIB or IIIC is about 75% reduced when compared to the AUC of a therapeutically effective amount of Compound 100C.

In some embodiments, the systemic exposure of a therapeutically effective amount of a compound of Formula IV that is not systemically absorbed (e.g., a compound of Formula IV that comprises a group L-K) is reduced when compared to the systemic exposure of a therapeutically effective amount of Compound 100A. In some embodiments, the AUC of a therapeutically effective amount of a compound of Formula IV that is not systemically absorbed (e.g., a compound of Formula I that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula IV that is not systemically absorbed (e.g., a compound of Formula IV that comprises a group L-K) is about 50% reduced when compared to the AUC of a therapeutically effective amount of Compound 100A. In other embodiments, the AUC of a therapeutically effective amount of a compound of Formula IV that is not systemically absorbed (e.g., a compound of Formula IV that comprises a group L-K) is about 75% reduced when compared to the AUC of a therapeutically effective amount of Compound 100A.

In some embodiments, the systemic exposure of a therapeutically effective amount of a compound of Formula V that is not systemically absorbed (e.g., a compound of Formula V that comprises a group L-K) is reduced when compared to the systemic exposure of a therapeutically effective amount of Compound 100A. In some embodiments, the AUC of a therapeutically effective amount of a compound of Formula V that is not systemically absorbed (e.g., a compound of Formula V that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula I that is not systemically absorbed (e.g., a compound of Formula V that comprises a group L-K) is about 50% reduced when compared to the AUC of a therapeutically effective amount of Compound 100A. In other embodiments, the AUC of a therapeutically effective amount of a compound of Formula I that is not systemically absorbed (e.g., a compound of Formula V that comprises a group L-K) is about 75% reduced when compared to the AUC of a therapeutically effective amount of Compound 100A.

In some embodiments, the systemic exposure of a therapeutically effective amount of a compound of Formula VI or VID that is not systemically absorbed (e.g., a compound of Formula VI or VID that comprises a group L-K) is reduced when compared to the systemic exposure of a therapeutically effective amount of Compound 100A. In some embodiments, the AUC of a therapeutically effective amount of a compound of Formula VI or VID that is not systemically absorbed (e.g., a compound of Formula VI or VID that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula VI or VID that is not systemically absorbed (e.g., a compound of Formula VI or VID that comprises a group L-K) is about 50% reduced when compared to the AUC of a therapeutically effective amount of Compound 100A. In other embodiments, the AUC of a therapeutically effective amount of a compound of Formula I that is not systemically absorbed (e.g., a compound of Formula VI or VID that comprises a group L-K) is about 75% reduced when compared to the AUC of a therapeutically effective amount of Compound 100A.

In certain embodiments, the Cmax of a therapeutically effective amount of any non-systemic ASBTI described herein (e.g., an ASBTI that comprises a group L-K) is at least 10%, at least 20%, at least 30%, at least 40%, at least 50%, at least 60%, at least 70%, at least 80% or at least 90% reduced when compared to the Cmax of any systemically absorbed ASBTI (e.g. Compound 100A).

By way of example, the Cmax of a therapeutically effective amount of a compound of Formula III, IIIA, IIIB or IIIC is about 10%, about 20%, about 30%, about 40%, about 50%, about 60%, about 70%, about 80% or about 90% reduced when compared to the Cmax of a therapeutically effective amount of Compound 100C. In some embodiments, the Cmax of a therapeutically effective amount of a compound of Formula III, IIIA, IIIB or IIIC is about 25% reduced when compared to the Cmax of a therapeutically effective amount of Compound 100C. In certain embodiments, the Cmax of a therapeutically effective amount of a compound of III, IIIA or IIIB is about 50% reduced when compared to the Cmax of a therapeutically effective amount of Compound 100C. In other embodiments, the Cmax of a therapeutically effective amount of a compound of Formula III, IIIA, IIIB or IIIC is about 75% reduced when compared to the Cmax of a therapeutically effective amount of Compound 100C.

In certain embodiments, provided herein is a method of treating a metabolic disease or a condition associated with a metabolic disease with an ASBTI and/or enteroendocrine peptide secretion enhancing agent and an optional carrier. In some embodiments, provided herein are methods of treating a metabolic disease comprising administering any composition as described herein. In some embodiments, provided herein is the use of any of the pharmaceutical compositions described herein in preparing a medicament for treating a metabolic disease. In specific embodiments, the metabolic disease is selected from, by way of non-limiting example, obesity, diabetes, necrotizing enterocolitis, gastritis, ulcerative colitis, inflammatory bowel disease, irritable bowel syndrome, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, gastric carcinogenesis following gastric or bowel resection, and a combination thereof. In some embodiments, provided herein is a method of treating a condition associated with a metabolic disease. In certain embodiments, provided herein is the use of any of the pharmaceutical compositions described herein in preparing a medicament for treating a condition associated with a metabolic disease. In some embodiments, conditions associated with a metabolic disease are selected from, by way of non-limiting example, necrosis or damage of ileal architecture or ileal cells, weight gain, food intake, appetite, impaired glucose tolerance, a glucose metabolic disorder, and insulin resistance. In certain embodiments, conditions associated with a metabolic disease are selected from, by way of non-limiting example, acute coronary syndrome, hibernating myocardium, ventricular dysfunction, cardiac risk, post myocardial infarction mortality, post-surgical catabolism, sepsis-related catabolism, critical illness-related catabolism, post-surgical mortality, sepsis-related mortality, critical illness-related mortality, critical illness-polyneuropathy, congestive heart failure, toxic hypervolemia, renal failure, ischemia-reperfusion injury, mortality and morbitity from stroke, mortality and morbitity from neurodegenerative disease, neuropathy, inflammatory bowel disease, bowel mucosal injury, impaired bowel integrity, irritable bowel disease, osteopenia, and a bone fracture or a bone disorder. It is to be understood that the term, "treating" includes controlling, suppressing, inhibiting, reducing the symptoms of and/or preventing.

Furthermore, in certain embodiments, provided herein is a method of decreasing intraenterocyte bile acids, decreasing necrosis and/or damage to ileal architecture, decreasing appetite, decreasing food intake, and/or decreasing appetite by administering a therapeutically effective amount of any enteroendocrine peptide secretion enhancing agent or composition described herein. In some embodiments, provided herein is an enteroendocrine peptide secretion enhancing agent or a composition used for preparing a medicament for decreasing appetite, decreasing food intake, and/or decreasing appetite.

In some embodiments, provided herein is a method of treating obesity, diabetes, or an inflammatory intestinal condition in an individual comprising delivering to ileal, colon, and/or rectal L-cells of the individual a therapeutically effective amount of any ASBTI and/or enteroendocrine peptide secretion enhancing agent described herein. In certain embodiments, the therapeutically effective amount of enteroendocrine peptide secretion enhancing agent stimulates or activates the L-cells to which the enteroendocrine peptide secretion enhancing agent is administered.

FIG. 11 illustrates the reduction of food intake in response to administration of anenteroendocrine peptide secretion enhancing agent. FIG. 11 illustrates that with increased amounts of enteroendocrine peptide secretion enhancing agent administered to the distal gastrointestinal tract, decreased amounts of calories were consumed by human subjects.

In some embodiments, provided herein is a method of treating diabetes in an individual comprising delivering to ileal, colon, and/or rectal L-cells of an individual in need thereof a therapeutically effective amount of any enteroendocrine peptide secretion enhancing agent described herein. In certain embodiments, provided herein is a method of treating diabetes in an individual comprising delivering to ileum, colon, and/or rectum of an individual in need thereof a therapeutically effective amount of any enteroendocrine peptide secretion enhancing agent described herein. In some embodiments, provided herein is a method of elevating insulin levels in an individual comprising delivering to ileum, colon, and/or rectum of an individual in need thereof (e.g., a diabetic individual) a therapeutically effective amount of any enteroendocrine peptide secretion enhancing agent described herein. In certain embodiments, provided herein is a method of reducing glucose levels in an individual comprising delivering to ileum, colon, and/or rectum of an individual in need thereof (e.g., a diabetic individual) a therapeutically effective amount of any enteroendocrine peptide secretion enhancing agent described herein. In some embodiments, the therapeutically effective amount of enteroendocrine peptide secretion enhancing agent stimulates or activates the L-cells of the ileum, colon, and/or rectum to which the enteroendocrine peptide secretion enhancing agent is administered.

FIG. 12 illustrates the insulin response to administration of an enteroendocrine peptide secretion enhancing agent. FIG. 12 illustrates that with increased amounts of enteroendocrine peptide secretion enhancing agent administered to the distal gastrointestinal tract, human diabetics demonstrated increased levels of insulin. FIG. 13 illustrates the incremental integrated response of insulin levels to administration of an enteroendocrine peptide secretion enhancing agent.

Figure 14:
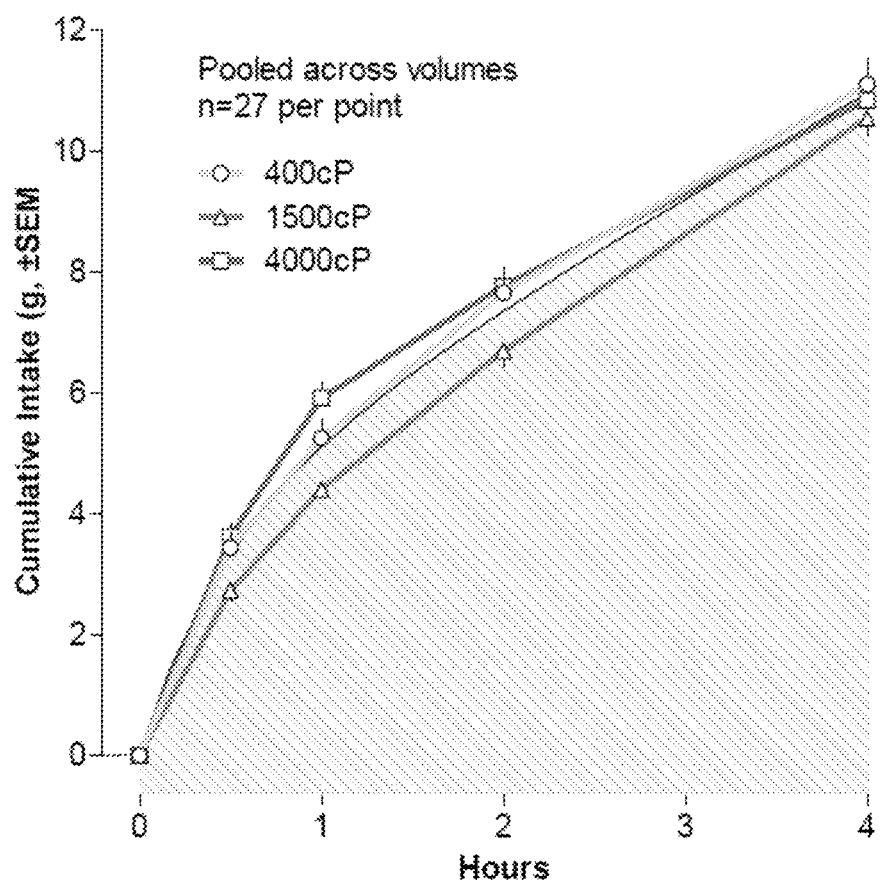
FIG. 14 illustrates the affect of the viscosity of a formulation described herein on the food intake of a subject.
Figure 15:
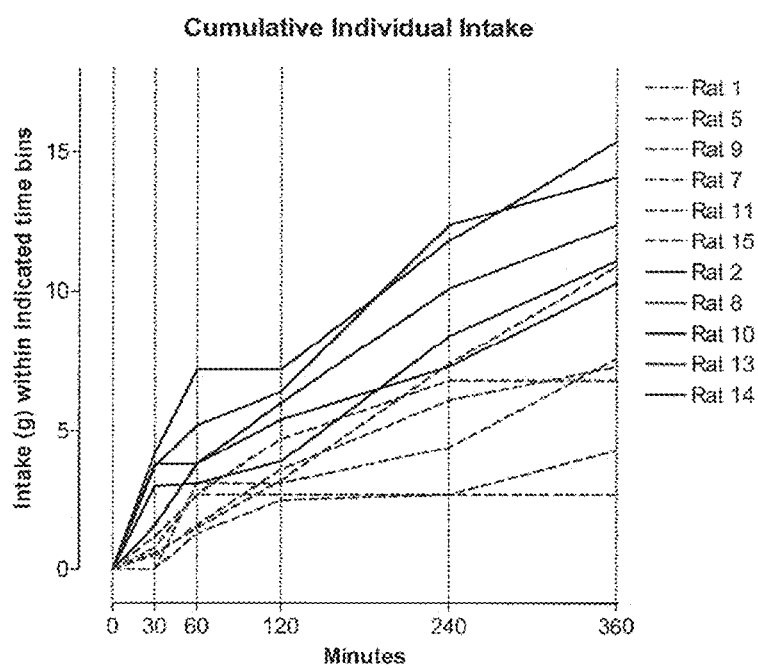
FIG. 15 illustrates the cumulative food intake of rats with (dotted lines) and without (solid lines) rectal administration of taurocholate.

FIG. 14 illustrates the glucose response to administration of anenteroendocrine peptide secretion enhancing agent. FIG. 14 illustrates that with increased amounts of enteroendocrine peptide secretion enhancing agent administered to the distal gastrointestinal tract, human diabetics demonstrated decreased levels of glucose. FIG. 15 illustrates the incremental integrated response of glucose levels to administration of an enteroendocrine peptide secretion enhancing agent.

In some embodiments, provided herein is a method of elevating GLP-1, PYY, oxyntomodulin, insulin, or a combination thereof levels in an individual comprising delivering to ileum, colon, and/or rectum of an individual in need thereof (e.g., a diabetic individual) a therapeutically effective amount of any enteroendocrine peptide secretion enhancing agent described herein. In some embodiments, provided herein is a method of elevating GLP-1, PYY, oxyntomodulin, and insulin levels in an individual comprising delivering to ileum, colon, and/or rectum of an individual in need thereof (e.g., a diabetic individual) a therapeutically effective amount of any enteroendocrine peptide secretion enhancing agent described herein.

In some embodiments, provided herein is a method of preventing or treating pancreatic or other cancers in an individual comprising delivering to ileal, colon, and/or rectal L-cells of an individual in need thereof a therapeutically effective amount of any enteroendocrine peptide secretion enhancing agent described herein. In certain embodiments, provided herein is a method of preventing or treating pancreatic or other cancers in an individual comprising delivering to ileum, colon, and/or rectum of an individual in need thereof a therapeutically effective amount of any enteroendocrine peptide secretion enhancing agent described herein. In some embodiments, the therapeutically effective amount of enteroendocrine peptide secretion enhancing agent stimulates or activates the L-cells of the ileum, colon, and/or rectum to which the enteroendocrine peptide secretion enhancing agent is administered. Other cancers include but are not limited to breast, rectal, colon and lung cancers.

In certain embodiments, the pharmaceutical composition administered includes a therapeutically effective amount of an enteroendocrine peptide secretion enhancing agent, an absorption inhibitor and a carrier (e.g., an orally suitable carrier or a rectally suitable carrier, depending on the mode of intended administration). In certain embodiments, the pharmaceutical composition used or administered comprises an enteroendocrine peptide secretion enhancing agent, an absorption inhibitor, a carrier, and one or more of a cholesterol absorption inhibitor, an enteroendocrine peptide, a peptidase inhibitor, a spreading agent, and a wetting agent.

In a specific embodiment, the pharmaceutical composition used to prepare a rectal dosage form or administered rectally comprises an enteroendocrine peptide secretion enhancing agent, an absorption inhibitor, a rectally suitable carrier, an optional cholesterol absorption inhibitor, an optional enteroendocrine peptide, an optional peptidase inhibitor, an optional spreading agent, and an optional wetting agent. In certain embodiments, rectally administered compositions evokes an anorectal response. In specific embodiments, the anorectal response is an increase in secretion of one or more enteroendocrine by cells (e.g., L-cells) in the colon and/or rectum (e.g., in the epithelial layer of the colon and/or rectum). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

In another specific embodiment, the pharmaceutical composition used to prepare an oral dosage form or administered orally comprises an enteroendocrine peptide secretion enhancing agent, an absorption inhibitor, an orally suitable carrier, an optional cholesterol absorption inhibitor, an optional enteroendocrine peptide, an optional peptidase inhibitor, an optional spreading agent, and an optional wetting agent. In certain embodiments, the orally administered compositions evokes an anorectal response. In specific embodiments, the anorectal response is an increase in secretion of one or more enteroendocrine by cells in the colon and/or rectum (e.g., in L-cells the epithelial layer of the colon and/or rectum). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

Provided herein are methods for prevention and/or treatment of congestive heart failure, ventricular dysfunction, toxic hypervolemia, polycystic ovary syndrome, inflammatory bowel disease, impaired bowel integrity, short bowel syndrome, gastritis, peptic ulcer, or irritable bowel disease comprising contacting the distal gastrointestinal tract (e.g., colon and/or rectum) of an individual in need thereof with an enteroendocrine peptide secretion enhancing agent and an optional absorption inhibitor. In some embodiments, the methods further comprise administration of a DPP-IV inhibitor, an enteroendocrine peptide enhancing agent, a biguanide, an incretin mimetic, or GLP-1 or an analog thereof. Provided herein are methods for prevention and/or treatment of radiation enteritis comprising contacting the distal gastrointestinal tract (e.g., colon and/or rectum) of an individual in need thereof with an enteroendocrine peptide secretion enhancing agent and an optional absorption inhibitor. In some embodiments, the methods further comprise administration of a DPP-IV inhibitor, an enteroendocrine peptide enhancing agent, a biguanide, an incretin mimetic, or GLP-1 or an analog thereof. Provided in certain embodiments herein is a method of promoting regeneration of the gastrointestinal tract by administering to the distal gastrointestinal tract (e.g., colon and/or rectum) of the individual, a therapeutically effective amount of an enteroendocrine peptide secretion enhancing agent and an optional absorption inhibitor. In some embodiments, the methods further comprise administration of a DPP-IV inhibitor, a TGR5 agonist, a biguanide, an incretin mimetic, or GLP-2 or an analog thereof. In some instances, radiation enteritis, or an inflammation of the intestine, is not only maj or complication of cancer radiation therapy, but occur after any accidental and intentional radiation exposure. In certain instances, GLP-2 secreted from L-cells (e.g., by administration thereto an enteroendocrine peptide secretion enhancing agent described herein) plays important role in regeneration of GI tract injuries.

Routes of Administration and Dosage

In some embodiments, the compositions described herein and the compositions administered in the methods described herein are formulated to enhance enteroendocrine peptide secretion and to evoke an anorectal response. In certain embodiments, the compositions described herein are formulated for rectal or oral administration. In some embodiments, such formulations are administered rectally or orally, respectively. In some embodiments, the compositions described herein are combined with a device for local delivery of the compositions to the rectum and/or colon (sigmoid colon, transverse colon, or ascending colon). In certain embodiments, for rectal administration the composition described herein are formulated as enemas, rectal gels, rectal foams, rectal aerosols, suppositories, jelly suppositories, or retention enemas. In some embodiments, for oral administration the compositions described herein are formulated for oral administration and enteric delivery to the colon.

In certain embodiments, the compositions or methods described herein are non-systemic. In some embodiments, compositions described herein deliver the enteroendocrine peptide secretion enhancing agent to the distal ileum, colon, and/or rectum and not systemically (e.g., a substantial portion of the enteroendocrine peptide secretion enhancing agent is not systemically absorbed). In some embodiments, oral compositions described herein deliver the enteroendocrine peptide secretion enhancing agent to the distal ileum, colon, and/or rectum and not systemically (e.g., a substantial portion of the enteroendocrine peptide secretion enhancing agent is not systemically absorbed). In some embodiments, rectal compositions described herein deliver the enteroendocrine peptide secretion enhancing agent to the distal ileum, colon, and/or rectum and not systemically (e.g., a substantial portion of the enteroendocrine peptide secretion enhancing agent is not systemically absorbed). In certain embodiments, non-systemic compositions described herein deliver less than 90% w/w of the enteroendocrine peptide secretion enhancing agent systemically. In certain embodiments, non-systemic compositions described herein deliver less than 80% w/w of the enteroendocrine peptide secretion enhancing agent systemically. In certain embodiments, non-systemic compositions described herein deliver less than 70% w/w of the enteroendocrine peptide secretion enhancing agent systemically. In certain embodiments, non-systemic compositions described herein deliver less than 60% w/w of the enteroendocrine peptide secretion enhancing agent systemically. In certain embodiments, non-systemic compositions described herein deliver less than 50% w/w of the enteroendocrine peptide secretion enhancing agent systemically. In certain embodiments, non-systemic compositions described herein deliver less than 40% w/w of the enteroendocrine peptide secretion enhancing agent systemically. In certain embodiments, non-systemic compositions described herein deliver less than 30% w/w of the enteroendocrine peptide secretion enhancing agent systemically. In certain embodiments, non-systemic compositions described herein deliver less than 25% w/w of the enteroendocrine peptide secretion enhancing agent systemically. In certain embodiments, non-systemic compositions described herein deliver less than 20% w/w of the enteroendocrine peptide secretion enhancing agent systemically. In certain embodiments, non-systemic compositions described herein deliver less than 15% w/w of the enteroendocrine peptide secretion enhancing agent systemically. In certain embodiments, non-systemic compositions described herein deliver less than 10% w/w of the enteroendocrine peptide secretion enhancing agent systemically. In certain embodiments, non-systemic compositions described herein deliver less than 5% w/w of the enteroendocrine peptide secretion enhancing agent systemically. In some embodiments, systemic absorption is determined in any suitable manner, including the total circulating amount, the amount cleared after administration, or the like.

In certain embodiments, the compositions and/or formulations described herein are administered at least once a day. In certain embodiments, the formulations containing the enteroendocrine peptide secretion enhancing agents are administered at least twice a day, while in other embodiments the formulations containing the enteroendocrine peptide secretion enhancing agents are administered at least three times a day. In certain embodiments, the formulations containing the enteroendocrine peptide secretion enhancing agents are administered up to five times a day. It is to be understood that in certain embodiments, the dosage regimen of composition containing the enteroendocrine peptide secretion enhancing agents described herein to is determined by considering various factors such as the patient's age, sex, and diet.

The concentration of the enteroendocrine peptide secretion enhancing agents administered in the formulations described herein ranges from about 1 mM to about 1 M. In certain embodiments the concentration of the enteroendocrine peptide secretion enhancing agents administered in the formulations described herein ranges from about 1 mM to about 750 mM. In certain embodiments the concentration of the enteroendocrine peptide secretion enhancing agents administered in the formulations described herein ranges from about 1 mM to about 500 mM. In certain embodiments the concentration of the enteroendocrine peptide secretion enhancing agents administered in the formulations described herein ranges from about 5 mM to about 500 mM. In certain embodiments the concentration of the enteroendocrine peptide secretion enhancing agents administered in the formulations described herein ranges from about 10 mM to about 500 mM. In certain embodiments the concentration of the enteroendocrine peptide secretion enhancing agents administered in the formulations described herein ranges from about 25 mM to about 500 mM. In certain embodiments the concentration of the enteroendocrine peptide secretion enhancing agents administered in the formulations described herein ranges from about 50 mM to about 500 mM. In certain embodiments the concentration of the enteroendocrine peptide secretion enhancing agents administered in the formulations described herein ranges from about 100 mM to about 500 mM. In certain embodiments the concentration of the enteroendocrine peptide secretion enhancing agents administered in the formulations described herein ranges from about 200 mM to about 500 mM.

In certain embodiments, any composition described herein comprises a therapeutically effective amount (e.g., to treat obesity and/or diabetes) of an enteroendocrine peptide secretion enhancing agent (e.g., bile acid). In some embodiments, compositions described herein comprise or methods described herein comprise administering about 0.01 mg to about 10 g of an enteroendocrine peptide secretion enhancing agent (e.g., bile acid). In certain embodiments, a composition described herein comprises or a method described herein comprises administering about 0.1 mg to about 500 mg of an enteroendocrine peptide secretion enhancing agent (e.g., bile acid). In certain embodiments, a composition described herein comprises or a method described herein comprises administering about 0.1 mg to about 100 mg of an enteroendocrine peptide secretion enhancing agent (e.g., bile acid). In certain embodiments, a composition described herein comprises or a method described herein comprises administering about 0.1 mg to about 50 mg of an enteroendocrine peptide secretion enhancing agent (e.g., bile acid). In certain embodiments, a composition described herein comprises or a method described herein comprises administering about 0.1 mg to about 10 mg of an enteroendocrine peptide secretion enhancing agent (e.g., bile acid). In certain embodiments, a composition described herein comprises or a method described herein comprises administering about 0.5 mg to about 10 mg of an enteroendocrine peptide secretion enhancing agent (e.g., bile acid). In some embodiments, compositions described herein comprise or methods described herein comprise administering about 0.1 mmol to about 1 mol of an enteroendocrine peptide secretion enhancing agent (e.g., bile acid). In certain embodiments, a composition described herein comprises or a method described herein comprises administering about 0.01 mmol to about 500 mmol of an enteroendocrine peptide secretion enhancing agent (e.g., bile acid). In certain embodiments, a composition described herein comprises or a method described herein comprises administering about 0.1 mmol to about 100 mmol of an enteroendocrine peptide secretion enhancing agent (e.g., bile acid). In certain embodiments, a composition described herein comprises or a method described herein comprises administering about 0.5 mmol to about 30 mmol of an enteroendocrine peptide secretion enhancing agent (e.g., bile acid). In certain embodiments, a composition described herein comprises or a method described herein comprises administering about 0.5 mmol to about 20 mmol of an enteroendocrine peptide secretion enhancing agent (e.g., bile acid). In certain embodiments, a composition described herein comprises or a method described herein comprises administering about 1 mmol to about 10 mmol of an enteroendocrine peptide secretion enhancing agent (e.g., bile acid). In certain embodiments, a composition described herein comprises or a method described herein comprises administering about 0.01 mmol to about 5 mmol of an enteroendocrine peptide secretion enhancing agent (e.g., bile acid). In certain embodiments, a composition described herein comprises or a method described herein comprises administering about 0.1 mmol to about 1 mmol of an enteroendocrine peptide secretion enhancing agent (e.g., bile acid). In various embodiments, certain enteroendocrine peptide secretion enhancing agents (e.g., bile acids) have different potencies and dosing is optionally adjusted accordingly. For example, the investigation in TGR5-transfected CHO cells of TGR5 agonist potency of natural bile acids indicates the following rank of potency: Lithocholic acid (LCA)>deoxycholic acid (DCA)>murocholic acid (Muro-CA)>lagodeoxycholic acid (lago-DCA)>chenodeoxycholic (CDCA)>cholic acid (CA)>hyodeoxycholic acid (HDCA>ursodeoxycholic acid (UDCA); and assays on TGR5-transfected CHO cells demonstrate that $EC_{50}$ (in µM) for UDCA was 36.4, TauroCA (TCA) 4.95 and LCA 0.58.

In certain embodiments, by targeting the distal gastrointestinal tract (e.g., distal ileum, colon, and/or rectum), compositions and methods described herein provide efficacy (e.g., in reducing food intake, treating obesity, treating diabetes) with a reduced dose of enteroendocrine peptide secretion enhancing agent (e.g., as compared to an oral dose that does not target the distal gastrointestinal tract).

Rectal Administration Formulations

The pharmaceutical compositions described herein for the non-systemic delivery of enteroendocrine peptide secretion enhancing agents to the rectum and/or colon are formulated for rectal administration as rectal enemas, rectal foams, rectal gels, and rectal suppositories. The components of such formulations are described herein. It is to be understood that as used herein, pharmaceutical compositions and compositions are or comprise the formulations as described herein.

Rectal Enemas

In certain embodiments, the compositions described herein are formulated as rectal enema formulations for non-systemic delivery of enteroendocrine peptide secretion enhancing agents. In certain embodiments, such rectal enemas are formulated as a solution, aqueous suspension or emulsion. In some embodiments, solution enemas contain a carrier vehicle, an enteroendocrine peptide secretion enhancing agent, an absorption inhibitor (e.g., of the enteroendocrine peptide secretion enhancing agent across the rectal or colonic mucosa), and one or more of the following: a solubilizer, a preservative, a chelating agent, a buffer for pH regulation, and a thickener. In certain embodiments, rectal enemas are formulated as an emulsion or aqueous suspension containing a carrier vehicle, at least one enteroendocrine peptide secretion enhancing agent, at least one agent for inhibiting absorption of the enteroendocrine peptide secretion enhancing agent across the rectal or colonic mucosa, and one or more of the following: a preservative, a chelating agent, a buffer for pH regulation, a solubilizer, a thickener, and an emulsifier/surfactant.

In certain embodiments, rectal enemas are formulated such that a enteroendocrine peptide secretion enhancing agent is dissolved or dispersed in a suitable flowable carrier vehicle, including but not limited to water, alcohol or an aqueous-alcoholic mixture. In certain embodiments, the carrier vehicle is thickened with natural or synthetic thickeners. In further embodiments the rectal enema formulations also contain a lubricant.

In some embodiments, unit dosages of such enema formulations are administered from prefilled bags or syringes.

In certain embodiments, the volume of enema administered using such rectal enema formulations is a volume suitable for achieving a desired result, e.g., from about 10 mL to about 1000 mL. In certain embodiments, the volume of enema administered using such rectal enema formulations is from about 10 mL to about 900 mL. In certain embodiments, the volume of enema administered using such rectal enema formulations is from about 10 mL to about 800 mL. In certain embodiments, the volume of enema administered using such rectal enema formulations is from about 10 mL to about 700 mL. In certain embodiments, the volume of enema administered using such rectal enema formulations is from about 10 mL to about 600 mL. In certain embodiments, the volume of enema administered using such rectal enema formulations is from about 10 mL to about 500 mL. In certain embodiments, the volume of enema administered using such rectal enema formulations is from about 10 mL to about 400 mL. In certain embodiments, the volume of enema administered using such rectal enema formulations is from about 10 mL to about 300 mL. In certain embodiments, the volume of enema administered using such rectal enema formulations is from about 10 mL to about 200 mL. In certain embodiments, the volume of enema administered using such rectal enema formulations is from about 10 mL to about 100 mL. In some embodiments, such enemas may have a volume of less than 1 L, less than 900 mL, less than 700 mL, less than 600 mL, less than 500 mL, less than 250 mL, less than 100 mL, less than 30 mL, less than 10 mL, less than 3 mL, or the like.

Rectal Foams

In certain instances, leakage is a problem associated with enemas. As such, it is often desirable or necessary for patients to lie down during administration of enemas. In some embodiments, rectal administration using foams overcomes the problem of leakage from the rectum following administration.

In certain embodiments, the pharmaceutical compositions are formulated as rectal foams. In some embodiments, rectal foams are used for the rectal administration and for local or non-systemic delivery of enteroendocrine peptide secretion enhancing agents to the rectum and/or colon. Such rectal foams formulations contain an enteroendocrine peptide secretion enhancing agent dissolved or suspended in a liquid carrier vehicle, an absorption inhibitor (e.g., of the enteroendocrine peptide secretion enhancing agent across the rectal or colonic mucosa), a surfactant/emulsifier with foaming properties and a propellant (e.g., a propellant gas). In certain embodiments, rectal foam formulations also contain one or more of the following: a suspending/solubilizing agent, a thickener, a preservative, a chelating agent, a buffer, an antioxidant, a tonicity modifiers, and a spreading agent. In certain embodiments, surfactants/emulsifiers include, by way of non-limiting example, non-ionic surfactants, anionic surfactants, cationic surfactants, and combinations thereof.

In certain embodiments, rectal foam formulations are filled in pressurized containers prior to rectal administration. In certain embodiments the pressurized container is a can. In certain embodiments, propellants used herein include, by way of non-limiting example, hydrocarbons (such as isobutane, N-butane or propane), fluorocarbons (e.g. dichlorodifluoromethane and dichlorotetrafluoroethane), chlorofluorocarbons, dimethyl ether, hydrofluorocarbons, compressed gases, freon (such as freon 12, freon 114), hydrochlorofluorocarbons, hydrofluorocarbons or mixtures thereof.

In some embodiments, the maximum amount of propellant used is determined by its miscibility with other components in the composition to form a mixture, such as a homogeneous mixture. In certain embodiments, the minimal level of propellant used in the composition is determined by the desired foam characteristics, and its ability to substantially or completely evacuate the container.

In some embodiments, the propellant concentration used in such rectal foam formulations is about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 50%, 55% to about 60% (w/w).

In certain embodiments, rectal foams are formed upon rectal administration, wherein the dispensing valve of the can allows rapid expansion of the propellant, triggering the foaming action of the surfactant and resulting foam forms within the rectum and colon. In other embodiments, the rectal foams used for rectal administration of the compositions described herein are formed within the dispensing container prior to rectal administration.

The distance the foam can reach within the colon and rectum is controlled by controlling the foam propelling properties by varying the type and quantity of propellant used. The volume of foam administered using such rectal foam formulations is from about 10 mL to about 1000 mL. In certain embodiments, the volume of a composition described herein (e.g., a foam) described herein or used in a method described herein (e.g., a foam, enema, or gel) is from about 10 mL to about 900 mL. In certain embodiments, the volume of a composition described herein (e.g., a foam) described herein or used in a method described herein (e.g., a foam, enema, or gel) is from about 10 mL to about 800 mL. In certain embodiments, the volume of a composition described herein (e.g., a foam) described herein or used in a method described herein (e.g., a foam, enema, or gel) is from about 10 mL to about 700 mL. In certain embodiments, the volume of a composition described herein (e.g., a foam) described herein or used in a method described herein (e.g., a foam, enema, or gel) is from about 10 mL to about 600 mL. In certain embodiments, the volume of a composition described herein (e.g., a foam) described herein or used in a method described herein (e.g., a foam, enema, or gel) is from about 10 mL to about 500 mL. In certain embodiments, the volume of a composition described herein (e.g., a foam) described herein or used in a method described herein (e.g., a foam, enema, or gel) is from about 10 mL to about 400 mL. In certain embodiments, the volume of a composition described herein (e.g., a foam) described herein or used in a method described herein (e.g., a foam, enema, or gel) is from about 10 mL to about 300 mL. In certain embodiments, the volume of a composition described herein (e.g., a foam) described herein or used in a method described herein (e.g., a foam, enema, or gel) is from about 10 mL to about 200 mL. In certain embodiments, the volume of a composition described herein (e.g., a foam) described herein or used in a method described herein (e.g., a foam, enema, or gel) is from about 10 mL to about 100 mL. In specific embodiments, the volume of a composition described herein (e.g., a foam) described herein or used in a method described herein (e.g., a foam, enema, or gel) is about 20 mL to about 60 mL, about 20 mL, about 40 mL, or about 60 mL.

Rectal Gels

In some embodiments, the pharmaceutical compositions described herein are formulated as rectal gels. In certain embodiments, the rectal gels are suitable for the regional or local non-systemic administration of one or more enteroendocrine peptide secretion enhancing agents to the rectum and/or colon. In some embodiments, rectal gel formulations contain at least one enteroendocrine peptide secretion enhancing agent dissolved or suspended in a solvent/liquid carrier vehicle, an absorption inhibitor (e.g., of the enteroendocrine peptide secretion enhancing agent across the rectal or colonic mucosa) and at least one thickening agents. In certain embodiments such rectal gel formulations also contain one or more of the following: a buffering agent(s), a preservative(s), and an antioxidant(s).

In certain embodiments, rectal gels have gel-like consistencies but are sufficiently flowable so as to be capable of local or regional administration through a catheter, needle, syringe, or other comparable means of local or regional administration.

In some embodiments, the concentration of a thickener used in a rectal gel formulation is in an amount or concentration suitable to achieve a desired thickness or viscosity, e.g., from about 0.05% to about 10% by weight. In certain embodiments, the concentration of the thickener used in such rectal gel formulations ranges from about 0.05% to about 8% by weight. In certain embodiments, the concentration of the thickener used in such rectal gel formulations ranges from about 0.05% to about 7% by weight. In certain embodiments, the concentration of the thickener used in such rectal gel formulations ranges from about 0.05% to about 6% by weight. In certain embodiments, the concentration of the thickener used in such rectal gel formulations ranges from about 0.05% to about 5% by weight. In certain embodiments, the concentration of the thickener used in such rectal gel formulations ranges from about 0.05% to about 4% by weight. In certain embodiments, the concentration of the thickener used in such rectal gel formulations ranges from about 0.05% to about 3% by weight. In certain embodiments, the concentration of the thickener used in such rectal gel formulations ranges from about 0.05% to about 2% by weight. In certain embodiments, the concentration of the thickener used in such rectal gel formulations ranges from about 0.05% to about 1% by weight. In certain embodiments the rectal gel formualtion includes methyl cellulose having a concentration from about 0.05% to about 2%, while in other embodiments the rectal gel formualtion includes methyl cellulose having a concentration of about 1%.

Figure 4:
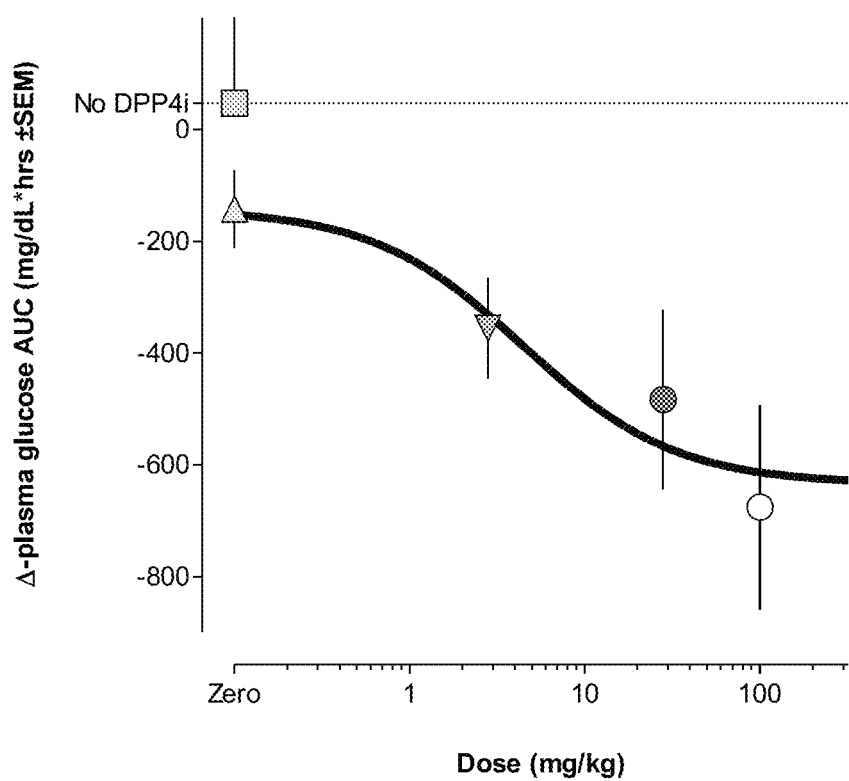
FIG. 4 illustrates the change in plasma glucose level in diabetic db/db mice after oral administration of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt at doses of 0, 3, 30, and 100 mg/kg.

In some embodiments, the any formulation described herein (e.g., arectal gel formulation) has a viscosity ranging from about 500 to about 50,000 centipoise (cP) at 25 C. In certain embodiments, the viscosity of the formulation described herein is from about 500 to about 40,000 centipoise (cP) at 25 C. In certain embodiments, the viscosity of the formulation described herein is from about 500 to about 30,000 centipoise (cP) at 25 C. In certain embodiments, the viscosity of the formulation described herein is from about 500 to about 20,000 centipoise (cP) at 25 C. In certain embodiments, the viscosity of the formulation described herein is from about 500 to about 10,000 centipoise (cP) at 25 C. In some embodiments, the formulation has a final viscosity of less than about 40,000 centipoises (cP), 20,000 cP, 15,000 cP, or 10,000 cP at 25 C. In some embodiments, the formulation has a viscosity of about 5,000 cP, 6,000 cP, 7,000 cP, 8,000 cP, 9,000 cP, 10,000 cP, 12,000 cP, 15,000 cP, 18,000 cP, 20,000 cP, 25,000 cP, 30,000 cP, 35,000 cP, or 40,000 cP at 25 C. In some embodiments, the formulation has a viscosity of about 1,000-20,000 cP, 5,000-15,000 cP, 6,000-12,000 cP, 7,000-10,000,500-3500 cP, 500-300cP, 1,000-2,000 cP, or about 1,500 cP at 25 C. In specific embodiments, the formulation has a viscosity of 1,000 cP to about 2,500 cP, or about 1,500 cP at 25 C. In certain embodiments, the amount of thickener used in a composition described herein is sufficient to achieve a viscosity as described herein. FIG. 4 illustrates the affect of the viscosity of a formulation described herein on the food intake of a subject.

In some embodiments, unit dosages of such rectal gel formulations are administered from prefilled bags or syringes.

Rectal Suppositories

In some embodiments, the pharmaceutical compositions described herein are also formulated as a suppository. In certain embodiments, suppositories are formulated for the regional or local non-systemic administration of one or more enteroendocrine peptide secretion enhancing agents to the rectum and/or colon.

In some embodiments, rectal suppository formulations contain a enteroendocrine peptide secretion enhancing agent, an absorption inhibitor (e.g., of the enteroendocrine peptide secretion enhancing agent across the rectal or colonic mucosa) and at least one pharmaceutically acceptable suppository base. In some embodiments, suppository formulation are prepared by combining an enteroendocrine peptide secretion enhancing agent with a pharmaceutically acceptable suppository base, melted, poured into a mould or moulds and cooled.

In certain embodiments, pharmaceutically acceptable suppository bases include, by way of non-limiting example, cocoa butter, beeswax, esterified fatty acids, glycerinated gelatin, semisynthetic glycerides of vegetable saturated fatty acids, polyethylene glycols, Witepsol, and polyoxyethylene sorbitan fatty acid esters.

In certain embodiments, the suppository formulations used to deliver one or more enteroendocrine peptide secretion enhancing agents to the rectum and/or colon also contain one or more of the following: buffering agents, preservatives, antioxidants, surfactants, and thickeners.

In some embodiments, suppositories contain from 0.5 to 10 mg of an enteroendocrine peptide secretion enhancing agent. In specific embodiments, suppositories contain from 1 to 5 mg of an enteroendocrine peptide secretion enhancing agent.

Components Used in Rectal Delivery/Administration Formulations

In certain embodiments, liquid carrier vehicles in the compositions and/or formulations described herein include, by way of non-limiting example, purified water, propylene glycol, polyethyleneglycol, ethanol, 1-propanol, 2-propanol, 1-propen-3-ol (allyl alcohol), propylene glycol, glycerol, 2-methyl-2-propanol, formamide, methyl formamide, dimethyl formamide, ethyl formamide, diethyl formamide, acetamide, methyl acetamide, dimethyl acetamide, ethyl acetamide, diethyl acetamide, 2-pyrrolidone, N-methyl-2-pyrrolidone, N-ethyl-2-pyrrolidone, tetramethyl urea, 1,3-dimethyl-2-imidazolidinone, propylene carbonate, 1,2-butylene carbonate, 2,3-butylene carbonate, dimethyl sulfoxide, diethyl sulfoxide, hexamethyl phosphoramide, pyruvic aldehyde dimethylacetal, dimethylisosorbide and combinations thereof.

In some embodiments, stabilizers used in compositions and/or formulations described herein include, but are not limited to, partial glycerides of polyoxyethylenic saturated fatty acids.

In certain embodiments, surfactants/emulsifiers used in the compositions and/or formulations described herein include, by way of non-limiting example, mixtures of cetostearylic alcohol with sorbitan esterified with polyoxyethylenic fatty acids, polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, petroleum derivatives, aliphatic amines, polysiloxane derivatives, sorbitan fatty acid esters, laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and combinations thereof.

In some embodiments, non-ionic surfactants used in compositions and/or formulations described herein include, by way of non-limiting example, phospholipids, alkyl poly (ethylene oxide), poloxamers, polysorbates, sodium dioctyl sulfosuccinate, Brij™-30 (Laureth-4), Brij™-58 (Ceteth-20) and Brij™-78 (Steareth-20), Brij™-721 (Steareth-21), Crillet-1 (Polysorbate 20), Crillet-2 (Polysorbate 40), Crillet-3 (Polysorbate 60), Crillet 45 (Polysorbate 80), Myrj-52 (PEG-40 Stearate), Myrj-53 (PEG-50 Stearate), Pluronic™ F77 (Poloxamer 217), Pluronic™ F87 (Poloxamer 237), Pluronic™ F98 (Poloxamer 288), Pluronic™ L62 (Poloxamer 182), Pluronic™ L64 (Poloxamer 184), Pluronic™ F68 (Poloxamer 188), Pluronic™ L81 (Poloxamer 231), Pluronic™ L92 (Poloxamer 282), Pluronic™ L101 (Poloxamer 331), Pluronic™ P103 (Poloxamer 333), Pluracare™ F 108 NF (Poloxamer 338), and Pluracare™ F 127 NF (Poloxamer 407) and combinations thereof. Pluronic™ polymers are commercially purchasable from BASF, USA and Germany.

In certain embodiments, anionic surfactants used in compositions and/or formulations described herein include, by way of non-limiting example, sodium laurylsulphate, sodium dodecyl sulfate (SDS), ammonium lauryl sulfate, alkyl sulfate salts, alkyl benzene sulfonate, and combinations thereof.

In some embodiments, the cationic surfactants used in compositions and/or formulations described herein include, by way of non-limiting example, benzalkonium chloride, benzethonium chloride, cetyl trimethylammonium bromide, hexadecyl trimethyl ammonium bromide, other alkyltrimethylammonium salts, cetylpyridinium chloride, polyethoxylated tallow and combinations thereof.

In certain embodiments, the thickeners used i in compositions and/or formulations described herein include, by way of non-limiting example, natural polysaccharides, semisynthetic polymers, synthetic polymers, and combinations thereof. Natural polysaccharides include, by way of non-limiting example, acacia, agar, alginates, carrageenan, guar, arabic, tragacanth gum, pectins, dextran, gellan and xanthan gums. Semi-synthetic polymers include, by way of non-limiting example, cellulose esters, modified starches, modified celluloses, carboxymethylcellulose, methyl cellulose, ethyl cellulose, hydroxyethyl cellulose, hydroxypropyl cellulose and hydroxypropyl methylcellulose. Synthetic polymers include, by way of non-limiting example, polyoxyalkylenes, polyvinyl alcohol, polyacrylamide, polyacrylates, carboxypolymethylene (carbomer), polyvinylpyrrolidone (povidones), polyvinylacetate, polyethylene glycols and poloxamer. Other thickeners include, by way of nonlimiting example, polyoxyethyleneglycol isostearate, cetyl alcohol, Polyglycol 300 isostearate, propyleneglycol, collagen, gelatin, and fatty acids (e.g., lauric acid, myristic acid, palmitic acid, stearic acid, palmitoleic acid, linoleic acid, linolenic acid, oleic acid and the like).

In some embodiments, chelating agents used in the compositions and/or formulations described herein include, by way of non-limiting example, ethylenediaminetetraacetic acid (EDTA) or salts thereof, phosphates and combinations thereof.

In some embodiments, the concentration of the chelating agent or agents used in the rectal formulations described herein is a suitable concentration, e.g., about 0.1%, 0.15%, 0.2%, 0.25%, 0.3%, 0.4%, or 0.5% (w/v).

In some embodiments, preservatives used in compositions and/or formulations described herein include, by way of non-limiting example, parabens, ascorbyl palmitate, benzoic acid, butylated hydroxyanisole, butylated hydroxytoluene, chlorobutanol, ethylenediamine, ethylparaben, methylparaben, butyl paraben, propylparaben, monothioglycerol, phenol, phenylethyl alcohol, propylparaben, sodium benzoate, sodium propionate, sodium formaldehyde sulfoxylate, sodium metabisulfite, sorbic acid, sulfur dioxide, maleic acid, propyl gallate, benzalkonium chloride, benzethonium chloride, benzyl alcohol, chlorhexidine acetate, chlorhexidine gluconate, sorbic acid, potassium sorbitol, chlorbutanol, phenoxyethanol, cetylpyridinium chloride, phenylmercuric nitrate, thimerosol, and combnations thereof.

In certain embodiments, antioxidants used in compositions and/or formulations described herein include, by way of non-limiting example, ascorbic acid, ascorbyl palmitate, butylated hydroxyanisole, butylated hydroxytoluene, hypophosphorous acid, monothioglycerol, propyl gallate, sodium ascorbate, sodium sulfite, sodium bisulfite, sodium formaldehyde sulfoxylate, potassium metabisulphite, sodium metabisulfite, oxygen, quinones, t-butyl hydroquinone, erythorbic acid, olive (olea eurpaea) oil, pentasodium penetetate, pentetic acid, tocopheryl, tocopheryl acetate and combinations thereof.

In some embodiments, concentration of the antioxidant or antioxidants used in the rectal formulations described herein is sufficient to achieve a desired result, e.g., about 0.1%, 0.15%, 0.2%, 0.25%, 0.3%, 0.4%, or 0.5% (w/v).

The lubricating agents used in compositions and/or formulations described herein include, by way of non-limiting example, natural or synthetic fat or oil (e.g., a tris-fatty acid glycerate and the like). In some embodiments, lubricating agents include, by way of non-limiting example, glycerin (also called glycerine, glycerol, 1,2,3-propanetriol, and trihydroxypropane), polyethylene glycols (PEGs), polypropylene glycol, polyisobutene, polyethylene oxide, behenic acid, behenyl alcohol, sorbitol, mannitol, lactose, polydimethylsiloxane and combinations thereof.

In certain embodiments, mucoadhesive and/or bioadhesive polymers are used in the compositions and/or formulations described herein as agents for inhibiting absorption of the enteroendocrine peptide secretion enhancing agent across the rectal or colonic mucosa. Bioadhesive or mucoadhesive polymers include, by way of non-limiting example, hydroxypropyl cellulose, polyethylene oxide homopolymers, polyvinyl ether-maleic acid copolymers, methyl cellulose, ethyl cellulose, propyl cellulose, hydroxyethyl cellulose, hydroxypropyl cellulose, hydroxypropylmethyl cellulose, carboxymethylcellulose, polycarbophil, polyvinylpyrrolidone, carbopol, polyurethanes, polyethylene oxide-polypropyline oxide copolymers, sodium carboxymethyl cellulose, polyethylene, polypropylene, lectins, xanthan gum, alginates, sodium alginate, polyacrylic acid, chitosan, hyaluronic acid and ester derivatives thereof, vinyl acetate homopolymer, calcium polycarbophil, gelatin, natural gums, karaya, tragacanth, algin, chitosan, starches, pectins, and combinations thereof.

In some embodiments, buffers/pH adjusting agents used in compositions and/or formulations described herein include, by way of non-limiting example, phosphoric acid, monobasic sodium or potassium phosphate, triethanolamine (TRIS), BICINE, HEPES, Trizma, glycine, histidine, arginine, lysine, asparagine, aspartic acid, glutamine, glutamic acid, carbonate, bicarbonate, potassium metaphosphate, potassium phosphate, monobasic sodium acetate, acetic acid, acetate, citric acid, sodium citrate anhydrous, sodium citrate dihydrate and combinations thereof. In certain embodiments, an acid or a base is added to adjust the pH. Suitable acids or bases include, by way of non-limiting example, HCL, NaOH and KOH.

In certain embodiments, concentration of the buffering agent or agents used in the rectal formulations described herein is sufficient to achieve or maintain a physiologically desirable pH, e.g., about 0.1%, 0.2%, 0.3%, 0.4%, 0.5%, 0.6%, 0.8%, 0.9%, or 1.0% (w/w).

The tonicity modifiers used in compositions and/or formulations described herein include, by way of non-limiting example o, sodium chloride, potassium chloride, sodium phosphate, mannitol, sorbitol or glucose.

Devices

In certain aspects of the methods and pharmaceutical compositions described herein, a device is used for rectal administration of the compositions and/or formulations described herein (e.g., the rectal gels, rectal foams, ememas and suppositories described herein). In certain embodiments, rectal gels or rectal enemas are administered using a bag or a syringe, while rectal foams are administered using a pressurized container.

In certain embodiments, a perfusion system is used to rectally administer the pharmaceutical compositions and/or formulations described herein. In some embodiments, the system comprises a tube surrounded by a semi-permeable membrane is rectally inserted and a solution containing a composition described herein is pumped into the membrane. In certain embodiments, the membrane expands to contact the rectal and/or colon walls, wherein the enterendocrine peptide secretion enhancing agents perfuse from the inside of the membrane to the outside. In certain embodiments, the solution is re-circulated as a continuous perfusion system.

Oral Administration for Colonic Delivery

In certain aspects, the composition or formulation containing one or more enteroendocrine peptide secretion enhancing agents is orally administered for local delivery of an ASBTI, a TGR5 agonist, or an enteroendocrine peptide secretion enhancing agent to the colon and/or rectum. Unit dosage forms of such compositions include a pill, tablet or capsules formulated for enteric delivery to colon. In certain embodiments, such pills, tablets or capsule contain the compositions described herein entrapped or embedded in microspheres. In some embodiments, microspheres include, by way of non-limiting example, chitosan microcores HPMC capsules and cellulose acetate butyrate (CAB) microspheres. In certain embodiments, oral dosage forms are prepared using conventional methods known to those in the field of pharmaceutical formulation. For example, in certain embodiments, tablets are manufactured using standard tablet processing procedures and equipment. An exemplary method for forming tablets is by direct compression of a powdered, crystalline or granular composition containing the active agent(s), alone or in combination with one or more carriers, additives, or the like. In alternative embodiments, tablets are prepared using wet-granulation or dry-granulation processes. In some embodiments, tablets are molded rather than compressed, starting with a moist or otherwise tractable material.

In certain embodiments, tablets prepared for oral administration contain various excipients, including, by way of non-limiting example, binders, diluents, lubricants, disintegrants, fillers, stabilizers, surfactants, preservatives, coloring agents, flavoring agents and the like. In some embodiments, binders are used to impart cohesive qualities to a tablet, ensuring that the tablet remains intact after compression. Suitable binder materials include, by way of non-limiting example, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), Veegum, and combinations thereof. In certain embodiments, diluents are utilized to increase the bulk of the tablet so that a practical size tablet is provided. Suitable diluents include, by way of non-limiting example, dicalcium phosphate, calcium sulfate, lactose, cellulose, kaolin, mannitol, sodium chloride, dry starch, powdered sugar and combinations thereof. In certain embodiments, lubricants are used to facilitate tablet manufacture; examples of suitable lubricants include, by way of non-limiting example, vegetable oils such as peanut oil, cottonseed oil, sesame oil, olive oil, corn oil, and oil of theobroma, glycerin, magnesium stearate, calcium stearate, stearic acid and combinations thereof. In some embodiments, disintegrants are used to facilitate disintegration of the tablet, and include, by way of non-limiting example, starches, clays, celluloses, algins, gums, crosslinked polymers and combinations thereof. Fillers include, by way of non-limiting example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. In certain embodiments, stabilizers are used to inhibit or retard drug decomposition reactions that include, by way of example, oxidative reactions. In certain embodiments, surfactants are anionic, cationic, amphoteric or nonionic surface active agents.

In some embodiments, ASBTIs, TGR5 agonists, or enteroendocrine peptide secretion enhancing agents described herein are orally administered in association with a carrier suitable for delivery of the enteroendocrine peptide secretion enhancing agents to the distal gastrointestinal tract (e.g., distal ileum, colon, and/or rectum).

In certain embodiments, a composition described herein comprises an ASBTI, a TGR5 agonist, or an enteroendocrine peptide secretion enhancing agent in association with a matrix (e.g., a matrix comprising hypermellose) that allows for controlled release of an active agent in the distal part of the ileum and/or the colon. In some embodiments, a composition comprises a polymer that is pH sensitive (e.g., a MMX™ matrix from Cosmo Pharmaceuticals) and allows for controlled release of an active agent in the distal part of the ileum. Examples of such pH sensitive polymers suitable for controlled release include and are not limited to poly-acrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of abut 7 to about 8). In some embodiments, a composition suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an enteroendocrine peptide secretion enhancing agent (e.g., bile acid) to the distal ileum. In some embodiments, a dosage form comprising an enteroendocrine peptide secretion enhancing agent (e.g., bile acid) is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the distal ileum and/or the colon. In some embodiments, bacterially activated systems are suitable for targeted delivery to the distal part of the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical composition described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences,* 20th Edition (2000), a film coating is provided around the formulation of the compound of Formula I. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

In certain embodiments, an oral formulation for use in any method described herein is, e.g., an ASBTI or an enteroendocrine peptide secretion enhancing agent in association with a labile bile acid sequestrant. A labile bile acid sequestrant is a bile acid sequestrant with a labile affinity for bile acids. In certain embodiments, a bile acid sequestrant described herein is an agent that sequesters (e.g., absorbs or is charged with) bile acid, and/or the salts thereof.

In specific embodiments, the labile bile acid sequestrant is an agent that sequesters (e.g., absorbs or is charged with) bile acid, and/or the salts thereof, and releases at least a portion of the absorbed or charged bile acid, and/or salts thereof in the distal gastrointestinal tract (e.g., the colon, ascending colon, sigmoid colon, distal colon, rectum, or any combination thereof). In certain embodiments, the labile bile acid sequestrant is an enzyme dependent bile acid sequestrant. In specific embodiments, the enzyme is a bacterial enzyme. In some embodiments, the enzyme is a bacterial enzyme found in high concentration in human colon or rectum relative to the concentration found in the small intestine. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like. In some embodiments, the labile bile acid sequestrant is a time dependent bile acid sequestrant (i.e., the bile acid sequesters the bile acid and/or salts thereof and after a time releases at least a portion of the bile acid and/or salts thereof). In some embodiments, a time dependent bile acid sequestrant is an agent that degrades in an aqueous environment over time. In certain embodiments, a labile bile acid sequestrant described herein is a bile acid sequestrant that has a low affinity for bile acid and/or salts thereof, thereby allowing the bile acid sequestrant to continue to sequester bile acid and/or salts thereof in an environ where the bile acids and/or salts thereof are present in high concentration and release them in an environ wherein bile acids and/or salts thereof are present in a lower relative concentration. In some embodiments, the labile bile acid sequestrant has a high affinity for a primary bile acid and a low affinity for a secondary bile acid, allowing the bile acid sequestrant to sequester a primary bile acid or salt thereof and subsequently release a secondary bile acid or salt thereof as the primary bile acid or salt thereof is converted (e.g., metabolized) to the secondary bile acid or salt thereof. In some embodiments, the labile bile acid sequestrant is a pH dependent bile acid sequestrant. In some embodiments, the pH dependent bile acid sequestrant has a high affinity for bile acid at a pH of 6 or below and a low affinity for bile acid at a pH above 6. In certain embodiments, the pH dependent bile acid sequestrant degrades at a pH above 6.

In some embodiments, labile bile acid sequestrants described herein include any compound, e.g., a macrostructured compound, that can sequester bile acids and/or salts thereof through any suitable mechanism. For example, in certain embodiments, bile acid sequestrants sequester bile acids and/or salts thereof through ionic interactions, polar interactions, static interactions, hydrophobic interactions, lipophilic interactions, hydrophilic interactions, steric interactions, or the like. In certain embodiments, macrostructured compounds sequester bile acids and/or sequestrants by trapping the bile acids and/or salts thereof in pockets of the macrostructured compounds and, optionally, other interactions, such as those described above. In some embodiments, bile acid sequestrants (e.g., labile bile acid sequestrants) include, by way of non-limiting example, lignin, modified lignin, polymers, polycationic polymers and copolymers, polymers and/or copolymers comprising anyone one or more of N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; or a combination thereof, or any combination thereof.

Covalent Linkage of the Drug with a Carrier

In some embodiments, strategies used for colon targeted delivery include, by way of non-limiting example, covalent linkage of the ASBTI and/or the enteroendocrine peptide secretion enhancing agents to a carrier, coating the dosage form with a pH-sensitive polymer for delivery upon reaching the pH environment of the colon, using redox sensitive polymers, using a time released formulation, utilizing coatings that are specifically degraded by colonic bacteria, using bioadhesive system and using osmotically controlled drug delivery systems.

In certain embodiments of such oral administration of a composition containing an ASBTI and or an enteroendocrine peptide secretion enhancing agent described herein involves covalent linking to a carrier wherein upon oral administration the linked moiety remains intact in the stomach and small intestine. Upon entering the colon the covalent linkage is broken by the change in pH, enzymes, and/or degradation by intestinal microflora. In certain embodiments, the covalent linkage between the ASBTI and/or enteroendocrine peptide secretion enhancing agent and the carrier includes, by way of non-limiting example, azo linkage, glycoside conjugates, glucuronide conjugates, cyclodextrin conjugates, dextran conjugates, and amino-acid conjugates (high hydrophilicity and long chain length of the carrier amino acid).

Coating with Polymers: pH-Sensitive Polymers

In some embodiments, the oral dosage forms described herein are coated with an enteric coating to facilitate the delivery of an ASBTI and/or an enteroendocrine peptide secretion enhancing agent to the colon and/or rectum. In certain embodiments, an enteric coating is one that remains intact in the low pH environment of the stomach, but readily dissolved when the optimum dissolution pH of the particular coating is reached which depends upon the chemical composition of the enteric coating. The thickness of the coating will depend upon the solubility characteristics of the coating material. In certain embodiments, the coating thicknesses used in such formulations described herein range from about 25 μm to about 200 μm.

In certain embodiments, the compositions or formulations described herein are coated such that an enteroendocrine peptide secretion enhancing agent of the composition or formulation is delivered to the colon and/or rectum without absorbing at the upper part of the intestine. In a specific embodiment, specific delivery to the colon and/or rectum is achieved by coating of the dosage form with polymers that degrade only in the pH environment of the colon. In alternative embodiments, the composition is coated with an enteric coat that dissolves in the pH of the intestines and an outer layer matrix that slowly erodes in the intestine. In some of such embodiments, the matrix slowly erodes until only a core composition comprising an enteroendocrine peptide secretion enhancing agent (and, in some embodiments, an absorption inhibitor of the agent) is left and the core is delivered to the colon and/or rectum.

In certain embodiments, pH-dependent systems exploit the progressively increasing pH along the human gastrointestinal tract (GIT) from the stomach (pH 1-2 which increases to 4 during digestion), small intestine (pH 6-7) at the site of digestion and it to 7-8 in the distal ileum. In certain embodiments, dosage forms for oral administration of the compositions described herein are coated with pH-sensitive polymer(s) to provide delayed release and protect the enteroendocrine peptide secretion enhancing agents from gastric fluid. In certain embodiments, such polymers are be able to withstand the lower pH values of the stomach and of the proximal part of the small intestine, but disintegrate at the neutral or slightly alkaline pH of the terminal ileum and/or ileocecal junction. Thus, in certain embodiments, provided herein is an oral dosage form comprising a coating, the coating comprising a pH-sensitive polymer. In some embodiments, the polymers used for colon and/or rectum targeting include, by way of non-limiting example, methacrylic acid copolymers, methacrylic acid and methyl methacrylate copolymers, Eudragit L100, Eudragit S100, Eudragit L-30D, Eudragit FS-30D, Eudragit L100-55, polyvinylacetate phthalate, hyrdoxypropyl ethyl cellulose phthalate, hyrdoxypropyl methyl cellulose phthalate 50, hyrdoxypropyl methyl cellulose phthalate 55, cellulose acetate trimelliate, cellulose acetate phthalate and combinations thereof.

In certain embodiments, oral dosage forms suitable for delivery to the colon and/or rectum comprise a coating that has a biodegradable and/or bacteria degradable polymer or polymers that are degraded by the microflora (bacteria) in the colon. In such biodegradable systems suitable polymers include, by way of non-limiting example, azo polymers, linear-type-segmented polyurethanes containing azo groups, polygalactomannans, pectin, glutaraldehyde crosslinked dextran, polysaccharides, amylose, guar gum, pectin, chitosan, inulin, cyclodextrins, chondroitin sulphate, dextrans, locust bean gum, chondroitin sulphate, chitosan, poly (-caprolactone), polylactic acid and poly(lactic-co-glycolic acid).

In certain embodiments of such oral administration of compositions containing one or more ASBTIs and/or enteroendocrine peptide secretion enhancing agents described herein, the compositions are delivered to the colon without absorbing at the upper part of the intestine by coating of the dosage forms with redox sensitive polymers that are degraded by the microflora (bacteria) in the colon. In such biodegradable systems such polymers include, by way of non-limiting example, redox-sensitive polymers containing an azo and/or a disulfide linkage in the backbone.

In some embodiments, compositions formulated for delivery to the colon and/or rectum are formulated for time-release. In some embodiments, time release formulations resist the acidic environment of the stomach, thereby delaying the release of the enteroendocrine peptide secretion enhancing agents until the dosage form enters the colon and/or rectum.

In certain embodiments the time released formulations described herein comprise a capsule (comprising an enteroendocrine peptide secretion enhancing agent and an optional absorption inhibitor) with hydrogel plug. In certain embodiments, the capsule and hydrogel plug are covered by a water-soluble cap and the whole unit is coated with an enteric polymer. When the capsule enters the small intestine the enteric coating dissolves and the hydrogels plug swells and dislodges from the capsule after a period of time and the composition is released from the capsule. The amount of hydrogel is used to adjust the period of time to the release the contents.

In some embodiments, provided herein is an oral dosage form comprising a multi-layered coat, wherein the coat comprises different layers of polymers having different pH-sensitivities. As the coated dosage form moves along GIT the different layers dissolve depending on the pH encountered. Polymers used in such formulations include, by way of non-limiting example, polymethacrylates with appropriate pH dissolution characteristics, Eudragit® RL and Eudragit®RS (inner layer), and Eudragit® FS (outer layer). In other embodiments the dosage form is an enteric coated tablets having an outer shell of hydroxypropylcellulose or hydroxypropylmethylcellulose acetate succinate (HPMCAS).

In some embodiments, provided herein is an oral dosage form that comprises coat with cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and combinations thereof.

Combination Therapy

In certain instances, provided herein are combination compositions and/or therapies comprising any compound described herein and an additional therapeutic agent. In some embodiments, the additional therapeutic agent is a L-cell endocrine peptide enhancer. In some instances, the L-cell endocrine peptide enhancer is a GLP-1 enhancer. In some embodiments, the GLP-1 enhancer is GLP-1, a GLP-1 secretion enhancer, a GLP-1 degradation inhibitor, the like, or a combination thereof. In certain instances, enhanced GLP-1 concentration provides a reduction in food intake and/or a reduction in gastric emptying in human subjects.

In some embodiments, the L-cell endocrine peptide enhancer is a GLP-2 enhancer. In certain instances, the GLP-2 enhancer is GLP-2, a GLP-2 secretion enhancer, a GLP-2 degradation inhibitor, the like, or a combination thereof. In certain instances, enhanced GLP-2 secretion inhibits gastric emptying and reduces intestinal permeability. In some instances, enhanced GLP-2 secretion inhibits gastric acid secretion. In some instances, enhanced GLP-2 secretion reduces or prevents inflammation in the gastrointestinal tract (gastrointestinal enteritis). In some instances, enhanced GLP-2 secretion regenerates and/or heals injury to gastrointestinal tissues (e.g., radiation enteritis).

In some instances, the L-cell endocrine peptide enhancer is a PYY enhancer. In some instances, enhanced secretion of PYY provides a reduction in sensation of hunger. In some instances, the L-cell endocrine peptide enhancer is an oxyntomodulin enhancer. In some instances, the enhanced secretion of oxyntomodulin inhibits meal-stimulated gastric secretion.

TGR5 Receptor Modulators

In some instances, the additional therapeutic agent modulates bile acid receptors in the gastrointestinal lumen. In some embodiments, the additional therapeutic agent agonizes or partially agonizes bile acid receptors (e.g., TGR5 receptors or Farnesoid-X receptors) in the gastrointestinal tract. In some embodiments, the additional therapeutic agent is a bile acid analog. In certain instances the additional therapeutic agent is a TGR5 agonist. In certain instances, administration of a TGR5 agonist in combination with any of the compounds described herein enhances the secretion of enteroendocrine peptides from L-cells. TGR5 modulators (e.g., agonists) include, and are not limited to, the compounds described in, WO 2008/091540, WO 2008/067219 and U.S. Appl. No. 2008/0221161.

Biguanides

In some embodiments, the additional therapeutic agent is a biguanide. In some instances, biguanides reduce blood and/or plasma glucose levels. Examples of biguanides include and are not limited to metformin, buformin, phenformin, proguanil or the like.

Incretin Mimetics

In some embodiments, the additional therapeutic agent is an incretin mimetic. In some embodiments, an incretic mimic augments pancreas response to ingestion of food, In some instances, administration of an incretin mimetic in combination with any of the compounds described herein lowers blood and/or plasma glucose levels. Examples of incretin mimetics include and are not limited to exenatide (Byetta®).

One currently used therapy for the treatment of diabetes is a subcutaneous injection of exenatide (Byetta®). In some embodiments, an oral combination of an ASBTI and a DPP-IV inhibitor is equally or more effective than an injection of exenatide in reducing plasma glucose levels. In some embodiments, an oral combination of an ASBTI and a DPP-IV inhibitor reduces or eliminates discomfort associated with injections of glucose-lowering medications.

Thiazolidinediones

In some embodiments, the additional therapeutic agent is a thiazolidinedione. In some instances thiazolidinediones reverse insulin resistance and lower blood and/or plasma glucose levels. Examples of thiazolidinediones include and are not limited to Rosiglitazone (Avandia), Pioglitazone (Actos), Troglitazone (Rezulin), MCC-555, rivoglitazone, ciglitazone or the like.

Enteroendocrine Peptides

In some embodiments, the additional therapeutic agent is an enteroendocrine peptide. In some embodiments, enteroendocrine peptides reverse insulin resistance and lower blood and/or plasma glucose levels. Examples of enteroendocrine peptides that are administered as additional therapeutic agents include and are not limited to GLP-1 or GLP-1 analogs such as Taspoglutide® (Ipsen), or the like.

Combination Therapy with ASBTI and DPP-IV Inhibitor

In specific embodiments, the additional therapeutic agent inhibits degradation of L-cell enteroendocrine peptides. In certain embodiments, the additional therapeutic agent is a DPP-IV inhibitor. In certain instances, administration of an ASBTI to an individual in need thereof enhances the secretion of GLP-1; administration of a DPP-IV inhibitor in combination with the ASBTI reduces or inhibits degradation of GLP-1 thereby prolonging the therapeutic benefit of enhanced levels of GLP-1. In some embodiments, administration of an ASBTI reduces weight of an individual. In some embodiments, administration of an ASBTI in combination with a DPP-IV inhibitor reduces weight of an individual.

Figure 2:
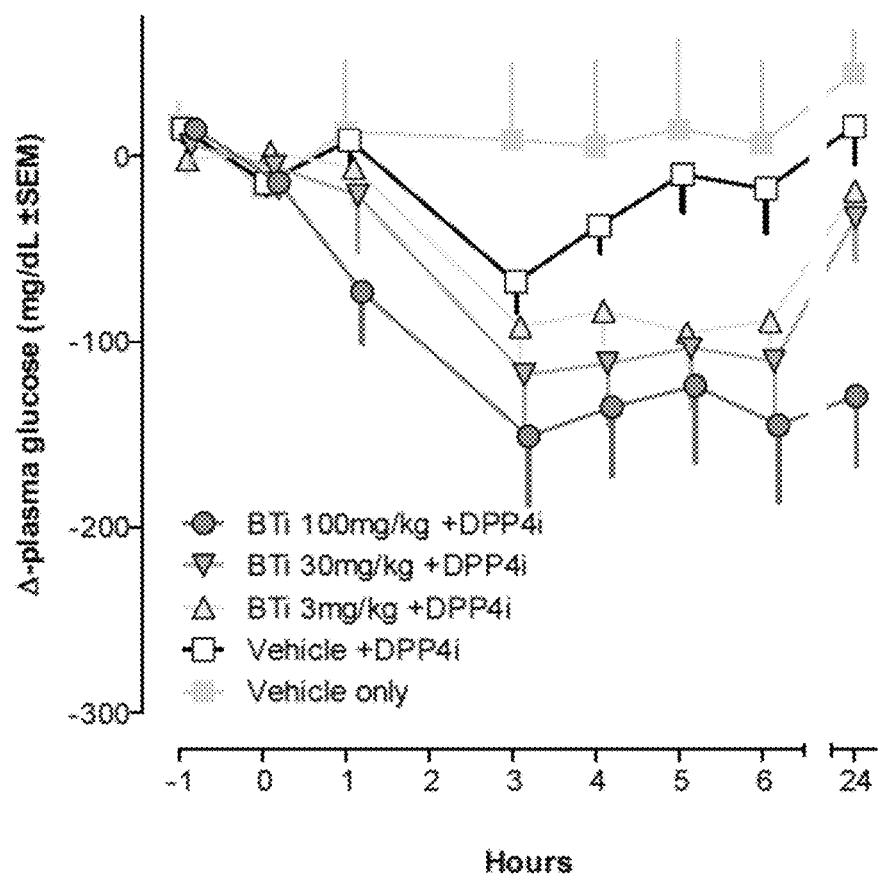
FIG. 2 illustrates the change in plasma glucose level in diabetic db/db mice after oral administration of a combination of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate at doses of 0, 3, 30, 100 mg/kg and 30 mg/kg sitagliptin (DPP-IV inhibitor).
Figure 3:
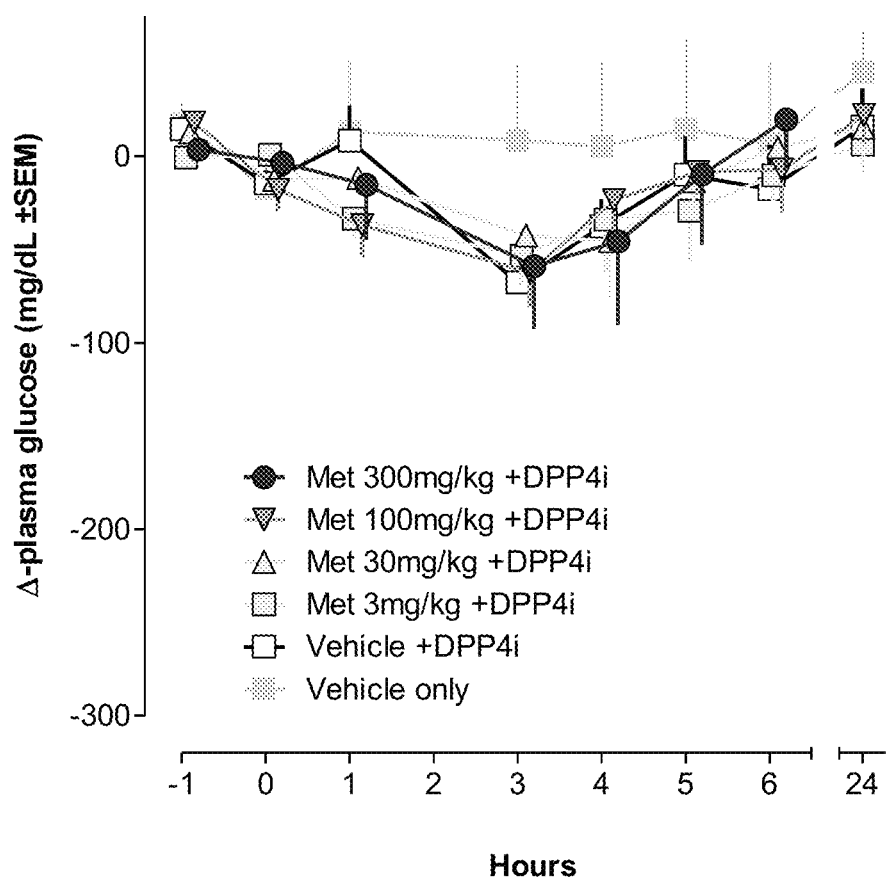
FIG. 3 illustrates the change in plasma glucose level in diabetic db/db mice after oral administration of a combination of metformin at doses of 0, 3, 30, 100, 300 mg/kg and 30 mg/kg sitagliptin (DPP-IV inhibitor).

Another therapy that is current standard of care for the treatment of diabetes is a combination of metformin and sitagliptin (Janumet®). At doses of 0, 3, 30, 100, 300 mg/kg doses of metformin in combination with 30 mg/kg of sitagliption, reductions in plasma glucose concentrations are observed from 3 hours till about 6 hours post-dose (FIG. 3). In some embodiments, a combination of an ASBTI and sitagliptin maintains reduced plasma glucose concentrations for a longer duration of time (e.g., at least 24 hours) compared to a combination of metformin and sitagliptin (about 6 hours) (FIGS. 1 and 2). In some instances ASBTI therapy eliminates side effects associated with metformin therapy and/or DPP-IV inhibitor therapy.

DPP-IV inhibitors suitable for use with the methods described herein include and are not limited to (2S)-1-{2-[(3-hydroxy-1-adamantyl)amino]acetyl}pyrrolidine-2-carbonitrile (vildagliptin), (3R)-3-amino-1-[9-(trifluoromethyl)-1,4,7,8-tetrazabicyclo[4.3.0]nona-6,8-d ien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin).

In some embodiments of any of the methods described herein, administration of an ASBT inhibitor described herein in combination with a DPP-IV inhibitor increases the level of GLP-1 in the blood and/or plasma of an individual by from about 1.1 times to about 30 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 1.1 times to about 20 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 1.5 times to about 10 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 2 times to about 8 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 2 times to about 6 times compared to the level of GLP-1 in the blood and/or plasma of the individual prior to administration of the ASBTI in combination with the DPP-IV inhibitor. In some instances, an increase in GLP-1 level of from about 2 times to about 3 times following the administration of an ASBT inhibitor described herein in combination with a DPP-IV inhibitor compared to the level of GLP-1 in the blood and/or plasma of the individual prior to administration of the ASBTI in combination with the DPP-IV inhibitor is associated with an anti-diabetic effect. In some instances, an increase in GLP-1 level of from about 3 times to about 8 times following the administration of an ASBT inhibitor described herein in combination with a DPP-IV inhibitor compared to the level of GLP-1 in the blood and/or plasma of the individual prior to administration of the ASBTI in combination with a DPP-IV inhibitor is associated with reduction in food intake and/or induction of satiety and/or weight loss.

In certain embodiments of any of the methods described herein, administration of an ASBTI in combination with a DPP-IV inhibitor reduces blood and/or plasma sugar levels by at least 20%, at least 30%, at least 40%, at least 50% at least 60%, at least 70% or at least 80% compared to blood and/or plasma sugar levels prior to administration of the ASBTI in combination with a DPP-IV inhibitor. In some embodiments of any of the methods described herein, administration of an ASBTI in combination with a DPP-IV inhibitor reduces blood and/or plasma sugar levels by at least 20% compared to blood and/or plasma sugar levels prior to administration of the ASBTI in combination with a DPP-IV inhibitor. In some embodiments of any of the methods described herein, administration of an ASBTI in combination with a DPP-IV inhibitor reduces blood and/or plasma sugar levels by at least 30% compared to blood and/or plasma sugar levels prior to administration of the ASBTI in combination with a DPP-IV inhibitor. In some embodiments of any of the methods described herein, administration of an ASBTI in combination with a DPP-IV inhibitor reduces blood and/or plasma sugar levels by at least 40% compared to blood and/or plasma sugar levels prior to administration of the ASBTI in combination with a DPP-IV inhibitor.

In some embodiments of any of the methods described herein, administration of an ASBTI in combination with a DPP-IV inhibitor reduces blood and/or plasma sugar levels for a longer period of time (e.g., at least 24 hours) compared to reduction in blood and/or plasma sugar levels upon administration of metformin in combination with a DPP-IV inhibitor. In some embodiments of any of the methods described herein, administration of a single dose of an ASBTI in combination with a DPP-IV inhibitor sustains reduced blood and/or plasma sugar levels for at least 6 hours, at least 12 hours, at least 14 hours, at least 16 hours, at least 18 hours, at least 20 hours, at least 24 hours, at least 30 hours, at least 36 hours or at least 48 hours compared to reduction in blood and/or plasma sugar levels upon administration of a single dose of metformin in combination with a DPP-IV inhibitor.

In some embodiments of any of the methods described herein, administration of an ASBTI in combination with a DPP-IV inhibitor results in lower levels of intraenterocyte bile acids in an individual compared to levels of intraenterocyte bile acids in an individual suffering from necrotizing enterocolitis. In some embodiments of any of the methods described herein, administration of an ASBTI in combination with a DPP-IV inhibitor results in lower levels of necrosis and/or damage to ileal architecture in an individual compared to levels of necrosis and/or damage to ileal architecture in an individual suffering from necrotizing enterocolitis. In some embodiments of any of the methods described herein, administration of an ASBTI in combination with a DPP-IV inhibitor results in higher levels of GLP-1 in blood and/or plasma of an individual compared to levels of GLP-1 in blood and/or plasma of a normal individual. In some embodiments of any of the methods described herein, administration of an ASBTI in combination with a DPP-IV inhibitor results in higher levels of GLP-1 in blood and/or plasma of an individual compared to levels of GLP-1 in blood and/or plasma of an individual undergoing therapy with metformin and/or a DPP-IV inhibitor.

Combination Therapy with ASBTI, Biliary Shunt and DPP-IV Inhibitor

In some embodiments, an ASBTI is administered in combination with a DPP-IV inhibitor and/or a biliary shunt. Examples of biliary shunts include and are not limited to the shunts described in WO 2007/0050628, the disclosure of biliary shunts described therein is incorporated herein by reference. In some of such embodiments, a biliary shunt moves bile acid to the distal ileum and/or the rectum and/or the colon thereby increasing the concentration of bile acids in the vicinity of L-cells present in the distal portion of the gastrointesinal tract. In some instances such an increase in the concentration of bile acids in the vicinity of L-cells increases the secretion of GLP-1 from L-cells thereby inducing safety and/or reduction in hunger and/or weight loss and/or reduction in plasma glucose levels or any combination thereof.

An ASBTI and a second active ingredient are used such that the combination is present in a therapeutically effective amount. That therapeutically effective amount arises from the use of a combination of an ASBTI and the other active ingredient (e.g., a DPP-IV inhibitor) wherein each is used in a therapeutically effective amount, or by virtue of additive or synergistic effects arising from the combined use, each can also be used in a subclinical therapeutically effective amount, i.e., an amount that, if used alone, provides for reduced effectiveness for the therapeutic purposes noted herein, provided that the combined use is therapeutically effective. In some embodiments, the use of a combination of an ASBTI and any other active ingredient as described herein encompasses combinations where the ASBTI or the other active ingredient is present in a therapeutically effective amount, and the other is present in a subclinical therapeutically effective amount, provided that the combined use is therapeutically effective owing to their additive or synergistic effects. As used herein, the term "additive effect" describes the combined effect of two (or more) pharmaceutically active agents that is equal to the sum of the effect of each agent given alone. A syngergistic effect is one in which the combined effect of two (or more) pharmaceutically active agents is greater than the sum of the effect of each agent given alone. Any suitable combination of an ASBIT with one or more of the aforementioned other active ingredients and optionally with one or more other pharmacologically active substances is contemplated as being within the scope of the methods described herein.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g, from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In certain embodiments, ASBTI compounds described herein are combined with or utilized in combination with one or more of the following therapeutic agents in any combination: insulin, insulin-mimetics, incretin mimetics, GLP-1 or analogs thereof, GLP-2 or analogs thereof, oxyntomodulin, PYY, DPP-IV inhibitors, or TGR5 modulators.

In certain embodiments, provided herein are combination therapies. In certain embodiments, the compositions described herein comprise an additional therapeutic agent. In some embodiments, the methods described herein comprise administration of a second dosage form comprising an additional therapeutic agent. In certain embodiments, combination therapies the compositions described herein are administered as part of a regimen. Therefore, additional therapeutic agents and/or additional pharmaceutical dosage form can be applied to a patient either directly or indirectly, and concomitantly or sequentially, with the compositions and formulations described herein.

In certain embodiments the compositions described herein are used in combination with at least one appetite suppressant (e.g., a 5HT transport inhibitor, a NE transport inhibitor, a CB-1 antagonist/inverse agonist, a ghrelin antagonist, a H3 antagonist/inverse agonist, a MCH1R antagonist, a MCH2R agonist/antagonist, a NPY1 antagonist, a NPY2 agonist, a mGluR5 antagonist, leptin, a leptin agonist/modulator, a leptin derivative, an opiod antagonist, an orexin antagonist, a BRS3 agonist, a CCK-A agonist, CNTF, a CNTF agonist/modulator, a CNTF derivative, a 5HT2c agonist, a Mc5r agonist, a monoamine reuptake inhibitor, a serotonin reuptake inhibitor, a GLP-1 agonist, axokine, fenfluramine, nalmafene, phentermine, rimonabant, sibutramine, topiramate, phytopharm compound 57, and combinations thereof). In certain embodiments the compositions or formulations described herein are used in combination with at least one metabolic rate enhancing agents (e.g., an ACC2 inhibitor, a β3 agonist, DGAT1 inhibitor, a DGAT2 inhibitor, a FAS inhibitor, a PDE inhibitor, a thyroid hormone β agonist, an UCP-1, 2, or 3 activator, an acyl-estrogen, a glucocorticoid antagonist, an 11 β HSD-1 inhibitor, a Mc3r agonist, a SCD-1, oleoyl-estrone, 3-[(3,5,7-trimethyl-1-adamantyl)methyl]-6,7,8,9-tetr-ahydro-5H-[1,2,4]triazolo[4,3-a]azepine; 3-(1-adamantyl)-4-ethyl-5-(e-thylthio)-4H-1,2,4-triazole; 3-adamantanyl-4,5,6,7,8,9,10,11,12,3a-de-cahydro-1,2,4-triazolo[4,3-a][11]annulene, 3-(1-adamantyl)-5-(3,4,5-trimethoxyphenyl)-4-methyl-4H-1,2,4-triazole and combinations thereof). In some embodiments, an enteroendocrine peptide secretion enhancing agent is combined or administered with a phosphodiesterase inhibitor. In certain embodiments, an enteroendocrine peptide secretion enhancing agent is combined or administered with caffeine. In certain embodiments the compositions or formulations described herein are used in combination with at least one nutrient absorption inhibitors (e.g., a lipase inhibitor; a fatty acid transporter inhibitor; a dicarboxylate transporter inhibitor; a glucose transporter inhibitor; a phosphate transporter inhibitor; orlistat and combinations thereof). In certain embodiments the compositions or formulations described herein are used in combination with at least one appetite suppressant and at least one metabolic rate enhancing agents. In certain embodiments the compositions or formulations described herein are used in combination with at least one appetite suppressant and at least one nutrient absorption inhibitors. In certain embodiments the compositions or formulations described herein are used in combination with at least one nutrient absorption inhibitors and at least one metabolic rate enhancing agents. In certain embodiments the compositions or formulations described herein are used in combination with at least one appetite suppressant, at least one metabolic rate enhancing agents and at least one nutrient absorption inhibitors.

Figure 16:
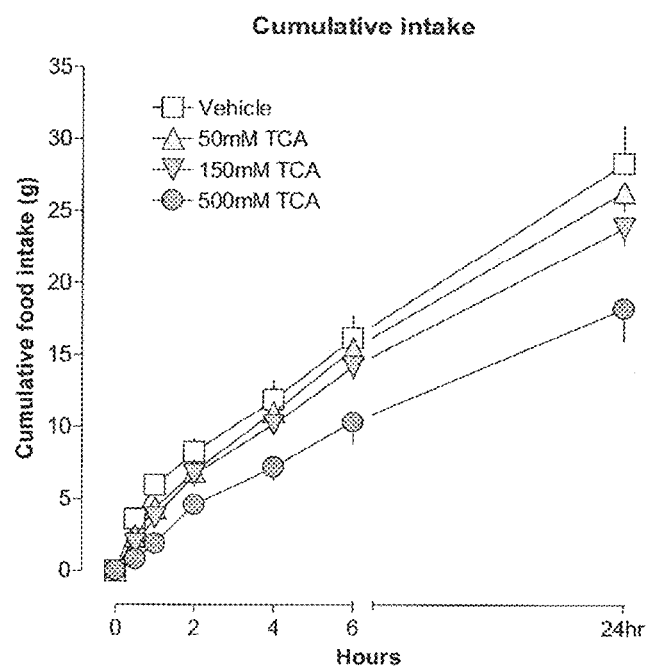
FIG. 16 illustrates the cumulative food intake of rats with rectal administration of three concentrations of taurocholate and the cumulative food intake of rats without rectal administration of taurocholate.
Figure 17:
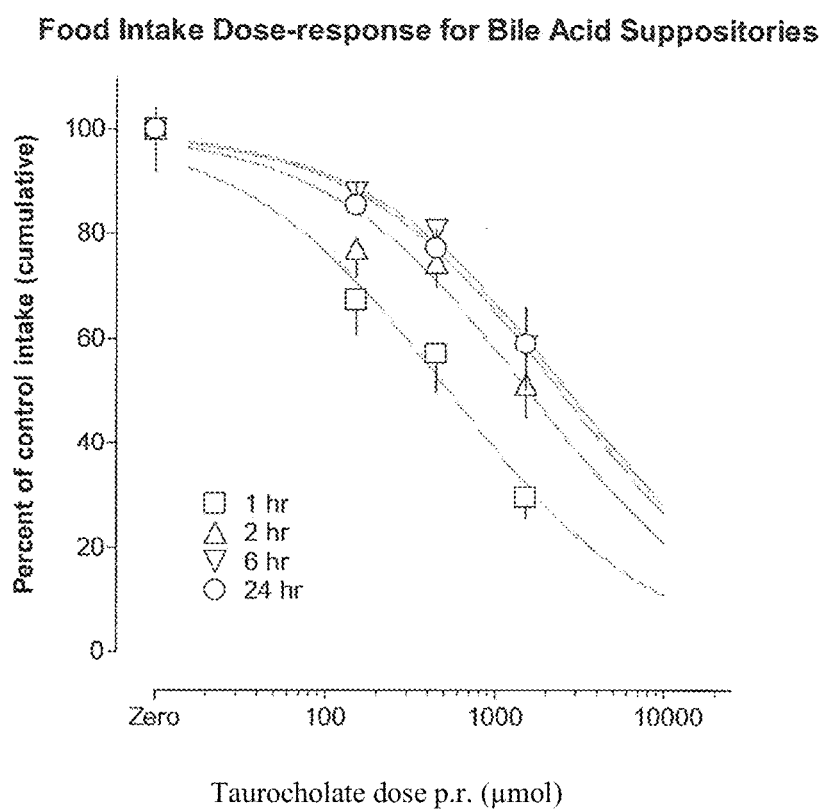
FIG. 17 illustrates the dose response in rats for the anorectic effect of rectally administered taurocholate.

In some embodiments, enteroendocrine peptide secretion enhancing agents therapies described herein are used in combination with biliary shunt treatments. In certain embodiments, a bilary shunt is a stented thin-walled catheter placed endoscopically within the common bile duct. In certain embodiments, the catheter runs a length down the gastrointestinal tract, providing for delivery of bile acids and/or salts to the distal gastrointestinal tract. FIG. 16 illustrates placement of a biliary shunt useful for delivery of endogenous bile acids and/or salts to the distal gastrointestinal tract (e.g., distal ileum, colon, and/or rectum).

In some embodiments, a combination described herein comprises a DPP-4 (used interchangeably herein with DPP-IV) inhibitor. In certain embodiments, a method described herein comprises administering a DPP-4 inhibitor. In some instances, inhibition of DPP-IV reduces the degradation of enteroendocrine peptide products (e.g. GLP-1) thereby prolonging the effect of GLP-1 in reducing blood glucose levels.

DPP-IV inhibitors suitable for use with the methods described herein include and are not limited to (2S)-1-{2-[(3-hydroxy-1-adamantyl)amino]acetyl}pyrrolidine-2-carbonitrile (vildagliptin), (3R)-3-amino-1-[9-(trifluoromethyl)-1,4,7,8-tetrazabicyclo[4.3.0]nona-6,8-d ien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin).

In some embodiments of any of the methods described herein, administration of an enteroendocrine peptide secretion enhancing agents described herein in combination with a DPP-IV inhibitor increases the level of GLP-1 in the blood and/or plasma of an individual by from about 1.1 times to about 30 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 1.1 times to about 20 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 1.5 times to about 10 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 2 times to about 8 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 2 times to about 6 times compared to the level of GLP-1 in the blood and/or plasma of the individual prior to administration of the enteroendocrine peptide secretion enhancing agent in combination with the DPP-IV inhibitor. In some instances, an increase in GLP-1 level of from about 2 times to about 3 times following the administration of an enteroendocrine peptide secretion enhancing agent inhibitor described herein in combination with a DPP-IV inhibitor compared to the level of GLP-1 in the blood and/or plasma of the individual prior to administration of the enteroendocrine peptide secretion enhancing agent in combination with the DPP-IV inhibitor is associated with an anti-diabetic effect. In some instances, an increase in GLP-1 level of from about 3 times to about 8 times following the administration of an enteroendocrine peptide secretion enhancing agent described herein in combination with a DPP-IV inhibitor compared to the level of GLP-1 in the blood and/or plasma of the individual prior to administration of the enteroendocrine peptide secretion enhancing agent in combination with a DPP-IV inhibitor is associated with reduction in food intake and/or induction of satiety and/or weight loss.

In certain embodiments of any of the methods described herein, administration of an enteroendocrine peptide secretion enhancing agent in combination with a DPP-IV inhibitor reduces blood and/or plasma sugar levels by at least 20%, at least 30%, at least 40%, at least 50% at least 60%, at least 70% or at least 80% compared to blood and/or plasma sugar levels prior to administration of the enteroendocrine peptide secretion enhancing agent in combination with a DPP-IV inhibitor. In some embodiments of any of the methods described herein, administration of an enteroendocrine peptide secretion enhancing agent in combination with a DPP-IV inhibitor reduces blood and/or plasma sugar levels by at least 20% compared to blood and/or plasma sugar levels prior to administration of the enteroendocrine peptide secretion enhancing agent in combination with a DPP-IV inhibitor. In some embodiments of any of the methods described herein, administration of an enteroendocrine peptide secretion enhancing agent in combination with a DPP-IV inhibitor reduces blood and/or plasma sugar levels by at least 30% compared to blood and/or plasma sugar levels prior to administration of the enteroendocrine peptide secretion enhancing agent in combination with a DPP-IV inhibitor. In some embodiments of any of the methods described herein, administration of an enteroendocrine peptide secretion enhancing agent in combination with a DPP-IV inhibitor reduces blood and/or plasma sugar levels by at least 40% compared to blood and/or plasma sugar levels prior to administration of the enteroendocrine peptide secretion enhancing agent in combination with a DPP-IV inhibitor.

In some embodiments of any of the methods described herein, administration of an enteroendocrine peptide secretion enhancing agent in combination with a DPP-IV inhibitor reduces blood and/or plasma sugar levels for a longer period of time (e.g., at least 24 hours) compared to reduction in blood and/or plasma sugar levels upon administration of metformin in combination with a DPP-IV inhibitor. In some embodiments of any of the methods described herein, administration of a single dose of an enteroendocrine peptide secretion enhancing agent in combination with a DPP-IV inhibitor sustains reduced blood and/or plasma sugar levels for at least 6 hours, at least 12 hours, at least 14 hours, at least 16 hours, at least 18 hours, at least 20 hours, at least 24 hours, at least 30 hours, at least 36 hours or at least 48 hours compared to reduction in blood and/or plasma sugar levels upon administration of a single dose of metformin in combination with a DPP-IV inhibitor.

In some embodiments of any of the methods described herein, administration of an enteroendocrine peptide secretion enhancing agent in combination with a DPP-IV inhibitor results in higher levels of GLP-1 in blood and/or plasma of an individual compared to levels of GLP-1 in blood and/or plasma of a normal individual. In some embodiments of any of the methods described herein, administration of an enteroendocrine peptide secretion enhancing agent in combination with a DPP-IV inhibitor results in higher levels of GLP-1 in blood and/or plasma of an individual compared to levels of GLP-1 in blood and/or plasma of an individual undergoing therapy with metformin and/or a DPP-IV inhibitor.

Kits

In another aspect, provided herein are kits containing a device for rectal administration pre-filled a pharmaceutical composition described herein. In certain embodiments, kits contain a device for rectal administration and a pharmaceutical composition (e.g., a rectal dosage form) as described herein. In certain embodiments the kits includes prefilled bags for administration of rectal enemas, while in other embodiments the kits include prefilled bags for administration of rectal gels. In certain embodiments the kits includes prefilled syringes for administration of rectal enemas, while in other embodiments the kits include prefilled syringes for administration of rectal gels. In certain embodiments the kits includes prefilled pressurized cans for administration of rectal foams.

Pharmaceutical Compositions

Provided herein, in certain embodiments, is a pharmaceutical composition comprising a therapeutically effective amount of any compound described herein. In certain instances, the pharmaceutical composition comprises an ASBT inhibitor (e.g., any ASBTI described herein).

In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition, as used herein, refers to a mixture of a compound described herein, such as, for example, a compound of Formula I-VI, with other chemical components, such as carriers, stabilizers, diluents, dispersing agents, suspending agents, thickening agents, and/or excipients. In certain instances, the pharmaceutical composition facilitates administration of the compound to an individual or cell. In certain embodiments of practicing the methods of treatment or use provided herein, therapeutically effective amounts of compounds described herein are administered in a pharmaceutical composition to an individual having a disease, disorder, or condition to be treated. In specific embodiments, the individual is a human. As discussed herein, the compounds described herein are either utilized singly or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

In certain embodiments, a pharmaceutical compositions described herein includes one or more compound described herein as an active ingredient in free-acid or free-base form, or in a pharmaceutically acceptable salt form. In some embodiments, the compounds described herein are utilized as an N-oxide or in a crystalline or amorphous form (i.e., a polymorph). In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be described herein.

A "carrier" includes, in some embodiments, a pharmaceutically acceptable excipient and is selected on the basis of compatibility with compounds described herein, such as, compounds of any of Formula I-VI, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Moreover, in certain embodiments, the pharmaceutical compositions described herein are formulated as a dosage form. As such, in some embodiments, provided herein is a dosage form comprising a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Release in Distal Ileum and/or Colon

In certain embodiments, a dosage form comprises a matrix (e.g., a matrix comprising hypermellose) that allows for controlled release of an active agent in the distal jejunum, proximal ileum, distal ileum and/or the colon. In some embodiments, a dosage form comprises a polymer that is pH sensitive (e.g., a MMX™ matrix from Cosmo Pharmaceuticals) and allows for controlled release of an active agent in the ileum and/or the colon. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a dosage form suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an ASBTI to the distal ileum. In some embodiments, a dosage form comprising an ASBTI is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the ileum and/or the colon. In some embodiments, bacterially activated systems are suitable for targeted delivery to the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences*, 20th Edition (2000), a film coating is provided around the formulation of the compound of Formula I-VI. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

An ASBT inhibitor (e.g., a compound of Formula I-VI) is used in the preparation of medicaments for the prophylactic and/or therapeutic treatment of obesity and/or diabetes. A method for treating any of the diseases or conditions described herein in an individual in need of such treatment, involves administration of pharmaceutical compositions containing at least one ASBT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

Screening Process

Provided in certain embodiments herein are processes and kits for identifying compounds suitable for treating obesity, metabolic disorders or disorders mediated by L-cell enteroendocrine peptides. In certain embodiments, provided herein are assays for identifying compounds that selectively inhibit the ASBT, or enhance the secretion of L-cell enteroendocrine peptides, or a combination thereof by:
 a. providing cells that are a model of intestinal L-cells (e.g., SLC-1 cells, GLUTag cells, NCI-H719 cells);
 b. contacting the cells with a compound (e.g., a compound as described herein);
 c. detecting or measuring the effect of the compound on the secretion of enteroendocrine peptides (e.g., GLP-1, GLP-2) from the cells.

In certain embodiments, provided herein are assays for identifying compounds that are non-systemic compounds by
 a. providing cells that are a model of intestinal permeability (e.g., Caco-2 cells);
 b. culturing the cells as a monolayer on semi-permeable plastic supports that are fitted into the wells of multiwell culture plates;
 c. contacting the apical or basolateral surface of the cells with a compound (e.g., a compound as described herein) and incubating for a suitable length of time;
 d. detecting or measuring the concentration of the compound on both sides of the monolayer by liquid-chromatography-mass spectrometry (LC-MS) and computing intestinal permeability of the compound.

In certain embodiments, non-systemic compounds are identified by suitable parallel artificial membrane permeability assays (PAMPA).

In certain embodiments, non-systemic compounds are identified by use of isolated vascular-perfused gut preparations.

In certain embodiments, provided herein are assays for identifying compounds that inhibit recycling of bile acid salts by
 a. providing cells that are a model of intestinal cells with apical bile acid transporters (e.g., BHK cells, CHO cells);
 b. incubating the cells with a compound (e.g., a compound as described herein) and/or a radiolabeled bile acid (e.g., $^{14}C$ taurocholate) for a suitable length of time;
 c. washing the cells with a suitable buffer (e.g. phosphate buffered saline);
 d. detecting or measuring the residual concentration of the radiolabeled bile acid in the cells.

EXAMPLES

Example 1

Synthesis of 1-phenethyl-1-((1,4-diazabicyclo[2.2.2] octanyl)pentyl)imidodicarbonimidic diamide, iodide salt

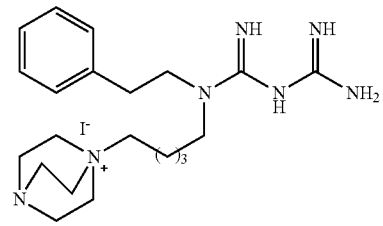

Step 1: Synthesis of 5-(1,4-diazabicyclo[2.2.2]octanyl)-1-iodo pentane, iodide salt

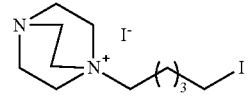

1,4-diazabicyclo[2.2.2]octane is suspended in THF. Diiodopentane is added dropwise and the mixture is refluxed overnight. The reaction mixture is filtered.

Step 2: Synthesis of N-phenethyl-5-(1,4-diazabicyclo[2.2.2]octanyl)-1-iodo pentane, iodide salt

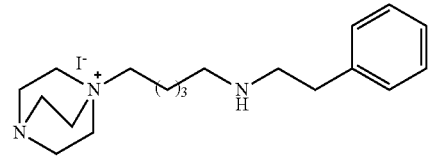

5-(1,4-diazabicyclo[2.2.2]octanyl)-1-iodo pentane, iodide salt is suspended in acetonitrile. Phenethylamine is added dropwise and the mixture is refluxed overnight. The reaction mixture is filtered.

Step 3: Synthesis of 1-phenethyl-1-((1,4-diazabicyclo[2.2.2]octanyl)pentyl)imidodicarbonimidic diamide, iodide salt N-phenethyl-5-(1,4-diazabicyclo[2.2.2]octanyl)-1-iodo pentane, iodide salt is heated with dicyanodiamide in n-butanol for 4 h. The reaction mixture is concentrated under reduced pressure.

The compounds in Table 1 are prepared using methods as described herein, and using appropriate starting materials.

TABLE 1
| Compound No. | Structure |
|---|---|
| 1 | 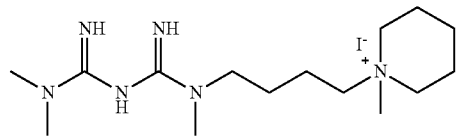 [SMILES: CN(C)C(=N)NC(=N)N(C)CCCC[N+]1(C)CCCCC1 ; [I-]] |
| 2 | 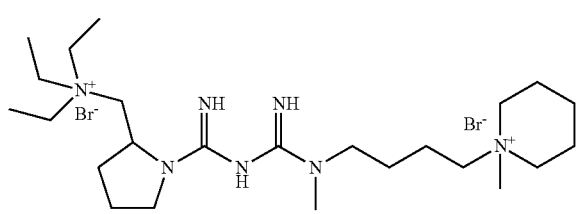 [SMILES: CC[N+](CC)(CC)CC1CCCN1C(=N)NC(=N)N(C)CCCC[N+]1(C)CCCCC1 ; [Br-] ; [Br-]] |
| 3 | 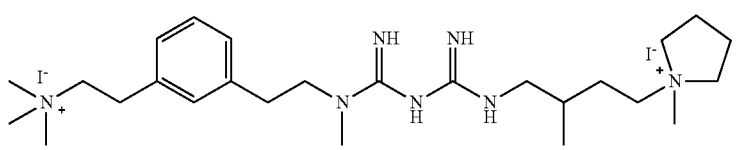 [SMILES: CC(CC[N+]1(C)CCCC1)CNC(=N)NC(=N)N(C)CCc1cccc(CC[N+](C)(C)C)c1 ; [I-] ; [I-]] |
| 4 | 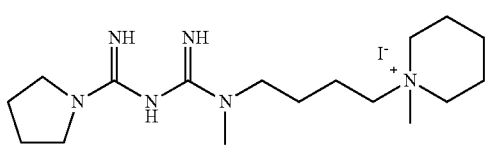 [SMILES: CN(CCCC[N+]1(C)CCCCC1)C(=N)NC(=N)N1CCCC1 ; [I-]] |
| 5 | 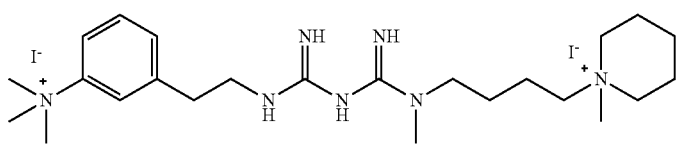 [SMILES: CN(CCCC[N+]1(C)CCCCC1)C(=N)NC(=N)NCCc1cccc([N+](C)(C)C)c1 ; [I-] ; [I-]] |
| 6 | 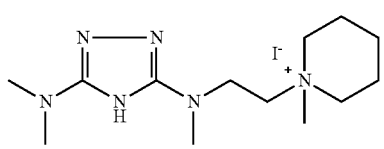 [SMILES: CN(C)c1nnc(N(C)CC[N+]2(C)CCCCC2)[nH]1 ; [I-]] |
| 7 | 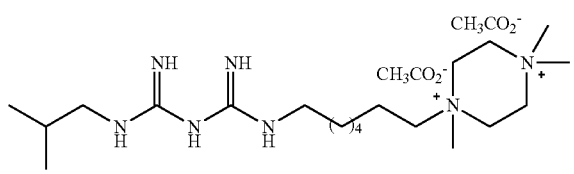 |
| 8 | 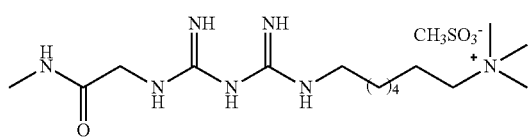 |
| 9 | 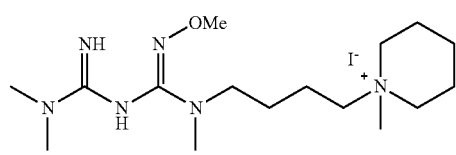 [SMILES: CO/N=C(/NC(=N)N(C)C)N(C)CCCC[N+]1(C)CCCCC1 ; [I-]] |

TABLE 1-continued

| Compound No. | Structure |
|---|---|
| 10 | 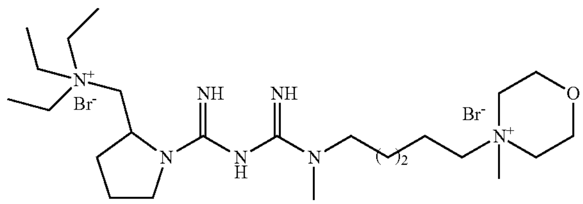 |
| 11 | 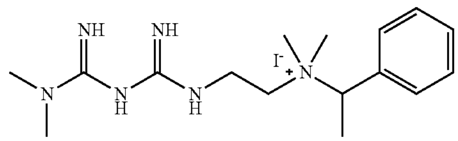 |

Example 2

In Vitro Assay for Inhibition of ASBT-Mediated Bile Acid Uptake

Baby hamster kidney (BHK) cells are transfected with cDNA of human ASBT. The cells are seeded in 96-well tissue culture plates at 60,000 cells/well. Assays are run within 24 hours of seeding.

On the day of the assay the cell monolayer is washed with 100 mL of assay buffer. The test compound is added to each well along with 6 mM [$^{14}$C]taurocholate in assay buffer (final concentration of 3 mM [$^{14}$C]taurocholate in each well). The cell cultures are incubated for 2 h at 37° C. The wells are washed with PBS. Scintillation counting fluid is added to each well, the cells are shaken for 30 minutes prior to measuring amount of radioactivity in each well. A test compound that has significant ASBT inhibitory activity provides an assay wherein low levels of radioactivity are observed in the cells.

Example 3

In Vitro Assay for Secretion of GLP-1

Human NCI-H716 cells are used as a model for L-cells. Two days before each assay experiment, cells are seeded in 12-well culture plates coated with Matrigel® to induce cell adhesion. On the day of the assay, cells are washed with buffer. The cells are incubated for 2 hours with medium alone, or with test compound. The extracellular medium is assayed for the presence of GLP-1. Peptides in the medium are collected by reverse phase adsorption and the extracts are stored until assay. The presence of GLP-1 is assayed using an antiserum directed against the carboxyl terminus of GLP-1 amide (total immunoreactive GLP-1; Affinity Research Products, Nottingham, UK). The detection of increased levels of GLP-1 in a well containing a test compound identifies the test compound as a compound that can enhance GLP-1 secretions from L-cells.

Example 4

In Vivo Bioavailability Assay

The test compounds are solubilized in saline solutions. Sprague Dawley rats are dosed at 2-10 mg/kg body weight by iv and oral dosing. Peripheral blood samples are taken from the femoral artery at selected time periods up to 8 hours. Plasma concentrations of the compounds are determined by quantitative HPLC and/or mass spectrometry. Clearance and AUC values are determined for the compounds.

For oral dosing, bioavailabilty is calculated by also drawing plasma samples from the portal vein. Cannulae are inserted in the femoral artery and the hepatic portal vein to obtain estimates of total absorption of drug without first-pass clearance in the liver. The fraction absorbed (F) is calculated by $$F = AUC_{po}/AUC_{iv}$$

Example 5

In Vivo Animal Model of Necrotizing Enterocolitis and Obesity

Sprague-Dawley (SD) rats are used as a model of necrotizing enterocolitis (NEC). NEC is induced by collecting premature SD rats by cesarean section 1 day prior to scheduled birth. SD rat pups are fed with cow's milk-based formula and subjected to asphyxia and cold stress twice daily to develop NEC.

A non-genetic mouse obesity model is used. Obesity is induced in a cohort of C57BL/6 (wild-type) mice, by a high-fat cafeteria diet. The mice are administered 30 mg/kg of compound 8 once daily as an oral solution in saline. The mice are weighed daily over a period of two weeks. Cafeteria dieting is continued throughout the experiment. Obese mice administered a saline solution alone (placebo) serve as negative controls. The weight gain in the control group is compared with the weight gain or loss of the test group.

Example 6

Histological Evaluations of Necrosis or Damage to Ileal Architecture or Ileal Cells in NEC Histological sections are obtained after administration of an ASBTI and/or an enteroendocrine peptide enhancing agent and/or a FXR agonist to the ileum of NEC suffering SD rats and compared to the corresponding histological sections of a normal SD rat. Histological changes are scored by a blind evaluator and graded using the following scoring system:

| Score | Histological observations |
|---|---|
| 0 | Normal, no necrosis or damage |
| 1 | Very mild, slight submucosal and/or lamina propria separation |
| 2 | Mild, some submucosal and/or lamina propria separation |
| 3 | Moderate, moderate submucosal and/or lamina propria separation |
| 4 | Severe, severe submucosal and/or lamina propria separation and/or severe edema in submucosa and muscular layers, regional villous sloughing |
| 5 | Necrosis, loss of villi and loss of ileal architecture |

Histological scores greater than or equal to 3 are considered to have developed NEC.

A single administration of (−)-(3R,5R)-trans-3-butyl-3-ethyl-2,3,4,5-tetrahydro-7,8-dimethoxy-5-phenyl-1,4-benzothiazepine 1,1-dioxide is administered to produce a dose-dependent reduction of the histological score. Control mice are treated with only the control vehicle (saline in 10% of DMSO).

Example 6B

Assay to Determine Ileal Intraenterocyte and Luminal Bile Acid Levels

Ileal luminal bile acid levels in SD rats are determined by flusing a 3-cm section of distal ileum with sterile, cold PBS. After flushing with additional PBS, the same section of ileum is weighed and then homogenized in fresh PBS for determination of interenterocyte bile acid levels. A LC/MS/MS system is used to evaluate cholic acid, DCA, LCA, chnodeoxycholic acid, and ursodeoxycholic acid levels.

Example 7A

In Vivo Assay for Reduction in Blood Glucose Levels

Male db/db mice 6-7 weeks (approx 30 g) were fasted for 2 h. A combination of (−)-(3R,5R)-trans-3-butyl-3-ethyl-2,3,4,5-tetrahydro-7,8-dimethoxy-5-phenyl-1,4-benzothiazepine 1,1-dioxide (Compound 100A) at doses of 0, 0.1, 1, 10, mg/kg in 10% of DMSO-water and 30 mg/kg sitagliptin (DPP-IV inhibitor) in a mixture of valine-pyrrolidine in water was administered orally to male db/db mice (n=7-10 per group). Blood sample (~1 µl from tail for glucose level testing) was taken at t=−24 h, 0, 60, 180, 240, 300, 360 min and 24 h after administration.

Figure 9:
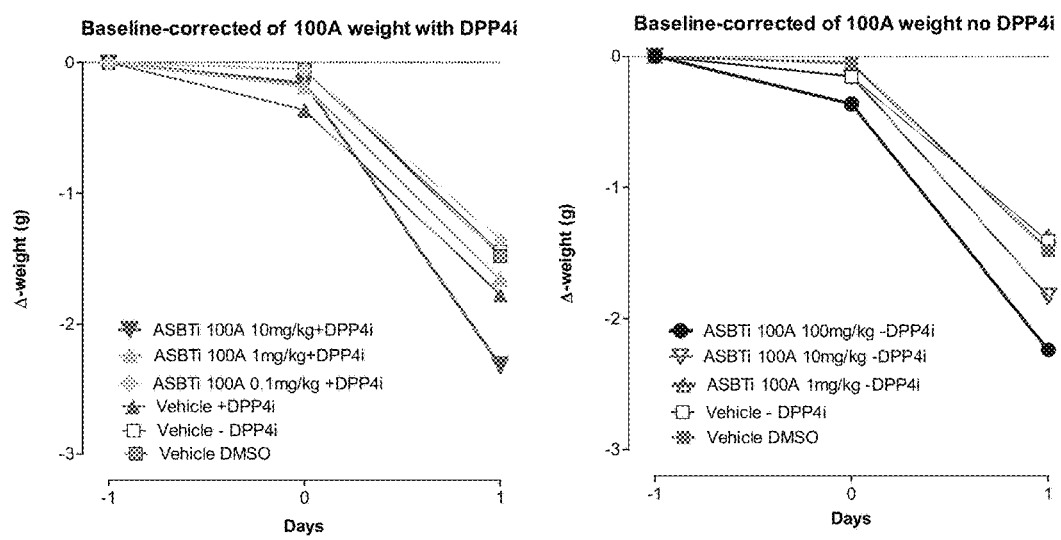
FIG. 9 illustrates the change in body weight 24 h after administration of the ASBTI (−)-(3R,5R)-trans-3-butyl-3-ethyl-2,3,4,5-tetrahydro-7,8-dimethoxy-5-phenyl-1,4-benzothiazepine 1,1-dioxide (100A) at doses of 0, 0.1, 1, 10 mg/kg in combination with 30 mg/kg sitagliptin (DPP-IV inhibitor) and the ASBTI alone.

A single administration of (−)-(3R,5R)-trans-3-butyl-3-ethyl-2,3,4,5-tetrahydro-7,8-dimethoxy-5-phenyl-1,4-benzothiazepinel 1,1-dioxide in combination with sitagliptin produced a dose-dependent reduction of the elevated blood glucose levels compared to the control mice treated with sitagliptin alone or with vehicle solution of 10% of DMSO (FIG. 1). Reductions in plasma glucose concentrations are observed from 3 hours up to 24 hours post-dose and accompanied after 6 hours by a 5.5%, 5.6%, 15% and 42.3% reduction in plasma glucose from baseline, (doses of 0, 01, 1 and 10 mg/kg of (−)-(3R,5R)-trans-3-butyl-3-ethyl-2,3,4,5-tetrahydro-7,8-dimethoxy-5-phenyl-1,4-benzothiazepine 1,1-dioxide respectively). Plasma glucose concentrations in the control mice treated with only the control vehicle (saline in 10% of DMSO) increased by 1.5% after 6 h. Administration of the ASBTI alone also lowers plasma glucose concentrations in male db/db mice as shown in FIG. 1. Weight loss is shown in FIG. 9.

Example 7B

In Vivo Assay for Reduction in Blood Glucose Levels

Male db/db mice 8-9 weeks (approx 40 g) were fasted for 2 h. A combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo [2.2.2]octane methane sulfonate (Compound 100B) at doses of 0, 3, 30, 100 mg/kg in saline-water and 30 mg/kg sitagliptin (DPP-IV inhibitor) in a mixture of valine-pyrrolidine in water was administered orally to male db/db mice (n=6-11 per group). Blood sample (~1 µl from tail for glucose level testing) was taken at t=−24 h, 0, 1, 3, 4, 5, 6 h and 24 h after administration.

Figure 8:
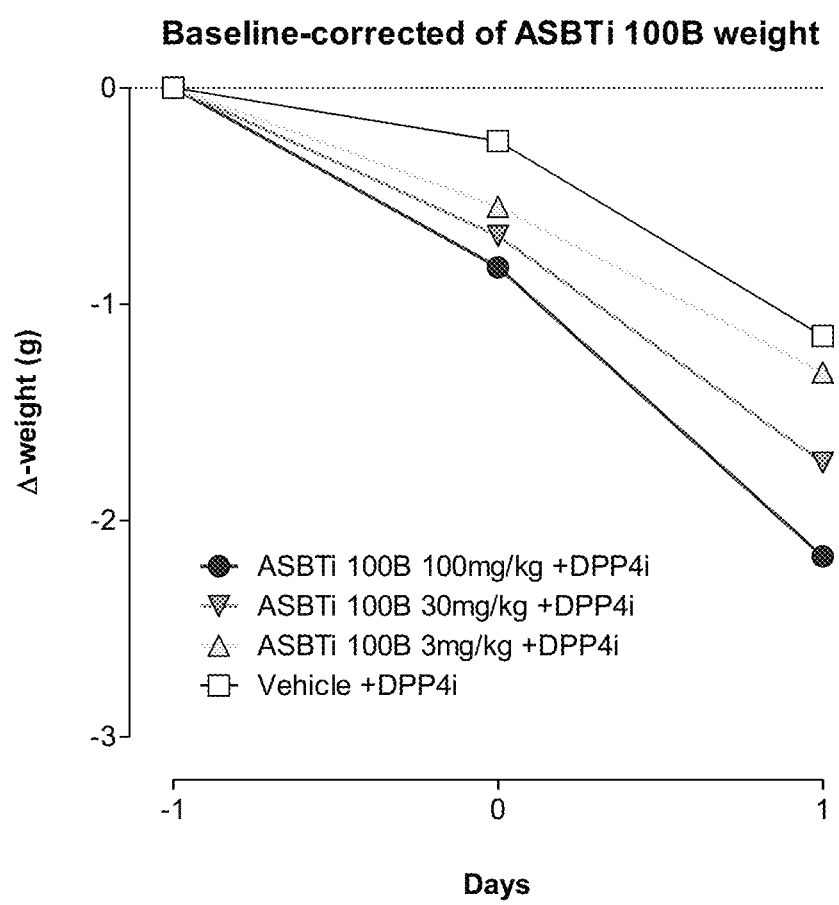
FIG. 8 illustrates the change in body weight 24 h after administration of ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (100B) at doses of 0, 3, 30, 100 mg/kg in combination with 30 mg/kg sitagliptin (DPP-IV inhibitor).

A single administration of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate in combination with sitagliptin produced a dose-dependent reduction of the elevated blood glucose levels compared to the control mice treated with sitagliptin alone or with vehicle solution of saline-water (FIG. 2). Reductions in plasma glucose concentrations are observed from 3 hours till 24 hours post-dose and accompanied after 6 hours by a 5.5%, 5.6%, 15% and 42.3% reduction in plasma glucose from baseline, (doses of 0, 3, 30 and 100 mg/kg of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate respectively). Plasma glucose concentrations in the control mice treated with only the control vehicle (saline-water) increased by 1.5% after 6 h (FIG. 2). Weight loss is shown in FIG. 8.

Administration of doses of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate alone also lowers plasma glucose levels in dose dependent manner (FIG. 4).

Example 8

Figure 5:
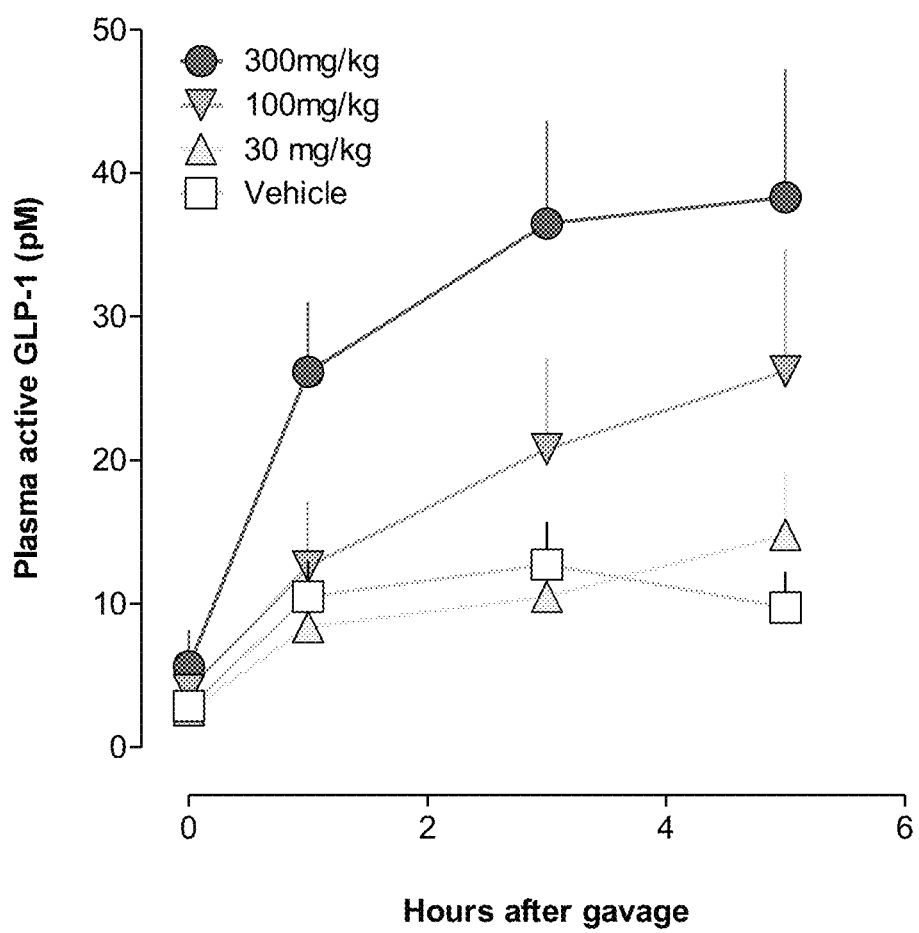
FIG. 5 illustrates a time course for dose-dependent increase in plasma GLP-1 level in normal rats upon administration of a combination of metformin (0, 30, 100, 300 mg/kg) and 30 mg/kg sitagliptin (DPP-IV inhibitor).

Investigation of Orally Delivered 1-[4-[4-[(4R,5R)-3,3-Dibutyl-7-(Dimethylamino)-2,3,4,5-Tetrahydro-4-Hydroxy-1,1-Dioxido-1-Benzothiepin-5-Yl]Phenoxy]Butyl]4-Aza-1-Azoniabicyclo[2.2.2]Octane Methane Sulfonate (Compound 100B) and Metformin in Combination with DPP-IV Inhibitor on Plasma GLP-1 Levels in Normal Rats 12-week-old male HSD rats were fasted for 16 h and given oral dose of 0, 3, 30, 100 mg/kg of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Synthesized by Nanosyn Inc., CA, USA) or metformin (Control, 0, 3, 30, 100, 300 mg/kg) in saline and a dose of 30 mg/kg sitaglipin in a mixture of valine-pyrrolidine in water (n=5 per group). Blood samples in volume of 0.6 ml for each time point were taken from the caudal vein with a heparinized capillary tube 0, 1, 3 and 5 h after the administration of compounds and plasma GLP-1 level were determined. Aprotinin and 10l of DPP-IV inhibitor per ml of blood were used for blood sample preservation during 10 min centrifugation and for storage at −70° C. or below. GLP-1 (Active pM) was tested by Millipore ELISA Kits (Millipore Corporation, 290 Concord Road, Billerica, Mass.). ASBTI alone or ASBTI in combination with sitagliptin elicited an elevation in GLP-1 levels in a dose-dependent manner (FIG. 6, FIG. 7) in normal rats. FIG. 5 shows elevation in GLP-1 levels in plasma of normal rats upon administration of a combination of metformin and sitagliptin.

Example 9

Figure 10:
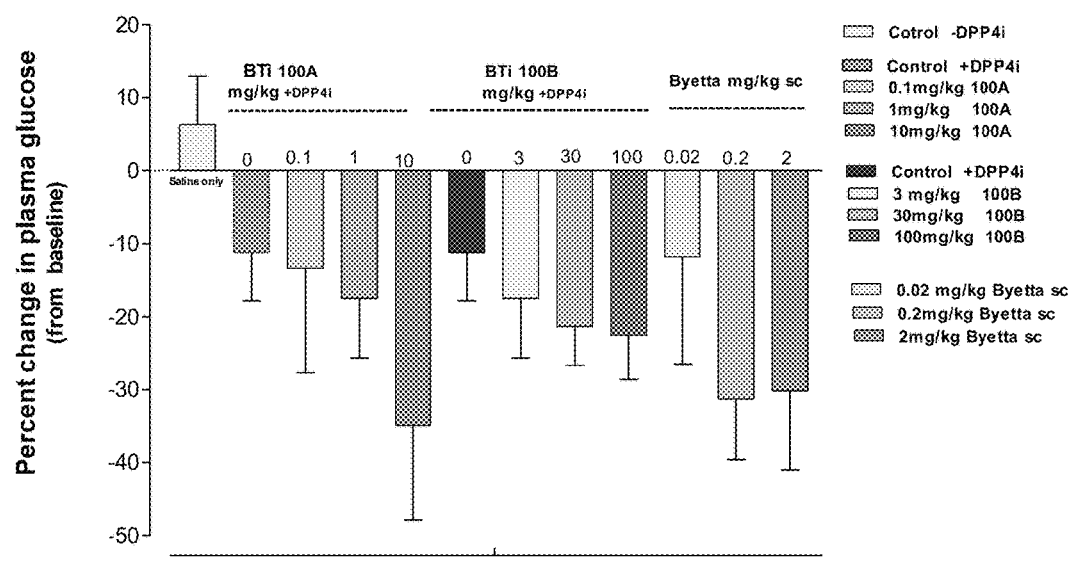
FIG. 10 illustrates (1) a comparison of orally administered combination of (−)-(3R,5R)-trans-3-butyl-3-ethyl-2,3,4,5-tetrahydro-7,8-dimethoxy-5-phenyl-1,4-benzothiazepine 1,1-dioxide (100A) at doses of 0, 0.1, 1, 10 mg/kg and 30 mg/kg sitagliptin (DPP-IV inhibitor) on blood glucose levels in diabetic db/db mice at 3 hours after dose; and (2) a comparison of orally administered combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt (100B) at doses of 0, 3, 30, 100 mg/kg and 30 mg/kg sitagliptin (DPP-IV inhibitor) on blood glucose levels in diabetic db/db mice at 3 hours after dose; versus (3) subcutaneously injected exenatide at doses of 0.02, 0.2 and 2 mg·kg on blood glucose levels in diabetic db/db mice at 3 hours after dose.

Investigation of Orally Delivered Compound 100A and 100B in Combination with DPP-IV Inhibitor Versus Subcutaneous Exenatide A similar experiment as described above is carried out to test doses of 0, 0.01, 1 and 10 mg/kg of the ASBTI (−)-(3R,5R)-trans-3-butyl-3-ethyl-2,3,4,5-tetrahydro-7,8-dimethoxy-5-phenyl-1,4-benzothiazepinel, 1-dioxide (Compound 100A) in combination with 30 mg/kg sitagliptin and a subcutaneous injection of exenatide. An oral dose of a combination of (−)-(3R,5R)-trans-3-butyl-3-ethyl-2,3,4,5-tetrahydro-7,8-dimethoxy-5-phenyl-1,4-benzothiazepine 1,1-dioxide (10 mg/kg) in combination with 30 mg/kg sitagliptin reduces plasma glucose levels by 35% while a sub-cutaneous injection of exenatide (0.2 mg/kg) reduces plasma glucose level by 31% at 3 hours post-dose (FIG. 10).

A similar experiment as described above is carried out to compare glucose lowering effect of orally administered doses of 0, 3, 30, and 100, mg/kg of the ABTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) in combination with a 30 mg/kg dose of sitagliptin versus 0.02, 0.2 and 2 mg/kg doses of exenatide. FIG. 10 shows that an oral combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate in combination with a 30 mg/kg dose of sitagliptin reduces blood glucose levels more than a single subcutaneous injection of 0.02 mg/kg exenatide at 3 hours after dosing.

Example 10

Tablet Formulation 10 kg of a compound of Formula I-VI is first screened through a suitable screen (e.g. 500 micron). 25 kg Lactose monohydrate, 8 kg hydroxypropylmethyl cellulose, the screened compound of Formula I-VI and 5 kg calcium hydrogen phosphate (anhydrous) are then added to a suitable blender (e.g. a tumble mixer) and blended. The blend is screened through a suitable screen (e.g. 500 micron) and reblended. About 50% of the lubricant (2.5 kg, magnesium stearate) is screened, added to the blend and blended briefly. The remaining lubricant (2 kg, magnesium stearate) is screened, added to the blend and blended briefly. The granules are screened (e.g. 200 micron) to obtain granulation particles of the desired size. In some embodiments, the granules are optionally coated with a drug release controlling polymer such as polyvinylpyrrolidine, hydroxypropylcellulose, hydroxypropylmethyl cellulose, methyl cellulose, or a methacrylic acid copolymer, to provide an extended release formulation. The granules are filled in gelatin capsules.

Example 11A

Human Clinical Trial of the Effect of (−)-(3R,5R)-Trans-3-Butyl-3-Ethyl-2,3,4,5-Tetrahydro-7,8-Dimethoxy-5-Phenyl-1,4-Benzothiazepine 1,1-Dioxide (Compound 100A) on Necrotizing Enterocolitis (NEC)

Objective:
The aim of a 6 month study is to show evidence of the efficacy (−)-(3R,5R)-trans-3-butyl-3-ethyl-2,3,4,5-tetrahydro-7,8-dimethoxy-5-phenyl-1,4-benzothiazepine 1,1-dioxide on reduction of incidence and severity of NEC in very low birth weight infants.

Study Design:
This is a 6 month study. A cohort of 1000 patients is divided into placebo group and drug treated groups. An optimized dose of (−)-(3R,5R)-trans-3-butyl-3-ethyl-2,3,4, 5-tetrahydro-7,8-dimethoxy-5-phenyl-1,4-benzothiazepine 1,1-dioxide will be administered with milk or formula.

Inclusion Criteria are: Infants with birth weight less than 1500 grams; gestational age 24 to 33 weeks; diagnosed with necrotizing enterocolitis based on Bell stage II or greater; or bowel perforation as evidenced by free intraperitoneal air seen on abdominal radiograph, stool, bile, or pus found at paracentesis or clinical evidence of perforation in the joint opinion of the attending surgeon or neonatologist.

Exclusion criteria are: healthy infants, maj or congenital abnormalities, chronic disorders of other organs, evidence of gastrointestinal anomaly.

Patient Response to (−)-(3R,5R)-trans-3-butyl-3-ethyl-2, 3,4,5-tetrahydro-7,8-dimethoxy-5-phenyl-1,4-benzothiazepine 1,1-dioxide therapy: Patient response is assessed via primary and secondary outcome measures.

Primary Outcome Measures: disease mortality, disease progression, treatment failure, time to recovery.

Secondary Outcome Measures: inflammatory cytokine concentration, duration of inflammation, weight gain, length of hospital stay.

Blood Sampling Serial blood is drawn by direct vein puncture before and after administration of Compound 100 analog. Venous blood samples (2 mL) for determination of serum concentrations are obtained at about 10 minutes prior to dosing and at approximately the following times after dosing: days 1, 2, 3, 4, 5, 6, 7, 14 and every 14 days later. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, 14 and every 14 days later. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Statistical Analysis: The association of (−)-(3R,5R)-trans-3-butyl-3-ethyl-2,3,4,5-tetrahydro-7,8-dimethoxy-5-phenyl-1,4-benzothiazepine 1,1-dioxide and reduction of necrotizing enterocolitis is analyzed by $\chi 2$ test.

Example 11B

A Human Clinical Trial similar to the trial in Example 11A is conducted to determine the effect of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) on reduction of necrotizing enterocolitis.

Example 11C

A Human Clinical Trial similar to the trial in Example 11A is conducted to determine the effect of 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine on reduction of necrotizing enterocolitis.

Example 11D

A Human Clinical Trial similar to the trial in Example 11A is conducted to determine the effect of 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine on reduction of necrotizing enterocolitis.

Example 11E

A Human Clinical Trial similar to the trial in Example 11A is conducted to determine the effect of 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine on reduction of necrotizing enterocolitis.

Example 11F

A Human Clinical Trial similar to the trial in Example 11A is conducted to determine the effect of 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl]amino]-1-deoxy-D-glucitol on reduction of necrotizing enterocolitis.

Example 11G

A Human Clinical Trial similar to the trial in Example 11A is conducted to determine the effect of Potassium((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl)sulphate ethanolate, hydrate on reduction of necrotizing enterocolitis.

Example 11H

A Human Clinical Trial similar to the trial in Example 11A is conducted to determine the effect of SD-5613 (Pfizer, a.k.a. 97-G) on reduction of necrotizing enterocolitis.

Example 11I

A Human Clinical Trial similar to the trial in Example 11A is conducted to determine the effect of combination of (−)-(3R,5R)-trans-3-butyl-3-ethyl-2,3,4,5-tetrahydro-7,8-dimethoxy-5-phenyl-1,4-benzothiazepine 1,1-dioxide and bile acids or mimetics on reduction of necrotizing enterocolitis.

Example 11J

A Human Clinical Trial similar to the trial in Example 11A is conducted to determine the effect of combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) bile acids or mimetics on reduction of necrotizing enterocolitis.

Example 11K

A Human Clinical Trial similar to the trial in Example 11A is conducted to determine the effect of combination of 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine bile acids or mimetics on reduction of necrotizing enterocolitis.

Example 11L

A Human Clinical Trial similar to the trial in Example 11A is conducted to determine the effect of combination of 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine bile acids or mimetics on reduction of necrotizing enterocolitis.

Example 11M

A Human Clinical Trial similar to the trial in Example 11A is conducted to determine the effect of combination of 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine bile acids or mimetics on reduction of necrotizing enterocolitis.

Example 11N

A Human Clinical Trial similar to the trial in Example 11A is conducted to determine the effect of combination of 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl]amino]-1-deoxy-D-glucitol bile acids or mimetics on reduction of necrotizing enterocolitis.

Example 11O

A Human Clinical Trial similar to the trial in Example 11A is conducted to determine the effect of combination of Potassium((2R,3R,4S,5R,6R)-4-benzyloxy-6-{3-[3-((3S, 4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl) sulphate ethanolate, hydrate bile acids or mimetics on reduction of necrotizing enterocolitis.

Example 11P

A Human Clinical Trial similar to the trial in Example 11A is conducted to determine the effect of combination of SD-5613 (Pfizer, a.k.a. 97-G) bile acids or mimetics on reduction of necrotizing enterocolitis.

Example 12A

Human Clinical Trial of the effect of (−)-(3R,5R)-trans-3-butyl-3-ethyl-2,3,4,5-tetrahydro-7,8-dimethoxy-5-phenyl-1,4-benzothiazepine 1,1-dioxide (Compound 100A) on satiety and reduction in food intake, plasma glucose and insulin levels Objective:

The aim of the 8 week study is to show evidence of the efficacy (−)-(3R,5R)-trans-3-butyl-3-ethyl-2,3,4,5-tetrahydro-7,8-dimethoxy-5-phenyl-1,4-benzothiazepine 1,1-dioxide to induce satiety and to reduce food intake. A secondary objective of the study is to determine the effect of (−)-(3R,5R)-trans-3-butyl-3-ethyl-2,3,4,5-tetrahydro-7,8-dimethoxy-5-phenyl-1,4-benzothiazepine-1,1-dioxide on food consumption (amount and composition) during a free meal (dinner); wellness after one week supplementation; the intermeal interval; and body weight and waist-hip ratio (WHR).

Study Design:

This is an 8 week study. A cohort of 500 patients is divided into placebo group and drug treated groups. 50 mg of (−)-(3R,5R)-trans-3-butyl-3-ethyl-2,3,4,5-tetrahydro-7,8-dimethoxy-5-phenyl-1,4-benzothiazepine 1,1-dioxide will be administered 30 minutes prior to ingestion of lunch and prior to ingestion of dinner for a total of 100 mg of (−)-(3R,5R)-trans-3-butyl-3-ethyl-2,3,4,5-tetrahydro-7,8-dimethoxy-5-phenyl-1,4-benzothiazepine 1,1-dioxide per day.

Inclusion Criteria are: a BMI≥27, 70 years of age or less, waist circumference ≥102 cm for men or ≥88 cm for women, eating disorders, diabetes Exclusion criteria are: Stroke/MI/unstable cardiovascular disease within 6 months, clinically significant renal, hepatic or psychiatric disease, participation in a formal weight loss program or lifestyle intervention, glaucoma or intraocular pressure, use of any antidiabetic medication.

Blood Sampling Serial blood is drawn by direct vein puncture before and after administration of Compound 100 analog. Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Patient Response to (−)-(3R,5R)-trans-3-butyl-3-ethyl-2,3,4,5-tetrahydro-7,8-dimethoxy-5-phenyl-1,4-benzothiazepine 1,1-dioxide therapy: Patient response is assessed via weekly hospital visits, weight and waist measurements and routine blood tests.

Primary Outcome Measures: Satiety scores (visual analog scores), wellness after one week supplementation.

Secondary Outcome Measures: Demonstrate an improvement over placebo in absolute weight loss and waist to hip ratio. Demonstrate an improvement in quality of life.

Example 12B

A Human Clinical Trial similar to the trial in Example 12A is conducted to determine the effect of 1-[4-[4-[(4R, 5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) on satiety and reduction in food intake, plasma glucose and insulin level

Example 13

Human Phase I Clinical Trial of (−)-(3R,5R)-trans-3-butyl-3-ethyl-2,3,4,5-tetrahydro-7,8-dimethoxy-5-phenyl-1,4-benzothiazepine 1,1-dioxide alone or in combination with sitagliptin on satiety and reduction in food intake, plasma glucose and insulin levels Aim of the study: A phase I dose-escalation study Patient population: Obese type II diabetic Study design: Randomized, double-blind, cross-over, single-dose placebo controlled Ten subjects will be administered a single dose of sitagliptin ten minutes before administration of a single dose of (−)-(3R,5R)-trans-3-butyl-3-ethyl-2,3,4,5-tetrahydro-7,8-dimethoxy-5-phenyl-1,4-benzothiazepine 1,1-dioxide prior to ingestion of food. A second group of ten subjects will be administered a single dose of (−)-(3R,5R)-trans-3-butyl-3-ethyl-2,3,4,5-tetrahydro-7,8-dimethoxy-5-phenyl-1,4-benzothiazepine 1,1-dioxide 30 minutes prior to ingestion of food. Rising dose levels of the ASBTI (1, 3, 10 and 30 mg/kg) will be administered at each visit. Each visit to test facility will be at least 72 hours apart.

A buffet style breakfast will be presented and ad-libitum food intake will be measured. Patients will record meal-related satiation, or hunger, and nausea on a chart. Satiogenic gut peptides will be measured post-prandially from plasma analytes. Insulin, glucose, GLP-1 and PYY levels in blood/plasma will be monitored for 24 hours. Subjects will be asked to record food intake for 72 hours after each dose.

Endpoints: Safety and tolerability, pharmacodynamics, food intake 24 hours after dosing.

Example 14

A Human Phase II Clinical Trial of (−)-(3R,5R)-trans-3-butyl-3-ethyl-2,3,4,5-tetrahydro-7,8-dimethoxy-5-phenyl-1,4-benzothiazepine 1,1-dioxide (Compound 100A) alone or in combination with sitagliptin and effect on obesity or diabetes Phase 2A: This will be a 16 week double-blind, parallel-group study. A single dose of sitagliptin in combination with (−)-(3R,5R)-trans-3-butyl-3-ethyl-2,3,4,5-tetrahydro-7,8-dimethoxy-5-phenyl-1,4-benzothiazepine 1,1-dioxide will be administered as described above. A second group of subjects will be administered a single dose of (−)-(3R,5R)-trans-3-butyl-3-ethyl-2,3,4,5-tetrahydro-7,8-dimethoxy-5-phenyl-1,4-benzothiazepine 1,1-dioxide 30 minutes prior to ingestion of food. A buffet style breakfast will be presented as described above and satiety and food intake will be measured.

Phase 2A: This will be a 6-week, single-blind, parallel-group study carried out as described above. Glucose levels in blood/plasma, body composition and a comprehensive assessment of food intake will be carried for the duration of the study.

Phase 2B: This will be a 16-week, double-blind, parallel group study dose-ranging study carried out as described above. Safety, dose-tolerance, glucose levels in blood/plasma, weight loss and HBA1c will be monitored for the duration of the study.

Example 15

A Human Phase II Clinical Trial similar to the trial in Example 14 is conducted to determine the effect of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) alone or in combination with sitagliptin and effect on obesity or diabetes

Example 16

A Human Phase II Clinical Trial similar to the trial in Example 14 is conducted to determine the effect of compound 4 alone or in combination with sitagliptin and effect on obesity or diabetes

Example 17

Human Phase I Clinical Trial of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) in combination with sitagliptin on satiety and reduction in food intake, plasma glucose and insulin level Aim of the study: A phase I dose-escalation study
Patient population: Obese type II diabetic
Study design: Randomized, double-blind, cross-over, single-dose placebo controlled Ten subjects will be administered a single dose of sitagliptin ten minutes before administration of a single dose of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate prior to ingestion of food. A second group often subjects will be administered a single dose of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate 30 minutes prior to ingestion of food. Rising dose levels of the ASBTI (1, 3, 10 and 30 mg/kg) will be administered at each visit. Each visit to test facility will be at least 72 hours apart.

A buffet style breakfast will be presented and ad-libitum food intake will be measured. Patients will record meal-related satiation, or hunger, and nausea on a chart. Satiogenic gut peptides will be measured post-prandially from plasma analytes. Insulin, glucose, GLP-1 and PYY levels in blood/plasma will be monitored for 24 hours. Subjects will be asked to record food intake for 72 hours after each dose.

Endpoints: Safety and tolerability, pharmacodynamics, food intake 24 hours after dosing.

Example 18

A Human Phase I Clinical Trial Similar to the Trial in Example 17 is Conducted to Determine the Effect of Compound 2 in Combination with Sitagliptin on Satiety and Reduction in Food Intake, Plasma Glucose And Insulin Level

Example 19

Human Clinical Trial of the Effect of Compound 4 on Satiety and Reduction in Food Intake Objective:
The aim of the 8 week study is to show evidence of the efficacy of compound 4 to induce satiety and to reduce food intake. A secondary objective of the study is to determine the effect of compound 4 on food consumption (amount and composition) during a free meal (dinner); wellness after one week supplementation; the intermeal interval; and body weight and waist-hip ratio (WHR).

Study Design:
This is an 8 week study. A cohort of 500 patients is divided into placebo group and drug treated groups. 50 mg of compound 4 will be administered 30 minutes prior to ingestion of lunch and prior to ingestion of dinner for a total of 100 mg of compound 4 per day.

Inclusion Criteria are: a BMI ≥27, 70 years of age or less, waist circumference ≥102 cm for men or >88 cm for women.

Exclusion criteria are: Stroke/MI/unstable cardiovascular disease within 6 months, clinically significant renal, hepatic or psychiatric disease, participation in a formal weight loss program or lifestyle intervention, glaucoma or intraocular pressure, use of any antidiabetic medication, previous bariatric surgery Blood Sampling Serial blood is drawn by direct vein puncture before and after administration of Compound 100 analog. Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Patient Response to Compound 4 therapy: Patient response is assessed via weekly hospital visits, weight and waist measurements and routine blood tests.

Primary Outcome Measures: Satiety scores (visual analog scores), wellness after one week supplementation.

Secondary Outcome Measures: Demonstrate an improvement over placebo in absolute weight loss and waist to hip ratio. Demonstrate an improvement in quality of life.

Example 20

Human Clinical Trial of the Effect of (−)-(3R,5R)-Trans-3-Butyl-3-Ethyl-2,3,4,5-Tetrahydro-7,8-Dimethoxy-5-Phenyl-1,4-Benzothiazepine 1,1-Dioxide (Compound 100a) on Risk of Pancreatic Cancer Objective:
The aim of a 1 year study is to show evidence of the efficacy (−)-(3R,5R)-trans-3-butyl-3-ethyl-2,3,4,5-tetrahydro-7,8-dimethoxy-5-phenyl-1,4-benzothiazepine 1,1-dioxide on reduction of risk of pancreatic cancer.

Study Design:
This is a 1 year study. A cohort of 1000 patients is divided into placebo group and drug treated groups. 50 mg of (−)-(3R,5R)-trans-3-butyl-3-ethyl-2,3,4,5-tetrahydro-7,8-dimethoxy-5-phenyl-1,4-benzothiazepine 1,1-dioxide will be administered 30 minutes prior to ingestion of lunch and prior to ingestion of dinner for a total of 100 mg of (−)-(3R,5R)-trans-3-butyl-3-ethyl-2,3,4,5-tetrahydro-7,8-dimethoxy-5-phenyl-1,4-benzothiazepine 1,1-dioxide per day.

Inclusion Criteria are: 70 years of age or less, waist circumference ≥102 cm for men or ≥88 cm for women, pancreatic ductal adenocarcinoma.

Exclusion criteria are: Stroke/MI/unstable cardiovascular disease within 6 months, clinically significant renal, hepatic or psychiatric disease, participation in a formal weight loss program or lifestyle intervention, glaucoma or intraocular pressure, use of any antidiabetic medication, prior history with cancer.

Patient Response to (−)-(3R,5R)-trans-3-butyl-3-ethyl-2,3,4,5-tetrahydro-7,8-dimethoxy-5-phenyl-1,4-benzothiazepine 1,1-dioxide therapy: Patient response is assessed via weekly hospital visits, weight and waist measurements and routine blood tests.

Blood Sampling Serial blood is drawn by direct vein puncture before and after administration of Compound 100 analog. Venous blood samples (5 mL) for determination of serum concentrations are obtained at about 10 minutes prior to dosing and at approximately the following times after dosing: days 1, 2, 3, 4, 5, 6, 7, 14 and every 14 days later. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, 14 and every 14 days later. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Patient Response to Compound 4 therapy: Patient response is assessed via weekly hospital visits, weight and waist measurements and routine blood tests.

Statistical Analysis: The association of (−)-(3R,5R)-trans-3-butyl-3-ethyl-2,3,4,5-tetrahydro-7,8-dimethoxy-5-phenyl-1,4-benzothiazepine 1,1-dioxide and risk of pancreatic cancer is analyzed in multivariable logistic regression models including age, sex, race, smoking, alcohol, BMI, family history of cancer, duration of diabetes, and insulin use. To control for reversal causality due to pancreatic cancer-caused diabetes, risk of pancreatic cancer is estimated after exclusion of those with duration of diabetes ≤2 years. HbA1c level (≤57% or >7%), a marker of glycemic control, is compared between placebo and users of (−)-(3R,5R)-trans-3-butyl-3-ethyl-2,3,4,5-tetrahydro-7,8-dimethoxy-5-phenyl-1,4-benzothiazepine-1,1-dioxide by $\chi^2$ test. The demographic and risk factors as well as duration of diabetes and insulin use are compared between (−)-(3R,5R)-trans-3-butyl-3-ethyl-2,3,4,5-tetrahydro-7,8-dimethoxy-5-phenyl-1,4-benzothiazepine 1,1-dioxide users and placebo by $\chi^2$ test.

Example 21

Rectal Foams a) 500 mM Sodium Taurocholate
Preparation Method:
Using a stainless steel dissolving vessel fitted with a propeller stirrer and turboemulsifier 26.88 grams of sodium taurocholate, 0.25 grams of potassium metabisulphite, 0.3 grams EDTA (disodium salt), 0.38 grams of sodium benzoate and 0.2 grams of xanthan gum are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

b) 500 mM Sodium Glycocholate
Preparation Method:
Using a stainless steel dissolving vessel fitted with a propeller stirrer and turboemulsifier 24.38 grams of sodium glycocholate, 0.25 grams of potassium metabisulphite, 0.3 grams EDTA (disodium salt), 0.38 grams of sodium benzoate and 0.2 grams of xanthan gum are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114into the can.

c) No Bile Salt (Control)
Preparation method:

Using a stainless steel dissolving vessel fitted with a propeller stirrer and turboemulsifier 0.25 grams of potassium metabisulphite, 0.3 grams EDTA (disodium salt), 0.38 grams of sodium benzoate and 0.2 grams of xanthan gum are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

Analysis of Food Intake

The sodium taurocholate rectal foam described above is rectally administered to 5 conscious overnight-fasted subjects (e.g., Sprague Dawley rats) and the control rectal foam without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

The sodium glycocholate rectal foam described above is rectally administered to 5 conscious overnight-fasted subjects (e.g., Sprague Dawley rats) and the control rectal foam without the sodium taurocholate is rectally administered to 5 conscious overnight-fasted subject (e.g., Sprague Dawley rats). Each subject is exposed to pre-weighed food and the cumulative consumption of the food is determined over a 6 hour period by weighing the food every 30 minutes.

Example 22

Rectal Enemas a) 500 mM Sodium Taurocholate
Preparation Method:

Using a stainless steel dissolving vessel fitted with a propeller stirrer 26.88 grams of sodium taurocholate, 0.25 grams of potassium metabisulphite, 0.3 grams EDTA (disodium salt), 0.38 grams of sodium benzoate are dissolved in 100 mL of purified water and stirring is continued for 10 minutes. The solution is then pulled into a syringe.

b) 500 mM Sodium Glycocholate
Preparation Method:

Using a stainless steel dissolving vessel fitted with a propeller stirrer and turboemulsifier 24.38 grams of sodium glycocholate, 0.25 grams of potassium metabisulphite, 0.3 grams EDTA (disodium salt), 0.38 grams of sodium benzoate are dissolved in 100 mL of purified water and stirring is continued for 10 minutes. The solution is then pulled into a syringe.

c) No Bile Salt (Control)
Preparation Method:

Using a stainless steel dissolving vessel fitted with a propeller stirrer and turboemulsifier 0.25 grams of potassium metabisulphite, 0.3 grams EDTA (disodium salt), 0.38 grams of sodium benzoate are dissolved in 100 mL of purified water and stirring is continued for 10 minutes. The solution is then pulled into a syringe.

Analysis of Food Intake

The sodium taurocholate rectal enema described above is rectally administered to 5 conscious overnight-fasted subjects (e.g., Sprague Dawley rats) and the control rectal enema without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

The sodium glycocholate rectal enema described above is rectally administered to 5 conscious overnight-fasted subjects (e.g., Sprague Dawley rats) and the control rectal enema without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

Example 23

Rectal Suppositories a) Sodium Taurocholate
Preparation Method:

Using a stainless steel dissolving vessel fitted with a propeller stirrer 2.69 grams of sodium taurocholate and 0.1 grams of methyl cellulose are added to 10 grams of higher saturated fatty acid triglycerides (Witepsol™S55; Dynamic Novel Aktiengesellschaft, West Germany) and the combination is melted at 50 C and stirred. While the composition is a liquid it is filled into suppository containers for rats (50 mg per container) and then quenched in ice-water.

b) 500 mM Sodium Glycocholate
Preparation Method:

Using a stainless steel dissolving vessel fitted with a propeller stirrer 2.69 grams of sodium glycocholate and 0.1 grams of methyl cellulose are added to 10 grams of higher saturated fatty acid triglycerides (Witepsol™S55; Dynamic Novel Aktiengesellschaft, West Germany) and the combination is melted at 50 C and stirred. While the composition is a liquid it is filled into suppository containers for rats (50 mg per container) and then quenched in ice-water.

c) No Bile Salt (Control)
Preparation Method:

Using a stainless steel dissolving vessel fitted with a propeller stirrer 0.1 grams of methyl cellulose is added to 10 grams of higher saturated fatty acid triglycerides (Witepsol™S55; Dynamic Novel Aktiengesellschaft, West Germany) and the combination is melted at 50 C and stirred. While the composition is a liquid it is filled into suppository containers for rats (50 mg per container) and then quenched in ice-water.

Analysis of Food Intake

The sodium taurocholate rectal suppository described above is rectally administered to 5 conscious overnight-fasted subjects (e.g., Sprague Dawley rats) and the control rectal suppository without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

The sodium glycocholate rectal suppository described above is rectally administered to 5 conscious overnight-fasted subjects (e.g., Sprague Dawley rats) and the control rectal suppository without the sodium glycocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

Example 24

Rectal Gels—Sodium Taurocholate/Control a) 500 mM Sodium Taurocholate
Preparation Method:

Using a stainless steel dissolving vessel fitted with a propeller stirrer 26.88 grams of sodium taurocholate and 1 gram of methyl cellulose are dissolved in 100 mL of purified water and stirred for 15 minutes. 6 syringes connected to gavage tubes were then each filled with 3 mL of the composition.

b) No Bile Salt (Control)
Preparation Method:

Using a stainless steel dissolving vessel fitted with a propeller stirrer 1 gram of methyl cellulose is dissolved in 100 mL of purified water and stirred for 15 minutes. 5 syringes connected to gavage tubes are then each filled with 3 mL of the composition.

Analysis of Food Intake

The sodium taurocholate rectal gel described above was rectally administered to 6 conscious overnight-fasted subjects (e.g., Sprague Dawley rats) and the control rectal gel without the sodium taurocholate was rectally administered to 5 conscious overnight-fasted subjects (e.g., Sprague Dawley rats). Each rat was then exposed to pre-weighed food and the cumulative consumption of the food was determined over a 6 hour period by weighing the food after 30 minutes, 60 minutes, 120 minutes, 240 minutes and 360 minutes.

Results

The cumulative food intake in rats instilled with taurocholate containing gels is reduced compared to rats instilled with gel alone (FIG. 5). FIG. 5 illustrates the individual food intake in rats with bile sat containing gel per rectum (dotted lines) or control vehicle (solid lines). The effect of the taurocholate on food intake is found to be statistically significant.

Example 5

Rectal Gels—Sodium Taurcholate Dose Response a) 50 mM Sodium Taurocholate
Preparation Method:

Using a stainless steel dissolving vessel fitted with a propeller stirrer 2.688 grams of sodium taurocholate and 1 gram of methyl cellulose are dissolved in 100 mL of purified water and stirred for 15 minutes. 12 syringes connected to gavage tubes are then each filled with 3 mL of the composition.

b) 150 mM Sodium Taurocholate
Preparation Method:

Using a stainless steel dissolving vessel fitted with a propeller stirrer 8.066 grams of sodium taurocholate and 1 gram of methyl cellulose are dissolved in 100 mL of purified water and stirred for 15 minutes. 12 syringes connected to gavage tubes are then each filled with 3 mL of the composition.

c) 500 mM Sodium Taurocholate
Preparation Method:

Using a stainless steel dissolving vessel fitted with a propeller stirrer 26.88 grams of sodium taurocholate and 1 gram of methyl cellulose are dissolved in 100 mL of purified water and stirred for 15 minutes. 12 syringes connected to gavage tubes are then each filled with 3 mL of the composition.

d) No Bile Salt (Control)
Preparation Method:

Using a stainless steel dissolving vessel fitted with a propeller stirrer 1 gram of methyl cellulose is dissolved in 100 mL of purified water and stirred for 15 minutes. 12 syringes connected to gavage tubes are then each filled with 3 mL of the composition.

Analysis of Food Intake

A 4×4 Latin Square design is used to monitor the effect of the different concentration of taurocholate on the food uptake of overnight-fasted Sprague Dawley rats. Each concentration is tested in triplicate with four rats used per replicate. Therefore, twelve rats were used for each rectal gel composition (50 mM gel, 150 mM gel, 500 mM gel and the control gel), and all rats received each of the 4 treatments. Following rectal administration of the gels, each rat is then exposed to pre-weighed food and the cumulative consumption of the food is determined over a 24 hour period by weighing the food after 30 minutes, 1 hour, 2 hours, 4 hours, 6 hours, 8 hours and 24 hours.

Results

Figure 6:
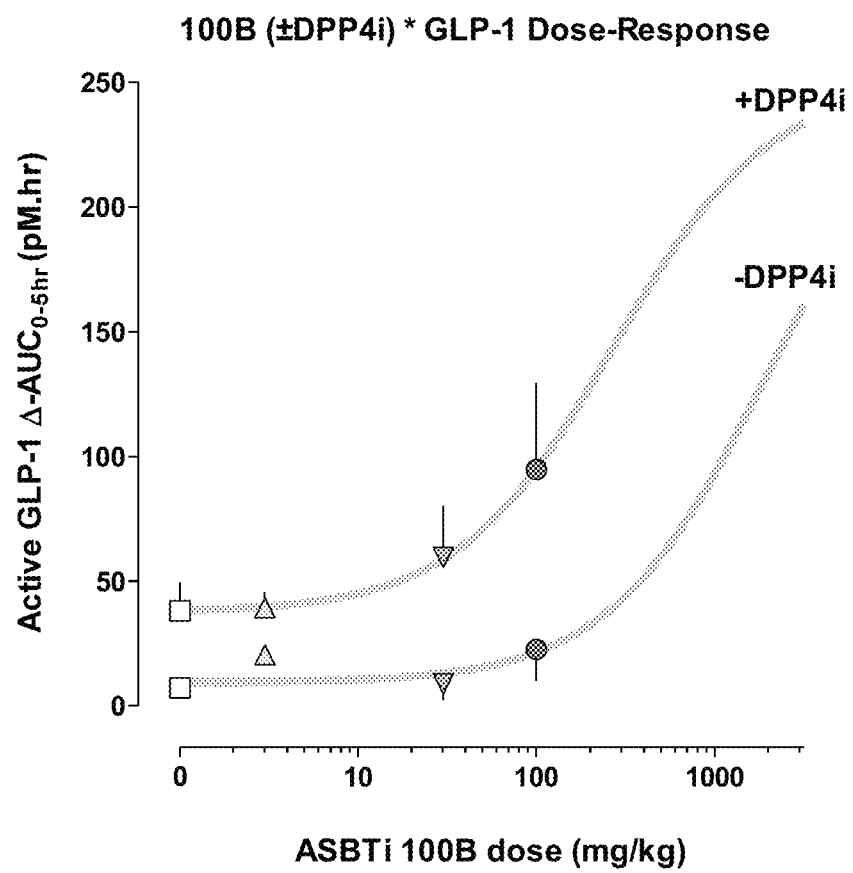
FIG. 6 illustrates a dose-dependent increase in plasma GLP-1 level in normal rats upon administration of a combination of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (100B) (0, 3, 30, 100 mg/kg) and 30 mg/kg sitagliptin (DPP-IV inhibitor) and the ASBTI alone.

The cumulative food intake in rats instilled with taurocholate containing gels is observed to be dose dependently related to the quantity of taurocholate administered (FIG. 6). Moreover, the differences in food uptake are observed to be maintained for at least 24 hours.

Figure 7A:
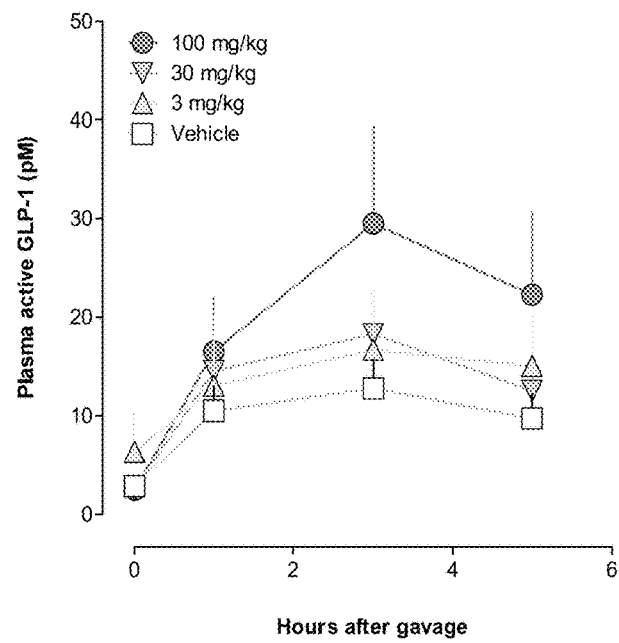
FIG. 7A and FIG. 7B illustrate a time course for dose-dependent increase in plasma GLP-1 level in normal rats upon administration of a combination of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (0, 3, 30, 100 mg/kg) and 30 mg/kg sitagliptin (DPP-IV inhibitor) and the ASBTI alone.
Figure 7B:
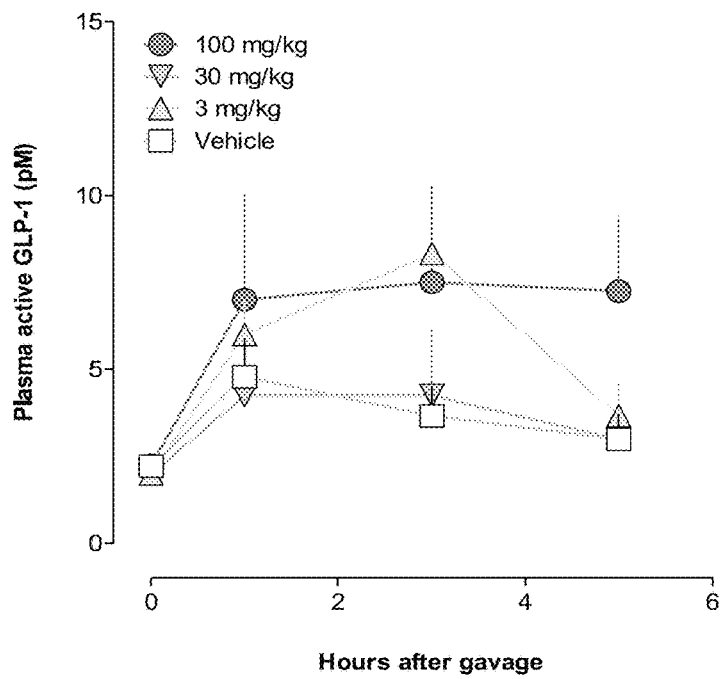

The ED50 for inhibition of food intake is obtained by plotting th normalizing the dose response for the anorectic effect of taurocholate to the control data as a log of taurocholate dose vs the percentage of control cumulative intake (FIG. 7). The ED50 for inhibition of food intake at 1 hour is 528 mM for 3 mL doses (1.6 mmol/rat) while for 24 hour intake the ED50 is 7.2 mmol/rat. Surprisingly, the dose dependency for inhibition of intake is not different between 8 and 24 hours, thereby indicating the longevity of the anorectic response.

Example 26

Rectal Gels—Sodium Glycocholate/Control a) 500 mM Sodium Glycocholate
Preparation Method:

Using a stainless steel dissolving vessel fitted with a propeller stirrer 24.38 grams of sodium glucocholate and 1 gram of methyl cellulose are dissolved in 100 mL of purified water and then stirred for 15 minutes. 6 syringes connected to gavage tubes are then each filled with 3 mL of the composition.

b) No Bile Salt (Control)
Preparation Method:

Using a stainless steel dissolving vessel fitted with a propeller stirrer 1 gram of methyl cellulose is dissolved in 100 mL of purified water and stirred for 15 minutes. 5 syringes connected to gavage tubes are then each filled with 3 mL of the composition.

Analysis of Food Intake

The sodium glycocholate rectal gel described above is rectally administered to 6 conscious overnight-fasted subjects (e.g., Sprague Dawley rats) and the control rectal gel without the sodium glycocholate is rectally administered to 5 conscious overnight-fasted subjects (e.g., Sprague Dawley rats). Each subject is then exposed to pre-weighed food and the cumulative consumption of the food is determined over a 6 hour period by weighing the food after 30 minutes, 60 minutes, 120 minutes, 240 minutes and 360 minutes.

Example 27

Rectal Gels—Sodium Glycocholate Dose Response a) 50 mM Sodium Glycocholate
Preparation Method:
Using a stainless steel dissolving vessel fitted with a propeller stirrer 2.44 grams of sodium glycocholate and 1 gram of methyl cellulose are dissolved in 100 mL of purified water and then stirred for 15 minutes. 12 syringes connected to gavage tubes are then each filled with 3 mL of the composition.

b) 150 mM Sodium Glycocholate
Preparation Method:
Using a stainless steel dissolving vessel fitted with a propeller stirrer 7.32 grams of sodium glycocholate and 1 gram of methyl cellulose are dissolved in 100 mL of purified water and then stirred for 15 minutes. 12 syringes connected to gavage tubes are then each filled with 3 mL of the composition.

c) 500 mM Sodium Glycocholate
Preparation Method:
Using a stainless steel dissolving vessel fitted with a propeller stirrer 24.38 grams of sodium glycocholate and 1 gram of methyl cellulose are dissolved in 100 mL of purified water and then stirred for 15 minutes. 12 syringes connected to gavage tubes are then each filled with 3 mL of the composition.

d) No Bile Salt (Control)
Preparation Method:
Using a stainless steel dissolving vessel fitted with a propeller stirrer 1 gram of methyl cellulose is dissolved in 100 mL of purified water and then stirred for 15 minutes. 12 syringes connected to gavage tubes are then each filled with 3 mL of the composition.

Analysis of Food Intake
A 4×4 Latin Square design as used to monitor the effect of the different concentration of glycocholate on the food uptake of overnight-fasted Sprague Dawley rats. Each concentration is tested in triplicate with four rats used per replicate. Therefore, twelve rats are used for each rectal gel composition (50 mM gel, 150 mM gel, 500 mM gel and the control gel), with all rats receiving each of the 4 treatments. Following rectal administration of the gels, each rat is then exposed to pre-weighed food and the cumulative consumption of the food is determined over a 24 hour period by weighing the food after 30 minutes, 1 hour, 2 hours, 4 hours, 6 hours, 8 hours and 24 hours.

Example 28

Enteric Coated Tablets a) 5 mg Sodium Taurocholate
Preparation Method:
Preparation of core: 5 mg sodium taurocholate, 25 mg microcrystalline cellulose, 20 mg mannitol, and 10 mg croscarmellose sodium are mixed in a Hobart Mixer for 15 minutes. The mixture is granulated with 20% polyvinl pyrrolidone (4 mg) solution until optimum granulation is obtained. The granulation is dried overnight at 50° C. The granulation is then passed through a #30 mesh. The granulation is then blended with 1 mg magnesium stearate. Using an F-Press ¼" standard concave round punch, the granulation is compressed into a tablet. Preparation of erodible polymer layer and dual matrix tablets: 415 mg hdroxypropyl methylcellulose, 75 mg microcrystalline cellulose, and 6 mg polyvinylpyrrolidone are uniformly mixed with a mortar. The powder mix is granulated with 50% v/v alcohol solution until optimum granulation is obtained. The granulation is dried overnight at 50° C. The granulation is then passed through a #40 mesh screen. The granulation is then blended with 2.5 mg magnesium stearate. Using a Carver Press and a ⁷⁄₁₆" standard concave round punch, half of the granulation is placed in the die cavity, the core is then placed in the cavity and the other half of the granulation is placed in the die cavity. The mass is compressed to 5,000 lbs to form the dual matrix tablet. Enteric coating: Using a propellar mixer, 42 g of hydroxypropyl methylcellulose phthalate and 4.2 g of distilled acetylated monoglycerides are dissolved in 514 mL of a mixture of a cetone and absolute alcohol (1:1). Using a spray system, the dual matrix tablets are then coated with the enteric coating solution. Approximately 60 mg of the coating material (dry basis) is applied per tablet.

b) 500 mM Sodium Glycocholate
Preparation Method:
Preparation of core: 5 mg sodium glycocholate, 25 mg microcrystalline cellulose, 20 mg mannitol, and 10 mg croscarmellose sodium are mixed in a Hobart Mixer for 15 minutes. The mixture is granulated with 20% polyvinl pyrrolidone (4 mg) solution until optimum granulation is obtained. The granulation is dried overnight at 50° C. The granulation is then passed through a #30 mesh. The granulation is then blended with 1 mg magnesium stearate. Using an F-Press ¼" standard concave round punch, the granulation is compressed into a tablet. Preparation of erodible polymer layer and dual matrix tablets: 415 mg hdroxypropyl methylcellulose, 75 mg microcrystalline cellulose, and 6 mg polyvinylpyrrolidone are uniformly mixed with a mortar. The powder mix is granulated with 50% v/v alcohol solution until optimum granulation is obtained. The granulation is dried overnight at 50° C. The granulation is then passed through a #40 mesh screen. The granulation is then blended with 2.5 mg magnesium stearate. Using a Carver Press and a ⁷⁄₁₆" standard concave round punch, half of the granulation is placed in the die cavity, the core is then placed in the cavity and the other half of the granulation is placed in the die cavity. The mass is compressed to 5,000 lbs to form the dual matrix tablet. Enteric coating: Using a propellar mixer, 42 g of hydroxypropyl methylcellulose phthalate and 4.2 g of distilled acetylated monoglycerides are dissolved in 514 mL of a mixture of a cetone and absolute alcohol (1:1). Using a spray system, the dual matrix tablets are then coated with the enteric coating solution. Approximately 60 mg of the coating material (dry basis) is applied per tablet.

c) No Bile Salt (Control)
Preparation Method:
Preparation of core: 25 mg microcrystalline cellulose, 20 mg mannitol, and 10 mg croscarmellose sodium are mixed in a Hobart Mixer for 15 minutes. The mixture is granulated with 20% polyvinl pyrrolidone (4 mg) solution until optimum granulation is obtained. The granulation is dried overnight at 50° C. The granulation is then passed through a #30 mesh. The granulation is then blended with 1 mg magnesium stearate. Using an F-Press ¼" standard concave round punch, the granulation is compressed into a tablet. Preparation of erodible polymer layer and dual matrix tablets: 415 mg hdroxypropyl methylcellulose, 75 mg microcrystalline cellulose, and 6 mg polyvinylpyrrolidone are uniformly mixed with a mortar. The powder mix is granulated with 50% v/v alcohol solution until optimum granulation is obtained. The granulation is dried overnight at 50° C. The granulation is then passed through a #40 mesh screen. The granulation is then blended with 2.5 mg magnesium stearate.

Using a Carver Press and a 7/16" standard concave round punch, half of the granulation is placed in the die cavity, the core is then placed in the cavity and the other half of the granulation is placed in the die cavity. The mass is compressed to 5,000 lbs to form the dual matrix tablet. Enteric coating: Using a propellar mixer, 42 g of hydroxypropyl methylcellulose phthalate and 4.2 g of distilled acetylated monoglycerides are dissolved in 514 mL of a mixture of acetone and absolute alcohol (1:1). Using a spray system, the dual matrix tablets are then coated with the enteric coating solution. Approximately 60 mg of the coating material (dry basis) is applied per tablet.

Analysis of Food Intake

The sodium taurocholate tablet described above (or, when necessary given the size and identity of a subject, a similar tablet having an appropriate dose and size) is orally administered to 5 conscious overnight-fasted subjects and the control tablet without the sodium taurocholate is orally administered to 5 conscious overnight-fasted subjects. Each subject is exposed to pre-weighed food and the cumulative consumption of the food is determined over a 6 hour period by weighing the food every 30 minutes.

The sodium glycocholate tablet described above (or, when necessary given the size and identity of a subject, a similar tablet having an appropriate dose and size) is orally administered to 5 conscious overnight-fasted subjects and the control tablet without the sodium taurocholate is orally administered to 5 conscious overnight-fasted subjects. Each subject is exposed to pre-weighed food and the cumulative consumption of the food is determined over a 6 hour period by weighing the food every 30 minutes.

Example 29

Absorption Inhibitors a) Control: 500mM Sodium Taurocholate
Preparation Method:

Using a stainless steel dissolving vessel fitted with a propeller stirrer and turboemulsifier 26.88 grams of sodium taurocholate, 0.25 grams of potassium metabisulphite, 0.3 grams EDTA (disodium salt) and 0.38 grams of sodium benzoate dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

b) 500 mM Sodium Taurocholate+Candidate Absorption Inhibitor
Preparation Method:

Using a stainless steel dissolving vessel fitted with a propeller stirrer and turboemulsifier 26.88 grams of sodium taurocholate, 0.25 grams of potassium metabisulphite, 0.3 grams EDTA (disodium salt), 0.38 grams of sodium benzoate and between 0.01 grams and 20 grams of a candidate absorption inhibitor are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

Analysis of Absorption Inhibition

The foams described above are rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes. Food intake is compared between the groups. The candidate absorption inhibitor inhibits absorption of the enteroendocrine peptide secretion enhancing agent (in this case sodium taurocholate) when the enteroendocrine peptide secretion enhancing agent is able to interact with the L-cells for a longer period of time (i.e., when it is not systemically absorbed), thereby reducing food intake when compared to the control formulation.

Alternatively, the ability of the absorption inhibitor to inhibit the absorption of the enteroendocrine peptide secretion enhancing agent (in this case sodium taurocholate) across the colon and/or rectum mucosa is determined by measuring the systemic concentration of enteroendocrine peptide secretion enhancing agent. Systemic concentration of enteroendocrine peptide secretion enhancing agent is measured prior to administration and at a time following administration of the enteroendocrine peptide secretion enhancing agent (e.g., after one hour). Decreased systemic concentration of the enteroendocrine peptide secretion enhancing agent indicate that the candidate absorption inhibitor inhibits the absorption of the enteroendocrine peptide secretion enhancing agent.

Example 30

Method of Inhibiting Food Intake

Studies are undertaken after an overnight fast following administration (8-10 hours prior to bile salt) of 100 mg Januvia (sitagliptin), a DDP-4 inhibitor that protects GLP-1 from inactivation by proteolysis. Dose escalation involves half-log increases in dose as tolerated. Planned doses are 1, 2, 7 and 20 mmoles of deoxycholic acid. Each dose is administered on a different day with at least three days between doses.

Subjects undergo complete physical examination with laboratory investigations including complete blood count, glucose, fasting lipids, liver function tests, urea and electrolytes, prothrombin time and partial thromboplastin time, haemoglobin $A_{1C}$, and urinalysis. Subjects are excluded if the fasting blood glucose is >300 mg/dl, if the haemoglobin $A_{1C}$ is >11%, or if there are abnormal liver function tests (such as transaminase levels >3× the upper limit of normal.

Subjects on oral medication will not receive such medication during the fasting period prior to the study or during the study period.

Subjects are studied on four separate occasions, e.g., at weekly intervals with at least three days gap between the different occasions. Subjects are studied after an overnight (10 hour) fast. Ten hours before the procedure, each subject will take 100 mg oral Januvia (sitagliptin), a DDP-4 inhibitor to protect GLP-1 (7-36) amide from degradation in the circulation. An indwelling catheter (Intracath) is placed in a forearm vein for blood sampling. An initial basal blood sample (5 ml) is taken and the catheter kept patent with normal saline. Blood samples are taken into EDTA Vacutainers (purple top). After 15 minutes a second blood sample (5 ml) will be collected. Placebo (vehicle) or sodium deoxycholate at doses of 1, 2, 7 and 20 mmoles, incorporated into 20 mL or 60 mL of 1% carboxymethyl cellulose is placed per rectum by syringe (type) over a period of one minute.

Further 5 ml blood samples are collected 10, 20, 30, 40, 50 and 60 minutes after instillation of the placebo or deoxycholate.

In plasma samples from each time point we will measure glucose, insulin, GLP-1 (active) and PYY (total), using assay kits (Linco) from the Millipore Corporation. Measures of these hormones provide an endpoint for determining efficacy in producing reduced food intake.

In addition, measured is food intake for a two hour period after the end of the infusion study. During this period, the subjects are offered a buffet lunch with food in such excess that all appetites will be satisfied. The amount of food is quantified preprandially and postprandially and the caloric intake calculated. Before, at the end of the infusion study, and two hours after presentation of a buffet lunch, appetite ratings are made on a 100 mm visual analogue scale (higher values indicating greater appetite) with the text expressing the most positive and most negative ratings at each end of the scale.

Example 31

In certain instances, placing bile salts or other enteroendocrine peptide enhancing agents into the rectum has several advantages and provides substantial information on the whole process of releasing the distal gut hormones, GLP-1, oxyntomodulin and PYY. In our human studies we have demonstrated the following:
Dose-responsive increase in GLP-1 and PYY levels in the bloodstream.
Consequent increase in insulin secretion and reduction in glucose levels.
Dose-responsive and substantial reduction in food intake.
Elevation of high local concentrations of bile salt in the rectum without diarrhea.

Example 32

Studies were undertaken after an overnight fast following administration (8-10 hours prior to bile salt) of 100 mg sitagliptin, a DPP-4 inhibitor that protects GLP-1 from inactivation by proteolysis. Dose escalation involved half-log increases in dose of taurocholic acid. The doses used were 0.66, 2.0, 6.66 and 20.0 mmoles (358, 1075, 3584, 10,754 mg) of taurocholic acid. The taurocholic acid was administered into the rectum by syringe in a total volume of 20 ml of 1% carboxymethyl cellulose gel. Each dose was administered on a different day with at least three days between doses. FIG. 9 illustrates the increase of circulating GLP-1 levels following rectal administration of taurocholic acid. FIG. 10 illustrates the increase of circulating PYY levels following rectal administration of taurocholic acid Example 33

Objective:
The aim of a 1 year study is to show evidence of the efficacy Sodium Taurocholate on reduction of risk of pancreatic cancer.
Study Design:
This is a 1 year study. A cohort of 1000 patients is divided into placebo group and drug treated groups. 50 mg of Sodium taurocholate will be rectally administered 30 minutes prior to ingestion of lunch and prior to ingestion of dinner for a total of 100 mg of Sodium taurocholate per day.

Inclusion Criteria are: 70 years of age or less, waist circumference ≥102 cm for men or ≥88 cm for women, pancreatic ductal adenocarcinoma.

Exclusion criteria are: Stroke/MI/unstable cardiovascular disease within 6 months, clinically significant renal, hepatic or psychiatric disease, participation in a formal weight loss program or lifestyle intervention, glaucoma or intraocular pressure, use of any antidiabetic medication, prior history with cancer.

Patient Response to sodium taurocholate therapy: Patient response is assessed via weekly hospital visits, weight and waist measurements and routine blood tests.

Blood Sampling Serial blood is drawn by direct vein puncture before and after administration of Compound 100 analog. Venous blood samples (5 mL) for determination of serum concentrations are obtained at about 10 minutes prior to dosing and at approximately the following times after dosing: days 1, 2, 3, 4, 5, 6, 7, 14 and every 14 days later. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, 14 and every 14 days later. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Patient Response to Compound 4 therapy: Patient response is assessed via weekly hospital visits, weight and waist measurements and routine blood tests.

Statistical Analysis: The association of sodium taurocholate and risk of pancreatic cancer is analyzed in multi-variable logistic regression models including age, sex, race, smoking, alcohol, BMI, family history of cancer, duration of diabetes, and insulin use. To control for reversal causality due to pancreatic cancer-caused diabetes, risk of pancreatic cancer is estimated after exclusion of those with duration of diabetes ≤2 years. HbA1c level (≤7% or >7%), a marker of glycemic control, is compared between placebo and users of sodium taurocholate by $\chi 2$ test. The demographic and risk factors as well as duration of diabetes and insulin use are compared between sodium taurocholate users and placebo by $\chi 2$ test.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating an inflammatory intestinal condition comprising orally administering for local delivery to the distal ileum, the colon, or the rectum of an individual in need thereof, a pharmaceutical composition consisting of a therapeutically effective amount of an Apical Sodium-dependent Bile Acid Transporter Inhibitor (ASBTI) and one or more pharmaceutical carriers, wherein the inflammatory intestinal condition is selected from the group consisting of gastritis, ulcerative colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastric carcinogenesis, and gastric carcinogenesis following gastric or bowel resection, wherein the ASBTI inhibitor is a compound of Formula II:

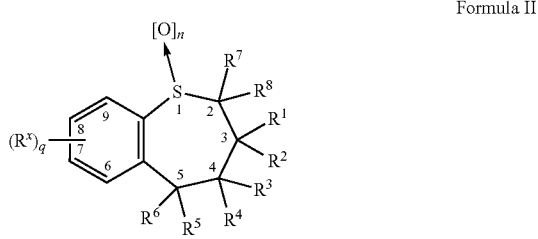

Formula II wherein:
q is an integer from 1 to 4,
n is an integer from 0 to 2,
$R^1$ and $R^2$ are independently selected from the consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or
$R^1$ and $R^2$ taken together with the carbon to which they are attached form $C_3$-$C_{10}$ cycloalkyl;
$R^3$ and $R^4$ are independently selected from the group consisting of H, alkyl, alkenyl, alkynl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above, or
$R^3$ and $R^4$ together =O, =NOR$^{11}$, =S, =NNR$^{11}$R$^{12}$, =NR$^9$, or =CR$^{11}$R$^{12}$,
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;
$R^5$ and $R^6$ are independently selected from the group consisting of H, alkyl, alkenyl, alkynyl, aryl, cycloalkyl, heterocycle, quaternary heterocycle, quaternary heteroaryl, $OR^9$, $SR^9$, $S(O)R^9$, $SO_2R^9$, $SO_3R^9$, and —$L_z$-$K_z$;
wherein z is 1, 2 or 3; each L is independently a substituted or unsubstituted alkyl, a substituted or unsubstituted heteroakyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^0R^{11}R^{12}A^-$,
wherein:
$A^+$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, P(O) $R^7R^8$, $P^+R^7R^8R^9A^-$, and $P(O)(OR^7)$ $OR^8$ and
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $P(O)R^7$, $P(O)R^7$, $P^+R^7R^8A^-$, or phenylene, and
$R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quatenary heteroaryl, and quaternary heteroarylalkyl,
wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, amino acid, peptide, or polypeptide, and
$R^{13}$, $R^{14}$ and $R^{15}$ are optionally substituted with one more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM,
wherein $R^{16}$ and $R^{17}$ are independently selected from the substituents constituting $R^9$ and M; or R¹⁴ and R¹⁵, together with the nitrogen atom to which they are attached, form a cyclic ring; and is selected from the group consisting of alkyl, alkenyl, alkynyl, cycloalky, aryl, acyl, heterocycle, ammoniumalkyl, alkylammoniumalkyl, and arylalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, S(O), $NR^{18}$, $NR^{13}R^{18}$, $NR^{18}R^{14}$, $N^+12^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)M, wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_3R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen or SH;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

2. The method of claim 1, wherein less than 10% of the ASBTI is systemically absorbed.

3. The method of claim 1, wherein the individual is a prematurely born infant, an enterally-fed infant, or a formula-fed infant.

4. The method of claim 1, wherein the non-systemically administered ASBTI reduces intraenterocyte bile acids or reduces necrosis and/or damage to ileal architecture in an individual in need thereof.

5. The method of claim 1, wherein the ASBTI is

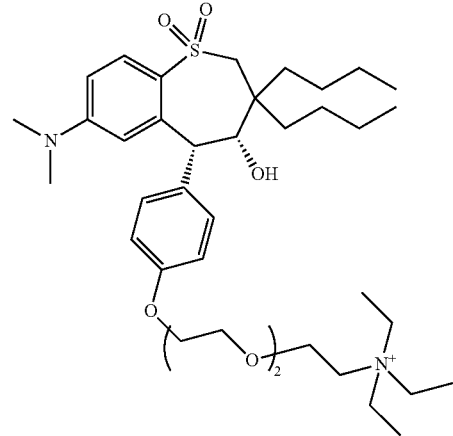

or a pharmaceutically acceptable salt or solvate thereof.

6. The method of claim 1, wherein the ASBTI is

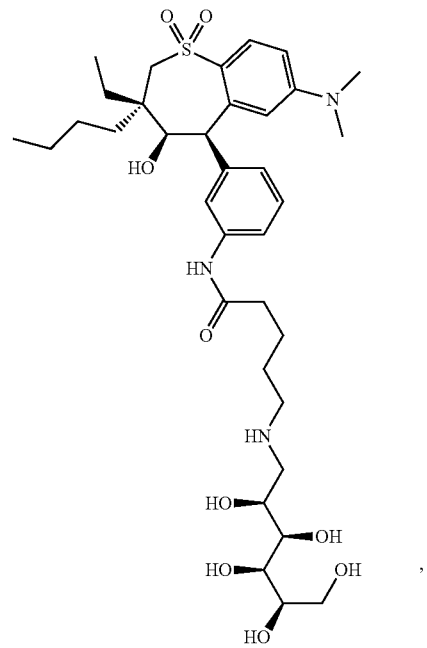 [SMILES: CCCC[C@]1(CC)CS(=O)(=O)c2ccc(N(C)C)cc2[C@@H](c2cccc(NC(=O)CCCCNC[C@H](O)[C@@H](O)[C@H](O)[C@H](O)CO)c2)[C@H]1O]

or a pharmaceutically acceptable salt or solvate thereof.

7. The method of claim 1, wherein the ASBTI is potassium((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydropyran-2-ylmethyl)sulphate ethanolate hydrate, or a pharmaceutically acceptable salt or solvate thereof.

8. The method of claim 1, wherein the ASBTI is

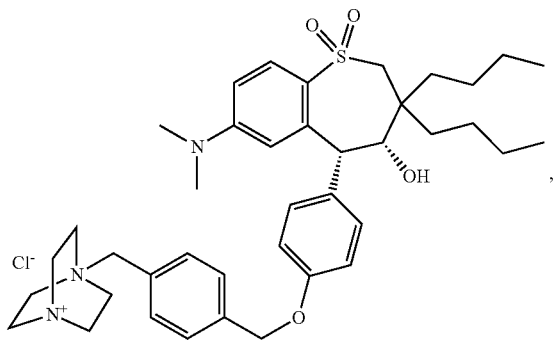

or a pharmaceutically acceptable salt or solvate thereof.

9. The method of claim 1, wherein the ASBTI is administered before ingestion of food, optionally wherein the ASBTI is administered less than about 60 minutes or less than about 30 minutes before ingestion of food.

10. The method of claim 1, wherein the ASBTI is administered orally, optionally wherein the ASBTI is administered as an ileal-pH sensitive release or an enterically coated formulation.

11. A method for treating an inflammatory intestinal condition comprising orally administering for local delivery to the distal ileum, the colon, or the rectum of an individual in need thereof, a pharmaceutical composition consisting of a therapeutically effective amount of 1) Apical Sodium-dependent Bile Acid Transporter Inhibitor (ASBTI), 2) a DPP-IV inhibitor, and 3) one or more pharmaceutical carriers, wherein the inflammatory intestinal condition is selected from the group consisting of gastritis, ulcerative colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastric carcinogenesis, and gastric carcinogenesis following gastric or bowel resection, wherein the ASBTI inhibitor is a compound of Formula II:

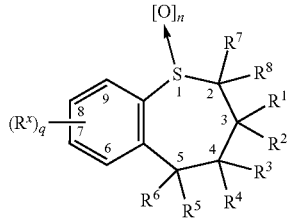

Formula II wherein
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or
$R^1$ and $R^2$ taken together with the carbon to which they are attached form $C_3$-$C_{10}$ cycloalkyl;
$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or
$R^3$ and $R^4$ together =O, =$NOR^{11}$, =S, =$NNR^{11}R^{12}$, =$NR^9$, or =$CR^{11}R^{12}$,
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ and $R^6$ are independently selected from the group consisting of H, alkyl, alkenyl, alkynyl, aryl, cycloalkyl, heterocycle, quaternary heterocycle, quaternary heteroaryl, $OR^9$, $SR^9$, $S(O)R^9$, $SO_2R^9$, $SO_3R^9$, and -$L_z$-$K_z$;
wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$,
wherein:
$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)$ $OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, amino acid, peptide, or polypeptide, and $R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, S(O), $NR^{18}$, $NR^{13}R^{18}$, $NR^{18}R^{14}$, $N^+12^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)M, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_3R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen or SH;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

12. The method of claim 11, wherein the DPP-IV inhibitor is sitagliptin.

\* \* \* \* \*